US008188255B2

(12) United States Patent
Litman et al.

(10) Patent No.: US 8,188,255 B2
(45) Date of Patent: May 29, 2012

(54) HUMAN MICRORNAS ASSOCIATED WITH CANCER

(75) Inventors: Thomas Litman, Værløse (DK); Søren Møller, Holte (DK); Søren Morgenthaler Echwald, Humlebæk (DK); Morten Lindow, København V (DK); Anders Martin Bøgild Jacobsen, København V (DK); Anders Stærmose Krogh, København Ø (DK); Sanne Nygaard, Brønshøj (DK); Rolf Søkilde, København N (DK)

(73) Assignee: Exiqon A/S, Vedbaek (DK)

( * ) Notice: Subject to any disclaimer, the term of this patent is extended or adjusted under 35 U.S.C. 154(b) by 25 days.

(21) Appl. No.: 11/975,644

(22) Filed: Oct. 19, 2007

(65) Prior Publication Data

US 2009/0239815 A1  Sep. 24, 2009

Related U.S. Application Data

(60) Provisional application No. 60/900,081, filed on Feb. 7, 2007, provisional application No. 60/853,410, filed on Oct. 20, 2006.

(51) Int. Cl.
*C07H 21/04* (2006.01)

(52) U.S. Cl. .................... 536/24.3; 536/23.1; 536/24.31; 536/24.33

(58) Field of Classification Search ........................ None
See application file for complete search history.

(56) References Cited

U.S. PATENT DOCUMENTS

| | | | |
|---|---|---|---|
| 3,687,808 | A | 8/1972 | Merigan et al. |
| 5,432,272 | A | 7/1995 | Benner |
| 6,043,060 | A | 3/2000 | Imanishi |
| 6,268,490 | B1 | 7/2001 | Imanishi et al. |
| 7,320,862 | B2 * | 1/2008 | Stahler et al. .................... 435/6 |
| 2005/0026164 | A1 * | 2/2005 | Zhou .................................. 435/6 |
| 2006/0154888 | A1 | 7/2006 | Rosenbohm et al. |
| 2007/0099196 | A1 | 5/2007 | Kauppinen et al. |

FOREIGN PATENT DOCUMENTS

| | | |
|---|---|---|
| EP | 1 072 679 A2 | 1/2001 |
| WO | WO 97/12896 A1 | 4/1997 |
| WO | WO 98/39352 A1 | 9/1998 |
| WO | WO 99/65928 A2 | 12/1999 |
| WO | WO 00/56746 A2 | 9/2000 |
| WO | WO 00/56748 A1 | 9/2000 |
| WO | WO 00/66604 A2 | 9/2000 |
| WO | WO 00/77214 A2 | 12/2000 |
| WO | WO 01/00641 A1 | 1/2001 |
| WO | WO 01/07455 A1 | 2/2001 |
| WO | WO 01/77384 A2 | 10/2001 |
| WO | WO 02/38589 A2 | 5/2002 |
| WO | WO 03/020739 A2 | 5/2003 |
| WO | WO 2004/024314 A2 | 5/2004 |
| WO | WO 2005/098029 A2 | 10/2005 |
| WO | WO 2006/015312 A2 | 2/2006 |
| WO | WO 2006/119365 A2 | 11/2006 |
| WO | WO 2007/073737 A1 | 7/2007 |
| WO | WO 2007/112754 A2 | 10/2007 |

OTHER PUBLICATIONS

Adams et al., "Hindered Dialkylamino Nucleoside Phosphite Reagents in the Synthesis of Two DNA 51-Mers," *J. Am. Chem. Soc.* 105:661-663, 1983.
Bartel et al., "MicroRNAs: Genomics, Biogenesis, Mechanism, and Function," *Cell* 116:281-297, 2004.
Bentwich et al., "Identification of Hundreds of Conserved and Nonconserved Human MicroRNAs," *Nat. Genet.* 37:766-770, 2005.
Bernstein et al., "Role for a Bidentate Ribonuclease in the Initiation Step of RNA Interference," *Nature* 409:363-366, 2001.
Bohnsack et al., "Exportin 5 is a RanGTP-Dependent dsRNA-Binding Protein that Mediates Nuclear Export of Pre-miRNAs," *RNA* 10:185-191, 2004.
Calin et al., "MicroRNA Profiling Reveals Distinct Signatures in B Cell Chronic Lymphocytic Leukemias," *Proc. Natl. Acad. Soc. U.S. A.* 101:11755-11760, 2004.
Caruthers et al., "Chemical Synthesis and Biological Studies on Mutated Gene-Control Regions," *Cold Spring Harbor Symp. Quant. Biol.* 47:411-418, 1982.
Cummins et al., "The Colorectal MicroRNAome," *Proc. Natl. Acad. Sci. U.S.A.* 103:3687-3692, 2006.
De Mesmaeker et al., "Backbone Modifications in Oligonucleotides and Peptide Nucleic Acid Systems," *Curr. Opin. Struct. Biol,* 5:343-355, 1995.
Englisch et al., "Chemically Modified Oligonucleotides as Probes and Inhibitors," *Angew. Chem. Int. Ed.* 30:613-629, 1991.
Freier et al., "The Ups and Downs of Nucleic Acid Duplex Stability: Structure-Stability Studies on Chemically Modified DNA:RNA Duplexes," *Nuc. Acids Res.* 25:4429-4443, 1997.
Gall et al., "Formation and Detection of RNA-DNA Hybrid Molecules in Cytological Preparations," *Proc. Natl. Acad. Sci., USA* 63:378-383, 1969.
Griffiths-Jones, "The MicroRNA Registry," *Nuc. Acids Res.* 32:D109-D111, 2004.
Guimaraes-Sternberg et al., "MicroRNA Modulation of Megakaryoblast Fate Involves Cholinergic Signaling," *Leukemia Res.* 30:583-595, 2006.
Håkansson et al., "Convenient Syntheses of 7-Hydroxy-1-(hydroxymethyl)-3-(thymin-1-yl)-2,5-dioxabicyclo[2.2.1] heptanes: α-L-Ribo- and α-L-Xylo-Configured LNA Nucleosides," *J. Org. Chem.* 65:5161-5166, 2000.
Håkansson et al., "The Adenine Derivative of α-L- LNA (α-L-ribo Configured Locked Nucleic Acid): Synthesis and High-Affinity Hybridization Towards DNA, RNA, LNA, and α-L-LNA Complementary Sequences," *Bioorg. Med. Chem. Lett,* 11:935-938, 2001.
Hames and Higgins (Ed.), *Nucleic Acid Hybridization: A Practical Approach*, IRL Press, p. 190-193, 1985.

(Continued)

*Primary Examiner* — Amy Bowman
(74) *Attorney, Agent, or Firm* — Clark & Elbing LLP; Kristina Bieker-Brady

(57) ABSTRACT

The invention provides new sequences for human microRNAs associated with cancer which may be used as molecular markers for cancer diagnostics or as therapeutic targets or agents.

26 Claims, 2 Drawing Sheets

OTHER PUBLICATIONS

Hutvagner et al., "A Cellular Function for the RNA-Interference Enzyme Dicer in the Maturation of the *let-7* Small Temporal RNA," *Science* 293:834-838, 2001.

Iorio et al., "MicroRNA Gene Expression Deregulation in Human Breast Cancer," *Cancer Res.* 65(16):7065-7070, 2005.

John et al., "RNA-DNA Hybrids at the Cytological Level," *Nature* 223:582-587, 1969.

Ke et al., "MicroRNAs: Key Participants in Gene Regulatory Networks," *Curr. Opin. Chem. Biol.* 7:516-523, 2003.

Ketting et al., "Dicer Functions in RNA Interference and in Synthesis of Small RNA Involved in Developmental Timing in *C. elegans*," *Genes Dev.* 15:2654-2659, 2001.

Khvorova et al., "Functional siRNAs and miRNAs Exhibit Strand Bias," *Cell* 115:209-216, 2003.

Koshkin et al., "A Simplified and Efficient Route to 2'-*O*, 4'-*C*-Methylene-Linked Bicyclic Ribonucleosides (Locked Nucleic Acid)," *J. Org. Chem.* 66:8504-8512, 2001.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," *Tetrahedron* 54:3607-3630, 1998.

Kroschwitz (Ed.), *Concise Encyclopedia of Polymer Science and Engineering*, John Wiley & Sons, p. 858-859, 1990.

Kumar et al., "The First Analogues of LNA (Locked Nucleic Acids): Phosphorothioate-LNA and 2'-Thio-LNA," *Bioorg. Med. Chem. Lett.* 8:2219-2222, 1998.

Kværnø et al., "Novel Bicyclic Nucleoside Analogue (1S,5S,6S)-6-Hydroxy-5-hydroxymethyl-1-(uracil-1-yl)-3,8-dioxabicyclo[3.2.1]octane: Synthesis and Incorporation Into Oligodeoxynucleotides," *J. Org. Chem.* 66:5498-5503, 2001.

Kværnø et al., "Synthesis of Abasic Locked Nucleic Acid and Two *seco*-LNA Derivatives and Evaluation of Their Hybridization Properties Compared With Their More Flexible DNA Counterparts," *J. Org. Chem.* 65:5167-5176, 2000.

Lagos-Quintana et al., "Identification of Novel Genes Coding for Small Expressed RNAs," *Science* 294:853-858, 2001.

Lau et al., "An Abundant Class of Tiny RNAs with Probable Regulatory Roles in *Caenorhabditis elegans*," *Science* 294:858-862, 2001.

Lee et al., "The Nuclear RNase III Drosha Initiates MicroRNA Processing," *Nature* 425:415-419, 2003.

Lipardi et al., "RNAi as Random Degradative PCR: siRNA Primers Convert mRNA Into dsRNAs That Are Degraded to Generate New siRNAs," *Cell* 107:297-307, 2001.

Lu et al., "MicroRNA Expression Profiles Classify Human Cancers," *Nature* 435:834-838, 2005.

Ma et al., "Molecular Classification of Human Cancers Using a 92-Gene Real-Time Quantitative Polymerase Chain Reaction Assay," *Arch. Pathol. Lab. Med.* 130:465-473, 2006.

Michael et al., "Reduced Accumulation of Specific MicroRNAs in Colorectal Neoplasia," *Mol. Cancer Res.* 1:882-891, 2003.

Morita et al., "2'-O,4'-C-Ethylene-Bridged Nucleic Acids (ENA): Highly Nuclease-Resistant and Thermodynamically Stable Oligonucleotides for Antisense Drug," *Bioorg. Med. Chem. Lett.* 12:73-76, 2002.

Muir, "Cancer of Unknown Primary Site," *Cancer* 75:353-356, 1995.

Nelson et al., "The MicroRNA World: Small is Mighty," *Trends Biochem. Sci.* 28: 534-540, 2003.

Nykänen et al. "ATP Requirements and Small Interfering RNA Structure in the RNA Interference Pathway," *Cell* 107:309-321 (2001).

Pfundheller et al., "Evaluation of Oligonucleotides Containing Two Novel 2'-O-Methyl Modified Nucleotide Monomers: A 3'-C-Allyl and a 2'-O,3'-C-Linked Bicyclic Derivative," *Nucleosides & Nucleotides* 18:2017-2030, 1999.

Reinhart et al., "MicroRNAs in Plants," *Genes Dev.* 16:1616-1626, 2002.

Reyes et al., "Metastasis of Unknown Origin: The Role of Fine-Needle Aspiration Cytology," *Diagn. Cytopathol.* 18:319-322, 1998.

Sanghvi, "Heterocyclic Base Modifications in Nucleic Acids and their Applications in Antisense Oligonucleotides," in *Antisense Research and Applications*, Crooke and Leblue (Ed.), Chapter 15, p. 273-288, 1993.

Válóczi et al., "Sensitive and Specific Detection of MicroRNAs by Northern Blot Analysis Using LNA-Modified Oligonucleotide Probes," *Nucleic Acids Res.* 32:e175, 7 pages, 2004.

Volinia et al., "A MicroRNA Expression Signature of Human Solid Tumors Defines Cancer Gene Targets," *Proc. Natl. Acad. Sci., USA* 103:2257-2261, 2006.

Weiler et al., "Anti-MiRNA Oligonucleotides (AMOs): Ammunition to Target miRNAs Implicated in Human Disease?" *Gene Ther.* 13:496-502, 2006.

Xie et al., "Systematic Discovery of Regulatory Motifs in Human Promoters and 3' UTRs by Comparison of Several Mammals," *Nature* 434:338-345, 2005.

Yanaihara et al., "Unique MircroRNA Molecular Profiles in Lung Cancer Diagnosis and Prognosis," *Cancer Cell* 9:189-198, 2006.

Yi et al., "Exportin-5 Mediates the Nuclear Export of Pre-MicroRNAs and Short Hairpin RNAs," *Genes Dev.* 17:3011-3016, 2003.

Zhang et al., "Human Dicer Preferentially Cleaves dsRNAs at Their Termini Without a Requirement for ATP," *EMBO J.* 21:5875-5885, 2002.

International Search Report for PCT/EP2007/061210, completed Feb. 4, 2008.

International Preliminary Report on Patentability for PCT/EP2007/061210, issued Apr. 22, 2009.

Written Opinion of the International Searching Authority for PCT/EP2007/061210, completed Feb. 4, 2008, mailed May 26, 2008.

Jagadeeswaran et al., "Deep Sequencing of Small RNA Libraries Reveals Dynamic Regulation of Conserved and Novel microRNAs and microRNA-stars During Silkworm Development," *BMC Genomics* 11:1-18 (2010).

"Dead miRNA Entry", http://www.mirbase.org/cgi-bin/mima_entry.pl?acc=MI0006441, accessed on Mar. 27, 2012.

* cited by examiner

```
                             SEQUENCE LISTING

<160> NUMBER OF SEQ ID NOS: 558

<210> SEQ ID NO 1
<211> LENGTH: 28
<212> TYPE: RNA
<213> ORGANISM: Homo sapiens

<400> SEQUENCE: 1
cgagccuggu gauagcuggu uguccaag                                          28

<210> SEQ ID NO 2
<211> LENGTH: 165
<212> TYPE: RNA
<213> ORGANISM: Homo sapiens

<400> SEQUENCE: 2
aagauucaug aguagcagug acaaaccuac cgagccuggu gauagcuggu uguccaagau        60
agaaucuuag acaacucccu auaccagauc cucuaauuaa uuuuaauaaa ggccuucuau       120
uuauacuagc cacaucaagc cuagccgucu acguacccac agaau                      165

<210> SEQ ID NO 3
<211> LENGTH: 18
<212> TYPE: RNA
<213> ORGANISM: Homo sapiens
```

```
<400> SEQUENCE: 3
gaggcugagg cgagaggu                                                 18

<210> SEQ ID NO 4
<211> LENGTH: 158
<212> TYPE: RNA
<213> ORGANISM: Homo sapiens

<400> SEQUENCE: 4
cgguguuucc ggccgccguc gcuguccagg gaggcugagg cgagagguag cuguccgggu    60
ggggagcccg cacuaccuuc uuccucuucc uccuccuccu ccgggugagg ggagcgaagg   120 uuggggqucc ccgagcccau ggaccaggag gaggcgga                           158

<210> SEQ ID NO 5
<211> LENGTH: 23
<212> TYPE: RNA
<213> ORGANISM: Homo sapiens

<400> SEQUENCE: 5
auuuguggcc gaguguaaca acc                                           23

<210> SEQ ID NO 6
<211> LENGTH: 163
<212> TYPE: RNA
<213> ORGANISM: Homo sapiens

<400> SEQUENCE: 6
aucacccucu gaucgccgau caccucugag acccaacuug cucauaaaca aaacugccca    60
ugucgguccu cugcccugga ccugugacac ucuggacuau uucuguguuu auuuguggcc   120
gaguguaaca accauauaau aaaucaccuc uuccgcuguu uua                     163

<210> SEQ ID NO 7
<211> LENGTH: 16
<212> TYPE: RNA
<213> ORGANISM: Homo sapiens

<400> SEQUENCE: 7
ucccuucgug gucgcc                                                   16

<210> SEQ ID NO 8
<211> LENGTH: 156
<212> TYPE: RNA
<213> ORGANISM: Homo sapiens

<400> SEQUENCE: 8
auccugccuu ggcuggaaaa gccagccuuc cacccagcgc cccuaaaaug aucggguuga    60
cuccaguuuu guuacgaaag gaggccgggc ugcugagagg cucccugagu ucccuucgug   120
gucgcccguc acauugcccu gcuguauacu uaauaa                             156

<210> SEQ ID NO 9
<211> LENGTH: 21
<212> TYPE: RNA
<213> ORGANISM: Homo sapiens

<400> SEQUENCE: 9
gcaggggaag aagccuuccg u                                             21

<210> SEQ ID NO 10
<211> LENGTH: 161
```

```
<212> TYPE: RNA
<213> ORGANISM: Homo sapiens

<400> SEQUENCE: 10
cagacaaaga ggggcgugag ggagcugccu gcaggggaag aagccuuccg uaucgagcug    60
ggcggucauu acacaggugc gcacagauau ggaugaggag gggcgugagg gagccacgug   120
cagggcagca aguccucuau aucuugagcu ggguggucau u                       161

<210> SEQ ID NO 11
<211> LENGTH: 25
<212> TYPE: RNA
<213> ORGANISM: Homo sapiens

<400> SEQUENCE: 11
acuuugagag uuagaaaugg uuacu                                          25

<210> SEQ ID NO 12
<211> LENGTH: 165
<212> TYPE: RNA
<213> ORGANISM: Homo sapiens

<400> SEQUENCE: 12
ugaaacuaac uagauuuauu ggauaucagu acuuugagag uuagaaaugg uuacugauug    60
ucaucuuuuc agugaagggu ucuauaguug aguaaaaaau uugucuaacu uuguaaguau   120
aguuuauauu guagaaauug cuuccaauuu guuggguaac uucau                   165

<210> SEQ ID NO 13
<211> LENGTH: 24
<212> TYPE: RNA
<213> ORGANISM: Homo sapiens

<400> SEQUENCE: 13
aaccaaugau guaaugauuc ugcc                                           24

<210> SEQ ID NO 14
<211> LENGTH: 164
<212> TYPE: RNA
<213> ORGANISM: Homo sapiens

<400> SEQUENCE: 14
auugaguagg gcaaauuuua aauggguauu auuuuucauc uucaaacagg cagaccuguu    60
auccuaaacu aggugaguca gcuuuuggua caugugauga uuuucagugu aaccaaugau   120
guaaugauuc ugccaaauga aauauaauga uaucacugua aaac                    164

<210> SEQ ID NO 15
<211> LENGTH: 20
<212> TYPE: RNA
<213> ORGANISM: Homo sapiens

<400> SEQUENCE: 15
augauucugu gacgccagcu                                                20

<210> SEQ ID NO 16
<211> LENGTH: 160
<212> TYPE: RNA
<213> ORGANISM: Homo sapiens

<400> SEQUENCE: 16
uuggcaggaa guuccauggg ccaugcagcc gcagggucac ccugagugcu uuucagggug    60
gcagggccuu gccucagaug gccacaaggg caccucuccu uggauacuuu augauucugu   120
```

```
gacgccagcu acuugguuug cuuuuguau uuuuaugcau                              160
```

<210> SEQ ID NO 17
<211> LENGTH: 22
<212> TYPE: RNA
<213> ORGANISM: Homo sapiens

<400> SEQUENCE: 17

```
gaaagcugag cgugaacgug gu                                                22
```

<210> SEQ ID NO 18
<211> LENGTH: 162
<212> TYPE: RNA
<213> ORGANISM: Homo sapiens

<400> SEQUENCE: 18

```
cuucaaguau gccuggucu ugcauaaacu gaaagcugag cgugaacgug guaucaccau        60
ugauaucucc uuguggaaau uugagaccag caaguacuau gugacuauca uugaugcccc       120
aggacucaga gacuucauca aaaacaugau uacagggaca uc                          162
```

<210> SEQ ID NO 19
<211> LENGTH: 23
<212> TYPE: RNA
<213> ORGANISM: Homo sapiens

<400> SEQUENCE: 19

```
uagcagcaca uaaugguuug aau                                               23
```

<210> SEQ ID NO 20
<211> LENGTH: 163
<212> TYPE: RNA
<213> ORGANISM: Homo sapiens

<400> SEQUENCE: 20

```
auagaaucau cuaaguauuc agacacugcu uuccuaggaa auguuaaacu ccuugaggca       60
ggcuggcuuc cucaccaccu ugugcacugc ugcucccaca ccacagugac uagcagcaca       120
uaaugguuug aauuaaagcu gaaguaaaaa auauccaggu cca                         163
```

<210> SEQ ID NO 21
<211> LENGTH: 19
<212> TYPE: RNA
<213> ORGANISM: Homo sapiens

<400> SEQUENCE: 21

```
uguuuagacg ggcucacau                                                    19
```

<210> SEQ ID NO 22
<211> LENGTH: 158
<212> TYPE: RNA
<213> ORGANISM: Homo sapiens

<400> SEQUENCE: 22

```
cuuaccuccu caaagcaaua cacugaaaau guuuagacgg gcucacauca ccccauaaac       60
aaauagguuu ggccuagcc uuucuauuag cuuaguaa gauuacacau gcaagcaucc          120
ccguuccagu gaguucaccc ucuaaaucac cacgauca                               158
```

<210> SEQ ID NO 23
<211> LENGTH: 24
<212> TYPE: RNA
<213> ORGANISM: Homo sapiens

```
<400> SEQUENCE: 23
ggaaauuuga gaccagcaag uacu                                              24

<210> SEQ ID NO 24
<211> LENGTH: 164
<212> TYPE: RNA
<213> ORGANISM: Homo sapiens

<400> SEQUENCE: 24
auuugagaag gaggcugcug agaugggaaa gugcuccuuc aaguaugccu gggucuugga       60
uaaacugaaa gcugagcgug aacaugguau caccauugau aucucuuugu ggaaauuuga      120
gaccagcaag uacuauguga cuaucauuga ugccccagga caca                      164

<210> SEQ ID NO 25
<211> LENGTH: 25
<212> TYPE: RNA
<213> ORGANISM: Homo sapiens

<400> SEQUENCE: 25
auuguauauc agcauggggga uuauu                                            25

<210> SEQ ID NO 26
<211> LENGTH: 165
<212> TYPE: RNA
<213> ORGANISM: Homo sapiens

<400> SEQUENCE: 26
ugccuaauac ugacucagau gcacaaucca guuacccag augugaga ucuuccgguu         60 ugaaagaacu guauuggcaa ggcaaaauca accauugua gaauauauuu auuguauauc      120 agcauggggga uuauuaauau ugcuaauaaa accauuauuu guaaa                    165

<210> SEQ ID NO 27
<211> LENGTH: 15
<212> TYPE: RNA
<213> ORGANISM: Homo sapiens

<400> SEQUENCE: 27
uuggaggcgu ggguu                                                        15

<210> SEQ ID NO 28
<211> LENGTH: 155
<212> TYPE: RNA
<213> ORGANISM: Homo sapiens

<400> SEQUENCE: 28
gggaaggaua aagggauggc auguggggg uuggaggcgu ggguuuuaga accauccccu       60
uucuagcccu gagcaaugcu ugccccagaa ggaguugggg cuaggcccau uccaauccuu     120
ccagccuaag auccagacuc caaggcaugc cccag                                155

<210> SEQ ID NO 29
<211> LENGTH: 22
<212> TYPE: RNA
<213> ORGANISM: Homo sapiens

<400> SEQUENCE: 29
aacgugcagc ggcugaagga gu                                                22

<210> SEQ ID NO 30
<211> LENGTH: 162
```

```
<212> TYPE: RNA
<213> ORGANISM: Homo sapiens

<400> SEQUENCE: 30
ucaaucugga ggagcucagg guggccggca uucacaagaa gguggcccgg accaucggca      60
uuucugugga uccgaggagg cggaacaagu ccacggaguc ccugcaggcg aacgugcagc     120
ggcugaagga guaccgcucc aaacucaucc ucuucccag ga                        162

<210> SEQ ID NO 31
<211> LENGTH: 19
<212> TYPE: RNA
<213> ORGANISM: Homo sapiens

<400> SEQUENCE: 31 aaugugagg cuugagugu                                                    19

<210> SEQ ID NO 32
<211> LENGTH: 159
<212> TYPE: RNA
<213> ORGANISM: Homo sapiens

<400> SEQUENCE: 32
accccaucca auuuaaucgg guguuauuua auuauacuac uauaauuguu guauuugcag      60
guuugacugu ucucagggaa cgcugaaggu ucauaacagu agugauuugu aaugugagg     120 cuugagugug gaauugaauu acuucauuag agaguaacc                            159

<210> SEQ ID NO 33
<211> LENGTH: 22
<212> TYPE: RNA
<213> ORGANISM: Homo sapiens

<400> SEQUENCE: 33
ugauaggauu gacauggagc ac                                               22

<210> SEQ ID NO 34
<211> LENGTH: 162
<212> TYPE: RNA
<213> ORGANISM: Homo sapiens

<400> SEQUENCE: 34
cuuauuuacg uuacuggcug aaagccuguc ugauaggauu gacauggagc acuaauuaau      60
caccuagggu cuccucauuu acuaaucaua uugcacaaaa cuucccugcu gacugaggcu     120
caagggcaaa cugugggcuu ccagccagcu uauuuucau aa                        162

<210> SEQ ID NO 35
<211> LENGTH: 20
<212> TYPE: RNA
<213> ORGANISM: Homo sapiens

<400> SEQUENCE: 35
aacggccgcg guacccuaac                                                  20

<210> SEQ ID NO 36
<211> LENGTH: 160
<212> TYPE: RNA
<213> ORGANISM: Homo sapiens

<400> SEQUENCE: 36
guuaaaaaaa guaaaggaa cucggcaaau cuuacccccgc cuguuuacca aaacaucac      60 cucuagcauu cucaguauua gaggcaccgc cugcccagug acaugcguuu aacggccgcg    120
```

```
guacccuaac ugugcaaagg uagcauaauc acuuguuccu                          160

<210> SEQ ID NO 37
<211> LENGTH: 25
<212> TYPE: RNA
<213> ORGANISM: Homo sapiens

<400> SEQUENCE: 37
ucuugccaag agaauuaaug ugcgu                                          25

<210> SEQ ID NO 38
<211> LENGTH: 165
<212> TYPE: RNA
<213> ORGANISM: Homo sapiens

<400> SEQUENCE: 38
uguuguaaac aaacaaguua agagcaagau ucuugccaag agaauuaaug ugcguauuga    60
gcacauuaag cacucugaga gcugggauag cuuccgaaa uacaugaagg aaaaugauca    120 gaaaagaaa gaagccaaag agaaagguac cuggguucaa cugaa                    165

<210> SEQ ID NO 39
<211> LENGTH: 24
<212> TYPE: RNA
<213> ORGANISM: Homo sapiens

<400> SEQUENCE: 39
aaucugagug agagguuagu ugcu                                           24

<210> SEQ ID NO 40
<211> LENGTH: 164
<212> TYPE: RNA
<213> ORGANISM: Homo sapiens

<400> SEQUENCE: 40
uucugaaggg uauauugcau guucauuauu aaucugagug agagguuagu ugcuauaaag    60
uuacaagauu uuccugauca cuuaaaauuu ucuuguaguc agagauuuga cucugaaucg    120
ucacuucaaa aauuugucuu uucagguacu auguaaagag aacu                    164

<210> SEQ ID NO 41
<211> LENGTH: 19
<212> TYPE: RNA
<213> ORGANISM: Homo sapiens

<400> SEQUENCE: 41
auuaaaaauu ucgguuggg                                                 19

<210> SEQ ID NO 42
<211> LENGTH: 159
<212> TYPE: RNA
<213> ORGANISM: Homo sapiens

<400> SEQUENCE: 42
ccgugaagag gcgggcauga cacagcaaga cgagaagacc cuauggagcu uuaauuuauu    60
aaugcaaaca guaccuaaca aacccacagg uccuaaacua ccaaaccugc auuaaaaauu    120
ucgguugggg cgaccucgga gcagaaccca accuccgag                          159

<210> SEQ ID NO 43
<211> LENGTH: 25
<212> TYPE: RNA
<213> ORGANISM: Homo sapiens
```

```
<400> SEQUENCE: 43
gauagcugcc agugacagga guagu                                         25

<210> SEQ ID NO 44
<211> LENGTH: 165
<212> TYPE: RNA
<213> ORGANISM: Homo sapiens

<400> SEQUENCE: 44
auucgugcug aaaaucucag acucauugau gauagcugcc agugacagga guaguguugc   60
cacuguaaga uacgccaucu uuguuaguua cucucaucua cucguuucuu guauucugcc  120
ucuuggucau cuuugauucu cauuuaucug caaauuuucu uggua                  165

<210> SEQ ID NO 45
<211> LENGTH: 18
<212> TYPE: RNA
<213> ORGANISM: Homo sapiens

<400> SEQUENCE: 45
gagccuggug auagcugg                                                 18

<210> SEQ ID NO 46
<211> LENGTH: 158
<212> TYPE: RNA
<213> ORGANISM: Homo sapiens

<400> SEQUENCE: 46
agauucauga guagcaguga caaaccuacc gagccuggug auagcugguu guccaagaua   60
gaaucuuaga caacucccua uaccagaucc ucuaauuaau uuuaauaaag gccuucuauu  120
uauacuagcc acaucaagcc uagccgucua cguaccca                          158

<210> SEQ ID NO 47
<211> LENGTH: 18
<212> TYPE: RNA
<213> ORGANISM: Homo sapiens

<400> SEQUENCE: 47
uggcgcggag cggagcgg                                                 18

<210> SEQ ID NO 48
<211> LENGTH: 158
<212> TYPE: RNA
<213> ORGANISM: Homo sapiens

<400> SEQUENCE: 48
aggcagcucg gcgggcggcg ggcggcauuc uggcgcggag cggagcggcg gcgggcgcag   60
cuagcgdduc ggccgcggag cggaggugca gcucggcuuc ccccggcacc ccucccccuc  120
gggcgccagc cccacccccuc cgccggccgg gccgaccc                         158

<210> SEQ ID NO 49
<211> LENGTH: 16
<212> TYPE: RNA
<213> ORGANISM: Homo sapiens

<400> SEQUENCE: 49
aggcggcgga ggggcg                                                   16

<210> SEQ ID NO 50
<211> LENGTH: 156
```

```
<212> TYPE: RNA
<213> ORGANISM: Homo sapiens

<400> SEQUENCE: 50
cggcccuguc cugcgggggu ccggucgcgg aggcggcgga ggggcgcggg gacacucccc        60
accuccacug uccgcccguc ggccccggug gccuuuucuc gccucgcgca cagcuccccc       120
gccgcagggc ugagagagag aguggccguc uggugc                                 156

<210> SEQ ID NO 51
<211> LENGTH: 21
<212> TYPE: RNA
<213> ORGANISM: Homo sapiens

<400> SEQUENCE: 51
augcgugcga gaagucagug g                                                  21

<210> SEQ ID NO 52
<211> LENGTH: 159
<212> TYPE: RNA
<213> ORGANISM: Homo sapiens

<400> SEQUENCE: 52
caggccuuuc ugaaggaguu auucugcuaa aaauggucuu aguugucuga aaagccagcu        60
cuugaaccuc uucacaacag uaucaacacu ggcuucuccc gguucauuuu augcgugcga       120
gaagucagug guaacugcug cagggcuuaa uacauuagu                              159

<210> SEQ ID NO 53
<211> LENGTH: 26
<212> TYPE: RNA
<213> ORGANISM: Homo sapiens

<400> SEQUENCE: 53
uguguuugag agcaacgcca uugccu                                             26

<210> SEQ ID NO 54
<211> LENGTH: 163
<212> TYPE: RNA
<213> ORGANISM: Homo sapiens

<400> SEQUENCE: 54
agcauuugag ggugaugaug gauucugugu guuugagagc aacgccauug ccuacuaugu        60
gagcaaugag gagcugcggg gaaguacucc agaggcagca gcccaggugg ugcagugggu       120
gagcuuugcu gauuccgaua uagugccccc agccaguacc ugg                         163

<210> SEQ ID NO 55
<211> LENGTH: 19
<212> TYPE: RNA
<213> ORGANISM: Homo sapiens

<400> SEQUENCE: 55
gcaugagugg uucaguggu                                                     19

<210> SEQ ID NO 56
<211> LENGTH: 159
<212> TYPE: RNA
<213> ORGANISM: Homo sapiens

<400> SEQUENCE: 56
auuuaaaacu gugucuuucu guguccuga aauucucaca cauggguacgu uucaaugag         60 cugauuuugu uucuccacuc aaugcaguaa uugagcuucu uugguucagu gcaugagugg      120
```

```
uucagugguu cauugggcau ccugguugag ggagggggcu                   159
```

<210> SEQ ID NO 57
<211> LENGTH: 19
<212> TYPE: RNA
<213> ORGANISM: Homo sapiens

<400> SEQUENCE: 57

```
aaggaaugag uuagcuuug                                          19
```

<210> SEQ ID NO 58
<211> LENGTH: 159
<212> TYPE: RNA
<213> ORGANISM: Homo sapiens

<400> SEQUENCE: 58

```
uuuaugguug cuacuguagg uuuauaauuu guuuauaauu uggccuaauu ccaucagcc   60 auacuaauau uggauuuuaa aaggaggcaa cuuuuuuucu uuuugaacca aaggaauag  120 uuagcuuuga aaacauaauu ugggauauua aguaugga                        159
```

<210> SEQ ID NO 59
<211> LENGTH: 20
<212> TYPE: RNA
<213> ORGANISM: Homo sapiens

<400> SEQUENCE: 59

```
acaagugaau acacugaggc                                          20
```

<210> SEQ ID NO 60
<211> LENGTH: 160
<212> TYPE: RNA
<213> ORGANISM: Homo sapiens

<400> SEQUENCE: 60

```
ccugcugggg uuggaguucu uaaugaacau acaagugaau acacugaggc aaaaaaauua   60
aagcucucca acuguggggu auucauucug uucacugugg ccaguguggu gaucaguacu  120
ggccacacca guggccaaag agaacugcau ucaucaugug                      160
```

<210> SEQ ID NO 61
<211> LENGTH: 22
<212> TYPE: RNA
<213> ORGANISM: Homo sapiens

<400> SEQUENCE: 61

```
cucgcgcccg cgucgcggca gc                                       22
```

<210> SEQ ID NO 62
<211> LENGTH: 162
<212> TYPE: RNA
<213> ORGANISM: Homo sapiens

<400> SEQUENCE: 62

```
ccucagcccc uucagagagc gacuuucaaa cucgcgcccg cgucgcggca gcaccugggc   60
agccccgcac gccgugcgcg ucccgagccc gcggggcagc uaccgcucgg ugagugcccc  120
cugauucucc ucucucccu cuuaucuccc ugcauuaggc ug                   162
```

<210> SEQ ID NO 63
<211> LENGTH: 21
<212> TYPE: RNA
<213> ORGANISM: Homo sapiens

```
<400> SEQUENCE: 63
gugguguuga ggaaagcaga c                                              21

<210> SEQ ID NO 64
<211> LENGTH: 161
<212> TYPE: RNA
<213> ORGANISM: Homo sapiens

<400> SEQUENCE: 64
cugaaaaguu ccagcauauu uugcgaguac ucaacaccaa caucgauggg cagcggaaaa    60
uagccuuugc caucacugcc auuaaggguc ugggccgaag auaugcucau gugguguuga   120
ggaaagcaga cacugaccuc accaagaggg cgggagaacu c                      161

<210> SEQ ID NO 65
<211> LENGTH: 21
<212> TYPE: RNA
<213> ORGANISM: Homo sapiens

<400> SEQUENCE: 65
guuuuuguga cugccuugag u                                              21

<210> SEQ ID NO 66
<211> LENGTH: 161
<212> TYPE: RNA
<213> ORGANISM: Homo sapiens

<400> SEQUENCE: 66
caugcuuuug guuguuacc aaaauauaca gugguggaa gguugacuga agaaguccag      60
uguguccagu uaaaacagaa auaaauuaaa cucuucauca acaaagaccu guuuuuguga   120
cugccuugag uuuuaucaga auuauuggcc uaguaauccu u                      161

<210> SEQ ID NO 67
<211> LENGTH: 24
<212> TYPE: RNA
<213> ORGANISM: Homo sapiens

<400> SEQUENCE: 67
aaggcacagc uggaaaugau ggug                                           24

<210> SEQ ID NO 68
<211> LENGTH: 164
<212> TYPE: RNA
<213> ORGANISM: Homo sapiens

<400> SEQUENCE: 68 cccaggguagg cauaggagaa aaaggugcug aaggcacagc uggaaaugau ggugcaagag   60
uaagugaaag uauuccuuuu cuagcugggc uaggaaccaa cauuacagua ucauaugagu   120
uucccugaac cuuccaaaau aaagucaguc auguuccuu ggua                     164

<210> SEQ ID NO 69
<211> LENGTH: 20
<212> TYPE: RNA
<213> ORGANISM: Homo sapiens

<400> SEQUENCE: 69
aaacuaggcg gcuauggau                                                 20

<210> SEQ ID NO 70
<211> LENGTH: 160
```

```
<212> TYPE: RNA
<213> ORGANISM: Homo sapiens

<400> SEQUENCE: 70
gggucaauag uacuugccgc aguacucuua aaacuaggcg gcuauggau aauacgccuc      60 acacucauuc ucaaccccccu gacaaaacac auagccuacc ccuuccuugu acauccccua   120
ugaggcauaa uuauaacaag cuccaucugc cuacgacaaa                          160

<210> SEQ ID NO 71
<211> LENGTH: 19
<212> TYPE: RNA
<213> ORGANISM: Homo sapiens

<400> SEQUENCE: 71 guggugucg uacgcugug                                                   19

<210> SEQ ID NO 72
<211> LENGTH: 159
<212> TYPE: RNA
<213> ORGANISM: Homo sapiens

<400> SEQUENCE: 72
ggcggcugcc gaagauggcg gaggugcagg ucccaguccu ccauggucga ggccaucucc    60
ugggccgccu ggcggccauc guggcuaagc agguaauguu gggcuggaag guggugucg    120 uacgcuguga gggcaucaac auuucuggca auucuaca                            159

<210> SEQ ID NO 73
<211> LENGTH: 22
<212> TYPE: RNA
<213> ORGANISM: Homo sapiens

<400> SEQUENCE: 73
gcugagugaa gcauuggacu gu                                              22

<210> SEQ ID NO 74
<211> LENGTH: 162
<212> TYPE: RNA
<213> ORGANISM: Homo sapiens

<400> SEQUENCE: 74
gcccaggacu ccagcucaug cgccgaauag uagguacagu guuccaaugu cuuugugguu     60
uguagagaac aaucaacggu cggcgaacau cagugggaua agguaaaaug gcugagugaa    120
gcauuggacu guaaaucuaa agacaggggc uaagccucuu uu                       162

<210> SEQ ID NO 75
<211> LENGTH: 20
<212> TYPE: RNA
<213> ORGANISM: Homo sapiens

<400> SEQUENCE: 75
agguucacau ggaaaagguu                                                 20

<210> SEQ ID NO 76
<211> LENGTH: 160
<212> TYPE: RNA
<213> ORGANISM: Homo sapiens

<400> SEQUENCE: 76
ugguguagag gcggagagga gccaagaaac uaaaggugaa aaauacacug gaacucuggg     60
gcaagacaug ucuaugguag cugagccaaa cacguaggau uuccguuuua agguucacau    120
```

```
ggaaaagguu auagcuuugc cuugagauug acucauuaaa              160
```

\<210\> SEQ ID NO 77
\<211\> LENGTH: 22
\<212\> TYPE: RNA
\<213\> ORGANISM: Homo sapiens

\<400\> SEQUENCE: 77

```
ccauugugua gcaagauguc au                                  22
```

\<210\> SEQ ID NO 78
\<211\> LENGTH: 162
\<212\> TYPE: RNA
\<213\> ORGANISM: Homo sapiens

\<400\> SEQUENCE: 78

```
gacuaaaacu auuugaucuu uuaauauuua auuaaugguu ccccguggcg uuuuuauagu    60 cuguuucua uugugagcaa cgagauuuua auaagcaggu ucaggacuuu ccauugugua    120 gcaauguc auugcuucca ugacacuaau uuggcuuuca ua                        162
```

\<210\> SEQ ID NO 79
\<211\> LENGTH: 24
\<212\> TYPE: RNA
\<213\> ORGANISM: Homo sapiens

\<400\> SEQUENCE: 79

```
ggaauaguu ugugacaaac uggg                                 24
```

\<210\> SEQ ID NO 80
\<211\> LENGTH: 164
\<212\> TYPE: RNA
\<213\> ORGANISM: Homo sapiens

\<400\> SEQUENCE: 80

```
cacauacuca aggagcccug uuuuacaggg cacuggagaa cuaauuaauu ugcaaugcag    60
aaagaaugca gugacaucug aaauauuggc cucggguauc acaggucauu ggaauaguu    120 ugugacaaac uggggguggag gguggggguc gggaaggcaa cucu                   164
```

\<210\> SEQ ID NO 81
\<211\> LENGTH: 21
\<212\> TYPE: RNA
\<213\> ORGANISM: Homo sapiens

\<400\> SEQUENCE: 81

```
cucucuucg ucuccucggu c                                   21
```

\<210\> SEQ ID NO 82
\<211\> LENGTH: 161
\<212\> TYPE: RNA
\<213\> ORGANISM: Homo sapiens

\<400\> SEQUENCE: 82

```
gggggaggcc ugcgcggagg agcaccgcuu ccucccgccg ggaggggag ucccgggcuc    60 cugcguccug ucuccuccc cggccgucug caggagcacg aagggagugc cucucuucg    120 ucuccucggu ccccguaacu ucucccccuca cuuccuccug g                     161
```

\<210\> SEQ ID NO 83
\<211\> LENGTH: 21
\<212\> TYPE: RNA
\<213\> ORGANISM: Homo sapiens

```
<400> SEQUENCE: 83
acuccagccc cacagccuca g                                              21

<210> SEQ ID NO 84
<211> LENGTH: 161
<212> TYPE: RNA
<213> ORGANISM: Homo sapiens

<400> SEQUENCE: 84
gucaaaaguc cccagagucu ucacacaagc cgugguguau gaagcugcau ccucaggacc    60
ugggcuuggg ugguaggagg aauuggugcu ggucuuucau uuuggauuug acuccagccc   120
cacagccuca gccaccccag ccaauuguca uaggagcugg a                       161

<210> SEQ ID NO 85
<211> LENGTH: 22
<212> TYPE: RNA
<213> ORGANISM: Homo sapiens

<400> SEQUENCE: 85
gccgcgagug ggagcgggag cg                                             22

<210> SEQ ID NO 86
<211> LENGTH: 162
<212> TYPE: RNA
<213> ORGANISM: Homo sapiens

<400> SEQUENCE: 86
gcgcggcgga ggggggggug gggccuuggg gccgcgagug ggagcgggag cgguucugcg    60
gccuccucgg gcuucuuggc ccugggcgga gugggauugg gugucccggc uguucgcagu   120
ggccgcgagu gcggccggac cuggaguagu accugagccg cu                      162

<210> SEQ ID NO 87
<211> LENGTH: 25
<212> TYPE: RNA
<213> ORGANISM: Homo sapiens

<400> SEQUENCE: 87
gcuugacuga guguggcugg acgug                                          25

<210> SEQ ID NO 88
<211> LENGTH: 165
<212> TYPE: RNA
<213> ORGANISM: Homo sapiens

<400> SEQUENCE: 88
gagaacaugg gucaccagca gggccugaga agagggagaa aauacggaaa ugugggauug    60
gggucgcuga gugcaggcau guaaguuaag uguuugggga acagagcagu gcuugacuga   120
guguggcugg acgugaguac ugagggggac aaaugagauu gaucc                   165

<210> SEQ ID NO 89
<211> LENGTH: 19
<212> TYPE: RNA
<213> ORGANISM: Homo sapiens

<400> SEQUENCE: 89
agucggugcc ugagguugc                                                 19

<210> SEQ ID NO 90
<211> LENGTH: 159
```

```
<212> TYPE: RNA
<213> ORGANISM: Homo sapiens

<400> SEQUENCE: 90
caggacggcc gccaucuugc gcgcagcugg agucggugcc ugagguugca gccgagagug      60
ugcgccagcc cgcggcccag ccgaagcucu ucccgccgc cucuccgcgc cucgcccagg     120
uucagcuccg ccugacccuc cgcuuggcac ggucccug                             159

<210> SEQ ID NO 91
<211> LENGTH: 20
<212> TYPE: RNA
<213> ORGANISM: Homo sapiens

<400> SEQUENCE: 91
agugaugagg augugcugau                                                  20

<210> SEQ ID NO 92
<211> LENGTH: 160
<212> TYPE: RNA
<213> ORGANISM: Homo sapiens

<400> SEQUENCE: 92
uuaggaaguc ugagaugaua aauauuucaa ggucagugaa gucuaucaau cauucccccc     60 uccucauca gcaauggcag auagaaaugu ccuaaacuuu ucuaaauccu agugaugagg     120
augugcugau auucaacaua guccuuaaag ugaaaacuga                          160

<210> SEQ ID NO 93
<211> LENGTH: 20
<212> TYPE: RNA
<213> ORGANISM: Homo sapiens

<400> SEQUENCE: 93
auugaguggg gcucaggauu                                                  20

<210> SEQ ID NO 94
<211> LENGTH: 160
<212> TYPE: RNA
<213> ORGANISM: Homo sapiens

<400> SEQUENCE: 94
agcuacuucc uuucuucagc cucuugcuuu cguucaaaau cucagcuuuu aucacauucu     60
uuucauggag agacaucuca augcccuuu ucgccuagga gaagaauguu auugaguggg     120
gcucaggauu uaaacccagg cagacuaauu gguaugugag                          160

<210> SEQ ID NO 95
<211> LENGTH: 18
<212> TYPE: RNA
<213> ORGANISM: Homo sapiens

<400> SEQUENCE: 95
gcaugggugg uucagugu                                                    18

<210> SEQ ID NO 96
<211> LENGTH: 158
<212> TYPE: RNA
<213> ORGANISM: Homo sapiens

<400> SEQUENCE: 96
cacauacauu ggcgaaaaga ccaacaaguc augauuguuc ugaaguuccc uuuaucaugu     60 ugucccuaa ucucuacuac caguaagccu uuguguuauc uuaggaugag gcaugggugg     120
```
uucaguguuu auaauaagac gagucuaaaa uggacaau          158

<210> SEQ ID NO 97
<211> LENGTH: 23
<212> TYPE: RNA
<213> ORGANISM: Homo sapiens

<400> SEQUENCE: 97
aacuguuaua uuaugauugu gac                          23

<210> SEQ ID NO 98
<211> LENGTH: 163
<212> TYPE: RNA
<213> ORGANISM: Homo sapiens

<400> SEQUENCE: 98
uguuuaaugc cugaaaucca agucuuccuc caugggaaaa uacguuaua ccaaauaauu   60 cuagaugagu aacaaagauc uuuuuaggcc uucauuuuau guuuuucuu aacguuaua   120 uuaugauugu gacauagauu auacuacuac uaauuuuugg aug                   163

<210> SEQ ID NO 99
<211> LENGTH: 24
<212> TYPE: RNA
<213> ORGANISM: Homo sapiens

<400> SEQUENCE: 99
uugcugugau gacuaucuua ggac                         24

<210> SEQ ID NO 100
<211> LENGTH: 164
<212> TYPE: RNA
<213> ORGANISM: Homo sapiens

<400> SEQUENCE: 100
cuuacggaaa aggaacagau uguuccuaaa ccagaagagg agguugccca gaagaaaaag   60 guaauaagu aguugcucgg uuuuguuugu gauaguagaa agauuugugg uugcugugau   120
gacuaucuua ggacaccuuu ggaauaacua ugaaagaaaa cuau                   164

<210> SEQ ID NO 101
<211> LENGTH: 22
<212> TYPE: RNA
<213> ORGANISM: Homo sapiens

<400> SEQUENCE: 101
agaauugagu gaucucaugg au                           22

<210> SEQ ID NO 102
<211> LENGTH: 162
<212> TYPE: RNA
<213> ORGANISM: Homo sapiens

<400> SEQUENCE: 102
cuaggaguga cucaugcaga cucaagcaga accuuggggc ccagggcaga agugugacuu   60
caggucucac ucagcacuca ucagaacacu cacucaguau gcuguaauu agaauugagu   120 gaucucaugg augaacugua cugggcuaac uugaagagca ca                    162

<210> SEQ ID NO 103
<211> LENGTH: 24
<212> TYPE: RNA
<213> ORGANISM: Homo sapiens

```
<400> SEQUENCE: 103
aaaacgaucu uucagauuua gagu                                            24

<210> SEQ ID NO 104
<211> LENGTH: 164
<212> TYPE: RNA
<213> ORGANISM: Homo sapiens

<400> SEQUENCE: 104
uaaaagcuga aaaucucagu uuaaaaauca aaauguuaac acaaagcuaa gauucaucag      60
agcccacccu auucuaagga accacaauaa cuuacucugg ccccagucuu aaaacgaucu     120
uucagauuua gagugacuau guaagaauuu aggauuuccu cuuu                     164

<210> SEQ ID NO 105
<211> LENGTH: 17
<212> TYPE: RNA
<213> ORGANISM: Homo sapiens

<400> SEQUENCE: 105
gcggucgggc ggcggcg                                                    17

<210> SEQ ID NO 106
<211> LENGTH: 157
<212> TYPE: RNA
<213> ORGANISM: Homo sapiens

<400> SEQUENCE: 106
ggccccgcgg ggcccguccg cuccuccagc cgcugccucc cgggcggcgc ucgccggcgc     60
ggcggcaaag acugagacag cuccgcugcc cgcugaacuc cauccucccg gcggucgggc    120
ggcggcggcu gcggucgguc gcggcagcgg cuccgcu                             157

<210> SEQ ID NO 107
<211> LENGTH: 22
<212> TYPE: RNA
<213> ORGANISM: Homo sapiens

<400> SEQUENCE: 107
augagaacuu gagcgacaga gu                                              22

<210> SEQ ID NO 108
<211> LENGTH: 162
<212> TYPE: RNA
<213> ORGANISM: Homo sapiens

<400> SEQUENCE: 108
cuccagguca ucaucagugu gguauuaucu augagaacuu gagcgacaga guauuucuug     60
augaauuuau agaucauuug agauguuuag uuacuuuugu uuuguuuuca aauagguaga    120
gacuauuaau guaaaaaaac aagaaaggaa aaugaaaugu gc                       162

<210> SEQ ID NO 109
<211> LENGTH: 18
<212> TYPE: RNA
<213> ORGANISM: Homo sapiens

<400> SEQUENCE: 109
auuggucgug guuguagu                                                   18

<210> SEQ ID NO 110
<211> LENGTH: 158
```

```
<212> TYPE: RNA
<213> ORGANISM: Homo sapiens

<400> SEQUENCE: 110 gugggaggu cgaugaauga gugguuaauu aauuuauua ggggguuaau uuugcguauu      60 gggucauug guguucuugu aguugaaaua caacgauggu uuucauauc auggucgug     120 guuguaguuc gugcgagaau aaugauguau gcuuuguu                          158

<210> SEQ ID NO 111
<211> LENGTH: 23
<212> TYPE: RNA
<213> ORGANISM: Homo sapiens

<400> SEQUENCE: 111
gaugagagaa caguggguac uuc                                           23

<210> SEQ ID NO 112
<211> LENGTH: 163
<212> TYPE: RNA
<213> ORGANISM: Homo sapiens

<400> SEQUENCE: 112
auucucagua uuggaucugc acauggagug uuuucucuc uaguguuac agaggaugaa     60 ugcauauuga gauaaagaag ugauuuuggu uccaaaagga uuuuaaggau gaugagagaa  120
caguggguac uucauugcca ggucaugucu uugcaagaag aaa                    163

<210> SEQ ID NO 113
<211> LENGTH: 23
<212> TYPE: RNA
<213> ORGANISM: Homo sapiens

<400> SEQUENCE: 113
caagguguag cccaugaggu ggc                                           23

<210> SEQ ID NO 114
<211> LENGTH: 163
<212> TYPE: RNA
<213> ORGANISM: Homo sapiens

<400> SEQUENCE: 114
agcacaagua cacacauaaa aacauuaggu caagguguag cccaugaggu ggcacgaaau    60
gggcuacauu uucuaugucc agaaaaucuc acaacauccu uuaggaaauc uaagggcuca  120
aggaggauuu agcaguaaac caagagcaga gugcuugguu gaa                    163

<210> SEQ ID NO 115
<211> LENGTH: 22
<212> TYPE: RNA
<213> ORGANISM: Homo sapiens

<400> SEQUENCE: 115
agcaccagcc uaggaagagg gu                                            22

<210> SEQ ID NO 116
<211> LENGTH: 162
<212> TYPE: RNA
<213> ORGANISM: Homo sapiens

<400> SEQUENCE: 116
cucaccucga uuccccag gccugggucc agcaccagcc uaggaagagg gugccccaug     60
cugucuagcu cuucucggg auggggggcu ccagguuccu ugguauuuug cuuuggccuu   120
```

```
uggagccuca gucaaaacug aggaaaggug ucauuucac au                         162

<210> SEQ ID NO 117
<211> LENGTH: 23
<212> TYPE: RNA
<213> ORGANISM: Homo sapiens

<400> SEQUENCE: 117
acuuuaacac ugcuguggaa ggc                                             23

<210> SEQ ID NO 118
<211> LENGTH: 163
<212> TYPE: RNA
<213> ORGANISM: Homo sapiens

<400> SEQUENCE: 118
gaaaauaaag gcaccugaaa agaaacuacu acuuuaacac ugcuguggaa ggccuuugcu     60
uuauaagaaa aauauuauua gcaugggaa aguaauguuc uuuauguaaa gacuuaaaaa     120
uagacuaaua guuuacagag uuauuauaua aaauacgaug uga                      163

<210> SEQ ID NO 119
<211> LENGTH: 24
<212> TYPE: RNA
<213> ORGANISM: Homo sapiens

<400> SEQUENCE: 119
auuugacaag aguaugccag gugu                                            24

<210> SEQ ID NO 120
<211> LENGTH: 164
<212> TYPE: RNA
<213> ORGANISM: Homo sapiens

<400> SEQUENCE: 120
cuaccugaag uuuuaagagu cuuggaaagu caggagugac uucugcuaaa cacggggcuu     60
uccagaguca gagaagcuag caagccugug guuuggacca gguacuaaau auuugacaag     120
aguaugccag guguaaugag cuacugucua uuccccuuua aagc                      164

<210> SEQ ID NO 121
<211> LENGTH: 18
<212> TYPE: RNA
<213> ORGANISM: Homo sapiens

<400> SEQUENCE: 121
cugggagcuu gaaaggag                                                   18

<210> SEQ ID NO 122
<211> LENGTH: 158
<212> TYPE: RNA
<213> ORGANISM: Homo sapiens

<400> SEQUENCE: 122
gcucuuucuc uucccucucg uuuaguuugc cugggagcuu gaaaggagaa agcacggggu     60
cgccccaaac ccccuucugcu ucugcccauc acaagugcca cuaccgccau gggccucacu    120
aucuccuccc ucuucucccg acuauuuggc aagaagca                            158

<210> SEQ ID NO 123
<211> LENGTH: 23
<212> TYPE: RNA
<213> ORGANISM: Homo sapiens
```

<400> SEQUENCE: 123
auuugggcag guugaaagaa uuu                                           23

<210> SEQ ID NO 124
<211> LENGTH: 163
<212> TYPE: RNA
<213> ORGANISM: Homo sapiens

<400> SEQUENCE: 124
uaguaaaugu aggcaguuuc uuuaggguua aucaucuuuc aaagggccuu aggaaugucc   60
uucaaacaga auauaaaugu caaagagaau aucucuuucu guuugaaauu auuugggcag  120
guugaaagaa uuugauaaag ggaaauucua uauuuaaucu uuc                    163

<210> SEQ ID NO 125
<211> LENGTH: 24
<212> TYPE: RNA
<213> ORGANISM: Homo sapiens

<400> SEQUENCE: 125
gugcuggagg ccaggcugag gccc                                          24

<210> SEQ ID NO 126
<211> LENGTH: 164
<212> TYPE: RNA
<213> ORGANISM: Homo sapiens

<400> SEQUENCE: 126
gugcccggga gguggacugg ggccuggguu gugcuggagg ccaggcugag gcccugccuu   60
gguuugggga ggagaucccu gcaccccgga acuccucugu ggcccacgga ggaucgcucu  120
gaacugccuc agcguggcgg ccagugggggg uaggggugga gaga                  164

<210> SEQ ID NO 127
<211> LENGTH: 18
<212> TYPE: RNA
<213> ORGANISM: Homo sapiens

<400> SEQUENCE: 127
gcuguuggug gagaaggu                                                 18

<210> SEQ ID NO 128
<211> LENGTH: 158
<212> TYPE: RNA
<213> ORGANISM: Homo sapiens

<400> SEQUENCE: 128
ccugaagagg aagagaugac uguuggaaag cguuccccuc ccccauacgg cagaacagcu   60
gcggcuccca ggggaaagcc cccgcaggac aguccucgug ggugugacg gcuguuggug   120 gagaagguuu ggcgcccuau uuucuuaucu gccuuucu                          158

<210> SEQ ID NO 129
<211> LENGTH: 22
<212> TYPE: RNA
<213> ORGANISM: Homo sapiens

<400> SEQUENCE: 129
auggcaguug gagagaaaga ac                                            22

<210> SEQ ID NO 130
<211> LENGTH: 162

```
<212> TYPE: RNA
<213> ORGANISM: Homo sapiens

<400> SEQUENCE: 130
gagaggaaaa guccagaccu aggacuaguu auggcaguug gagagaaaga acaucgggau    60
guuugaaaau augccauuga cuaucuuaac uacuguaauu uuaucauuuc caacgucauc   120
uaacugggga cuagaacaaa cugugaauuc acuuucagca ac                     162

<210> SEQ ID NO 131
<211> LENGTH: 25
<212> TYPE: RNA
<213> ORGANISM: Homo sapiens

<400> SEQUENCE: 131
gcagauaaac ucaugccaga gaacu                                         25

<210> SEQ ID NO 132
<211> LENGTH: 165
<212> TYPE: RNA
<213> ORGANISM: Homo sapiens

<400> SEQUENCE: 132
ucuuaaaagu uuuauuaaag gggaggggca aauauuggca auuaguuggc aguggccugu    60
uacgguuggg auggugggg ugguuuagg uaauuguuua guuaugauu gcagauaaac     120 ucaugccaga gaacuuaaag ucuuagaaug gaaaaguaa agaaa                   165

<210> SEQ ID NO 133
<211> LENGTH: 17
<212> TYPE: RNA
<213> ORGANISM: Homo sapiens

<400> SEQUENCE: 133
agugccaggu ggggagg                                                  17

<210> SEQ ID NO 134
<211> LENGTH: 157
<212> TYPE: RNA
<213> ORGANISM: Homo sapiens

<400> SEQUENCE: 134
gcccagcacc cucugucucu uuaugcaauc agugccaggu ggggagggau gcauucuguc    60
caaugacaug caggcacuuu agagggcuug cauucauucc caaguccagc ggcacacuuu   120
auacauccuu ggcuggucau ugaggggaac accggag                            157

<210> SEQ ID NO 135
<211> LENGTH: 18
<212> TYPE: RNA
<213> ORGANISM: Homo sapiens

<400> SEQUENCE: 135
gacucuuagc gguggauc                                                 18

<210> SEQ ID NO 136
<211> LENGTH: 158
<212> TYPE: RNA
<213> ORGANISM: Homo sapiens

<400> SEQUENCE: 136
cacgcuugug gugaaaucag gaauuuuuag gacucuuagc gguggaucaa aaagaaaaaa    60
gaaaacagga cagaguaaaa ucuugcucca aagcuugugu ucuggcaaau accgucugug   120
```

```
ucucgaaugu gaaguuguuu ccacuccuca gagcccac                                    158

<210> SEQ ID NO 137
<211> LENGTH: 21
<212> TYPE: RNA
<213> ORGANISM: Homo sapiens

<400> SEQUENCE: 137 cguugcggg acccggggug u                                                        21

<210> SEQ ID NO 138
<211> LENGTH: 161
<212> TYPE: RNA
<213> ORGANISM: Homo sapiens

<400> SEQUENCE: 138
uggauuucgc ccccgcuccc ucccggaaac uccuccuggu gccugcgacc guucucacug             60
agcaugugca gacggcggug cgcaugcucu guugcgqucc gcuucgguuu cguugcggg            120 acccggggug ucuccuagcg caaccggaac uagccuucug g                               161

<210> SEQ ID NO 139
<211> LENGTH: 21
<212> TYPE: RNA
<213> ORGANISM: Homo sapiens

<400> SEQUENCE: 139
uuaaagcugc cauuuguuac u                                                       21

<210> SEQ ID NO 140
<211> LENGTH: 161
<212> TYPE: RNA
<213> ORGANISM: Homo sapiens

<400> SEQUENCE: 140
cacuguagca uaagcaaggg cuuaguuccu gaacugaguu acagcuuuau uuucuuuug             60 auucagcaug uuuuuaauga uccauaaguu aaaagcugcu ggguguuuua uuaaagcugc           120
cauuuguuac uaaccaggcu cugugugacu ccuaagugga a                               161

<210> SEQ ID NO 141
<211> LENGTH: 22
<212> TYPE: RNA
<213> ORGANISM: Homo sapiens

<400> SEQUENCE: 141
gagcagaggc gauaguugaa gu                                                      22

<210> SEQ ID NO 142
<211> LENGTH: 162
<212> TYPE: RNA
<213> ORGANISM: Homo sapiens

<400> SEQUENCE: 142
agccacaccc cagcagugug caagggauca gacacaaggu ugaauccauc acaaaagcag            60
aaucaccaug gcaacugcau ccuuugauuc uugagugugc ccagcaaccu gagcagaggc           120
gauaguugaa gugaaccaag uucuccugag aaauggaggg ga                              162

<210> SEQ ID NO 143
<211> LENGTH: 24
<212> TYPE: RNA
<213> ORGANISM: Homo sapiens
```

```
<400> SEQUENCE: 143
gaugacaugg gcuuuggucu uuuu                                            24

<210> SEQ ID NO 144
<211> LENGTH: 164
<212> TYPE: RNA
<213> ORGANISM: Homo sapiens

<400> SEQUENCE: 144
gcaaagaaag aagaaucuga ggagucugau gaugacaugg gcuuuggucu uuuugacuaa     60
accucuuuua uaauguguuc aauaaaaagc ugaacuuuaa aaaaaagauu gggguuuauc    120
auguaauugu uucauuuugu uguauucugu guuaagauuu cuaa                    164

<210> SEQ ID NO 145
<211> LENGTH: 18
<212> TYPE: RNA
<213> ORGANISM: Homo sapiens

<400> SEQUENCE: 145
agaaagggcc uuguguuu                                                   18

<210> SEQ ID NO 146
<211> LENGTH: 158
<212> TYPE: RNA
<213> ORGANISM: Homo sapiens

<400> SEQUENCE: 146
aggaagggga aacucaauca gcaggacuuc agaaagggcc uuguguuuau agcuuuguca     60
aguaaauuug gacgcagcug gagcacaggc ccuguuuguu ugcacauaau aaucuguuu    120 aucacuuuaa aaaauucagu aauaucucag cagucagg                            158

<210> SEQ ID NO 147
<211> LENGTH: 26
<212> TYPE: RNA
<213> ORGANISM: Homo sapiens

<400> SEQUENCE: 147
acucggcgug gcgucggucg ugguag                                          26

<210> SEQ ID NO 148
<211> LENGTH: 164
<212> TYPE: RNA
<213> ORGANISM: Homo sapiens

<400> SEQUENCE: 148
acucccugac agauaucucc cucuuccauu ucaucaagac ccagcugagu cacgucacu      60 gccuaccaau cucgaccgga ccucgaccgg cucgucugug uugccaaucg acucggcgug    120
gcgucggucg ugguagauag gcggucaugc auacgaauuu ucag                    164

<210> SEQ ID NO 149
<211> LENGTH: 20
<212> TYPE: RNA
<213> ORGANISM: Homo sapiens

<400> SEQUENCE: 149
guguuuagug aguauuuguu                                                 20

<210> SEQ ID NO 150
<211> LENGTH: 160
```

```
<212> TYPE: RNA
<213> ORGANISM: Homo sapiens

<400> SEQUENCE: 150
agggacaaug ccauauuuau ccuucuagcc cugacaccuc acacaaugca gagaacggaa    60
gggaguucaa uaacgguag caaagugcca acuccuugag aauagggccu uguguuuagug   120 aguauuuguu aagagaauga auaaaugaug uacaguugua                         160

<210> SEQ ID NO 151
<211> LENGTH: 20
<212> TYPE: RNA
<213> ORGANISM: Homo sapiens

<400> SEQUENCE: 151
acugcugcug cugcuuggcc                                                20

<210> SEQ ID NO 152
<211> LENGTH: 160
<212> TYPE: RNA
<213> ORGANISM: Homo sapiens

<400> SEQUENCE: 152
ccccgcucac cuccucuauc cccacagugu acugcugcug cugcuuggcc aacguuucac    60
ugccuggcau cggggcacc auuccugagu ccaaaccuuu cuucuacgug aacguggcug    120
acaucgagag ccuggaggua gagguguccu auguggccug                         160

<210> SEQ ID NO 153
<211> LENGTH: 25
<212> TYPE: RNA
<213> ORGANISM: Homo sapiens

<400> SEQUENCE: 153
ugcagagugg gguuuugcag uccuu                                          25

<210> SEQ ID NO 154
<211> LENGTH: 165
<212> TYPE: RNA
<213> ORGANISM: Homo sapiens

<400> SEQUENCE: 154
aauuaaagug gcugauuugc guucaguuga ugcagagugg gguuuugcag uccuuagcug    60
uugcagaaau uaaguauugc aacuuacuga gggcuuugaa ggcucuuggu cuguauuuaa   120
ccuaaauuuc uauaagauua uuaguauaaa aggggagaua gguag                   165

<210> SEQ ID NO 155
<211> LENGTH: 21
<212> TYPE: RNA
<213> ORGANISM: Homo sapiens

<400> SEQUENCE: 155
augaccacca aacccaggag c                                              21

<210> SEQ ID NO 156
<211> LENGTH: 161
<212> TYPE: RNA
<213> ORGANISM: Homo sapiens

<400> SEQUENCE: 156
uuuuauaacc auagagugga gacagucagu augaccacca aacccaggag ccauauauua    60
aaauacugau aaauuuaacu auauaaaaaa auuuuugccg ggugcggugg cucacaccug   120
```

```
ugauucuagc agaaaaucag aucaggagau cacagaaggu c          161
```

<210> SEQ ID NO 157
<211> LENGTH: 20
<212> TYPE: RNA
<213> ORGANISM: Homo sapiens

<400> SEQUENCE: 157

```
cagagucugu agaagaggcg                                   20
```

<210> SEQ ID NO 158
<211> LENGTH: 160
<212> TYPE: RNA
<213> ORGANISM: Homo sapiens

<400> SEQUENCE: 158

```
guccucccac uggccgcacu cugugcccca uggcccuccu gcgccccgcc cggcguccuc   60
ucacggccuc ugucugugcu gagcuugggu aacuuguguu cuuaccucca cagagucugu  120
agaagaggcg acaccagggc uuccaaauga acaaccgaaa                        160
```

<210> SEQ ID NO 159
<211> LENGTH: 19
<212> TYPE: RNA
<213> ORGANISM: Homo sapiens

<400> SEQUENCE: 159

```
ccuugacuuc ugccagagu                                    19
```

<210> SEQ ID NO 160
<211> LENGTH: 159
<212> TYPE: RNA
<213> ORGANISM: Homo sapiens

<400> SEQUENCE: 160

```
agcccagaac cccucucacc ccagaaccuu ccuugacuuc ugccagaguu gagcagccgg   60
cccucuggua ggcgcaugug aguggaugug ggcacaugug gcccacugga ucgguggau   120
guggucgcgu cuggccccu ggaucggug ggugugggc                           159
```

<210> SEQ ID NO 161
<211> LENGTH: 24
<212> TYPE: RNA
<213> ORGANISM: Homo sapiens

<400> SEQUENCE: 161

```
aucacugacu gaucaaguag aggu                              24
```

<210> SEQ ID NO 162
<211> LENGTH: 164
<212> TYPE: RNA
<213> ORGANISM: Homo sapiens

<400> SEQUENCE: 162

```
ucauuucugc cacagucuuu uuuguugaag caaguuagca agcacuaagc acaucuacaa   60
ucaaggagag gggcaggcuu uaccuuuuga aggaagaagu augaaagugu aucacugacu  120
gaucaaguag agguaagcag uggaggacac ucagaauacc uuuu                   164
```

<210> SEQ ID NO 163
<211> LENGTH: 22
<212> TYPE: RNA
<213> ORGANISM: Homo sapiens

```
<400> SEQUENCE: 163
aaggauugga caggguuaga uu                                              22

<210> SEQ ID NO 164
<211> LENGTH: 162
<212> TYPE: RNA
<213> ORGANISM: Homo sapiens

<400> SEQUENCE: 164
augguuacuu auaugggaag ggugggauaac aaggauugga caggguuaga uuagaccccu    60
cugaagguac cuuguuuuau aguuguaacu uuuuuuuuuu uugagaugga gucuugcucu   120
gucacccagg cuggagugca guggugcgau cucagcucac ug                      162

<210> SEQ ID NO 165
<211> LENGTH: 19
<212> TYPE: RNA
<213> ORGANISM: Homo sapiens

<400> SEQUENCE: 165
aggccaaggc ugcggggguu                                                 19

<210> SEQ ID NO 166
<211> LENGTH: 159
<212> TYPE: RNA
<213> ORGANISM: Homo sapiens

<400> SEQUENCE: 166
gggcagccgu ggggcgugga agccgcgcag aggccaaggc ugcggggguuc uucgucgucu    60 acaggcuuuc gcggcucagu guggaaaacc cgccguuucc ucgcgcccca cguccgaccc   120
aggccuccug ggcacccuuc ggggaggccg cgaucucgg                          159

<210> SEQ ID NO 167
<211> LENGTH: 21
<212> TYPE: RNA
<213> ORGANISM: Homo sapiens

<400> SEQUENCE: 167
aacgggaggc gcuagccaug g                                               21

<210> SEQ ID NO 168
<211> LENGTH: 161
<212> TYPE: RNA
<213> ORGANISM: Homo sapiens

<400> SEQUENCE: 168
accgcaacuc ccuuucccccc acuuucccca aacgggaggc gcuagccaug gaacauggca    60
cauccagggc uaccuccucc caaguuaccc agaggucaug uguacaagca gcaauucuaa   120
caacaguccc ucaggcguga gcggcauuuu acaguuugca a                       161

<210> SEQ ID NO 169
<211> LENGTH: 22
<212> TYPE: RNA
<213> ORGANISM: Homo sapiens

<400> SEQUENCE: 169
accuuucagu gcaguuucuu uu                                              22

<210> SEQ ID NO 170
<211> LENGTH: 162
```

```
<212> TYPE: RNA
<213> ORGANISM: Homo sapiens

<400> SEQUENCE: 170
aaccagaacg ugguuugccu gaggcuguaa cugagagaaa gauucugggg cuguguuaug      60
aaaauauaga cauucucaca uaagcccagu ucaucaccau uccuccuuu accuucagu      120 gcaguuucuu uucacauuag gcuguugguu caaacuuuug gg                       162

<210> SEQ ID NO 171
<211> LENGTH: 20
<212> TYPE: RNA
<213> ORGANISM: Homo sapiens

<400> SEQUENCE: 171
auuuugggug gaagaggcau                                                 20

<210> SEQ ID NO 172
<211> LENGTH: 160
<212> TYPE: RNA
<213> ORGANISM: Homo sapiens

<400> SEQUENCE: 172 gugugugpau auauguauac auauauguau guguaugugu auauagagag agagcugaga     60
guuauucuau uuauuccuuu ucucuccuaa ucugaaaaug ggugugucgu auuuugggug    120
gaagaggcau agaaggggau gugguuguc ucuuaagauu                           160

<210> SEQ ID NO 173
<211> LENGTH: 18
<212> TYPE: RNA
<213> ORGANISM: Homo sapiens

<400> SEQUENCE: 173
ggaaugagga gcuuugac                                                   18

<210> SEQ ID NO 174
<211> LENGTH: 158
<212> TYPE: RNA
<213> ORGANISM: Homo sapiens

<400> SEQUENCE: 174
agacagaaau caggacuaag uccucugcuu caguuucauu guuaacgggc cuuauucuga     60
ucucaccugu cgcguagcuc uaauauucac auaaacugaa auaaagaagu ggaaugagga   120
gcuuugacau ucaaauuaug ugauguaauu uaucuucc                            158

<210> SEQ ID NO 175
<211> LENGTH: 20
<212> TYPE: RNA
<213> ORGANISM: Homo sapiens

<400> SEQUENCE: 175
aaaagcuggg uugagaggau                                                 20

<210> SEQ ID NO 176
<211> LENGTH: 160
<212> TYPE: RNA
<213> ORGANISM: Homo sapiens

<400> SEQUENCE: 176
uauguguaag auagaaugaa uauugagcag gaugcuuuaa aagugaccaa gcagauuuga     60
aaaacauuaa aaauguuggc cuucucgucc caguucuucc caaaguugag aaaagcuggg   120
```

```
uugagaggau gaaagaaaa aaaaagaaaa auuuagugga                              160
```

<210> SEQ ID NO 177
<211> LENGTH: 22
<212> TYPE: RNA
<213> ORGANISM: Homo sapiens

<400> SEQUENCE: 177

```
aguaagguca gcuaaauaag cu                                                22
```

<210> SEQ ID NO 178
<211> LENGTH: 162
<212> TYPE: RNA
<213> ORGANISM: Homo sapiens

<400> SEQUENCE: 178

```
cuccgugcua ccuaucacac cacguccuaa aguaagguca gcuaaauaag cugucaggcc       60
cauaccccaa aaauguuggu uacauccuuc cuguacuaau uaaccuauua gcucagcuua      120
ucaucuacuu uacuauuucu acagguaccc uuaucacaau gc                        162
```

<210> SEQ ID NO 179
<211> LENGTH: 17
<212> TYPE: RNA
<213> ORGANISM: Homo sapiens

<400> SEQUENCE: 179

```
gaauugacgg aagggac                                                      17
```

<210> SEQ ID NO 180
<211> LENGTH: 157
<212> TYPE: RNA
<213> ORGANISM: Homo sapiens

<400> SEQUENCE: 180

```
cuucaggagu uggugugugu gacugggagu gaauugacgg aagggaccau gggaauuuau        60
auaucauuuu gaaacuuaug aaaccuuuug ucaaaguuuc acuuucugac ucaggcucag      120
uccaggacau uguucaauuc cccuggugua ggcauca                              157
```

<210> SEQ ID NO 181
<211> LENGTH: 18
<212> TYPE: RNA
<213> ORGANISM: Homo sapiens

<400> SEQUENCE: 181

```
uugugucuug ugucuuuu                                                     18
```

<210> SEQ ID NO 182
<211> LENGTH: 158
<212> TYPE: RNA
<213> ORGANISM: Homo sapiens

<400> SEQUENCE: 182

```
ggaaguuugg gauaguaaag uuuguugccu uugugucuug ugucuuuuuu ccuuucuuc        60 cuuucuuggg ggagauagau agauagacag acagacagac agacagacac agagagagag      120
agagagagag agagacagau aguguucaug gauccugu                             158
```

<210> SEQ ID NO 183
<211> LENGTH: 16
<212> TYPE: RNA
<213> ORGANISM: Homo sapiens

```
<400> SEQUENCE: 183
ucccuggugg ucuagu                                                    16

<210> SEQ ID NO 184
<211> LENGTH: 156
<212> TYPE: RNA
<213> ORGANISM: Homo sapiens

<400> SEQUENCE: 184
guaaaaugaa aucacagugg uaugggccuc augggguuau cgaaagaaug ggcugagguc    60
augugggcca ugggcuuggu acagugccug agacauaaug aauacucagu ucccuggugg   120
ucuagugguu agaaaaauaa uaauaauaau aauaau                             156

<210> SEQ ID NO 185
<211> LENGTH: 25
<212> TYPE: RNA
<213> ORGANISM: Homo sapiens

<400> SEQUENCE: 185
ugaggcugua acugagagaa agauu                                          25

<210> SEQ ID NO 186
<211> LENGTH: 165
<212> TYPE: RNA
<213> ORGANISM: Homo sapiens

<400> SEQUENCE: 186
cagaacccac caaccagaac gugguuugcc ugaggcugua acugagagaa agauucuggg    60
gcuguguuau gaaauauag acauucucac auaagcccag uucaucacca uuccuccuu    120 uaccuuucag ugcaguuucu uuucacauua ggcuguuggu ucaaa                   165

<210> SEQ ID NO 187
<211> LENGTH: 23
<212> TYPE: RNA
<213> ORGANISM: Homo sapiens

<400> SEQUENCE: 187
uuagggcccu ggcuccaucu ccu                                            23

<210> SEQ ID NO 188
<211> LENGTH: 163
<212> TYPE: RNA
<213> ORGANISM: Homo sapiens

<400> SEQUENCE: 188
ugaaaucaac gaaucaccua ccuaacuggg uuagggcccu ggcuccaucu ccuuuaggaa    60
aaccuucugu ggggaguggg gcuucgaccc uaacccaggu gggcuguaac acugcugugu   120
uuucuaaggg gcagaguuuu cuacuacuuu uccgcuggcc cag                     163

<210> SEQ ID NO 189
<211> LENGTH: 24
<212> TYPE: RNA
<213> ORGANISM: Homo sapiens

<400> SEQUENCE: 189
gagugugagu ggacgcguga gugu                                           24

<210> SEQ ID NO 190
<211> LENGTH: 164
```

```
<212> TYPE: RNA
<213> ORGANISM: Homo sapiens

<400> SEQUENCE: 190
guggcgucgc gugugaggcg cgugcagggu gagugugagu ggacgcguga gugugugagu      60
gugcgcgcuu ggagcguguu aggcgagugc gugcgcccac cccugcgccc cuccucccgc    120
uuacacuuug aucuuauuug aucggaucgu gaccccagcc ccgc                     164

<210> SEQ ID NO 191
<211> LENGTH: 22
<212> TYPE: RNA
<213> ORGANISM: Homo sapiens

<400> SEQUENCE: 191
auugagucug gcagucccug uu                                              22

<210> SEQ ID NO 192
<211> LENGTH: 162
<212> TYPE: RNA
<213> ORGANISM: Homo sapiens

<400> SEQUENCE: 192
gggcuagugu guugucuuu ccauucuaag auugagucug gcagucccug uuuuuuugca      60 uuggggauaac ugcucuuuga uuuuuuuaa uugcaguauu ugugugauug caauaauaaa    120 guuuggouug guuuuuacag ucaugcgcag ggacgauccu ug                       162

<210> SEQ ID NO 193
<211> LENGTH: 21
<212> TYPE: RNA
<213> ORGANISM: Homo sapiens

<400> SEQUENCE: 193
aaaauguuua gacgggcuca c                                               21

<210> SEQ ID NO 194
<211> LENGTH: 161
<212> TYPE: RNA
<213> ORGANISM: Homo sapiens

<400> SEQUENCE: 194
uguagcuuac cuccucaaag caauacacug aaaauguuua gacgggcuca caucaccccca    60 uaaacaaaua gguuuggucc uagccuuucu auuagcucuu aguaagauua cacaugcaag   120 caucccgu ccagugaguu cacccucuaa aucaccacga u                         161

<210> SEQ ID NO 195
<211> LENGTH: 20
<212> TYPE: RNA
<213> ORGANISM: Homo sapiens

<400> SEQUENCE: 195
gaauguuuau ggcaccugac                                                 20

<210> SEQ ID NO 196
<211> LENGTH: 160
<212> TYPE: RNA
<213> ORGANISM: Homo sapiens

<400> SEQUENCE: 196
gugguauuug ugauuugguu aaucuguaua aaaauuguaa guagaaaggu uuauauuuca      60
ucuuaauucu uuugauguug uaaacguacu uuuuaaaga uggauuauuu gaauguuuau    120
```

```
ggcaccugac uuguaaaaaa aaaaaacuac aaaaaaaucc                          160

<210> SEQ ID NO 197
<211> LENGTH: 21
<212> TYPE: RNA
<213> ORGANISM: Homo sapiens

<400> SEQUENCE: 197
ggaaauuuga gaccagcaag u                                              21

<210> SEQ ID NO 198
<211> LENGTH: 161
<212> TYPE: RNA
<213> ORGANISM: Homo sapiens

<400> SEQUENCE: 198
ugauauuacu caccauugau accucuguuu ggaaauuuga gaccagcaag ugacuaucgc    60
uguugccuua ggccacagag acuuuaucaa aaacgugauu acaggacau aucagguggg    120 cuguuguc cugauuauug cugcuggugu uggcaacuuu g                         161

<210> SEQ ID NO 199
<211> LENGTH: 22
<212> TYPE: RNA
<213> ORGANISM: Homo sapiens

<400> SEQUENCE: 199
acaguagggc cuuuggagug au                                             22

<210> SEQ ID NO 200
<211> LENGTH: 162
<212> TYPE: RNA
<213> ORGANISM: Homo sapiens

<400> SEQUENCE: 200
gaaggauggu uauucccgcc uggagauccc acaguagggc cuuuggagug auagacaucc    60
ccaucucccu ccacaccug cccuaccgcc ccccaacccc caaagcuuca acaaaggcuc    120 cuuuuaaag uuuccgguh cccuuugcuc uuuguuugcc uu                        162

<210> SEQ ID NO 201
<211> LENGTH: 25
<212> TYPE: RNA
<213> ORGANISM: Homo sapiens

<400> SEQUENCE: 201
cuugaagucu ggugaugcug ccauu                                          25

<210> SEQ ID NO 202
<211> LENGTH: 165
<212> TYPE: RNA
<213> ORGANISM: Homo sapiens

<400> SEQUENCE: 202
ugguaagaaa cuggaagaug gcccuaaauu cuugaagucu ggugaugcug ccauuguuga    60
uacgguuccu ggcaagcccu ugugguuga gagcuucuca gacuauccac cuguggucg     120 cuuugcuguu caugaucuga gacagacagu ugucguggu gucau                    165

<210> SEQ ID NO 203
<211> LENGTH: 15
<212> TYPE: RNA
<213> ORGANISM: Homo sapiens
```

```
<400> SEQUENCE: 203
agaugagcug aaggg                                                        15

<210> SEQ ID NO 204
<211> LENGTH: 155
<212> TYPE: RNA
<213> ORGANISM: Homo sapiens

<400> SEQUENCE: 204
ccuaaaauuc ucaauuaggc uauaaaugca agaugagcug aagggaaaua ggugauuucc       60
auucuguagu guguauauau gagguuuuau ucucaugaca agaaacagac uaugcaaauc      120
ucuuuaauuu cuggcauuuc agcuuucuag aauua                                 155

<210> SEQ ID NO 205
<211> LENGTH: 18
<212> TYPE: RNA
<213> ORGANISM: Homo sapiens

<400> SEQUENCE: 205
aaaaagggag ccaagaag                                                    18

<210> SEQ ID NO 206
<211> LENGTH: 158
<212> TYPE: RNA
<213> ORGANISM: Homo sapiens

<400> SEQUENCE: 206
ggcaagaaca aguaccuuac gaaagacagc aaaaagggag ccaagaagug gcugauccau       60
uuucuuuuuu ucuuuuuucu uuuuuugag acagucuugc ucuaucccc uggcuggaau        120 acaauggugu gaucucagcu cacugcaacc uccgccuc                              158

<210> SEQ ID NO 207
<211> LENGTH: 22
<212> TYPE: RNA
<213> ORGANISM: Homo sapiens

<400> SEQUENCE: 207
aguuuugugu guuggcugcu cc                                               22

<210> SEQ ID NO 208
<211> LENGTH: 162
<212> TYPE: RNA
<213> ORGANISM: Homo sapiens

<400> SEQUENCE: 208
cacuacggcc ucuggccaug caccaguugu aguuugugu guuggcugcu ccacuguugu       60
cugccagccc acaggaggga aagugaggcu ccuggaagga cgcuccuuca gauggaagca     120
gcacuggaag agcccaagu ugaggugcau gggacacaaa cu                         162

<210> SEQ ID NO 209
<211> LENGTH: 18
<212> TYPE: RNA
<213> ORGANISM: Homo sapiens

<400> SEQUENCE: 209
gguuuaguga gcagaguu                                                    18

<210> SEQ ID NO 210
<211> LENGTH: 158
```

```
<212> TYPE: RNA
<213> ORGANISM: Homo sapiens

<400> SEQUENCE: 210
gaaugaauga uuuuauagau ugacuauagu gguuuaguga gcagaguuac aauuaugagc    60
auuaauuccc agaccaguuc cccuaacuca ccuugugcuc aaauaugaaa aaggauacca   120
cagaaaaugu caguuacucu cagauuaagu aaaaaugg                           158

<210> SEQ ID NO 211
<211> LENGTH: 25
<212> TYPE: RNA
<213> ORGANISM: Homo sapiens

<400> SEQUENCE: 211
aagacgagaa gacccuaugg agcuu                                          25

<210> SEQ ID NO 212
<211> LENGTH: 165
<212> TYPE: RNA
<213> ORGANISM: Homo sapiens

<400> SEQUENCE: 212
acuuguuccc uaaauaggga cuuguacgaa uugcuacacg aggguucagc ugucucuuac    60
uuuuaaucag ugaaauugac cuaucuguga agagguggau auaaaaaaau aagacgagaa   120
gacccuaugg agcuuuaauu cauuaauaca aauaaaaacu caaac                   165

<210> SEQ ID NO 213
<211> LENGTH: 22
<212> TYPE: RNA
<213> ORGANISM: Homo sapiens

<400> SEQUENCE: 213
agcagggugc aggcuuggag uc                                             22

<210> SEQ ID NO 214
<211> LENGTH: 162
<212> TYPE: RNA
<213> ORGANISM: Homo sapiens

<400> SEQUENCE: 214
uggacacaga agaaacgagg gagcccgggu cuccuccgag ugugcaacaa gcuggccugg    60 ggcccccga aaggacgcug gagagaagcc caggaucacc cagucuuugc agcagggugc    120
aggcuuggag uccccccaag ggcggcuaga aucaggucca gg                      162

<210> SEQ ID NO 215
<211> LENGTH: 20
<212> TYPE: RNA
<213> ORGANISM: Homo sapiens

<400> SEQUENCE: 215
auguuggguu guuacagagu                                                20

<210> SEQ ID NO 216
<211> LENGTH: 160
<212> TYPE: RNA
<213> ORGANISM: Homo sapiens

<400> SEQUENCE: 216 ugugcuuuu aaacuggaaa aucuucuagc auguuggguu guuacagagu auauuuugu      60 cugcagcugu uguugccccc auuccuaaga ggaguuuauc cauccugacu uguagcugug   120
```

```
<210> SEQ ID NO 217
<211> LENGTH: 20
<212> TYPE: RNA
<213> ORGANISM: Homo sapiens

<400> SEQUENCE: 217
acugaguuga cguucccuu                                                        20

<210> SEQ ID NO 218
<211> LENGTH: 160
<212> TYPE: RNA
<213> ORGANISM: Homo sapiens

<400> SEQUENCE: 218
cagaagugac uuuacuuucu caaguuugau acugaguuga cguucccuu aucccucacc            60 cuccccuuc ccuuuccuaa ggcauagug cacaacuuag guuauuuug cuuccgaauu             120 ugaaugaaaa acuuaaugcc auggauuuuu ucuuuugca                                 160

<210> SEQ ID NO 219
<211> LENGTH: 22
<212> TYPE: RNA
<213> ORGANISM: Homo sapiens

<400> SEQUENCE: 219
acugggcagu gacaagcacg au                                                    22

<210> SEQ ID NO 220
<211> LENGTH: 162
<212> TYPE: RNA
<213> ORGANISM: Homo sapiens

<400> SEQUENCE: 220
ucacucgcca guaaccuguc ugcaugcaag acugggcagu gacaagcacg augugcucac            60
ugcccaagau uuugcuuuga uuuuguuuua cugcccaaga ucugaacauu uuuugcaaac           120
auagcagcuu cucuaccucu gcugcauuga cauauguuug aa                             162

<210> SEQ ID NO 221
<211> LENGTH: 24
<212> TYPE: RNA
<213> ORGANISM: Homo sapiens

<400> SEQUENCE: 221
agaaagcgug aguguccaga gccu                                                  24

<210> SEQ ID NO 222
<211> LENGTH: 164
<212> TYPE: RNA
<213> ORGANISM: Homo sapiens

<400> SEQUENCE: 222
agaagaaaac aaguuaauuu gaagagaguc agaaagcgug aguguccaga gccuacugag            60
cccuggaagu cacggauaaa aacaagaagu gaagucaaca cucucgguga gaaagggagc           120
gguacugaca aacuucuacc auccagugu gcccgguugc uccc                            164

<210> SEQ ID NO 223
<211> LENGTH: 21
<212> TYPE: RNA
<213> ORGANISM: Homo sapiens
```

-continued

<400> SEQUENCE: 223
gcuugagggc aguuggugcg g                                              21

<210> SEQ ID NO 224
<211> LENGTH: 160
<212> TYPE: RNA
<213> ORGANISM: Homo sapiens

<400> SEQUENCE: 224
cccucccggc gcgguugggu ggcgccucag cggguggggca gcaugggggcg gggagggugu   60 ccccuccgcg ccguuaaaau gaaacucuag uggcuggagu ccgggcagag cuugagggca   120
guuggugcgg ucgdgguuggu ucuuacaccc cggcgggagc                         160

<210> SEQ ID NO 225
<211> LENGTH: 25
<212> TYPE: RNA
<213> ORGANISM: Homo sapiens

<400> SEQUENCE: 225
ccgagccugg ugauagcugg uuguc                                          25

<210> SEQ ID NO 226
<211> LENGTH: 162
<212> TYPE: RNA
<213> ORGANISM: Homo sapiens

<400> SEQUENCE: 226
gauucaugag uagcagugac aaaccuaccg agccugguga uagcugguug uccaagauag   60
aaucuuagac aacucccuau accagauccu cuaauuaauu uuaauaaagg ccuucuauuu   120
auacuagcca caucaagccu agccgucuac guacccacag aa                      162

<210> SEQ ID NO 227
<211> LENGTH: 25
<212> TYPE: RNA
<213> ORGANISM: Homo sapiens

<400> SEQUENCE: 227
uggagauggc uggcagaaug guucu                                          25

<210> SEQ ID NO 228
<211> LENGTH: 165
<212> TYPE: RNA
<213> ORGANISM: Homo sapiens

<400> SEQUENCE: 228
gccuguugag aaagaccucu ggggcccugu uggagauggc uggcagaaug guucucuuga   60
ugagcuucau gauaaagcag acuugccaau aauaccaaga gagaagacug gcucuacucu   120
ccaaaggagu ccagggacag agagucagac agaugacauc agaag                   165

<210> SEQ ID NO 229
<211> LENGTH: 20
<212> TYPE: RNA
<213> ORGANISM: Homo sapiens

<400> SEQUENCE: 229
aaguagaagc cucagggaag                                                20

<210> SEQ ID NO 230
<211> LENGTH: 160

```
<212> TYPE: RNA
<213> ORGANISM: Homo sapiens

<400> SEQUENCE: 230
ccaggagagg aaaaggaaau gggaccucag aaguagaagc cucagggaag gaguaaagua      60
gaaaucagaa gaaaagaagc uucacuugau aguaauaagg uuuuuaacuu caaguaccuu    120
cagaaaaugu gauuuugaua agaggaaagg gcaaauuuag                          160

<210> SEQ ID NO 231
<211> LENGTH: 20
<212> TYPE: RNA
<213> ORGANISM: Homo sapiens

<400> SEQUENCE: 231
augguucugg acaguggauu                                                 20

<210> SEQ ID NO 232
<211> LENGTH: 160
<212> TYPE: RNA
<213> ORGANISM: Homo sapiens

<400> SEQUENCE: 232
agaaauaaua augcagggu ucuucaaaau augguucugg acaguggauu auaguuaccu      60
ggagagcuug uguuaaaaua ucugaggaug auuccaagua ccagggcuua uacacaggaa    120
uacuugagaa ccacugcacu caagcauuua aaauuuuccu                          160

<210> SEQ ID NO 233
<211> LENGTH: 18
<212> TYPE: RNA
<213> ORGANISM: Homo sapiens

<400> SEQUENCE: 233
gaugagucag gcuaggcu                                                   18

<210> SEQ ID NO 234
<211> LENGTH: 158
<212> TYPE: RNA
<213> ORGANISM: Homo sapiens

<400> SEQUENCE: 234
uccuagggcu uugacaccaa aaucuacuau gaugagucag gcuaggcuau aaacuugcaa      60
ggacuuagag cccagaaagu gacaagccca acuagccugc cucuuggagg aaaaaagaag    120
aauagcucaa aacacuuaag aagguaagga guccaagc                            158

<210> SEQ ID NO 235
<211> LENGTH: 22
<212> TYPE: RNA
<213> ORGANISM: Homo sapiens

<400> SEQUENCE: 235
augugagagc agcagaggcg gu                                              22

<210> SEQ ID NO 236
<211> LENGTH: 162
<212> TYPE: RNA
<213> ORGANISM: Homo sapiens

<400> SEQUENCE: 236
gggagggugg acaguccuua acugcucugc agguccagga uguuagaaag gggcagggac      60
aacaaauggg ugaccccaac cucaaccugc ugcuucucuc uccaguccc augugagagc    120
```

```
agcagaggcg gucuucaaca uccugccagc cccacacagc ua            162
```

<210> SEQ ID NO 237
<211> LENGTH: 21
<212> TYPE: RNA
<213> ORGANISM: Homo sapiens

<400> SEQUENCE: 237

```
guuuuaagga cuuaagggua u                                   21
```

<210> SEQ ID NO 238
<211> LENGTH: 161
<212> TYPE: RNA
<213> ORGANISM: Homo sapiens

<400> SEQUENCE: 238

```
uaggucuguu auuucacau acacuuggua acucagacug gucugaauau aaaguagaaa   60
uagcuaagaa ccauuguaa ugaaugcaac ucuuauugu uuuuaauggu guuuaagga   120 cuuaaggua uuagaacuga caacaguuua uucaguuaag c                     161
```

<210> SEQ ID NO 239
<211> LENGTH: 20
<212> TYPE: RNA
<213> ORGANISM: Homo sapiens

<400> SEQUENCE: 239

```
ugauauguuu gauauugggu                                     20
```

<210> SEQ ID NO 240
<211> LENGTH: 160
<212> TYPE: RNA
<213> ORGANISM: Homo sapiens

<400> SEQUENCE: 240

```
accccaaag cucuccugcc ugcuucgugu ugauauguuu gauauugggu uguuuaauua   60
ggaaccaacu aaaugucaaa cauauucuua cagcagcagg ugauucagca ccacccucuu  120
ucauacuuca aucucugggg cuccugucuc uuuuacugaa                      160
```

<210> SEQ ID NO 241
<211> LENGTH: 21
<212> TYPE: RNA
<213> ORGANISM: Homo sapiens

<400> SEQUENCE: 241

```
agaaagccag gagcugugau u                                   21
```

<210> SEQ ID NO 242
<211> LENGTH: 161
<212> TYPE: RNA
<213> ORGANISM: Homo sapiens

<400> SEQUENCE: 242

```
auccguuuug gaaccugcgu cuggggcucc agucgcugcu cuugcuggcg uccaucgccg   60
ccucggacgg ccgugcauuu ucucgucuca cgcaguucga ggaggacccu agaaagccag   120
gagcugugau ugacaguagc uguagguuac cagacggcaa c                     161
```

<210> SEQ ID NO 243
<211> LENGTH: 21
<212> TYPE: RNA
<213> ORGANISM: Homo sapiens -continued

```
<400> SEQUENCE: 243
auucuaaguc agucagucau c                                              21

<210> SEQ ID NO 244
<211> LENGTH: 161
<212> TYPE: RNA
<213> ORGANISM: Homo sapiens

<400> SEQUENCE: 244
uacauuuuag ggugguagag cuacuccuua cuuuaaaugc uaccacuca cugugacacu     60 guuuaauaaa ugguuauuga cuagagaagu agggaucucu gcaccuagc auucaaguc     120 agucagucau caguuuugu agguuaucuc agaagcaaua g                        161

<210> SEQ ID NO 245
<211> LENGTH: 23
<212> TYPE: RNA
<213> ORGANISM: Homo sapiens

<400> SEQUENCE: 245
uucucuguuu uggccaugug ugu                                            23

<210> SEQ ID NO 246
<211> LENGTH: 163
<212> TYPE: RNA
<213> ORGANISM: Homo sapiens

<400> SEQUENCE: 246
uucuucuuca gcaaacauua ggagaguauc uucucuguuu uggccaugug uacucaca     60 gccccucaca cauggccgaa acagagaagu acuuuccua auauuugccu ccuuggagug    120
ucucaagucc uggaagcaag agauaauaag caauuaauau aca                     163

<210> SEQ ID NO 247
<211> LENGTH: 23
<212> TYPE: RNA
<213> ORGANISM: Homo sapiens

<400> SEQUENCE: 247
uucuaagcca guuucugucu gau                                            23

<210> SEQ ID NO 248
<211> LENGTH: 163
<212> TYPE: RNA
<213> ORGANISM: Homo sapiens

<400> SEQUENCE: 248
cccgacagau cgacuauguu gaucuaacuu uucuaagcca guuucugucu gauaugccag    60
cuugagcagc uccuuugucc cagcuccccu gggcaucuag cugaugggag cucauuuuc    120 uguuuuuuca uuucagguuu auuguuggcc aaaaccaggc uuu                     163

<210> SEQ ID NO 249
<211> LENGTH: 20
<212> TYPE: RNA
<213> ORGANISM: Homo sapiens

<400> SEQUENCE: 249
gguuuugaca ugucacuguu                                                20

<210> SEQ ID NO 250
<211> LENGTH: 160
```

```
<212> TYPE: RNA
<213> ORGANISM: Homo sapiens

<400> SEQUENCE: 250
gggucaugga ccagcgccuc agugcauuag ucauucgcuu uuccuuacag acaaaucaga    60
uaacucuucc ccagugauug ucaaauguau gaauguaucu cuguaaaugu gguuuugaca   120
ugucacuguu acugaaggag aguauggaau ccccacagga                         160

<210> SEQ ID NO 251
<211> LENGTH: 22
<212> TYPE: RNA
<213> ORGANISM: Homo sapiens

<400> SEQUENCE: 251
cucgcccgug gucucucguc uu                                             22

<210> SEQ ID NO 252
<211> LENGTH: 162
<212> TYPE: RNA
<213> ORGANISM: Homo sapiens

<400> SEQUENCE: 252
ggugaggccc cgcgcgugug ucccggcugc ggucggccgc gcucgagggg uccccguggc    60
gucccccuuc ccgccggccg ccuuucucgc gccuucccg ucgccccggc cucgcccgug   120
gucucucguc uucucccggc ccgcucuucc gaaccggguc gg                     162

<210> SEQ ID NO 253
<211> LENGTH: 25
<212> TYPE: RNA
<213> ORGANISM: Homo sapiens

<400> SEQUENCE: 253
aacacgcaua cgguuaaggc auugc                                          25

<210> SEQ ID NO 254
<211> LENGTH: 165
<212> TYPE: RNA
<213> ORGANISM: Homo sapiens

<400> SEQUENCE: 254
acaaggaugg aagaggcccu cgggccugac aacacgcaua cgguuaaggc auugccaccu    60 acuucgugge aucuaaccau cguuuuuuuu uuuuggugu uuuguuuuu auuuucuuc     120 agacggaguc uuauucuguc gcccagacug gagugcaaug gcgcg                   165

<210> SEQ ID NO 255
<211> LENGTH: 25
<212> TYPE: RNA
<213> ORGANISM: Homo sapiens

<400> SEQUENCE: 255
ugaaacagca ucugaucuug aacuu                                          25

<210> SEQ ID NO 256
<211> LENGTH: 165
<212> TYPE: RNA
<213> ORGANISM: Homo sapiens

<400> SEQUENCE: 256
acaugcaggg ugaaauccuc acauuuuuua ugaaacagca ucugaucuug aacuuuuaug    60 acucacccuca gucacuucac cuguauuuug gcccugucag aucaugucuu uauuuaaacu  120
```
uuugauauuu uauucuuuau auguuuuugc auuaguuuuu auuuu                    165

<210> SEQ ID NO 257
<211> LENGTH: 25
<212> TYPE: RNA
<213> ORGANISM: Homo sapiens

<400> SEQUENCE: 257
gcguaaagag uguuuuagau caccc                                          25

<210> SEQ ID NO 258
<211> LENGTH: 165
<212> TYPE: RNA
<213> ORGANISM: Homo sapiens

<400> SEQUENCE: 258
cacacgauua acccaaguca auagaagccg gcguaaagag uguuuuagau caccccaucc    60
ccaauaaagc uaaaacucac cugaguugua aaaaaccuca guugcacaaa aauagacuac    120
gaaaguggcu uuaacauauc ugaacacaca auagcuaaga cccaa                   165

<210> SEQ ID NO 259
<211> LENGTH: 24
<212> TYPE: RNA
<213> ORGANISM: Homo sapiens

<400> SEQUENCE: 259
guccguuucc ugucagagug aucc                                           24

<210> SEQ ID NO 260
<211> LENGTH: 164
<212> TYPE: RNA
<213> ORGANISM: Homo sapiens

<400> SEQUENCE: 260
cagagcaacu ggcuccuggc agcugugcuu guccguuucc ugucagagug auccaugguu   60
uccuccuggc ccgucccaug gucccuccac aggaguguga gaggauggggg gaagcacugu 120 gggaagacca ccaaagaugg cuggacagug ggagagagca cguu                   164

<210> SEQ ID NO 261
<211> LENGTH: 24
<212> TYPE: RNA
<213> ORGANISM: Homo sapiens

<400> SEQUENCE: 261
ccaucgguga ucccagugac aagu                                           24

<210> SEQ ID NO 262
<211> LENGTH: 164
<212> TYPE: RNA
<213> ORGANISM: Homo sapiens

<400> SEQUENCE: 262
aucaaacacu uauccuauua aacacagcau ccaucgguga ucccagugac aaguaauuga   60
auguuaguuc uggagucuuu ccuggggugu uggccuggag aagccucucu uuuaaggauu   120
agauucagag guagagguaa augagugug agcaccagga agag                    164

<210> SEQ ID NO 263
<211> LENGTH: 23
<212> TYPE: RNA
<213> ORGANISM: Homo sapiens

```
<400> SEQUENCE: 263
gaaauguuga guguuuaccc ugu                                           23

<210> SEQ ID NO 264
<211> LENGTH: 163
<212> TYPE: RNA
<213> ORGANISM: Homo sapiens

<400> SEQUENCE: 264
guuggcuuuu ccagggccag cgugaguggu gaggccagcu cucucaguga ccaucagaga    60
caaggccuug gccaguccag gggucuuggg gcuccacuuu ucugaauuau gaaauguuga   120
guguuuaccc ugucaauaua uauaucauuu auauauuuuu ugu                    163

<210> SEQ ID NO 265
<211> LENGTH: 21
<212> TYPE: RNA
<213> ORGANISM: Homo sapiens

<400> SEQUENCE: 265
gaagaaacag cucaugaggc u                                             21

<210> SEQ ID NO 266
<211> LENGTH: 161
<212> TYPE: RNA
<213> ORGANISM: Homo sapiens

<400> SEQUENCE: 266
gaaagagaaa gccaagaucc acuaccggaa gaagaaacag cucaugaggc uacggaaaca    60
ggccgagaag aacguggaga agaaaaauuga caaauacaca gagguccuca agacccacgg   120
acuccugguc ugagcccaau aaagacuguu aauuccucaa a                      161

<210> SEQ ID NO 267
<211> LENGTH: 23
<212> TYPE: RNA
<213> ORGANISM: Homo sapiens

<400> SEQUENCE: 267
augaaccacc aguccaagaa ucu                                           23

<210> SEQ ID NO 268
<211> LENGTH: 163
<212> TYPE: RNA
<213> ORGANISM: Homo sapiens

<400> SEQUENCE: 268
gaagcccaag uuugaauugg gaaggcucau ggagcuucau ggugaaggca guaguucugg    60
aaaagccacu ggggaugaga caggugcuaa aguuggacga gcugauggau augaaccacc   120
aguccaagaa ucuguuuaaa guucagacuu caaauagugg caa                    163

<210> SEQ ID NO 269
<211> LENGTH: 17
<212> TYPE: RNA
<213> ORGANISM: Homo sapiens

<400> SEQUENCE: 269
ggaagguugg ggggugu                                                  17

<210> SEQ ID NO 270
<211> LENGTH: 157
```

```
<212> TYPE: RNA
<213> ORGANISM: Homo sapiens

<400> SEQUENCE: 270
cucucagcuc ugcagcuguc ugcggugggg ggaagguugg ggggugucug gaggcauguu      60
ccccucacca cccccgugg gucucaggga ggccgggugu gaccucaucu uucucauggu      120
gcuauccugg ugcuauuggg gugggagcu cccuccc                               157

<210> SEQ ID NO 271
<211> LENGTH: 18
<212> TYPE: RNA
<213> ORGANISM: Homo sapiens

<400> SEQUENCE: 271
uucuagguug uggcauuu                                                    18

<210> SEQ ID NO 272
<211> LENGTH: 158
<212> TYPE: RNA
<213> ORGANISM: Homo sapiens

<400> SEQUENCE: 272
auccuuuagc acguuggau aaaguuggcc uucuagguug uggcauuuca acugguuaug      60
guccugcugu gaacacugcc aagcuggagc cuggcucugu uugugccauc uuuggccugg      120
gaggauuugg aucggggguu accaugggcu guaaagug                             158

<210> SEQ ID NO 273
<211> LENGTH: 24
<212> TYPE: RNA
<213> ORGANISM: Homo sapiens

<400> SEQUENCE: 273
ugauauguuu gauauggggu uguu                                             24

<210> SEQ ID NO 274
<211> LENGTH: 164
<212> TYPE: RNA
<213> ORGANISM: Homo sapiens

<400> SEQUENCE: 274
acccccaaag cucuccugcc ugcuucugug ugauauguuu gauauggggu uguuaauua      60 ggaaccaacu aaaugucaaa cauauucuua cagcagcagg ugauucagca ccacccucuu      120
ucauacuuca aucucugggg cuccugcucu uuuuacugaa ccuc                      164

<210> SEQ ID NO 275
<211> LENGTH: 22
<212> TYPE: RNA
<213> ORGANISM: Homo sapiens

<400> SEQUENCE: 275
agaauacagc agaauuggcc uc                                               22

<210> SEQ ID NO 276
<211> LENGTH: 162
<212> TYPE: RNA
<213> ORGANISM: Homo sapiens

<400> SEQUENCE: 276
cauuaauuag guaauauuuu ccucauuucu uuacugcugc cauuuccuc accaguauuc      60 cagagauggu cauagcucau uacucuacca ccaagaaccu aaaaggaauu agaauacagc      120
```

```
agaauuggcc ucagugaaga gcuuaaaauu guucuccucg ua                 162

<210> SEQ ID NO 277
<211> LENGTH: 21
<212> TYPE: RNA
<213> ORGANISM: Homo sapiens

<400> SEQUENCE: 277
cugauggaga gaagaaggca u                                         21

<210> SEQ ID NO 278
<211> LENGTH: 161
<212> TYPE: RNA
<213> ORGANISM: Homo sapiens

<400> SEQUENCE: 278 uggugugcc aaggccaaca cugagucgac cugauggaga gaagaaggca uguguccacu  60
ggcuccugau gaccaugcuu uggauguugc caacaaaauu gggaucaucu aaucugaguc 120
cagcuugcua auucuaaagg uauauaugua ucuuuucacc a                   161

<210> SEQ ID NO 279
<211> LENGTH: 22
<212> TYPE: RNA
<213> ORGANISM: Homo sapiens

<400> SEQUENCE: 279
acucggcgug gcgucggucg ug                                        22

<210> SEQ ID NO 280
<211> LENGTH: 162
<212> TYPE: RNA
<213> ORGANISM: Homo sapiens

<400> SEQUENCE: 280
acucccugac agauaucucc cucuuccauu ucaucaagac ccagcugagu cacugucacu  60
gccuaccaau cucgaccgga ccucgaccgg cucgucugug uugccaaucg acucggcgug 120
gcgucggucg ugguagauag gcggucaugc auacgaauuu uc                  162

<210> SEQ ID NO 281
<211> LENGTH: 22
<212> TYPE: RNA
<213> ORGANISM: Homo sapiens

<400> SEQUENCE: 281
augagguggc aagaaauggg cu                                        22

<210> SEQ ID NO 282
<211> LENGTH: 162
<212> TYPE: RNA
<213> ORGANISM: Homo sapiens

<400> SEQUENCE: 282
auauaaaaac auuaggucaa gguacagccu augagguggc aagaaauggg cuacauuuuc  60
uauauccggc aaaucucaca acaaccuuua ugaaaucuaa gggcucaagg aggauuuagu 120
aguaaaccaa gcgcagagug cuugguugaa uaaggccaug aa                  162

<210> SEQ ID NO 283
<211> LENGTH: 25
<212> TYPE: RNA
<213> ORGANISM: Homo sapiens
```

```
<400> SEQUENCE: 283
aauuuugaca gaugcucaag gcugu                                              25

<210> SEQ ID NO 284
<211> LENGTH: 165
<212> TYPE: RNA
<213> ORGANISM: Homo sapiens

<400> SEQUENCE: 284
uuucauuuuc ugugauuauu uuuaaauuag cuucugugua aacucacuaa cuuguuccca        60
caugacaauu uauagcaguc caaagauuuu uuuauagcca ugguuguuau aauuuugaca       120
gaugcucaag gcuguguuu gcauuguucu ucagaauuuc aucuu                        165

<210> SEQ ID NO 285
<211> LENGTH: 18
<212> TYPE: RNA
<213> ORGANISM: Homo sapiens

<400> SEQUENCE: 285
aaaagcuggg uugagaag                                                      18

<210> SEQ ID NO 286
<211> LENGTH: 158
<212> TYPE: RNA
<213> ORGANISM: Homo sapiens

<400> SEQUENCE: 286
cauuacacuc cagccugggc aacaagagca aaacucuguc ucaaaaaaau gaaaagaaaa        60
gaaaauaccu ccauggggcc uucucuuccc aguucuuccu ggagucgggg aaaagcuggg       120
uugagaaggu gaaaagaaaa aacaaaccuu gacugggc                               158

<210> SEQ ID NO 287
<211> LENGTH: 23
<212> TYPE: RNA
<213> ORGANISM: Homo sapiens

<400> SEQUENCE: 287
auugaugguu aagcucagcu uuu                                                23

<210> SEQ ID NO 288
<211> LENGTH: 163
<212> TYPE: RNA
<213> ORGANISM: Homo sapiens

<400> SEQUENCE: 288
ggaguagcug uaacauuaug uggaaagcaa gugggagaau caugaaaaaa aauaauccca        60
uagauggaga agaauagaaa gaaggaaagg agcauugccu agguugguu auugaugguu       120 aagcucagcu uuuauuuauu caauaggccu gcagauguag acu                        163

<210> SEQ ID NO 289
<211> LENGTH: 24
<212> TYPE: RNA
<213> ORGANISM: Homo sapiens

<400> SEQUENCE: 289
auggauugag augugaucaa aggc                                               24

<210> SEQ ID NO 290
<211> LENGTH: 164
```

```
<212> TYPE: RNA
<213> ORGANISM: Homo sapiens

<400> SEQUENCE: 290
uguaggauuu uuuguuuuug uagcuaacuu auggauugag augugaucaa aggcuuuauu    60
aaauuuguac uucagcauau gauggcugcg uucugcauuu cauuccgcca uaugccugga   120
ccguucacac uuggguaucu gggcuuaggg agcauguagg cuuc                    164

<210> SEQ ID NO 291
<211> LENGTH: 23
<212> TYPE: RNA
<213> ORGANISM: Homo sapiens

<400> SEQUENCE: 291
auuuggcauu uggaagauag guu                                            23

<210> SEQ ID NO 292
<211> LENGTH: 163
<212> TYPE: RNA
<213> ORGANISM: Homo sapiens

<400> SEQUENCE: 292
ucuagcucug uuauaaagaa aacauuuagg aaauucucuc uuucucucuu ucaccuaucc    60
uacuuuuugu guguccuuug uaguuuugca ccaucauucc uaacgaauuu auuuggcauu   120
uggaagauag guuagcaaaa auuuuacuau auuugaaagg cua                     163

<210> SEQ ID NO 293
<211> LENGTH: 23
<212> TYPE: RNA
<213> ORGANISM: Homo sapiens

<400> SEQUENCE: 293
acugcugagg aacugucacu ugu                                            23

<210> SEQ ID NO 294
<211> LENGTH: 163
<212> TYPE: RNA
<213> ORGANISM: Homo sapiens

<400> SEQUENCE: 294
ggucaccagg cugagaaagc aggagaugcu acugcugagg aacugucacu ugcauuuca    60 agguccacuc cuccacccuc uggcagcaug agucgcucug aaagauuuug aagcugggac   120
aggagagggu gagugaggug aggccuccgc augccagguu uuc                     163

<210> SEQ ID NO 295
<211> LENGTH: 24
<212> TYPE: RNA
<213> ORGANISM: Homo sapiens

<400> SEQUENCE: 295
aggugagggg caggaccuga aggu                                           24

<210> SEQ ID NO 296
<211> LENGTH: 164
<212> TYPE: RNA
<213> ORGANISM: Homo sapiens

<400> SEQUENCE: 296
auucaucucu gguuuucuug ccacccucug ggaguccca ucccauuuuc auccugagcc    60
caaccaggcc cugccauugg ccucuugucc cuuggcacac uuguacccac aggugagggg   120
```

```
caggaccuga agguauuggc cguucaaca aucagucauc augg            164

<210> SEQ ID NO 297
<211> LENGTH: 20
<212> TYPE: RNA
<213> ORGANISM: Homo sapiens

<400> SEQUENCE: 297
agugucugug ugugcuugcu                                      20

<210> SEQ ID NO 298
<211> LENGTH: 160
<212> TYPE: RNA
<213> ORGANISM: Homo sapiens

<400> SEQUENCE: 298 acuauaagc uacaaaacau uuaaaugacu agugucugug ugugcuugcu aguauuauua    60
uaccaucaga aaguaaaaau ggacauacau guuaugcauu aaacccacaa gagagaaaac  120
uugaggacug auuaauuuaa guaguaaaug aauccaagaa                        160

<210> SEQ ID NO 299
<211> LENGTH: 20
<212> TYPE: RNA
<213> ORGANISM: Homo sapiens

<400> SEQUENCE: 299
acgaagaugg cgaccguaac                                      20

<210> SEQ ID NO 300
<211> LENGTH: 160
<212> TYPE: RNA
<213> ORGANISM: Homo sapiens

<400> SEQUENCE: 300
acuguuuaua agucgguguu guaaaucuga ugugaauuuu uguuucuuuu uucuuagauu    60
uuugccuuua ugacgacagc uuguuauggu ugcaguuugg gucuggcuuu acgaagaugg  120
cgaccguaac acuccuuaga aacuggcagu cguauguuag                        160

<210> SEQ ID NO 301
<211> LENGTH: 23
<212> TYPE: RNA
<213> ORGANISM: Homo sapiens

<400> SEQUENCE: 301
aacuggaaug gcggcaaggu ccu                                  23

<210> SEQ ID NO 302
<211> LENGTH: 163
<212> TYPE: RNA
<213> ORGANISM: Homo sapiens

<400> SEQUENCE: 302
aguaggcaac ugaggacuga uuucucaggg ugauuagaaa ggaaagggug gcggccuccu    60
uucauacuuc ggaaagucuu gucccauca gccuuuccuc auggugccau aacuggaaug   120
gcggcaaggu ccucuuuccu gugccugugu cuuaaguuuc ugg                    163

<210> SEQ ID NO 303
<211> LENGTH: 21
<212> TYPE: RNA
<213> ORGANISM: Homo sapiens
```

<400> SEQUENCE: 303
aguugaguca gggccugugu g                                     21

<210> SEQ ID NO 304
<211> LENGTH: 161
<212> TYPE: RNA
<213> ORGANISM: Homo sapiens

<400> SEQUENCE: 304
gcgcccccaa agugccccu ccugcuguga cuucuagcca agaagacauu ucucccaugg    60
ccaagugauc ucgauagau ccguaggac cacugaaguc agacaggaca aguugaguca   120
gggccugugu guccagugcg cagcaugcuu ggggagugac a                     161

<210> SEQ ID NO 305
<211> LENGTH: 19
<212> TYPE: RNA
<213> ORGANISM: Homo sapiens

<400> SEQUENCE: 305
gccgcccggg gccauggcg                                        19

<210> SEQ ID NO 306
<211> LENGTH: 159
<212> TYPE: RNA
<213> ORGANISM: Homo sapiens

<400> SEQUENCE: 306
uaacgcaugc gcggggaggg cggagcuggg cguugccgug gcuacuggga acgcauuuca    60
cgggggcggg gcgugguucc ggggcggggc gcggccgccg gaagugcgug gccgcccggg   120
gccauggcga cacucagcuu cgucuuccug cugcugggg                         159

<210> SEQ ID NO 307
<211> LENGTH: 24
<212> TYPE: RNA
<213> ORGANISM: Homo sapiens

<400> SEQUENCE: 307
aagucuaagu cuaacauucg gugu                                  24

<210> SEQ ID NO 308
<211> LENGTH: 164
<212> TYPE: RNA
<213> ORGANISM: Homo sapiens

<400> SEQUENCE: 308
ucgaugggug uucuuuuaaa auacgguucu aagucuaagu cuaacauucg guguaucuaa    60
ccgaauguua auugauggag acaaggugau acggguucag aaaauagaau ucagaaaaga   120
aaaggaagaa uuggcaaaau ucagaaauca auuuuaagaa aaau                   164

<210> SEQ ID NO 309
<211> LENGTH: 16
<212> TYPE: RNA
<213> ORGANISM: Homo sapiens

<400> SEQUENCE: 309
cggcgggagc ccgggg                                           16

<210> SEQ ID NO 310
<211> LENGTH: 156

```
<212> TYPE: RNA
<213> ORGANISM: Homo sapiens

<400> SEQUENCE: 310
cccacggauu cgccccgccg cgccucuccg cgcguagauu ggccggagcg aggcgaacgg      60
gcccggccuu gguagccgcc gaccgagcgc uggcugnccu ggaaccuagg cggcgggagc     120
ccggggcgcc ucgcggcacg gaagagcggc gagaug                               156

<210> SEQ ID NO 311
<211> LENGTH: 21
<212> TYPE: RNA
<213> ORGANISM: Homo sapiens

<400> SEQUENCE: 311
acguggaugg cguggaggug c                                                21

<210> SEQ ID NO 312
<211> LENGTH: 161
<212> TYPE: RNA
<213> ORGANISM: Homo sapiens

<400> SEQUENCE: 312
ccuguccccc ccaaaaccca aggacacucu caugaucucc cggaccccug aggucacgug      60
cgugguggug gacgcgagcc aggaagaccc cgagguccag uucaacuggu acguggaugg     120
cguggaggug cauaaugcca agacaaagcc gcgggaggag c                         161

<210> SEQ ID NO 313
<211> LENGTH: 18
<212> TYPE: RNA
<213> ORGANISM: Homo sapiens

<400> SEQUENCE: 313
guuuagacgg gcucacau                                                    18

<210> SEQ ID NO 314
<211> LENGTH: 158
<212> TYPE: RNA
<213> ORGANISM: Homo sapiens

<400> SEQUENCE: 314
uuuuacauaa guagacacag gugggaaacu guuuagacgg gcucacauca ccccauaaac      60
aaauagguuu gguccuagcc uuucuauuag cucuuaguaa gauuacacau gcaagcaucc     120 ccauccagu gaguucaccc ucuaaaucac cacgauga                              158

<210> SEQ ID NO 315
<211> LENGTH: 21
<212> TYPE: RNA
<213> ORGANISM: Homo sapiens

<400> SEQUENCE: 315
auuucugcag ucaggugaga c                                                21

<210> SEQ ID NO 316
<211> LENGTH: 161
<212> TYPE: RNA
<213> ORGANISM: Homo sapiens

<400> SEQUENCE: 316
uggaaaucac agcaacccau ugaaaacugc ccuccccacc agaacgugcu acguucuuuc      60
uucaugccua ugugugcucc auccucauu ucuacuuggc ucaagaaaac auuucugcag     120
```

```
ucaggugaga cuuuuacaaa agaggagaaa aucaaugccu c                161
```

<210> SEQ ID NO 317
<211> LENGTH: 22
<212> TYPE: RNA
<213> ORGANISM: Homo sapiens

<400> SEQUENCE: 317

```
aagaaugacc gcugaagaac gu                                      22
```

<210> SEQ ID NO 318
<211> LENGTH: 162
<212> TYPE: RNA
<213> ORGANISM: Homo sapiens

<400> SEQUENCE: 318

```
cugaucauag uauucuguca gauaaugccu aagaaugacc gcugaagaac guugacccau   60
uugaguaccc ggucucaguc gucauuuuua agccaguga gcauugggu aguguucuu    120 agauugcagu uucuuauguu uugaguuuga aguugauuuu ca                    162
```

<210> SEQ ID NO 319
<211> LENGTH: 20
<212> TYPE: RNA
<213> ORGANISM: Homo sapiens

<400> SEQUENCE: 319

```
aaauaugagc cacugggugu                                          20
```

<210> SEQ ID NO 320
<211> LENGTH: 160
<212> TYPE: RNA
<213> ORGANISM: Homo sapiens

<400> SEQUENCE: 320

```
aaagucuuag aauggaaaaa guaaagaaau caacuuccc aaguuggcaa guaacuccca    60
augauuuagu uuuuuccccc ccaguuugaa uugggaagcu gggggaaguu aaauaugagc   120
cacugggugu accagugcau uaauuugggc aaggaaagug                       160
```

<210> SEQ ID NO 321
<211> LENGTH: 23
<212> TYPE: RNA
<213> ORGANISM: Homo sapiens

<400> SEQUENCE: 321

```
aagguccucu gaggcagcag gcu                                     23
```

<210> SEQ ID NO 322
<211> LENGTH: 163
<212> TYPE: RNA
<213> ORGANISM: Homo sapiens

<400> SEQUENCE: 322

```
gaagaucacu acaacaauuu gucugccucc aagguccucu gaggcagcag gcucggggc    60 uucugcuguc cuuuggaggg ugucuucugg guagagggau gggaaggaag ggacccuuac   120
ccccggcucu ucuccugacc ugccaauaaa aauuuauggu cca                   163
```

<210> SEQ ID NO 323
<211> LENGTH: 21
<212> TYPE: RNA
<213> ORGANISM: Homo sapiens

```
<400> SEQUENCE: 323
gucgaggucu uuggugggguu g                                        21

<210> SEQ ID NO 324
<211> LENGTH: 161
<212> TYPE: RNA
<213> ORGANISM: Homo sapiens

<400> SEQUENCE: 324
caccccgugc cuuuugaucu agcacagacc cuucaccccu caccucgaug cagccaguag    60
cuuggauccu ugugggcaug auccauaauc gguuucaagg uaacgauggu gucgaggucu   120 uuggugggguu gaacuauguu agaaaaggcc auuaauuugc c                      161

<210> SEQ ID NO 325
<211> LENGTH: 21
<212> TYPE: RNA
<213> ORGANISM: Homo sapiens

<400> SEQUENCE: 325
gguuucgggu uugaaggcag c                                         21

<210> SEQ ID NO 326
<211> LENGTH: 161
<212> TYPE: RNA
<213> ORGANISM: Homo sapiens

<400> SEQUENCE: 326
cccucuggca ugguucauua gggccaauua augguggcugg guuauuugca acuuaaacug    60
ggggauaaug ucgcuugagg gagcguuuuc guuuuaggaa auauuguuuu gguuucgggu   120
uugaaggcag cugucaaaaa agcggcaugg aaauucauug g                       161

<210> SEQ ID NO 327
<211> LENGTH: 22
<212> TYPE: RNA
<213> ORGANISM: Homo sapiens

<400> SEQUENCE: 327
gcuggugagu gcaggcugcu uc                                        22

<210> SEQ ID NO 328
<211> LENGTH: 162
<212> TYPE: RNA
<213> ORGANISM: Homo sapiens

<400> SEQUENCE: 328
gagcuaguac cuucuccccu uagcaacuuc cucauucuaa aauggggggug gcagaaccau    60 uguuuggcuc caguugaccu cagaaaggug gcuuccagau gccagugacu gcuggugagu   120
gcaggcugcu ucaguauuuc cuggccagcu gacaaggugu ua                      162

<210> SEQ ID NO 329
<211> LENGTH: 20
<212> TYPE: RNA
<213> ORGANISM: Homo sapiens

<400> SEQUENCE: 329
gacagaggug gcaucaagcu                                           20

<210> SEQ ID NO 330
<211> LENGTH: 160
```

```
<212> TYPE: RNA
<213> ORGANISM: Homo sapiens

<400> SEQUENCE: 330
aaucccuguu ugcuucaggg cgagaugugu gacagaggug gcaucaagcu cuuacagucc    60
caacccucca acggaaaugg gcgaagaucu caggaauggc aucggucaca ggaaaucgau   120
aguggcuggc ugcuagcaug gccacuuggg gcuuaggcag                         160

<210> SEQ ID NO 331
<211> LENGTH: 23
<212> TYPE: RNA
<213> ORGANISM: Homo sapiens

<400> SEQUENCE: 331
cugcccuggc ccgagggacc gac                                            23

<210> SEQ ID NO 332
<211> LENGTH: 163
<212> TYPE: RNA
<213> ORGANISM: Homo sapiens

<400> SEQUENCE: 332
ggaaccugcu uggacaaguc uucuggcucg accucgacau gcuccaucgg augaauuguu    60
gguguuagcc cugcggcccc acgcaccagg guaagagaga cucucgcuuc cugcccuggc   120
ccgagggacc gacuggcugg gccugccuuc ugcccagcuc acc                     163

<210> SEQ ID NO 333
<211> LENGTH: 20
<212> TYPE: RNA
<213> ORGANISM: Homo sapiens

<400> SEQUENCE: 333
ucgugucgcg uggggggcgg                                                20

<210> SEQ ID NO 334
<211> LENGTH: 160
<212> TYPE: RNA
<213> ORGANISM: Homo sapiens

<400> SEQUENCE: 334
ucgcgggucu guggcgcggg gccccggugg ucgugucgcg uggggggcgg guggugggg     60 cguccgguuc gccgcgcccc gccccggccc caccggugccc ggccgccgcc cccgcgcccg  120 cucgcuccu cccguccgcc cguccgcggc ccguccgucc                          160

<210> SEQ ID NO 335
<211> LENGTH: 25
<212> TYPE: RNA
<213> ORGANISM: Homo sapiens

<400> SEQUENCE: 335
gggaugccag gcaagugagc agguc                                          25

<210> SEQ ID NO 336
<211> LENGTH: 165
<212> TYPE: RNA
<213> ORGANISM: Homo sapiens

<400> SEQUENCE: 336
ggucaacaag gugagucugg augaggggca gggaugccag gcaagugagc aggucgggga    60
gucaggccuu gcucaggccc uguucuucuc ccuugcagcu ucugucuggc cccaaagaga   120
```

```
ccccugcugc ccagagcccc accagaggcc ccucugacac caaga          165

<210> SEQ ID NO 337
<211> LENGTH: 25
<212> TYPE: RNA
<213> ORGANISM: Homo sapiens

<400> SEQUENCE: 337
agggccguca ggacacggga ggguu                                25

<210> SEQ ID NO 338
<211> LENGTH: 165
<212> TYPE: RNA
<213> ORGANISM: Homo sapiens

<400> SEQUENCE: 338
cuguguugug uccugacacc uccaaguucu agggccguca ggacacggga ggguugggg   60 acagaguguc cuuccucugu ccucucaucc caguccugau ggccgcuugg ugagugucug  120
gugcccuggu ggccugcccc agcucucuuc uggcuuucug agcag                 165

<210> SEQ ID NO 339
<211> LENGTH: 21
<212> TYPE: RNA
<213> ORGANISM: Homo sapiens

<400> SEQUENCE: 339
gaaaagcugg guugagaggg u                                    21

<210> SEQ ID NO 340
<211> LENGTH: 160
<212> TYPE: RNA
<213> ORGANISM: Homo sapiens

<400> SEQUENCE: 340
uuacaauggu ucuaugagga cguggcccca caguaaguug aggagcacug gguauguaug   60
aauaaaaugg caugacaggc cuucucuuuc caguucuucc cagaauuggg aaaagcuggg  120
uugagagggu aagaaaagaa aaacaaauaa auuuuuaaa                        160

<210> SEQ ID NO 341
<211> LENGTH: 17
<212> TYPE: RNA
<213> ORGANISM: Homo sapiens

<400> SEQUENCE: 341
aacuagcuag ggguucg                                         17

<210> SEQ ID NO 342
<211> LENGTH: 157
<212> TYPE: RNA
<213> ORGANISM: Homo sapiens

<400> SEQUENCE: 342
gcgagacucu uuuuucucc aggaccugcg gagcagccag gcuucaugag uuaaaugcag    60
aucugaacca uacccaguug ggauuggggu acacacucua cuccucugaa aacuagcuag  120
ggguucgaac uggugagag ggagaguggg acagagc                           157

<210> SEQ ID NO 343
<211> LENGTH: 23
<212> TYPE: RNA
<213> ORGANISM: Homo sapiens
```

```
<400> SEQUENCE: 343
ggguuugggg gaugucagag ggc                                              23

<210> SEQ ID NO 344
<211> LENGTH: 163
<212> TYPE: RNA
<213> ORGANISM: Homo sapiens

<400> SEQUENCE: 344
aaguucugag aguccaggag gcagaggcug ggguuugggg gaugucagag ggcaaaucug      60
gggcuugggg ggcccaggaa gcagagauga agguuuuaga gucuccagag aacaaaucug    120
guacuuuuaa ggcccaggaa gcggaggcug gggucuuggg aaa                      163

<210> SEQ ID NO 345
<211> LENGTH: 22
<212> TYPE: RNA
<213> ORGANISM: Homo sapiens

<400> SEQUENCE: 345
ugaagggaga ugugaagaag cc                                              22

<210> SEQ ID NO 346
<211> LENGTH: 162
<212> TYPE: RNA
<213> ORGANISM: Homo sapiens

<400> SEQUENCE: 346
aauuugaaaa uccauauaaa gguacgucca cauuuauguu auuaugagug agucauauug      60
gugaagucag gacaauggcc ugucauuaga ucuuugauuc uuguuugcag ugaagggaga    120
ugugaagaag ccauguucuc ugaacgugcu gcuuggagga cu                       162

<210> SEQ ID NO 347
<211> LENGTH: 20
<212> TYPE: RNA
<213> ORGANISM: Homo sapiens

<400> SEQUENCE: 347 agaaaguccha aguguucagg                                                20

<210> SEQ ID NO 348
<211> LENGTH: 160
<212> TYPE: RNA
<213> ORGANISM: Homo sapiens

<400> SEQUENCE: 348
ucucuaauua gcuuucccag uauacuucuu agaaaguccha aguguucagg acuuuuauac     60
cuguuauacu uggcuuggu uuccaugauu cuuacuuuau uagccaguu uaucaccaau      120 aauacuugac ggaaggcuca guaauuaguu augaauaugg                          160

<210> SEQ ID NO 349
<211> LENGTH: 18
<212> TYPE: RNA
<213> ORGANISM: Homo sapiens

<400> SEQUENCE: 349
ugaacgggua uuuuacug                                                   18

<210> SEQ ID NO 350
<211> LENGTH: 158
```

```
<212> TYPE: RNA
<213> ORGANISM: Homo sapiens

<400> SEQUENCE: 350
uuuuuuuuuu aacaccuaua uaucacccau ugaacgggua uuuuacugaa cacaguacag      60
uagacuguuu aaaacucaca uccugguaac uuucacuacu ugaaauuaca aagugcuuuu    120
guuaauugca uauuuuugcu cagccaucuu agaauugu                            158

<210> SEQ ID NO 351
<211> LENGTH: 21
<212> TYPE: RNA
<213> ORGANISM: Homo sapiens

<400> SEQUENCE: 351
cugagacaug cacuucuggu u                                               21

<210> SEQ ID NO 352
<211> LENGTH: 161
<212> TYPE: RNA
<213> ORGANISM: Homo sapiens

<400> SEQUENCE: 352
aagcuggccc uggcuggaga uggcuagccc cugagacaug cacuucuggu uugaaauga      60 cucugucugu ggggcagcag aaacuagaga aggcaagugg cugccccacc ccaaggcgug    120
accaggagga acagccugca gcucacucca ugccacacgg g                        161

<210> SEQ ID NO 353
<211> LENGTH: 21
<212> TYPE: RNA
<213> ORGANISM: Homo sapiens

<400> SEQUENCE: 353
aauugaggau gugugagguu u                                               21

<210> SEQ ID NO 354
<211> LENGTH: 161
<212> TYPE: RNA
<213> ORGANISM: Homo sapiens

<400> SEQUENCE: 354 uuggugugu guauaagaau guuucuugcu aauugaggau gugugagguu uaaggcugug      60
agcugaucuu ugaaaaauag uuccuguuu cuaaagugac auuacccagu auuugcuuac    120
ugcuuugugc cuuaucuccc gcuuucuuuu uaguauuucu g                        161

<210> SEQ ID NO 355
<211> LENGTH: 24
<212> TYPE: RNA
<213> ORGANISM: Homo sapiens

<400> SEQUENCE: 355
aguuucuaug aguguauacc auuu                                            24

<210> SEQ ID NO 356
<211> LENGTH: 164
<212> TYPE: RNA
<213> ORGANISM: Homo sapiens

<400> SEQUENCE: 356
ucauucugag gucacauaac acauaaaauu aguuucuaug aguguauacc auuuaaagaa      60 uuuuuuuuc aguaaaaggg aauauuacaa uguuggagga gagauaaguu auagggagcu    120
```

```
ggauuucaaa acguggucca agauucaaaa auccuauuga uagu          164
```

<210> SEQ ID NO 357
<211> LENGTH: 25
<212> TYPE: RNA
<213> ORGANISM: Homo sapiens

<400> SEQUENCE: 357

```
agguggagau caagcccgag augau                                25
```

<210> SEQ ID NO 358
<211> LENGTH: 165
<212> TYPE: RNA
<213> ORGANISM: Homo sapiens

<400> SEQUENCE: 358

```
ugggcgucua caacggcaag accuucaacc agguggagau caagcccgag augaucgacc    60
acuaccuggg cgaguucucc aucaccuaca agcccauaaa gcacggcggg cccggcaucg   120
gggccagcca cuccucccgc uucaucccuc ucaagcagug gcuca                   165
```

<210> SEQ ID NO 359
<211> LENGTH: 21
<212> TYPE: RNA
<213> ORGANISM: Homo sapiens

<400> SEQUENCE: 359

```
gaagacagca auaaccacag u                                    21
```

<210> SEQ ID NO 360
<211> LENGTH: 161
<212> TYPE: RNA
<213> ORGANISM: Homo sapiens

<400> SEQUENCE: 360

```
guagcccaca uggauagcac aguugucaga caagauuccu ucagauuccg agugccuac     60
cgguuguuuu cguuguuguu guuguuguuu uucuuuuucu uuuuuuuuu gaagacagca    120
auaaccacag uacauauuac cuaguucuc uauaguuuua c                        161
```

<210> SEQ ID NO 361
<211> LENGTH: 24
<212> TYPE: RNA
<213> ORGANISM: Homo sapiens

<400> SEQUENCE: 361

```
guuucuguug agugugggguu uagu                                24
```

<210> SEQ ID NO 362
<211> LENGTH: 164
<212> TYPE: RNA
<213> ORGANISM: Homo sapiens

<400> SEQUENCE: 362

```
aguccgugcg agaauaauga uguaugcuuu guuucuguug agugugggu uaguaauggg     60
guuugugggg uuucuuucua agccuucucc uauuuauggg gguuuaguac ugauuguuag   120
cggugugguc gggguguuua uuauucgaa uuuugggga gguu                      164
```

<210> SEQ ID NO 363
<211> LENGTH: 21
<212> TYPE: RNA
<213> ORGANISM: Homo sapiens

```
<400> SEQUENCE: 363
aucgccgugg agugggagag c                                               21

<210> SEQ ID NO 364
<211> LENGTH: 161
<212> TYPE: RNA
<213> ORGANISM: Homo sapiens

<400> SEQUENCE: 364
ugccugguca aaggcuucua ccccagcgac aucgccgugg agugggagag cagcgggcag     60
ccggagaaca acuacaacac cacgccuccc augcuggacu ccgacggcuc cuucuuccuc    120
uacagcaagc ucaccgugga caagagcagg uggcagcagg g                        161

<210> SEQ ID NO 365
<211> LENGTH: 23
<212> TYPE: RNA
<213> ORGANISM: Homo sapiens

<400> SEQUENCE: 365
ggaugaagug cacugaggcu cuu                                             23

<210> SEQ ID NO 366
<211> LENGTH: 163
<212> TYPE: RNA
<213> ORGANISM: Homo sapiens

<400> SEQUENCE: 366
guaagauggu uaucgauagu aguuaaugau ggaugaagug cacugaggcu cuuaaaagau     60
acuuaggauu uuugacuuua cucguaggu ucuaaaguaa acauauga gguuuuaau        120 uucucagaua cuauaccugc agcucuuuuu gcugacucaa gau                      163

<210> SEQ ID NO 367
<211> LENGTH: 27
<212> TYPE: RNA
<213> ORGANISM: Homo sapiens

<400> SEQUENCE: 367
uccuguuggc cgaguggaga cuggugu                                         27

<210> SEQ ID NO 368
<211> LENGTH: 165
<212> TYPE: RNA
<213> ORGANISM: Homo sapiens

<400> SEQUENCE: 368
ucuacaaaau uggugguauu gguacuguuc cuguuggccg aguggagacu gguguucuca     60
aaccuggugu ggugucacc uuugcuccag ucaacauuac aacagaagua aaaucugucg    120
aaaugcacca ugaagcuuug agugaagcuc uuccugggga caaug                    165

<210> SEQ ID NO 369
<211> LENGTH: 24
<212> TYPE: RNA
<213> ORGANISM: Homo sapiens

<400> SEQUENCE: 369
guggagucug ucaucgaggu gcgu                                            24

<210> SEQ ID NO 370
<211> LENGTH: 164
```

```
<212> TYPE: RNA
<213> ORGANISM: Homo sapiens

<400> SEQUENCE: 370
gucacucagg acagacuucu ugaaguaggu ggcccuucaa cugagcugaa gggaagagaa      60
gggcauugca ggcugaggga ugaucccagg gugccccccca gaucuaaagu guggagucug   120
ucaucgaggu gcguagccuc uccagaggug ucacuguguu ccau                     164

<210> SEQ ID NO 371
<211> LENGTH: 24
<212> TYPE: RNA
<213> ORGANISM: Homo sapiens

<400> SEQUENCE: 371
uugcagcugc cugggaguga cuuc                                            24

<210> SEQ ID NO 372
<211> LENGTH: 164
<212> TYPE: RNA
<213> ORGANISM: Homo sapiens

<400> SEQUENCE: 372
cugcaaacag ccuuuccacu gacgcagugc cuuggggggcu cugccaagcg accccuagaa    60
uggggauugu gggggggucgc ucuaggcacc gcagcacugu gcggggaug uugcagcugc   120 cugggaguga cuucacacag uccucucugc cuccaggguc accc                     164

<210> SEQ ID NO 373
<211> LENGTH: 22
<212> TYPE: RNA
<213> ORGANISM: Homo sapiens

<400> SEQUENCE: 373
ugcagccagc gucccaugcu cg                                              22

<210> SEQ ID NO 374
<211> LENGTH: 162
<212> TYPE: RNA
<213> ORGANISM: Homo sapiens

<400> SEQUENCE: 374
guggauauga gugaagacgg ggcaggcagg ccacaucucu uagaagagga aggugauugc     60
cacgucuccu uccuccaugc ugauggcaag gcgugcgggc uguguucucu ugcagccagc   120
gucccaugcu cgguggcccc agaaaaguca guguguaggc cu                       162

<210> SEQ ID NO 375
<211> LENGTH: 17
<212> TYPE: RNA
<213> ORGANISM: Homo sapiens

<400> SEQUENCE: 375
aguuuugugu guuggcu                                                    17

<210> SEQ ID NO 376
<211> LENGTH: 157
<212> TYPE: RNA
<213> ORGANISM: Homo sapiens

<400> SEQUENCE: 376
aggaaacaca agaagaaacg ccuggugcag agccccaauu ccuacuucau ggaugugaaa     60
ugcccaagau gcuauaaaau caccacgguc uuuagccaug cacaaacggu aguuuugugu   120
```

```
guuggcugcu ccacuguccu cugccagccu auaggag                              157
```

<210> SEQ ID NO 377
<211> LENGTH: 22
<212> TYPE: RNA
<213> ORGANISM: Homo sapiens

<400> SEQUENCE: 377

```
acggccaagc agaaaauguu uu                                              22
```

<210> SEQ ID NO 378
<211> LENGTH: 162
<212> TYPE: RNA
<213> ORGANISM: Homo sapiens

<400> SEQUENCE: 378

```
cauagauaug uauucagcuu gucuucaaau acggccaagc agaaaauguu uauauuuua      60
uaaaucaucu uuugacucug uauuuaaauu cuaugauacu gaaaauaaag gcauucgga     120
aaaauacuga cugauuuugg ugcagaaguu uugaguauca ag                       162
```

<210> SEQ ID NO 379
<211> LENGTH: 24
<212> TYPE: RNA
<213> ORGANISM: Homo sapiens

<400> SEQUENCE: 379

```
gauuagggug cuuagcuguu aacu                                            24
```

<210> SEQ ID NO 380
<211> LENGTH: 164
<212> TYPE: RNA
<213> ORGANISM: Homo sapiens

<400> SEQUENCE: 380

```
ggcggcggga gaaguagauu gaagccaguu gauuagggug cuuagcuguu aacuaagugu     60
uuguggguuu aagucccauu ggucuaguaa gggcuuagcu uaauuaaagu ggcugauuug    120
cguucaguug augcagagug ggguuuugca guccuuagcu guug                     164
```

<210> SEQ ID NO 381
<211> LENGTH: 21
<212> TYPE: RNA
<213> ORGANISM: Homo sapiens

<400> SEQUENCE: 381

```
ccuucgaggc ggcugagacc c                                               21
```

<210> SEQ ID NO 382
<211> LENGTH: 161
<212> TYPE: RNA
<213> ORGANISM: Homo sapiens

<400> SEQUENCE: 382

```
cguucuccgc acuccugcuc cgcgagggcc ccuucgaggc ggcugagacc cgagugccgg     60
acucccgccg cuggagcggg gcucgggaau cggcagccgga aggagugug ccccggggc     120
gcuggggggc gccugaagguc ccgaggggag gcaagauggg a                       161
```

<210> SEQ ID NO 383
<211> LENGTH: 23
<212> TYPE: RNA
<213> ORGANISM: Homo sapiens

<400> SEQUENCE: 383
aggugguggc agcuggaggg acc                                              23

<210> SEQ ID NO 384
<211> LENGTH: 163
<212> TYPE: RNA
<213> ORGANISM: Homo sapiens

<400> SEQUENCE: 384
agccugugac cccucgggac ugccuggugc aggugguggc agcuggaggg acccaugcag      60
cacccagguc agagcagacc cuccccugcc ggccugcgcc agcuggaccu gauggccccc     120
uguggcgccu ugaccugcug ggccaggcug cccugggacu cuc                       163

<210> SEQ ID NO 385
<211> LENGTH: 23
<212> TYPE: RNA
<213> ORGANISM: Homo sapiens

<400> SEQUENCE: 385
agaagaagga cggcaagaag cgc                                              23

<210> SEQ ID NO 386
<211> LENGTH: 163
<212> TYPE: RNA
<213> ORGANISM: Homo sapiens

<400> SEQUENCE: 386
ggccccgcau ccgcguucgu cuaggcgcuc uugucaccuc gccaugccgg agccaucgcg      60 ggcgguccg gcuucuaaaa agggcuccaa gaaggccauu accaaggcgc agaagaagga     120
cggcaagaag cgcaagcgcg gccgcaagga gagcuauucu auc                       163

<210> SEQ ID NO 387
<211> LENGTH: 23
<212> TYPE: RNA
<213> ORGANISM: Homo sapiens

<400> SEQUENCE: 387
aaaagcaaau guugggugaa cgg                                              23

<210> SEQ ID NO 388
<211> LENGTH: 163
<212> TYPE: RNA
<213> ORGANISM: Homo sapiens

<400> SEQUENCE: 388
gaaacaucuu aaugcacagc cacaaguuac aaugcaacag ccugcugcuc auguacaagg      60
ucaggaaccu uugacugcuu ccauguuggu aucgcccau gcucaagagc aaaagcaaau     120
guugggugaa cggcuguuuc cucuuauuca agccaugcac cuu                       163

<210> SEQ ID NO 389
<211> LENGTH: 19
<212> TYPE: RNA
<213> ORGANISM: Homo sapiens

<400> SEQUENCE: 389
ggcggagggg ccgcgggcc                                                   19

<210> SEQ ID NO 390
<211> LENGTH: 159

```
<212> TYPE: RNA
<213> ORGANISM: Homo sapiens

<400> SEQUENCE: 390 cagagugggga ccggcagcuc ccagacuuga ggcggagggg ccgcgggccg gagcucccug      60
cagccgcuag ccugggaaga cuggagugcg cugcccaccg agggucugcg ccgcgccggc     120
cgccccgggc cgcuuugugc gcgcccgcgc ggucuguac                            159

<210> SEQ ID NO 391
<211> LENGTH: 19
<212> TYPE: RNA
<213> ORGANISM: Homo sapiens

<400> SEQUENCE: 391
uugcagcugc cugggagug                                                   19

<210> SEQ ID NO 392
<211> LENGTH: 159
<212> TYPE: RNA
<213> ORGANISM: Homo sapiens

<400> SEQUENCE: 392
cugcaaacag ccuuuccacu gacgcagugc cuuggggggcu cugccaagcg accccuagaa     60
uggggauugu gggggucgc ucuaggcacc gcagcacugu gcggggaug uugcagcugc       120 cugggaguga cuucacacag uccucucugc cuccagggu                            159

<210> SEQ ID NO 393
<211> LENGTH: 24
<212> TYPE: RNA
<213> ORGANISM: Homo sapiens

<400> SEQUENCE: 393
ucucuccagg ugacagaaag ggcu                                             24

<210> SEQ ID NO 394
<211> LENGTH: 164
<212> TYPE: RNA
<213> ORGANISM: Homo sapiens

<400> SEQUENCE: 394
acauaaaauc uuaucuaugu gcagcaugac ucucuccagg ugacagaaag ggcucuagac      60
agcugagagg accugaucau guagggaggg acggggaggg gagccaggac ccaggagcug     120
cauggcugua agaggaaggu ccuuggaggg uaucagcagu cuca                      164

<210> SEQ ID NO 395
<211> LENGTH: 21
<212> TYPE: RNA
<213> ORGANISM: Homo sapiens

<400> SEQUENCE: 395
cguucuugcu cugccucggu c                                                21

<210> SEQ ID NO 396
<211> LENGTH: 161
<212> TYPE: RNA
<213> ORGANISM: Homo sapiens

<400> SEQUENCE: 396
gggcagaagu cugagccagu guuucaucau cguucuugcu cugccucggu cuguacaucu      60
gugaaauggg acucccucuc uguugguggag gcccugggga cagcugggag gacuggaggg    120
```

-continued

```
gugguggga ggugugguc cuuauuagac auucagauac c            161
```

<210> SEQ ID NO 397
<211> LENGTH: 22
<212> TYPE: RNA
<213> ORGANISM: Homo sapiens

<400> SEQUENCE: 397

```
augccaagag ggccagguc uu                                22
```

<210> SEQ ID NO 398
<211> LENGTH: 162
<212> TYPE: RNA
<213> ORGANISM: Homo sapiens

<400> SEQUENCE: 398

```
aaacaauaaa aaacuggcug cuaucgaagc ccuaaaugau ggugaacucc agaaagccau    60
ugacuuauuc acagaugcca ucaagcugaa uccucacuug gcccuuugu augccaagag   120
ggccaguguc uucgucaaau uacagaagcc aaauacugcc au                     162
```

<210> SEQ ID NO 399
<211> LENGTH: 22
<212> TYPE: RNA
<213> ORGANISM: Homo sapiens

<400> SEQUENCE: 399

```
uuugugugu guguuuguuu uu                                22
```

<210> SEQ ID NO 400
<211> LENGTH: 162
<212> TYPE: RNA
<213> ORGANISM: Homo sapiens

<400> SEQUENCE: 400

```
cugguuauau caggauaaau ucauaaaggg uuugugugu guguuuguuu uguuguugu     60
uguuuagggu uuuuuuuuu uaaacagggu cuugcuuugu ugcccaggau gaaaugcaau   120
cacacacaau cauggcucau ugcaucacua ucuauguauu ca                     162
```

<210> SEQ ID NO 401
<211> LENGTH: 25
<212> TYPE: RNA
<213> ORGANISM: Homo sapiens

<400> SEQUENCE: 401

```
augaggaaca cugacuuuau uaagc                            25
```

<210> SEQ ID NO 402
<211> LENGTH: 165
<212> TYPE: RNA
<213> ORGANISM: Homo sapiens

<400> SEQUENCE: 402

```
ucaguuaagc caauacauuu aaaguuuugc augaggaaca cugacuuuau uaagcauuuu    60
cagaugugu gguuguauuu uugccccaag agguguuugg auaaccacac aaaagcauga   120
ugaaaaggcu ucuuguaguc ccauaauuuc uugugaacua auguu                  165
```

<210> SEQ ID NO 403
<211> LENGTH: 24
<212> TYPE: RNA
<213> ORGANISM: Homo sapiens

<400> SEQUENCE: 403
gggucggagu uagcucaagc gguu                                              24

<210> SEQ ID NO 404
<211> LENGTH: 164
<212> TYPE: RNA
<213> ORGANISM: Homo sapiens

<400> SEQUENCE: 404
uuuagaaguu ucagucgcac acuccacccc gggucggagu uagcucaagc gguuaccucc       60
ucaugccgga cuuucuaucu guccaucucu gugcuggggu ucgagacccg cgggugcuua      120
cugacccuuu uaugcaauaa auucgguaua aucgucacu cuga                        164

<210> SEQ ID NO 405
<211> LENGTH: 19
<212> TYPE: RNA
<213> ORGANISM: Homo sapiens

<400> SEQUENCE: 405
ggagguucag aguuggaag                                                    19

<210> SEQ ID NO 406
<211> LENGTH: 159
<212> TYPE: RNA
<213> ORGANISM: Homo sapiens

<400> SEQUENCE: 406
aguugcgaca agacagaguu ggagaauaga ggagguucag aguuggaaga aaugggagua       60
ggugauggca acaccgaguu gucagaguga gcugaggcaa cauccucuac uucuagcuca      120
cugaugaaaa uauccaggau agcgggucug gguccagu                              159

<210> SEQ ID NO 407
<211> LENGTH: 23
<212> TYPE: RNA
<213> ORGANISM: Homo sapiens

<400> SEQUENCE: 407
gagagucuca ggaaagaaag guc                                               23

<210> SEQ ID NO 408
<211> LENGTH: 163
<212> TYPE: RNA
<213> ORGANISM: Homo sapiens

<400> SEQUENCE: 408
auaaugagua aaauguuuca ucuuuaauaa agcaaaaaua gagcaaccca ccaaauaguu       60
aacacuugcc uggagagauu uaggaacacc aguauuccac ugagauugcu gagagucuca      120
ggaaagaaag gucuaacuua aauuguauuu uaccauuucu gag                        163

<210> SEQ ID NO 409
<211> LENGTH: 43
<212> TYPE: DNA
<213> ORGANISM: artificial
<220> FEATURE:
<223> OTHER INFORMATION: PCR PRIMER
<220> FEATURE:
<221> NAME/KEY: misc_feature
<222> LOCATION: (22)..(25)
<223> OTHER INFORMATION: n is a, c, g, or t

<400> SEQUENCE: 409

```
gcctccctcg cgccatcagc tnnnngacct tggctgtcac tca                    43
```

<210> SEQ ID NO 410
<211> LENGTH: 61
<212> TYPE: DNA
<213> ORGANISM: artificial
<220> FEATURE:
<223> OTHER INFORMATION: PCR PRIMER

<400> SEQUENCE: 410

```
gccttgccag cccgctcaga cgagacatcg ccccgctttt tttttttttt tttttttttt    60
t                                                                    61
```

<210> SEQ ID NO 411
<211> LENGTH: 21
<212> TYPE: RNA
<213> ORGANISM: Homo sapiens

<400> SEQUENCE: 411

```
acccgucccg uucguccccg g                                              21
```

<210> SEQ ID NO 412
<211> LENGTH: 96
<212> TYPE: RNA
<213> ORGANISM: Homo sapiens

<400> SEQUENCE: 412

```
ccggccgcug ggcgcacccg ucccguucgu ccccggacgu ugcucucuac cccgggaacg    60
ucgagacugg agcgcccgaa cugagccacc uucgcg                              96
```

<210> SEQ ID NO 413
<211> LENGTH: 19
<212> TYPE: RNA
<213> ORGANISM: Homo sapiens

<400> SEQUENCE: 413

```
accgggugcu guaggcuuu                                                 19
```

<210> SEQ ID NO 414
<211> LENGTH: 94
<212> TYPE: RNA
<213> ORGANISM: Homo sapiens

<400> SEQUENCE: 414

```
ucucggaagc uaagcagggu cgggccuggu uaguacuugg acgggagacc gccugggaau    60
accgggugcu guaggcuuuu ucuuuggcuu uuug                                94
```

<210> SEQ ID NO 415
<211> LENGTH: 94
<212> TYPE: RNA
<213> ORGANISM: Homo sapiens

<400> SEQUENCE: 415

```
ucuuggaagc uaagcagggu cgggccuggu uaguacuugg augggagacc accugggaau    60
accgggugcu guaggcuuug gccgggcgug gugg                                94
```

<210> SEQ ID NO 416
<211> LENGTH: 29
<212> TYPE: RNA
<213> ORGANISM: Homo sapiens

<400> SEQUENCE: 416

-continued

```
acgcggguga ugcgaacugg agucugagc                                      29

<210> SEQ ID NO 417
<211> LENGTH: 104
<212> TYPE: RNA
<213> ORGANISM: Homo sapiens

<400> SEQUENCE: 417
ggcguagggg ggccggccug cugugaugac auuccaauua aagcacgugu uagacugcug    60
acgcggguga ugcgaacugg agucugagcc ugcccgagcg gagc                    104

<210> SEQ ID NO 418
<211> LENGTH: 20
<212> TYPE: RNA
<213> ORGANISM: Homo sapiens

<400> SEQUENCE: 418
acucggcgug gcgucggucg                                                20

<210> SEQ ID NO 419
<211> LENGTH: 95
<212> TYPE: RNA
<213> ORGANISM: Homo sapiens

<400> SEQUENCE: 419
cacugucacu gccuaccaau cucgaccgga ccucgaccgg cucgucugug uugccaaucg    60
acucggcgug gcgucggucg ugguagauag gcggu                              95

<210> SEQ ID NO 420
<211> LENGTH: 21
<212> TYPE: RNA
<213> ORGANISM: Homo sapiens

<400> SEQUENCE: 420
acucggcgug gcgucggucg u                                              21

<210> SEQ ID NO 421
<211> LENGTH: 24
<212> TYPE: RNA
<213> ORGANISM: Homo sapiens

<400> SEQUENCE: 421
acucggcgug gcgucggucg uggu                                           24

<210> SEQ ID NO 422
<211> LENGTH: 21
<212> TYPE: RNA
<213> ORGANISM: Homo sapiens

<400> SEQUENCE: 422
agagcagugu guguugccug g                                              21

<210> SEQ ID NO 423
<211> LENGTH: 96
<212> TYPE: RNA
<213> ORGANISM: Homo sapiens

<400> SEQUENCE: 423
ugcugcaggu guuggagagc agugugeguu gccuggggac uguguggacu gguaucaccc    60
agacagcuug cacugacucc agacccugcc gucaug                             96
```

```
<210> SEQ ID NO 424
<211> LENGTH: 22
<212> TYPE: RNA
<213> ORGANISM: Homo sapiens

<400> SEQUENCE: 424
agaguugagu cuggacgucc cg                                              22

<210> SEQ ID NO 425
<211> LENGTH: 97
<212> TYPE: RNA
<213> ORGANISM: Homo sapiens

<400> SEQUENCE: 425
cgccccgggc cgcggcuccu gauuguccaa acgcaauucu cgagucuaug gcuccggccg    60
agaguugagu cuggacgucc cgagccgccg cccccaa                             97

<210> SEQ ID NO 426
<211> LENGTH: 19
<212> TYPE: RNA
<213> ORGANISM: Homo sapiens

<400> SEQUENCE: 426
aggacggugg ccauggaag                                                  19

<210> SEQ ID NO 427
<211> LENGTH: 94
<212> TYPE: RNA
<213> ORGANISM: Homo sapiens

<400> SEQUENCE: 427
aguaccaaga aguuaucauu uccauaugac ugucauugcu uaaaacuagc uaguaugagc    60
aggacggugg ccauggaagu cgaaauucgc uaag                                94

<210> SEQ ID NO 428
<211> LENGTH: 20
<212> TYPE: RNA
<213> ORGANISM: Homo sapiens

<400> SEQUENCE: 428
aggacggugg ccauggaagu                                                 20

<210> SEQ ID NO 429
<211> LENGTH: 21
<212> TYPE: RNA
<213> ORGANISM: Homo sapiens

<400> SEQUENCE: 429
aguuggugga gugauuuguc u                                               21

<210> SEQ ID NO 430
<211> LENGTH: 22
<212> TYPE: RNA
<213> ORGANISM: Homo sapiens

<400> SEQUENCE: 430
aguuggugga gugauuuguc ug                                              22

<210> SEQ ID NO 431
<211> LENGTH: 23
<212> TYPE: RNA
<213> ORGANISM: Homo sapiens

<400> SEQUENCE: 431
```

```
aguuggugga gugauuuguc ugg                                            23

<210> SEQ ID NO 432
<211> LENGTH: 24
<212> TYPE: RNA
<213> ORGANISM: Homo sapiens

<400> SEQUENCE: 432
aguuggugga gugauuuguc uggu                                           24

<210> SEQ ID NO 433
<211> LENGTH: 96
<212> TYPE: RNA
<213> ORGANISM: Homo sapiens

<400> SEQUENCE: 433
gggauugaca gauugacagc ucuuucucga uucuguggu ggugguagcau ggccauucuu    60 aguuggugga gugauuuguc ugguuaauuc ugauaa                              96

<210> SEQ ID NO 434
<211> LENGTH: 19
<212> TYPE: RNA
<213> ORGANISM: Homo sapiens

<400> SEQUENCE: 434
agaacgcggu cugaguggu                                                 19

<210> SEQ ID NO 435
<211> LENGTH: 94
<212> TYPE: RNA
<213> ORGANISM: Homo sapiens

<400> SEQUENCE: 435
ugcaacugcc gucagccauu gaugaucguu cuucucuccg uauuggggag ugagagggag    60
agaacgcggu cugagugguu uuccuucuu gaug                                 94

<210> SEQ ID NO 436
<211> LENGTH: 19
<212> TYPE: RNA
<213> ORGANISM: Homo sapiens

<400> SEQUENCE: 436
augaggaugg auagcaagg                                                 19

<210> SEQ ID NO 437
<211> LENGTH: 94
<212> TYPE: RNA
<213> ORGANISM: Homo sapiens

<400> SEQUENCE: 437
auacguguaa uugugaugag gauggauagc aaggaagccg cucccaccug acccucacgg    60
ccuccguguu accugccuc uagguggggac gcuc                                94

<210> SEQ ID NO 438
<211> LENGTH: 20
<212> TYPE: RNA
<213> ORGANISM: Homo sapiens

<400> SEQUENCE: 438
cggagcuggg gauugugggu                                                20
```

```
<210> SEQ ID NO 439
<211> LENGTH: 95
<212> TYPE: RNA
<213> ORGANISM: Homo sapiens

<400> SEQUENCE: 439
gggugugaga agccggaucc uguggugacc caguggccua auggauaagg caucagccuc    60
cggagcuggg gauugugggu ucgagcccca ucugg                               95

<210> SEQ ID NO 440
<211> LENGTH: 22
<212> TYPE: RNA
<213> ORGANISM: Homo sapiens

<400> SEQUENCE: 440
cggcggcucc agggaccugg cg                                             22

<210> SEQ ID NO 441
<211> LENGTH: 97
<212> TYPE: RNA
<213> ORGANISM: Homo sapiens

<400> SEQUENCE: 441
ccgggagcgg ggaggcggcg gcuccaggga ccuggcggcc gccgaucggg gcugcgaggc    60
cccauggcgc cgcccccagc cccgcuccug gcgccga                             97

<210> SEQ ID NO 442
<211> LENGTH: 20
<212> TYPE: RNA
<213> ORGANISM: Homo sapiens

<400> SEQUENCE: 442
cggcggggac ggcgauuggu                                                20

<210> SEQ ID NO 443
<211> LENGTH: 95
<212> TYPE: RNA
<213> ORGANISM: Homo sapiens

<400> SEQUENCE: 443
gggccgggaa ugccgcggcg gggacggcga uugguccgua uguguggugc caccggccgc    60
cggcuccgcc ccggccccg ccccacacgc cgcau                                95

<210> SEQ ID NO 444
<211> LENGTH: 29
<212> TYPE: RNA
<213> ORGANISM: Homo sapiens

<400> SEQUENCE: 444
cggggaucgc cgagggccgg ucggccgcc                                      29

<210> SEQ ID NO 445
<211> LENGTH: 104
<212> TYPE: RNA
<213> ORGANISM: Homo sapiens

<400> SEQUENCE: 445 ugguggggg agccgcgggg aucgccgagg gccggucggc cgccccgggu gccgcgcggu    60
gccgccggcg gcggugaggc cccgcgcgug uguccggcu gcgg                     104

<210> SEQ ID NO 446
<211> LENGTH: 104
```

```
<212> TYPE: RNA
<213> ORGANISM: Homo sapiens

<400> SEQUENCE: 446
ggggaggaga cgguuccggg ggaccggccg cgacugcggc ggcgguggug gggggagccg    60
cggggaucgc cgagggccgg ucggccgccc cgggugccgc gcgg                    104

<210> SEQ ID NO 447
<211> LENGTH: 23
<212> TYPE: RNA
<213> ORGANISM: Homo sapiens

<400> SEQUENCE: 447
cucggcgugg cgucggucgu ggu                                            23

<210> SEQ ID NO 448
<211> LENGTH: 98
<212> TYPE: RNA
<213> ORGANISM: Homo sapiens

<400> SEQUENCE: 448
acugucacug ccuaccaauc ucgaccggac cucgaccggc ucgucugugu ugccaaucga    60
cucggcgugg cgucggucgu gguagauagg cggucaug                            98

<210> SEQ ID NO 449
<211> LENGTH: 19
<212> TYPE: RNA
<213> ORGANISM: Homo sapiens

<400> SEQUENCE: 449
cugcccagug cucugaaug                                                 19

<210> SEQ ID NO 450
<211> LENGTH: 94
<212> TYPE: RNA
<213> ORGANISM: Homo sapiens

<400> SEQUENCE: 450
aaugcagugu gauuucugcc cagugcucug aaugucaaag ugaagaaauu cagagaagcc    60
uggguagccg ggcguggugg cucacaccug uaau                                94

<210> SEQ ID NO 451
<211> LENGTH: 27
<212> TYPE: RNA
<213> ORGANISM: Homo sapiens

<400> SEQUENCE: 451
cugcccagug cucugaaugu caaagug                                        27

<210> SEQ ID NO 452
<211> LENGTH: 24
<212> TYPE: RNA
<213> ORGANISM: Homo sapiens

<400> SEQUENCE: 452
cugcccuggc ccgagggacc gacu                                           24

<210> SEQ ID NO 453
<211> LENGTH: 99
<212> TYPE: RNA
<213> ORGANISM: Homo sapiens

<400> SEQUENCE: 453
```

```
augaauuguu ggguguuagcc cugcggcccc acgcaccagg guaagagaga cucucgcuuc    60
cugcccuggc ccgagggacc gacuggcugg gccugccuu                            99
```

<210> SEQ ID NO 454
<211> LENGTH: 18
<212> TYPE: RNA
<213> ORGANISM: Homo sapiens

<400> SEQUENCE: 454

```
cuggaggagc uggccugu                                                   18
```

<210> SEQ ID NO 455
<211> LENGTH: 93
<212> TYPE: RNA
<213> ORGANISM: Homo sapiens

<400> SEQUENCE: 455

```
cuucuccca gccagaggug gagccaagug guccagcguc acuccagugc ucagcugugg      60
cuggaggagc uggccugugg cacagcccug agu                                  93
```

<210> SEQ ID NO 456
<211> LENGTH: 21
<212> TYPE: RNA
<213> ORGANISM: Homo sapiens

<400> SEQUENCE: 456

```
cuuggcaccu agcaagcacu c                                               21
```

<210> SEQ ID NO 457
<211> LENGTH: 96
<212> TYPE: RNA
<213> ORGANISM: Homo sapiens

<400> SEQUENCE: 457

```
gcacccagau cagugcuugg caccuagcaa gcacucagua aauauuuguu gagugccugc     60
uaugugccag gcauugugcu gagggcuuug uggga                                96
```

<210> SEQ ID NO 458
<211> LENGTH: 21
<212> TYPE: RNA
<213> ORGANISM: Homo sapiens

<400> SEQUENCE: 458

```
gacuauagaa cuuuccccu c                                                21
```

<210> SEQ ID NO 459
<211> LENGTH: 96
<212> TYPE: RNA
<213> ORGANISM: Homo sapiens

<400> SEQUENCE: 459

```
aguugguaga gggcagaggg augaggggga aaguucuaua guccugagau cuaauuacag     60
gacuauagaa cuuuccccu caucccucua cccuua                                96
```

<210> SEQ ID NO 460
<211> LENGTH: 22
<212> TYPE: RNA
<213> ORGANISM: Homo sapiens

<400> SEQUENCE: 460

```
gagagcagug uguguugccu gg                                              22
```

<210> SEQ ID NO 461
<211> LENGTH: 97
<212> TYPE: RNA
<213> ORGANISM: Homo sapiens

<400> SEQUENCE: 461
gugcugcagg uguuggagag cagugugugu ugccugggga cuguguggac ugguaucacc    60
cagacagcuu gcacugacuc cagacccugc cgucaug                            97

<210> SEQ ID NO 462
<211> LENGTH: 17
<212> TYPE: RNA
<213> ORGANISM: Homo sapiens

<400> SEQUENCE: 462
gaggaaggug gggaugc                                                  17

<210> SEQ ID NO 463
<211> LENGTH: 92
<212> TYPE: RNA
<213> ORGANISM: Homo sapiens

<400> SEQUENCE: 463
gagggcggga gacaaaaucu cgcaauucug accugccuuu ggacauaauu gaggcuuuau    60
gaggaaggug gggaugcggg aguggcgauc cc                                 92

<210> SEQ ID NO 464
<211> LENGTH: 30
<212> TYPE: RNA
<213> ORGANISM: Homo sapiens

<400> SEQUENCE: 464
gagugagagg gagagaacgc ggucugagug                                    30

<210> SEQ ID NO 465
<211> LENGTH: 105
<212> TYPE: RNA
<213> ORGANISM: Homo sapiens

<400> SEQUENCE: 465
ggcguugcuu ggcugcaacu gccgucagcc auugaugauc guucuucucu ccguauuggg    60
gagugagagg gagagaacgc ggucugagug guuuuuccuu cuuga                  105

<210> SEQ ID NO 466
<211> LENGTH: 21
<212> TYPE: RNA
<213> ORGANISM: Homo sapiens

<400> SEQUENCE: 466
gaugccuggg aguugcgauc u                                             21

<210> SEQ ID NO 467
<211> LENGTH: 96
<212> TYPE: RNA
<213> ORGANISM: Homo sapiens

<400> SEQUENCE: 467
ugugagacga auuuugagc ggguaaaggu cgcccucaag gugacccgcc uacuuugcgg     60
gaugccuggg aguugcgauc ugcccgaccu uauuca                             96

-continued

```
<210> SEQ ID NO 468
<211> LENGTH: 23
<212> TYPE: RNA
<213> ORGANISM: Homo sapiens

<400> SEQUENCE: 468
gaugccuggg aguugcgauc ugc                                              23

<210> SEQ ID NO 469
<211> LENGTH: 18
<212> TYPE: RNA
<213> ORGANISM: Homo sapiens

<400> SEQUENCE: 469 gcauggugg uucagugg                                                     18

<210> SEQ ID NO 470
<211> LENGTH: 93
<212> TYPE: RNA
<213> ORGANISM: Homo sapiens

<400> SEQUENCE: 470
gugaacggcg gcuggugcg aguuccgcug ugccagcuuc cguuggcguu ugccaucggu       60 gcauggugg uucaguggua gaauucucgc cug                                    93

<210> SEQ ID NO 471
<211> LENGTH: 19
<212> TYPE: RNA
<213> ORGANISM: Homo sapiens

<400> SEQUENCE: 471 gcauggugg uucaguggu                                                    19

<210> SEQ ID NO 472
<211> LENGTH: 31
<212> TYPE: RNA
<213> ORGANISM: Homo sapiens

<400> SEQUENCE: 472 gcauggugg uucaguggua gaauucucgc c                                      31

<210> SEQ ID NO 473
<211> LENGTH: 19
<212> TYPE: RNA
<213> ORGANISM: Homo sapiens

<400> SEQUENCE: 473
gcauuggugg uucaguggu                                                   19

<210> SEQ ID NO 474
<211> LENGTH: 94
<212> TYPE: RNA
<213> ORGANISM: Homo sapiens

<400> SEQUENCE: 474
ccaucaccac ugugaaucag agcaacaaaa cagcuggagg cagaacagca cucagcugga      60
gcauuggugg uucaguggua gaauucucgc cugc                                  94

<210> SEQ ID NO 475
<211> LENGTH: 19
<212> TYPE: RNA
<213> ORGANISM: Homo sapiens

<400> SEQUENCE: 475
```

```
gcguuggugg uauaguggu                                              19

<210> SEQ ID NO 476
<211> LENGTH: 94
<212> TYPE: RNA
<213> ORGANISM: Homo sapiens

<400> SEQUENCE: 476
cgaggaagua gugaccugcc acuggccacc ugcggaacca gaguucccca cuggagggcc   60
gcguuggugg uauaguggug agcauagcug ccuu                              94

<210> SEQ ID NO 477
<211> LENGTH: 23
<212> TYPE: RNA
<213> ORGANISM: Homo sapiens

<400> SEQUENCE: 477
gcguuggugg uauaguggug agc                                          23

<210> SEQ ID NO 478
<211> LENGTH: 19
<212> TYPE: RNA
<213> ORGANISM: Homo sapiens

<400> SEQUENCE: 478
gcuguggcug ugacuggcg                                               19

<210> SEQ ID NO 479
<211> LENGTH: 94
<212> TYPE: RNA
<213> ORGANISM: Homo sapiens

<400> SEQUENCE: 479
ccgacccggg ccugggcugu ggcugugacu ggcgcugccg ugggcgccgc agcccucgcg   60
ggagccggac gcgguaaugc cccagcggcg cagc                              94

<210> SEQ ID NO 480
<211> LENGTH: 19
<212> TYPE: RNA
<213> ORGANISM: Homo sapiens

<400> SEQUENCE: 480
ggacgguggc cauggaagu                                               19

<210> SEQ ID NO 481
<211> LENGTH: 94
<212> TYPE: RNA
<213> ORGANISM: Homo sapiens

<400> SEQUENCE: 481
guaccaagaa guuaucauuu ccauaugacu gucauugcuu aaaacuagcu aguaugagca   60
ggacgguggc cauggaaguc gaaauucgcu aagg                              94

<210> SEQ ID NO 482
<211> LENGTH: 19
<212> TYPE: RNA
<213> ORGANISM: Homo sapiens

<400> SEQUENCE: 482
ggggauguag cucaguggu                                               19
```

```
<210> SEQ ID NO 483
<211> LENGTH: 94
<212> TYPE: RNA
<213> ORGANISM: Homo sapiens

<400> SEQUENCE: 483
cugcugagag uaggugggga uguagcucag ugguagagcg caugcuuugc auguaugagg    60
ccccggguuc gauccccggc aucuccagug uagu                               94

<210> SEQ ID NO 484
<211> LENGTH: 18
<212> TYPE: RNA
<213> ORGANISM: Homo sapiens

<400> SEQUENCE: 484
gguucccuca gaccuggu                                                 18

<210> SEQ ID NO 485
<211> LENGTH: 93
<212> TYPE: RNA
<213> ORGANISM: Homo sapiens

<400> SEQUENCE: 485
gccgacagcc agcuggaucu ccugucccga gcccugggua cuggggugc cccugaguug     60 gguucccuca gaccugguga ucgggcccug gag                                93

<210> SEQ ID NO 486
<211> LENGTH: 26
<212> TYPE: RNA
<213> ORGANISM: Homo sapiens

<400> SEQUENCE: 486
ggaaaguuug gcugcgcggg uucccc                                        26

<210> SEQ ID NO 487
<211> LENGTH: 101
<212> TYPE: RNA
<213> ORGANISM: Homo sapiens

<400> SEQUENCE: 487
cucccucucc uccccggggg uucggugcgc ggcggggcc ggaguucgcu gcaagucggc     60
ggaaaguuug gcugcgcggg uuccccgaa guucaggugc g                       101

<210> SEQ ID NO 488
<211> LENGTH: 25
<212> TYPE: RNA
<213> ORGANISM: Homo sapiens

<400> SEQUENCE: 488
ggaauaccgg gugcuguagg cuuuu                                         25

<210> SEQ ID NO 489
<211> LENGTH: 100
<212> TYPE: RNA
<213> ORGANISM: Homo sapiens

<400> SEQUENCE: 489
gucugaucuc agaagcuaag caaggucggg ucuaguuagu acuuggaugg gagacugccu    60
ggaauaccgg gugcuguagg cuuuuggccu aucguucccu                        100

<210> SEQ ID NO 490
<211> LENGTH: 23
```

<212> TYPE: RNA
<213> ORGANISM: Homo sapiens

<400> SEQUENCE: 490
gugaacgggc gccaucccga ggc                                          23

<210> SEQ ID NO 491
<211> LENGTH: 98
<212> TYPE: RNA
<213> ORGANISM: Homo sapiens

<400> SEQUENCE: 491
agagagcccc ggggugcaga uccuugggag cccuguuaga cucuggauuu uacacuugga   60
gugaacgggc gccaucccga ggcuuugcac aggggcaa                          98

<210> SEQ ID NO 492
<211> LENGTH: 24
<212> TYPE: RNA
<213> ORGANISM: Homo sapiens

<400> SEQUENCE: 492
gugaacgggc gccaucccga ggcu                                         24

<210> SEQ ID NO 493
<211> LENGTH: 25
<212> TYPE: RNA
<213> ORGANISM: Homo sapiens

<400> SEQUENCE: 493
gugaacgggc gccaucccga ggcuu                                        25

<210> SEQ ID NO 494
<211> LENGTH: 26
<212> TYPE: RNA
<213> ORGANISM: Homo sapiens

<400> SEQUENCE: 494
gugaacgggc gccaucccga ggcuuu                                       26

<210> SEQ ID NO 495
<211> LENGTH: 21
<212> TYPE: RNA
<213> ORGANISM: Homo sapiens

<400> SEQUENCE: 495
guugguggag cgauuugucu g                                            21

<210> SEQ ID NO 496
<211> LENGTH: 96
<212> TYPE: RNA
<213> ORGANISM: Homo sapiens

<400> SEQUENCE: 496
ggauugacag auugauagcu cuuucucgau uccgugggug guggugcaug gccguucuua   60
guugguggag cgauuugucu gguuaauucc gauaac                            96

<210> SEQ ID NO 497
<211> LENGTH: 22
<212> TYPE: RNA
<213> ORGANISM: Homo sapiens

<400> SEQUENCE: 497
guugguggag cgauuugucu gg                                           22

```
<210> SEQ ID NO 498
<211> LENGTH: 23
<212> TYPE: RNA
<213> ORGANISM: Homo sapiens

<400> SEQUENCE: 498
guugguggag cgauuugucu ggu                                          23

<210> SEQ ID NO 499
<211> LENGTH: 20
<212> TYPE: RNA
<213> ORGANISM: Homo sapiens

<400> SEQUENCE: 499
guugguggag ugauuugucu                                              20

<210> SEQ ID NO 500
<211> LENGTH: 95
<212> TYPE: RNA
<213> ORGANISM: Homo sapiens

<400> SEQUENCE: 500
ggauugacag auugacagcu cuuucucgau ucugugggug guggugcaug gccauucuua  60
guugguggag ugauuugucu gguuaauucu gauaa                             95

<210> SEQ ID NO 501
<211> LENGTH: 21
<212> TYPE: RNA
<213> ORGANISM: Homo sapiens

<400> SEQUENCE: 501
guugguggag ugauuugucu g                                            21

<210> SEQ ID NO 502
<211> LENGTH: 18
<212> TYPE: RNA
<213> ORGANISM: Homo sapiens

<400> SEQUENCE: 502
gaacgcgguc ugaguggu                                                18

<210> SEQ ID NO 503
<211> LENGTH: 93
<212> TYPE: RNA
<213> ORGANISM: Homo sapiens

<400> SEQUENCE: 503
gcaacugccg ucagccauug augaucguuc uucucuccgu auuggggagu gagagggaga  60
gaacgcgguc ugagugguuu uuccuucuug aug                               93

<210> SEQ ID NO 504
<211> LENGTH: 20
<212> TYPE: RNA
<213> ORGANISM: Homo sapiens

<400> SEQUENCE: 504
uaccgggugc uguaggcuuu                                              20

<210> SEQ ID NO 505
<211> LENGTH: 95
<212> TYPE: RNA
<213> ORGANISM: Homo sapiens
```

```
<400> SEQUENCE: 505
aucuuggaag cuaagcaggg ucgggccugg uuaguacuug gaugggagac caccugggaa    60
uaccgggugc uguaggcuuu ggccgggcgu ggugg                               95

<210> SEQ ID NO 506
<211> LENGTH: 95
<212> TYPE: RNA
<213> ORGANISM: Homo sapiens

<400> SEQUENCE: 506
aucucggaag cuaagcaggg ucgggccugg uuaguacuug gacgggagac cgccugggaa    60
uaccgggugc uguaggcuuu uucuuuggcu uuuug                               95

<210> SEQ ID NO 507
<211> LENGTH: 20
<212> TYPE: RNA
<213> ORGANISM: Homo sapiens

<400> SEQUENCE: 507
uccuguacug agcugccccg                                                20

<210> SEQ ID NO 508
<211> LENGTH: 95
<212> TYPE: RNA
<213> ORGANISM: Homo sapiens

<400> SEQUENCE: 508
auccucccug gggcauccug uacugagcug ccccgaggcc cuucaugcug cccagcucgg    60
ggcagcucag uacaggauac ucggguggg aguca                                95

<210> SEQ ID NO 509
<211> LENGTH: 21
<212> TYPE: RNA
<213> ORGANISM: Homo sapiens

<400> SEQUENCE: 509
ucgaggagcu cacagucuag u                                              21

<210> SEQ ID NO 510
<211> LENGTH: 96
<212> TYPE: RNA
<213> ORGANISM: Homo sapiens

<400> SEQUENCE: 510
acaucaagug acugcuuug gcugugggc uaccaagaug aagaaggaau gcuccugccc     60
ucgaggagcu cacagucuag ugggagggaa caaugc                              96

<210> SEQ ID NO 511
<211> LENGTH: 20
<212> TYPE: RNA
<213> ORGANISM: Homo sapiens

<400> SEQUENCE: 511
ucggacaccg gcgcgucucu                                                20

<210> SEQ ID NO 512
<211> LENGTH: 95
<212> TYPE: RNA
<213> ORGANISM: Homo sapiens

<400> SEQUENCE: 512
```

```
ggggcucgcg acccggccc agagggcggc ggug gcggca gcuacuuuc uggucagggc    60 ucggacaccg gcgcgucucu caagcucgcc ucuuc                              95

<210> SEQ ID NO 513
<211> LENGTH: 19
<212> TYPE: RNA
<213> ORGANISM: Homo sapiens

<400> SEQUENCE: 513
ucugcccagu gcucugaau                                                19

<210> SEQ ID NO 514
<211> LENGTH: 94
<212> TYPE: RNA
<213> ORGANISM: Homo sapiens

<400> SEQUENCE: 514
uaaugcagug ugauuucugc ccagugcucu gaaugucaaa gugaagaaau cagagaagc    60 cugguagcc gggcguggug gcucacaccu guaa                                94

<210> SEQ ID NO 515
<211> LENGTH: 21
<212> TYPE: RNA
<213> ORGANISM: Homo sapiens

<400> SEQUENCE: 515
ucugcaagug ucagaggcga g                                             21

<210> SEQ ID NO 516
<211> LENGTH: 96
<212> TYPE: RNA
<213> ORGANISM: Homo sapiens

<400> SEQUENCE: 516
guuccuugug uucuuccagu ccgcccucug ucaccuugca gacggcuuuc ucuccgaaug    60
ucugcaagug ucagaggcga ggaguggcag cugcau                             96

<210> SEQ ID NO 517
<211> LENGTH: 22
<212> TYPE: RNA
<213> ORGANISM: Homo sapiens

<400> SEQUENCE: 517
ucugcaagug ucagaggcga gg                                            22

<210> SEQ ID NO 518
<211> LENGTH: 22
<212> TYPE: RNA
<213> ORGANISM: Homo sapiens

<400> SEQUENCE: 518
ucuucucugu uuuggccaug ug                                            22

<210> SEQ ID NO 519
<211> LENGTH: 97
<212> TYPE: RNA
<213> ORGANISM: Homo sapiens

<400> SEQUENCE: 519
aacauuagga gaguaucuuc ucuguuuugg ccaugugugu acucacagcc ccucacacau    60
ggccgaaaca gagaaguuac uuuccuaaua uuugccu                            97
```

```
<210> SEQ ID NO 520
<211> LENGTH: 22
<212> TYPE: RNA
<213> ORGANISM: Homo sapiens

<400> SEQUENCE: 520
ugauauguuu gauauugggu ug                                              22

<210> SEQ ID NO 521
<211> LENGTH: 97
<212> TYPE: RNA
<213> ORGANISM: Homo sapiens

<400> SEQUENCE: 521
cugccugcuu cugugugaua uguuugauau ugggguuguuu aauuaggaac caacuaaaug    60
ucaaacauau ucuuacagca gcaggugauu cagcacc                             97

<210> SEQ ID NO 522
<211> LENGTH: 23
<212> TYPE: RNA
<213> ORGANISM: Homo sapiens

<400> SEQUENCE: 522
ugauugucca aacgcaauuc ucg                                             23

<210> SEQ ID NO 523
<211> LENGTH: 98
<212> TYPE: RNA
<213> ORGANISM: Homo sapiens

<400> SEQUENCE: 523
ccgggccgcg gcuccugauu guccaaacgc aauucucgag ucuauggcuc cggccgagag    60
uugagucugg acgucccgag ccgccgcccc caaaccuc                            98

<210> SEQ ID NO 524
<211> LENGTH: 22
<212> TYPE: RNA
<213> ORGANISM: Homo sapiens

<400> SEQUENCE: 524
ugcuggauca gguucgag uc                                                22

<210> SEQ ID NO 525
<211> LENGTH: 97
<212> TYPE: RNA
<213> ORGANISM: Homo sapiens

<400> SEQUENCE: 525
guugugcugu ccaggugcug gaucaguggu ucgagucuga gccuuuaaaa gccacucuag    60
ccacagaugc agugauugga gccaugacaa gucccca                             97

<210> SEQ ID NO 526
<211> LENGTH: 20
<212> TYPE: RNA
<213> ORGANISM: Homo sapiens

<400> SEQUENCE: 526
uuagggcccu ggcuccaucu                                                 20

<210> SEQ ID NO 527
<211> LENGTH: 95
```

```
<212> TYPE: RNA
<213> ORGANISM: Homo sapiens

<400> SEQUENCE: 527
accuaccuaa cugggguuagg gcccuggcuc caucuccuuu aggaaaaccu ucuguggga        60 gugggggcuuc gacccuaacc caggugggcu guaac                                  95

<210> SEQ ID NO 528
<211> LENGTH: 22
<212> TYPE: RNA
<213> ORGANISM: Homo sapiens

<400> SEQUENCE: 528
uucucuguuu uggccaugug ug                                                 22

<210> SEQ ID NO 529
<211> LENGTH: 97
<212> TYPE: RNA
<213> ORGANISM: Homo sapiens

<400> SEQUENCE: 529
cauuaggaga guaucuucuc uguuuuggcc augugguac ucacagcccc ucacacaugg          60
ccgaaacaga gaaguuacuu uccuaauauu ugccucc                                 97

<210> SEQ ID NO 530
<211> LENGTH: 17
<212> TYPE: RNA
<213> ORGANISM: Homo sapiens

<400> SEQUENCE: 530
uucugcccag ugcucug                                                       17

<210> SEQ ID NO 531
<211> LENGTH: 92
<212> TYPE: RNA
<213> ORGANISM: Homo sapiens

<400> SEQUENCE: 531
uaccucccag cuguguucug cccagugcuc ugcugacugg acgccucugu guccuuagac         60
caugugcagg gccugaugca ggaaagagcu ga                                      92

<210> SEQ ID NO 532
<211> LENGTH: 20
<212> TYPE: RNA
<213> ORGANISM: Homo sapiens

<400> SEQUENCE: 532
uucugcccag ugcucugaau                                                    20

<210> SEQ ID NO 533
<211> LENGTH: 95
<212> TYPE: RNA
<213> ORGANISM: Homo sapiens

<400> SEQUENCE: 533
uuaaugcagu gugauuucug cccagugcuc ugaaugucaa agugaagaaa uucagagaag         60
ccuggguagc cgggcguggu ggcucacacc uguaa                                   95

<210> SEQ ID NO 534
<211> LENGTH: 24
<212> TYPE: RNA
<213> ORGANISM: Homo sapiens
```

```
<400> SEQUENCE: 534
uugcagcugc cugggaguga cuuc                                              24

<210> SEQ ID NO 535
<211> LENGTH: 99
<212> TYPE: RNA
<213> ORGANISM: Homo sapiens

<400> SEQUENCE: 535
accccuagaa ugggauugu gggggucgc ucuaggcacc gcagcacugu gcuggggaug         60
uugcagcugc cugggaguga cuucacacag uccucucug                             99

<210> SEQ ID NO 536
<211> LENGTH: 21
<212> TYPE: RNA
<213> ORGANISM: Homo sapiens

<400> SEQUENCE: 536
uuggccaugg ggcugcgcgg g                                                 21

<210> SEQ ID NO 537
<211> LENGTH: 96
<212> TYPE: RNA
<213> ORGANISM: Homo sapiens

<400> SEQUENCE: 537
ucguccagcg agggcgcgcu ggcccugggc agcguguggc ugaaggucac cauguucucc       60
uuggccaugg ggcugcgcgg ggccagcagg uccacg                                 96

<210> SEQ ID NO 538
<211> LENGTH: 20
<212> TYPE: RNA
<213> ORGANISM: Homo sapiens

<400> SEQUENCE: 538
uuggggaaac ggccgcugag                                                   20

<210> SEQ ID NO 539
<211> LENGTH: 95
<212> TYPE: RNA
<213> ORGANISM: Homo sapiens

<400> SEQUENCE: 539
cagcuccgca ggguuuggg gaaacggccg cugagugagg cgucggcugu guuucucacc        60
gcggucuuuu ccucccacuc uuggcugguu ggacc                                  95

<210> SEQ ID NO 540
<211> LENGTH: 21
<212> TYPE: RNA
<213> ORGANISM: Homo sapiens

<400> SEQUENCE: 540
uuggggaaac ggccgcugag u                                                 21

<210> SEQ ID NO 541
<211> LENGTH: 19
<212> TYPE: RNA
<213> ORGANISM: Homo sapiens

<400> SEQUENCE: 541
uugguggagc gauuugucu                                                    19
```

<210> SEQ ID NO 542
<211> LENGTH: 94
<212> TYPE: RNA
<213> ORGANISM: Homo sapiens

<400> SEQUENCE: 542
gauugacaga uugauagcuc uuucucgauu ccgugggugg uggugcaugg ccguucuuag    60
uugguggagc gauuugucug guuaauuccg auaa                                94

<210> SEQ ID NO 543
<211> LENGTH: 20
<212> TYPE: RNA
<213> ORGANISM: Homo sapiens

<400> SEQUENCE: 543
uugguggagc gauuugucug                                                20

<210> SEQ ID NO 544
<211> LENGTH: 20
<212> TYPE: RNA
<213> ORGANISM: Homo sapiens

<400> SEQUENCE: 544
uuuccggcuc gcguggugu                                                 20

<210> SEQ ID NO 545
<211> LENGTH: 95
<212> TYPE: RNA
<213> ORGANISM: Homo sapiens

<400> SEQUENCE: 545
ccggcggggc gaagcccgcg gcugcuggac cacccggcc gggaauagug cuccugguug     60
uuuccggcuc gcguggugu gucggcggcg gggcc                                95

<210> SEQ ID NO 546
<211> LENGTH: 17
<212> TYPE: RNA
<213> ORGANISM: Homo sapiens

<400> SEQUENCE: 546
aaagcugggu gagaggg                                                   17

<210> SEQ ID NO 547
<211> LENGTH: 92
<212> TYPE: RNA
<213> ORGANISM: Homo sapiens

<400> SEQUENCE: 547
ccugagcaag gucacaaagc ugggugagag gggcugggau ucacauucaa gcacuguguu    60
ccuaggcccc uugaccccug gcaucugugg gg                                  92

<210> SEQ ID NO 548
<211> LENGTH: 17
<212> TYPE: RNA
<213> ORGANISM: Homo sapiens

<400> SEQUENCE: 548
aaagcugggu ugagagg                                                   17

<210> SEQ ID NO 549
<211> LENGTH: 18

```
<212> TYPE: RNA
<213> ORGANISM: Homo sapiens

<400> SEQUENCE: 549
aaagcugggu ugagaggg                                                  18

<210> SEQ ID NO 550
<211> LENGTH: 19
<212> TYPE: RNA
<213> ORGANISM: Homo sapiens

<400> SEQUENCE: 550
aaagcugggu ugagagggc                                                 19

<210> SEQ ID NO 551
<211> LENGTH: 92
<212> TYPE: RNA
<213> ORGANISM: Homo sapiens

<400> SEQUENCE: 551
cugaaauguc uucaaaugua ucaauaagcc uucucuuccc aguucuucuu ggagucagga    60
aaagcugggu ugagaggagc agaaaagaaa aa                                  92

<210> SEQ ID NO 552
<211> LENGTH: 92
<212> TYPE: RNA
<213> ORGANISM: Homo sapiens

<400> SEQUENCE: 552
guauguauga auaaaauggc augacaggcc uucucuuucc aguucuuccc agaauuggga    60
aaagcugggu ugagagggua agaaaagaaa aa                                  92

<210> SEQ ID NO 553
<211> LENGTH: 92
<212> TYPE: RNA
<213> ORGANISM: Homo sapiens

<400> SEQUENCE: 553
ucuucuaccu aagaauucug ucucuuaggc uuucucuucc cagauuuccc aaaguuggga    60
aaagcugggu ugagagggca aaaggaaaaa aa                                  92

<210> SEQ ID NO 554
<211> LENGTH: 92
<212> TYPE: RNA
<213> ORGANISM: Homo sapiens

<400> SEQUENCE: 554
gaaacuagug uuucaaaaau aaauuaaucc cucucuuucu aguucuuccu agagugagga    60
aaagcugggu ugagagggca aacaaauuaa cu                                  92

<210> SEQ ID NO 555
<211> LENGTH: 18
<212> TYPE: RNA
<213> ORGANISM: Homo sapiens

<400> SEQUENCE: 555
aaccuuggag agcugagc                                                  18

<210> SEQ ID NO 556
<211> LENGTH: 93
<212> TYPE: RNA
<213> ORGANISM: Homo sapiens
```

```
<400> SEQUENCE: 556
cgcggugggg aagccaaccu uggagagcug agcgugcgac cggcccggcg cggggucuc        60 cgggagcugg cgagucgcua gcaccgaguc aca                                   93

<210> SEQ ID NO 557
<211> LENGTH: 18
<212> TYPE: RNA
<213> ORGANISM: Homo sapiens

<400> SEQUENCE: 557
aagcuggguu gagagggc                                                    18

<210> SEQ ID NO 558
<211> LENGTH: 93
<212> TYPE: RNA
<213> ORGANISM: Homo sapiens

<400> SEQUENCE: 558
cuucuaccua agaauucugu cucuuaggcu uucucuuccc agauuuccca aaguugggaa      60
aagcuggguu gagagggcaa aaggaaaaaa aaa                                   93
```

HUMAN MICRORNAS ASSOCIATED WITH CANCER

CROSS REFERENCE TO RELATED APPLICATIONS

This application claims the benefit of the filing date of U.S. Provisional Patent Application No. 60/900,081, filed Feb. 7, 2007, and U.S. Provisional Patent Application No. 60/853,410, filed Oct. 20, 2006, each of which is hereby incorporated by reference.

The present invention provides compounds which comprise novel nucleobase sequences which correspond to previously unknown miRNA sequences associated with cancer. The compounds may be used in therapeutics or diagnostics. The invention provides methods for treatment of cancer, and methods for the detection and analysis of non-coding RNAs associated with cancer, such as breast cancer. The invention furthermore relates to collections of oligonucleotide probes for detection and analysis of non-coding RNAs associated with cancer, such as breast cancer.

BACKGROUND OF THE INVENTION

The present invention relates to the detection and analysis of target nucleotide sequences associated with cancer. The invention provides novel microRNAs, oligonucleotide probes which can detect the novel microRNAs, and methods employing the use of oligonucleotide probes that are useful for detecting and analysing target nucleotide sequences associated with cancer.

MicroRNAs (miRNAs) have rapidly emerged as an important class of short endogenous RNAs that act as post-transcriptional regulators of gene expression by base-pairing with their target mRNAs. The 19-25 nucleotide (nt) mature miRNAs are processed sequentially from longer hairpin transcripts by the RNAse III ribonucleases Drosha (Lee, Y., et al., 2003. Nature 425: 415-419.) and Dicer (Hutvagner, G., et al., 2001. Science 293: 834-838, Ketting, R. F., et al., 2001. Genes Dev. 15: 2654-2659.). To date more than 3400 microRNAs have been annotated in vertebrates, invertebrates and plants according to the miRBase database release 7.1 in October 2005 (Griffiths-Jones, S. 2004. NAR 32 (Database issue), D109-D111), and many miRNAs that correspond to putative genes have also been identified. Some miRNAs have multiple loci in the genome (Reinhart, B. J., et al., 2002. Genes Dev. 16, 1616-1626.) and occasionally, several miRNA genes are arranged in tandem clusters (Lagos-Quintana, M., et al., 2001. Science 294: 853-858.). Recent bioinformatic predictions combined with array analyses, small RNA cloning and Northern blot validation indicate that the total number of miRNAs in vertebrate genomes is significantly higher than previously estimated and maybe as many as 1000 (Bentwich, I., et al., 2005. Nat. Genet. 37: 766-770, Berezikov, E., et al., 2005. Cell 120: 21-24, Xie, X., Lu, J., et al., 2005. Nature 434: 338-345.).

In a series of publications during recent years, it has become clear that microRNAs are extensively involved in cancer pathogenesis, and microRNA has been shown to be differentially expressed in a number of cancers (Breast cancer: Iorio et al Cancer Res 2005; 65: 7065. Lung cancer: Yanaihara et al Cell Science 2006; 9: 189-198. Chronic lymphocytic leukaemia (CLL): Galin et al PNAS, 2004 101(32): 11755-11760. Colon cancer: Cummins et al PNAS 2006, 103 (10):3687-3692. Prostate cancer: Volinia et al PNAS 2006; 103: 2257). In fact, in a landmark paper Lu et al (Nature 2005; 435:834-838) demonstrated that differential expression of microRNA in multiple cancers types, and that signatures based on approximately 200 microRNAs improve classification of poorly differentiated cancers over mRNA profiles.

Furthermore, the expected complexity of the "microRNA'nome" is far smaller than the human transcriptome with the total number of microRNAs being approximately limited to between 800 to 1000. Therefore, a microRNA cancer signature can be predicted to include from 5-20 microRNAs, suggesting that microRNA based theranostics will be of limited complexity and far more robust than mRNA profiles.

Taken together microRNA constitutes a new class of non-coding RNAs that plays a significant role in determining gene expression, microRNAs are differentially expressed in human cancers and a series of recent publication show that microRNA classify human cancers; in some cases improvement over mRNA classification is observed.

The present invention allows for the determination of microRNA signatures that improve the classification of early diagnosed cancers. The microRNA signatures—following from the role of microRNAs in cancer—reveal the true cancerous potential of the tumor, and enable physicians to select the appropriate treatment. microRNA based cancer classification may significantly benefit patient care, because recurrence rate may be improved due to adequate treatment of traditionally classified low risk patients, and suitable therapy, such as adjuvant chemotherapy for breast cancer may be deselected for the large group of patients that do not benefit from it.

PCT/DK2005/000838, and U.S. application Ser. No. 11/324,177, both hereby incorporated by reference, discloses methods for the detection of microRNAs (miRNAs) using oligonucleotides which comprise nucleotide analogues, such as locked nucleic acids (LNAs).

WO2005/098029, hereby incorporated by reference, discloses a method using oligonucleotides for the detection, quantification, monitoring of expression of siRNA and/or miRNA. It is suggested that the method can be used for determining the differences between nucleic acid samples from e.g. a cancer patient.

The Sanger Institute publishes known miRNA sequences in the miRBase database (http://microrna.sanger.ac.uk/seauences/index.shtml). To date there are 533 human siRNAs present in the miRBase database.

WO2006/015312 discloses sets of genetic markers which can be correlated with a prognosis of breast cancer.

Iorio et al, (Cancer Res 2005; 65 (16), pp 7065-7070) discloses miRNAs whose expression profile is altered between breast cancer tumors and non tumor cells.

SUMMARY OF THE INVENTION

The invention provides a compound which comprises a contiguous sequence of nucleobases of between 8 and 30 nucleobases in length, wherein the nucleobase sequence of the contiguous sequence corresponds to a contiguous nucleic acid or nucleobase sequence present in a nucleobase sequence selected from the group consisting of: SEQ ID No 1 and/or 2; SEQ ID No 3 and/or 4; SEQ ID No 5 and/or 6; SEQ ID No 7 and/or 8; SEQ ID No 9 and/or 10; SEQ ID No 11 and/or 12; SEQ ID No 13 and/or 14; SEQ ID No 15 and/or 16; SEQ ID No 17 and/or 18; SEQ ID No 19 and/or 20; SEQ ID No 21 and/or 22; SEQ ID No 23 and/or 24; SEQ ID No 25 and/or 26; SEQ ID No 27 and/or 28; SEQ ID No 29 and/or 30; SEQ ID No 31 and/or 32; SEQ ID No 33 and/or 34; SEQ ID No 35 and/or 36; SEQ ID No 37 and/or 38; SEQ ID No 39 and/or 40; SEQ ID No 41 and/or 42; SEQ ID No 43 and/or 44;

SEQ ID No 45 and/or 46; SEQ ID No 47 and/or 48; SEQ ID No 49 and/or 50; SEQ ID No 51 and/or 52; SEQ ID No 53 and/or 54; SEQ ID No 55 and/or 56; SEQ ID No 57 and/or 58; SEQ ID No 59 and/or 60; SEQ ID No 61 and/or 62; SEQ ID No 63 and/or 64; SEQ ID No 65 and/or 66; SEQ ID No 67 and/or 68; SEQ ID No 69 and/or 70; SEQ ID No 71 and/or 72; SEQ ID No 73 and/or 74; SEQ ID No 75 and/or 76; SEQ ID No 77 and/or 78; SEQ ID No 79 and/or 80; SEQ ID No 81 and/or 82; SEQ ID No 83 and/or 84; SEQ ID No 85 and/or 86; SEQ ID No 87 and/or 88; SEQ ID No 89 and/or 90; SEQ ID No 91 and/or 92; SEQ ID No 93 and/or 94; SEQ ID No 95 and/or 96; SEQ ID No 97 and/or 98; SEQ ID No 99 and/or 100; SEQ ID No 101 and/or 102; SEQ ID No 103 and/or 104; SEQ ID No 105 and/or 106; SEQ ID No 107 and/or 108; SEQ ID No 109 and/or 110; SEQ ID No 111 and/or 112; SEQ ID No 113 and/or 114; SEQ ID No 115 and/or 116; SEQ ID No 117 and/or 118; SEQ ID No 119 and/or 120; SEQ ID No 121 and/or 122; SEQ ID No 123 and/or 124; SEQ ID No 125 and/or 126; SEQ ID No 127 and/or 128; SEQ ID No 129 and/or 130; SEQ ID No 131 and/or 132; SEQ ID No 133 and/or 134; SEQ ID No 135 and/or 136; SEQ ID No 137 and/or 138; SEQ ID No 139 and/or 140; SEQ ID No 141 and/or 142; SEQ ID No 143 and/or 144; SEQ ID No 145 and/or 146; SEQ ID No 147 and/or 148; SEQ ID No 149 and/or 150; SEQ ID No 151 and/or 152; SEQ ID No 153 and/or 154; SEQ ID No 155 and/or 156; SEQ ID No 157 and/or 158; SEQ ID No 159 and/or 160; SEQ ID No 161 and/or 162; SEQ ID No 163 and/or 164; SEQ ID No 165 and/or 166; SEQ ID No 167 and/or 168; SEQ ID No 169 and/or 170; SEQ ID No 171 and/or 172; SEQ ID No 173 and/or 174; SEQ ID No 175 and/or 176; SEQ ID No 177 and/or 178; SEQ ID No 179 and/or 180; SEQ ID No 181 and/or 182; SEQ ID No 183 and/or 184; SEQ ID No 185 and/or 186; SEQ ID No 187 and/or 188; SEQ ID No 189 and/or 190; SEQ ID No 191 and/or 192; SEQ ID No 193 and/or 194; SEQ ID No 195 and/or 196; SEQ ID No 197 and/or 198; SEQ ID No 199 and/or 200; SEQ ID No 201 and/or 202; SEQ ID No 203 and/or 204; SEQ ID No 205 and/or 206; SEQ ID No 207 and/or 208; SEQ ID No 209 and/or 210; SEQ ID No 211 and/or 212; SEQ ID No 213 and/or 214; SEQ ID No 215 and/or 216; SEQ ID No 217 and/or 218; SEQ ID No 219 and/or 220; SEQ ID No 221 and/or 222; SEQ ID No 223 and/or 224; SEQ ID No 225 and/or 226; SEQ ID No 227 and/or 228; SEQ ID No 229 and/or 230; SEQ ID No 231 and/or 232; SEQ ID No 233 and/or 234; SEQ ID No 235 and/or 236; SEQ ID No 237 and/or 238; SEQ ID No 239 and/or 240; SEQ ID No 241 and/or 242; SEQ ID No 243 and/or 244; SEQ ID No 245 and/or 246; SEQ ID No 247 and/or 248; SEQ ID No 249 and/or 250; SEQ ID No 251 and/or 252; SEQ ID No 253 and/or 254; SEQ ID No 255 and/or 256; SEQ ID No 257 and/or 258; SEQ ID No 259 and/or 260; SEQ ID No 261 and/or 262; SEQ ID No 263 and/or 264; SEQ ID No 265 and/or 266; SEQ ID No 267 and/or 268; SEQ ID No 269 and/or 270; SEQ ID No 271 and/or 272; SEQ ID No 273 and/or 274; SEQ ID No 275 and/or 276; SEQ ID No 277 and/or 278; SEQ ID No 279 and/or 280; SEQ ID No 281 and/or 282; SEQ ID No 283 and/or 284; SEQ ID No 285 and/or 286; SEQ ID No 287 and/or 288; SEQ ID No 289 and/or 290; SEQ ID No 291 and/or 292; SEQ ID No 293 and/or 294; SEQ ID No 295 and/or 296; SEQ ID No 297 and/or 298; SEQ ID No 299 and/or 300; SEQ ID No 301 and/or 302; SEQ ID No 303 and/or 304; SEQ ID No 305 and/or 306; SEQ ID No 307 and/or 308; SEQ ID No 309 and/or 310; SEQ ID No 311 and/or 312; SEQ ID No 313 and/or 314; SEQ ID No 315 and/or 316; SEQ ID No 317 and/or 318; SEQ ID No 319 and/or 320; SEQ ID No 321 and/or 322; SEQ ID No 323 and/or 324; SEQ ID No 325 and/or 326; SEQ ID No 327 and/or 328; SEQ ID No 329 and/or 330; SEQ ID No 331 and/or 332; SEQ ID No 333 and/or 334; SEQ ID No 335 and/or 336; SEQ ID No 337 and/or 338; SEQ ID No 339 and/or 340; SEQ ID No 341 and/or 342; SEQ ID No 343 and/or 344; SEQ ID No 345 and/or 346; SEQ ID No 347 and/or 348; SEQ ID No 349 and/or 350; SEQ ID No 351 and/or 352; SEQ ID No 353 and/or 354; SEQ ID No 355 and/or 356; SEQ ID No 357 and/or 358; SEQ ID No 359 and/or 360; SEQ ID No 361 and/or 362; SEQ ID No 363 and/or 364; SEQ ID No 365 and/or 366; SEQ ID No 367 and/or 368; SEQ ID No 369 and/or 370; SEQ ID No 371 and/or 372; SEQ ID No 373 and/or 374; SEQ ID No 375 and/or 376; SEQ ID No 377 and/or 378; SEQ ID No 379 and/or 380; SEQ ID No 381 and/or 382; SEQ ID No 383 and/or 384; SEQ ID No 385 and/or 386; SEQ ID No 387 and/or 388; SEQ ID No 389 and/or 390; SEQ ID No 391 and/or 392; SEQ ID No 393 and/or 394; SEQ ID No 395 and/or 396; SEQ ID No 397 and/or 398; SEQ ID No 399 and/or 400; SEQ ID No 401 and/or 402; SEQ ID No 403 and/or 404; SEQ ID No 405 and/or 406 and SEQ ID No 407 and/or 408, SEQ ID NOs 411 and/or 412; SEQ ID NOs 413; 414 and/or 415; SEQ ID NOs 416 and/or 417; SEQ ID NOs 418; 420; 421 and/or 419; SEQ ID NOs 422 and/or 423; SEQ ID NOS 424 and/or 425; SEQ ID NOS 426; 428 and/or 427; SEQ ID NOS 429; 430; 431; 432 and/or 433; SEQ ID NOS 434 and/or 435; SEQ ID NOS 436 and/or 437; SEQ ID NOS 438 and/or 439; SEQ ID NOS 440 and/or 441, SEQ ID NOS 442 and/or 443, SEQ ID NOS 444, 445 and/or 446, SEQ ID NOS 447 and/or 448, SEQ ID NOS 449, 451 and/or 450, SEQ ID NOS 452 and/or 453, SEQ ID NOS 454 and/or 455, SEQ ID NOS 456 and/or 457, SEQ ID NOS 458 and/or 459, SEQ ID NOS 460 and/or 461, SEQ ID NOS 462 and/or 463, SEQ ID NOS 464 and/or 465, SEQ ID NOS 466, 468 and/or 467, SEQ ID NOS 469, 471, 472 and/or 470, SEQ ID NOS 473 and/or 474, SEQ ID NOS 475, 477 and/or 476, SEQ ID NOS 478 and/or 479, SEQ ID NOS 480 and/or 481, SEQ ID NOS 482 and/or 483, SEQ ID NOS 484 and/or 485, SEQ ID NOS 486 and/or 487, SEQ ID NOS 488 and/or 489, SEQ ID NOS 490, 492, 493 494, and/or 491, SEQ ID NOS 495, 497, 498, 499, 501, 496 and/or 500; SEQ ID NOS 502 and/or 503; SEQ ID NOS 504; 505 and/or 506; SEQ ID NOS 507 and/or 508; SEQ ID NOS 509 and/or 510; SEQ ID NOS 511 and/or 512; SEQ ID NOS 513 and/or 514; SEQ ID NOS 515, 517; and/or 516; SEQ ID NOS 518 and/or 519; SEQ ID NOS 520 and/or 521; SEQ ID NOS 522 and/or 523; SEQ ID NOS 524 and/or 525; SEQ ID NOS 526 and/or 527; SEQ ID NOS 528 and/or 529; SEQ ID NOS 530 and/or 531; SEQ ID NOS 532 and/or 533; SEQ ID NOS 534 and/or 535; SEQ ID NOS 536 and/or 537; SEQ ID NOS 538; 540 and/or 539; SEQ ID NOS 541; 543 and/or 542; SEQ ID NOS 544 and/or 545; SEQ ID NOS 546 and/or 547; SEQ ID NOS 548; 551; 552; 553; and/or 554; SEQ ID NOS 549; 552; 553 and/or 554; SEQ ID NOS 550; 553 and/or 554; SEQ ID NOS 555 and/or 556; SEQ ID NOS 557 and/or 558; and allelic variants thereof.

The above sequences and their naturally occurring allelic variants are referred to as 'target nucleotide(s)' or 'target sequence(s)' herein. Preferred groups of target sequences are according to the preferred groups or individual nucleobase sequences referred to herein.

The invention also provides for new molecular markers for cancer, and the use of such markers in the methods according to the invention, and for use in the collection of probes and/or kits according to the invention.

The invention also provides detection probes which comprise a continuous sequence of nucleobases according to the compound of the invention. In this respect, in the above list of sequences, from SEQ ID 1 to SEQ ID 408, the list is prepared to highlight pairs of sequences, the first being an odd number (e.g. SEQ ID NO 1), and the second being an even number (e.g. SEQ ID NO 2)—written as 'SEQ ID NO 1 and/or 2', in the above list. The odd number sequence in each pair corresponds to the mature miRNA sequence, whereas the even number corresponds to the pre-mature pre-miRNA sequence. This pairing of SEQ IDs is particularly important when considered the case where the compound of the invention is in the form of a detection probe, where pairs of detection probes (detection probe pairs) may be used to determine the level of a specific miRNA sequence present in the sample, compared to the level of the precursor form of that miRNA. This may provide useful diagnostic information, for example in cancer derived samples.

However, for SEQ ID NOs 411-558 the miRNAs and their corresponding pre-miRNAs, in addition to related miRNA (and/or related pre-miRNAs) are shown in Table 3. It will be noted that for some miRNAs there are more than one possible pre-miRNA precursor, and in some cases, some pre-miRNAs may result in more than one mature miRNA. Suitably the detection probe pairs may be selected from one (or more) miRNA and one (or more) of the corresponding pre-miRNAs.

DESCRIPTION OF INVENTION

Definitions

For the purposes of the subsequent detailed description of the invention the following definitions are provided for specific terms, which are used in the disclosure of the present invention:

In the present context "ligand" means something, which binds. Ligands may comprise biotin and functional groups such as: aromatic groups (such as benzene, pyridine, naphtalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, $C_1$-$C_{20}$ alkyl groups optionally interrupted or terminated with one or more heteroatoms such as oxygen atoms, nitrogen atoms, and/or sulphur atoms, optionally containing aromatic or mono/polyunsaturated hydrocarbons, polyoxyethylene such as polyethylene glycol, oligo/polyamides such as poly-β-alanine, polyglycine, polylysine, peptides, oligo/polysaccharides, oligo/polyphosphates, toxins, antibiotics, cell poisons, and steroids, and also "affinity ligands", i.e. functional groups or biomolecules that have a specific affinity for sites on particular proteins, antibodies, poly- and oligosaccharides, and other biomolecules.

The singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

"Transcriptome" refers to the complete collection of transcriptional units of the genome of any species. In addition to protein-coding mRNAs, it also represents non-coding RNAs, such as small nucleolar RNAs, siRNAs, microRNAs and antisense RNAs, which comprise important structural and regulatory roles in the cell.

A "multi-probe library" or "library of multi-probes" comprises a plurality of multi-probes, such that the sum of the probes in the library are able to recognise a major proportion of a transcriptome, including the most abundant sequences, such that about 60%, about 70%, about 80%, about 85%, more preferably about 90%, and still more preferably 95%, of the target nucleic acids in the transcriptome, are detected by the probes.

"Sample" refers to a sample of cells, or tissue or fluid isolated from an organism or organisms, including but not limited to, for example, skin, plasma, serum, spinal fluid, lymph fluid, synovial fluid, urine, tears, blood cells, organs, tumors, and also to samples of in vitro cell culture constituents (including but not limited to conditioned medium resulting from the growth of cells in cell culture medium, recombinant cells and cell components).

The terms "Detection probes" or "detection probe" or "detection probe sequence" refer to an oligonucleotide or oligonucleotide analogue, which oligonucleotide or oligonucleotide analogue comprises a recognition sequence complementary to a nucleotide target, such as an RNA (or DNA) target sequence. It is preferable that the detection probe(s) are oligonucleotides, preferably where said recognition sequence is substituted with high-affinity nucleotide analogues, e.g. LNA, to increase the sensitivity and specificity of conventional oligonucleotides, such as DNA oligonucleotides, for hybridization to short target sequences, e.g. mature miRNAs, stem-loop precursor miRNAs, pri-miRNAs, siRNAs or other non-coding RNAs as well as miRNA binding sites in their cognate mRNA targets, mRNAs, mRNA splice variants, RNA-edited mRNAs, antisense RNAs and small nucleolar RNAs (snRNA).

The terms "miRNA" and "microRNA" refer to about 18-25 nt non-coding RNAs derived from endogenous genes. They are processed from longer (ca 75 nt) hairpin-like precursors termed pre-miRNAs. MicroRNAs assemble in complexes termed miRNPs and recognize their targets by antisense complementarity. If the microRNAs match 100% their target, i.e. the complementarity is complete, the target mRNA is cleaved, and the miRNA acts like a siRNA. If the match is incomplete, i.e. the complementarity is partial, then the translation of the target mRNA is blocked.

The terms "Small interfering RNAs" or "siRNAs" refer to 21-25 nt RNAs derived from processing of linear double-stranded RNA. siRNAs assemble in complexes termed RISC (RNA-induced silencing complex) and target homologous RNA sequences for endonucleolytic cleavage. Synthetic siRNAs also recruit RISCs and are capable of cleaving homologous RNA sequences The term "RNA interference" (RNAi) refers to a phenomenon where double-stranded RNA homologous to a target mRNA leads to degradation of the targeted mRNA. More broadly defined as degradation of target mRNAs by homologous siRNAs.

The terms "microRNA precursor" or "miRNA precursor" or "pre-miRNA" or "premature miRNA" refer to polynucleotide sequences (approximately 70 nucleotides in length) that form hairpin-like structures having a loop region and a stem region. The stem region includes a duplex cre-ated by the pairing of opposite ends of the pre-miRNA polynucleotide sequence. The loop region connects the two halves of the stem region. The pre-miRNAs are transcribed as mono- or polycistronic, long, primary precursor transcripts (pri-miRNAs) that are then cleaved into individual pre-miRNAs by a nuclear RNAse III-like enzyme. Subsequently pre-miRNA hairpins are exported to the cytoplasm where they are processed by a second RNAse III-like enzyme into miRNAs. The target nucleic acid may be present in a premature miRNA sequence.

The fragments from the opposing arm, called the miRNA* (or "miRNA-star") sequences (Lau et al, Science (2001) 294: 858-862) are found in libraries of cloned miRNAs but typically at much lower frequency than are the miRNAs. For example, in an effort that identified over 3400 clones representing 80 *C. elegans* miRNAs, only 38 clones representing 14 miRNAs* were found. This approximately 100-fold difference in cloning frequency indicates that the miRNA: miRNA* duplex is generally short lived compared to the miRNA single strand (Bartel et al, Cell (2004) 116:281-297). The target nucleic acid may be present in a miRNA* sequence.

The "miRNA precursor loop sequence" or "loop sequence of the miRNA precursor" or "loop region" of an miRNA precursor is the portion of an miRNA precursor that is not present in the stem region and that is not retained in the mature miRNA (or its complement) upon cleavage by a RNAse III-like enzyme.

The "miRNA precursor stem sequence" or "stem sequence of the miRNA precursor" or "stem region" of an miRNA precursor is the portion of an miRNA precursor created by the pairing of opposite ends of the pre-miRNA polynucleotide sequence, and in-cluding the portion of the miRNA precursor that will be retained in the "mature miRNA."

The term "Recognition sequence" refers to a nucleotide sequence that is complementary to a region within the target nucleotide sequence essential for sequence-specific hybridization between the target nucleotide sequence and the recognition sequence.

The terms "corresponding to" and "corresponds to" refer to the comparison between the nucleobase sequence of the compound of the invention, and the equivalent nucleotide sequence or the reverse complement thereof. Nucleobases sequences which "correspond to" a SEQ ID, therefore have between 8 and 30 contiguous nucleobases which form a sequence which is found with i) either the one or more of the SEQ ID(s), or ii) the reverse complement thereof. Nucleotide analogues are compared directly to their equivalent or corresponding natural nucleotides. Sequences which form the reverse complement of a SEQ ID are referred to as the complement sequence of the SEQ ID. In a preferably embodiment, the term complementary refers to fully or perfectly complementary.

The terms "homologues", "variants" and "fragments" in the context of 'homologues, variants and fragments thereof' in relation to detection probe sequences and specific detection probes, refers to any sequence which has at least 8 consecutive nucleotide residues (or nucleotide analogues), such as at least 10 consecutive residues (or nucleotide analogues), such as at least 14 consecutive nucleotides (or nucleotide analogues), in common with at least one of the sequences, allowing for no more than 1 mismatch per 8 nucleotides (or nucleotide analogues), preferably with no more than 1 mismatch or no mismatch.

The term 'natural allelic variants' and the term 'allelic variants' encompasses both variants which although have a slightly different sequence (such as a homologue, fragment or variant), originate from the same chromosomal position, or the same position on an allelic chromosome, as the non-coding RNAs, and precursors thereof herein listed. The term 'natural allelic variants' and the term 'allelic variants' also encompasses mature non-coding RNAs encompasses, which may be differentially processed by the processing enzymes, as this may lead to variants of the same microRNAs having different lengths e.g. shortened by 1 or 2 nucleotides, despite originating from the same allelic chromosome position.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetric, X-ray diffraction or absorption, magnetism, enzymatic activity, and the like.

As used herein, the terms "nucleic acid", "polynucleotide" and "oligonucleotide" refer to primers, probes, oligomer fragments to be detected, oligomer controls and unlabeled blocking oligomers and shall be generic to polydeoxyribonucleotides (containing 2-deoxy-D-ribose), to polyribonucleotides (containing D-ribose), to any other type of polynucleotide which is an N glycoside of a purine or pyrimidine base, or modified purine or pyrimidine bases, and in one embodiment, nucleobases (a collective term used to describe both nucleotides and nucleotide analogues, such as LNA). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA. The oligonucleotide is comprised of a sequence of approximately at least 3 nucleotides, preferably at least about 6 nucleotides, and more preferably at least about 8-30 nucleotides corresponding to a region of the designated target nucleotide sequence. "Corresponding" means identical to or complementary to the designated sequence. The oligonucleotide is not necessarily physically derived from any existing or natural sequence but may be generated in any manner, including chemical synthesis, DNA replication, reverse transcription or a combination thereof.

The terms "oligonucleotide" or "nucleic acid" intend a polynucleotide of genomic DNA or RNA, cDNA, semi synthetic, or synthetic origin which, by virtue of its origin or manipulation: (1) is not associated with all or a portion of the polynucleotide with which it is associated in nature; and/or (2) is linked to a polynucleotide other than that to which it is linked in nature; and (3) is not found in nature. Because mononucleotides are reacted to make oligonucleotides in a manner such that the 5'-phosphate of one mononucleotide pentose ring is attached to the 3' oxygen of its neighbour in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have a 5' and 3' ends. When two different, non-overlapping oligonucleotides anneal to different regions of the same linear complementary nucleic acid sequence, the 3' end of one oligonucleotide points toward the 5' end of the other; the former may be called the "upstream" oligonucleotide and the latter the "downstream" oligonucleotide.

By the term "SBC nucleobases" is meant "Selective Binding Complementary" nucleobases, i.e. modified nucleobases that can make stable hydrogen bonds to their complementary nucleobases, but are unable to make stable hydrogen bonds to other SBC nucleobases. As an example, the SBC nucleobase A', can make a stable hydrogen bonded pair with its complementary unmodified nucleobase, T. Likewise, the SBC nucleobase T' can make a stable hydrogen bonded pair with its complementary unmodified nucleobase, A. However, the SBC nucleobases A' and T' will form an unstable hydrogen bonded pair as compared to the base pairs A'-T and A-T'. Likewise, a SBC nucleobase of C is designated C' and can make a stable hydrogen bonded pair with its complementary unmodified nucleobase G, and a SBC nucleobase of G is designated G' and can make a stable hydrogen bonded pair with its complementary unmodified nucleobase C, yet C' and G' will form an unstable hydrogen bonded pair as compared to the base pairs C'-G and C-G'. A stable hydrogen bonded pair is obtained when 2 or more hydrogen bonds are formed e.g. the pair between A' and T, A and T', C and G', and C' and G. An unstable hydrogen bonded pair is obtained when 1 or no hydrogen bonds is formed e.g. the pair between A' and T', and C' and G'. Especially interesting SBC nucleobases are 2,6-diaminopurine (A', also called D) together with 2-thio-uracil (U', also called $^{2S}$U)(2-thio-4-oxo-pyrimidine) and 2-thio-thymine (T', also called $^{2S}$T)(2-thio-4-oxo-5-methyl-pyrimidine). FIG. 4 in PCT Publication No. WO 2004/024314 illustrates that the pairs A-$^{2S}$T and D-T have 2 or more than 2 hydrogen bonds whereas the D-$^{2S}$T pair forms a single (unstable) hydrogen bond. Likewise the SBC nucleobases pyrrolo-[2,3-d]pyrimidine-2(3H)-one (C', also called PyrroloPyr) and hypoxanthine (G', also called I)(6-oxo-purine) are shown in FIG. 4 in PCT Publication No. WO 2004/024314 where the pairs PyrroloPyr-G and C-I have 2 hydrogen bonds each whereas the PyrroloPyr-I pair forms a single hydrogen bond.

"SBC LNA oligomer" refers to a "LNA oligomer" containing at least one LNA monomer where the nucleobase is a "SBC nucleobase". By "LNA monomer with an SBC nucleobase" is meant a "SBC LNA monomer". Generally speaking SBC LNA oligomers include oligomers that besides the SBC LNA monomer(s) contain other modified or naturally occurring nucleotides or nucleosides. By "SBC monomer" is meant a non-LNA monomer with a SBC nucleobase. By "isosequential oligonucleotide" is meant an oligonucleotide with the same sequence in a Watson-Crick sense as the corresponding modified oligonucleotide e.g. the sequences agT-tcATg is equal to agTscD$^{25}$Ug where s is equal to the SBC DNA monomer 2-thio-t or 2-thio-u, D is equal to the SBC LNA monomer LNA-D and $^{25}$U is equal to the SBC LNA monomer LNA $^{25}$U.

The complement of a nucleic acid sequence as used herein refers to an oligonucleotide which, when aligned with the nucleic acid sequence such that the 5' end of one sequence is paired with the 3' end of the other, is in "antiparallel association." Bases not commonly found in natural nucleic acids may be included in the nucleic acids of the present invention include, for example, inosine and 7-deazaguanine. Complementarity may not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

Stability of a nucleic acid duplex is measured by the melting temperature, or "$T_m$". The $T_m$ of a particular nucleic acid duplex under specified conditions is the temperature at which half of the duplexes have disassociated.

The term "nucleobase" covers the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4$,$N^4$-ethanocytosin, $N^6$,$N^6$-ethano-2,6-diaminopurine, 5-methylcytosine, 5-($C^3$-$C^6$)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272 and Susan M. Freier and Karl-Heinz Altmann, *Nucleic Acid Research*, 25: 4429-4443, 1997. The term "nucleobase" thus includes not only the known purine and pyrimidine heterocycles, but also heterocyclic analogues and tautomers thereof. Further naturally and non naturally occurring nucleobases include those disclosed in U.S. Pat. No. 3,687,808; in chapter 15 by Sanghvi, in *Antisense Research and Application*, Ed. S. T. Crooke and B. Lebleu, CRC Press, 1993; in Englisch, et al., *Angewandte Chemie, International Edition*, 30: 613-722, 1991 (see, especially pages 622 and 623, and in the *Concise Encyclopedia of Polymer Science and Engineering*, J. I. Kroschwitz Ed., John Wiley & Sons, pages 858-859, 1990, Cook, *Anti-Cancer DrugDesign* 6: 585-607, 1991, each of which are hereby incorporated by reference in their entirety).

The term "nucleosidic base" or "nucleobase analogue" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole or a 5-nitroindole. Other preferred compounds include pyrene and pyridyloxazole derivatives, pyrenyl, pyrenylmethylglycerol derivatives and the like. Other preferred universal bases include, pyrrole, diazole or triazole derivatives, including those universal bases known in the art.

By "oligonucleotide," "oligomer," or "oligo" is meant a successive chain of monomers (e.g., glycosides of heterocyclic bases) connected via internucleoside linkages. The linkage between two successive monomers in the oligo consist of 2 to 4, desirably 3, groups/atoms selected from —$CH_2$—, —O—, —S—, —$NR^H$, >C=O, >C=$NR^H$, >C=S, —Si($R''$)$_2$—, —SO—, —S(O)$_2$—, —P(O)$_2$—, —PO($BH_3$)—, —P(O,S)—, —P(S)$_2$—, —PO(R'')—, —PO($OCH_3$)—, and —PO($NHR^H$)—, where $R^H$ is selected from hydrogen and $C_{1-4}$-alkyl, and R'' is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$C(=$NR^H$)—$NR^H$—, —$NR^H$—CO—$CH_2$—$NR^H$—, —O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N= (including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH= (including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$—, —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R'')—O—, —O—PO($OCH_3$)—O—, —O—PO($OCH_2CH_3$)—O—, —O—PO($OCH_2CH_2$S—R)—O—, —O—PO($BH_3$)—O—, —O—PO($NHR^N$)—O—, —O—P(O)$_2$—$NR^H$—, —$NR^H$—P(O)$_2$—O—, —O—P(O, $NR^H$—O—, —$CH_2$—P(O)$_2$—O—, —O—P(O)$_2$—$CH_2$—, and —O—Si(R")$_2$—O—; among which —$CH_2$—CO—$NR^H$—, —$CH_2$—$NR^H$—O—, —S—$CH_2$—O—, —O—P(O)$_2$—O—, —O—P(O,S)—O—, —O—P(S)$_2$—O—, —$NR^H$—P(O)$_2$—O—, —O—P(O,$NR^H$)—O—, —O—PO(R")—O—, —O—PO($CH_3$)—O—, and —O—PO($NHR^N$)—O—, where $R^H$ is selected form hydrogen and $C_{1-4}$-alkyl, and R" is selected from $C_{1-6}$-alkyl and phenyl, are especially desirable. Further illustrative examples are given in Mesmaeker et. al., Current Opinion in Structural Biology 1995, 5, 343-355 and Susan M. Freier and Karl-Heinz Altmann, Nucleic Acids Research, 1997, vol 25, pp 4429-4443. The left-hand side of the internucleoside linkage is bound to the 5-membered ring as substituent P* at the 3'-position, whereas the right-hand side is bound to the 5'-position of a preceding monomer.

By "LNA" or "LNA monomer" (e.g., an LNA nucleoside or LNA nucleotide) or an LNA oligomer (e.g., an oligonucleotide or nucleic acid) is meant a nucleoside or nucleotide analogue that includes at least one LNA monomer. LNA monomers as disclosed in PCT Publication WO 99/14226 are in general particularly desirable modified nucleic acids for incorporation into an oligonucleotide of the invention. Additionally, the nucleic acids may be modified at either the 3' and/or 5' end by any type of modification known in the art. For example, either or both ends may be capped with a protecting group, attached to a flexible linking group, attached to a reactive group to aid in attachment to the substrate surface, etc. Desirable LNA monomers and their method of synthesis also are disclosed in U.S. Pat. No. 6,043,060, U.S. Pat. No. 6,268,490, PCT Publications WO 01/07455, WO 01/00641, WO 98/39352, WO 00/56746, WO 00/56748 and WO 00/66604 as well as in the following papers: Morita et al., Bioorg. Med. Chem. Lett. 12(1):73-76, 2002; Hakansson et al., Bioorg. Med. Chem. Lett. 11(7):935-938, 2001; Koshkin et al., J. Org. Chem. 66(25):8504-8512, 2001; Kvaerno et al., J. Org. Chem. 66(16):5498-5503, 2001; Hakansson et al., J. Org. Chem. 65(17):5161-5166, 2000; Kvaerno et al., J. Org. Chem. 65(17):5167-5176, 2000; Pfundheller et al., Nucleosides Nucleotides 18(9):2017-2030, 1999; and Kumar et al., Bioorg. Med. Chem. Lett. 8(16):2219-2222, 1998.

Preferred LNA monomers, also referred to as "oxy-LNA" are LNA monomers which include bicyclic compounds as disclosed in PCT Publication WO 03/020739 wherein the bridge between $R^{4'}$ and $R^{2'}$ as shown in formula (I) below together designate —$CH_2$—O— or —$CH_2$—$CH_2$—O—.

By "LNA modified oligonucleotide" or "LNA substituted oligonucleotide" is meant a oligonucleotide comprising at least one LNA monomer of formula (I), described infra, having the below described illustrative examples of modifications:

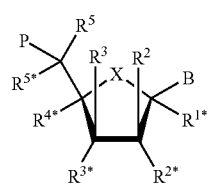

(I)

wherein X is selected from —O—, —S—, —N($R^N$)—, —O—C($R^6R^{6*}$)—, —O—C($R^7R^{7*}$)—, —C($R^6R^{6*}$)—O—, —S—C($R^7R^{7*}$), —C($R^6R^{6*}$)—S—, —N($R^{N*}$)—C($R^7R^{7*}$)—, —C($R^6R^{6*}$)—N($R^{N*}$), and C($R^6R^{6*}$)—C($R^7R^{7*}$).

B is selected from a modified base as discussed above e.g. an optionally substituted carbocyclic aryl such as optionally substituted pyrene or optionally substituted pyrenylmethylglycerol, or an optionally substituted heteroalicylic or optionally substituted heteroaromatic such as optionally substituted pyridyloxazole, optionally substituted pyrrole, optionally substituted diazole or optionally substituted triazole moieties; hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands.

P designates the radical position for an internucleoside linkage to a succeeding monomer, or a 5'-terminal group, such internucleoside linkage or 5'-terminal group optionally including the substituent $R^5$. One of the substituents $R^2$, $R^{2*}$, $R^3$, and $R^{3*}$ is a group P* which designates an internucleoside linkage to a preceding monomer, or a 2'/3'-terminal group. The substituents of $R^{1*}$, $R^{4*}$, $R^5$, $R^{5*}$, $R^6$, $R^{6*}$, $R^7$, $R^{7*}$, $R^N$, and the ones of $R^2$, $R^{2*}$, $R^3$, and $R^{3*}$ not designating P* each designates a biradical comprising about 1-8 groups/atoms selected from —C($R^aR^b$)—, —C($R^a$)=C($R^a$)—, —C($R^a$)=N—, —C($R^a$)—O—, —O—, —Si($R^a$)$_2$—, —C($R^a$)—S, —S—, —$SO_2$—, —C($R^a$)—N($R^b$)—, N($R^a$)—, and >C=Q, wherein Q is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, hetero-aryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents $R^a$ and $R^b$ together may designate optionally substituted methylene (=$CH_2$), and wherein two non-geminal or geminal substituents selected from $R^a$, $R^b$, and any of the substituents $R^{1*}$, $R^2$, $R^{2*}$, $R^3$, $R^{3*}$, $R^{4*}$, $R^5$, $R^{5*}$, $R^6$ and $R^{6*}$, $R^7$, and $R^{7*}$ which are present and not involved in P, P or the biradical(s) together may form an associated biradical selected from biradicals of the same kind as defined before; the pair(s) of non-geminal substituents thereby forming a mono- or bicyclic entity together with (i) the atoms to which said non-geminal substituents are bound and (ii) any intervening atoms.

Each of the substituents $R^{1*}$, $R^2$, $R^{2*}$, $R^3$, $R^4$, $R^5$, $R^{5*}$, $R^6$ and $R^{6*}$, $R^7$, and $R^{7*}$ which are present and not involved in P, P* or the biradical(s), is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di-($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1-5 carbon atom(s) alkylene chain which is optionally interrupted and/or terminated by one or more heteroatoms/groups selected from —O—, —S—, and —(NR$^N$)— where R$^N$ is selected from hydrogen and C$_{1-4}$-alkyl, and where two adjacent (non-geminal) substituents may designate an additional bond resulting in a double bond; and R$^{N*}$, when present and not involved in a biradical, is selected from hydrogen and C$_{1-4}$-alkyl; and basic salts and acid addition salts thereof.

Exemplary 5', 3', and/or 2' terminal groups include —H, —OH, halo (e.g., chloro, fluoro, iodo, or bromo), optionally substituted aryl, (e.g., phenyl or benzyl), alkyl (e.g., methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamino, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethoxytrityl, monomethoxytrityl, or trityl(triphenylmethyl)), linkers (e.g., a linker containing an amine, ethylene glycol, quinone such as anthraquinone), detectable labels (e.g., radiolabels or fluorescent labels), and biotin.

It is understood that references herein to a nucleic acid unit, nucleic acid residue, LNA monomer, or similar term are inclusive of both individual nucleoside units and nucleotide units and nucleoside units and nucleotide units within an oligonucleotide.

A "modified base" or other similar terms refer to a composition (e.g., a non-naturally occurring nucleobase or nucleosidic base), which can pair with a natural base (e.g., adenine, guanine, cytosine, uracil, and/or thymine) and/or can pair with a non-naturally occurring nucleobase or nucleosidic base. Desirably, the modified base provides a T$_m$ differential of 15, 12, 10, 8, 6, 4, or 2° C. or less as described herein. Exemplary modified bases are described in EP 1 072 679 and WO 97/12896.

The term "chemical moiety" refers to a part of a molecule. "Modified by a chemical moiety" thus refer to a modification of the standard molecular structure by inclusion of an unusual chemical structure. The attachment of said structure can be covalent or non-covalent.

The term "inclusion of a chemical moiety" in an oligonucleotide probe thus refers to attachment of a molecular structure. Such as chemical moiety include but are not limited to covalently and/or non-covalently bound minor groove binders (MGB) and/or intercalating nucleic acids (INA) selected from a group consisting of asymmetric cyanine dyes, DAPI, SYBR Green I, SYBR Green II, SYBR Gold, PicoGreen, thiazole orange, Hoechst 33342, Ethidium Bromide, 1-O-(1-pyrenylmethyl)glycerol and Hoechst 33258. Other chemical moieties include the modified nucleobases, nucleosidic bases or LNA modified oligonucleotides.

"Oligonucleotide analogue" refers to a nucleic acid binding molecule capable of recognizing a particular target nucleotide sequence. A particular oligonucleotide analogue is peptide nucleic acid (PNA) in which the sugar phosphate backbone of an oligonucleotide is replaced by a protein like backbone. In PNA, nucleobases are attached to the uncharged polyamide backbone yielding a chimeric pseudopeptide-nucleic acid structure, which is homomorphous to nucleic acid forms.

"High affinity nucleotide analogue" or "affinity-enhancing nucleotide analogue" refers to a non-naturally occurring nucleotide analogue that increases the "binding affinity" of an oligonucleotide probe to its complementary recognition sequence when substituted with at least one such high-affinity nucleotide analogue.

As used herein, a probe with an increased "binding affinity" for a recognition sequence compared to a probe which comprises the same sequence but does not comprise a stabilizing nucleotide, refers to a probe for which the association constant (K$_a$) of the probe recognition segment is higher than the association constant of the complementary strands of a double-stranded molecule. In another preferred embodiment, the association constant of the probe recognition segment is higher than the dissociation constant (K$_d$) of the complementary strand of the recognition sequence in the target sequence in a double stranded molecule.

Monomers are referred to as being "complementary" if they contain nucleobases that can form hydrogen bonds according to Watson-Crick base-pairing rules (e.g. G with C, A with T or A with U) or other hydrogen bonding motifs such as for example diaminopurine with T, 5-methyl C with G, 2-thiothymidine with A, inosine with C, pseudoisocytosine with G, etc.

The term "succeeding monomer" relates to the neighbouring monomer in the 5'-terminal direction and the "preceding monomer" relates to the neighbouring monomer in the 3'-terminal direction.

The term "target nucleic acid" or "target ribonucleic acid" refers to any relevant nucleic acid of a single specific sequence, e.g., a biological nucleic acid, e.g., derived from a patient, an animal (a human or non-human animal), a cell, a tissue, an organism, etc. In one embodiment, the target nucleic acid is derived from a patient, e.g., a human patient. In this embodiment, the invention optionally further includes selecting a treatment, diagnosing a disease, or diagnosing a genetic predisposition to a disease, based upon detection of the target nucleic acid. Whilst the target may be a miRNA, such as the miRNA or pre-miRNA sequences disclosed herein, such as in the context of the target of a detection probe, the target is also used in the context as the target of the miRNA, i.e. the mRNA whose expression is regulated by the miRNA. Table 11 includes human genes whose mRNAs are targeted by the miRNAs disclosed herein.

"Target sequence" refers to a specific nucleic acid sequence within any target nucleic acid.

The term "stringent conditions", as used herein, is the "stringency" which occurs within a range from about T$_m$–5° C. (5° C. below the melting temperature (T$_m$) of the probe) to about 20° C. to 25° C. below T$_m$. As will be understood by those skilled in the art, the stringency of hybridization may be altered in order to identify or detect identical or related polynucleotide sequences. Hybridization techniques are generally described in *Nucleic Acid Hybridization, A Practical Approach*, Ed. Hames, B. D. and Higgins, S. J., IRL Press, 1985; Gall and Pardue, *Proc. Natl. Acad. Sci., USA* 63: 378-383, 1969; and John, et al. *Nature* 223: 582-587, 1969.

In one embodiment the term "specifically hybridise" is determined by whether the oligonucleotide or compound of the invention hybridises to the target nucleic acid sequence (e.g. a SEQ selected from SEQ ID NO 1-408) under stringent conditions.

The terms "contiguous sequence of nucleobases" and "contiguous nucleobase sequence" are used interchangeably.

DETAILED DESCRIPTION OF THE INVENTION

New microRNA Markers

The invention provides 558 new microRNA markers which have not previously been recognised as miRNAs and/or indicated in cancer. The 558 miRNAs were identified in cancer tissue and are considered to be useful indicators of cancer. The present invention provides a detailed expression analysis of both the pre- and mature forms of the miRNAs in various cancers and corresponding healthy tissues, and as such the present invention provides an extensive collection of miRNA sequences which, when in the form of detection probes, can be used, individually, or in the form of collections for cancer diagnostics, and for determining the origin of secondary cancers.

The new microRNA markers include mature miRNAs and the premature (pre-processed) miRNAs from which they originate.

The odd numbered SEQ IDs from 1 to 407 are novel mature miRNAs. The even numbers from 2 to 408 are the corresponding pre-mature miRNAs. For SEQ ID Nos 411-558 the miRNAs and their corresponding pre-miRNAs, in addition to related miRNA (and/or related pre-miRNAs) are shown in Table 3.

The invention provides for a nucleic acid or nucleobase sequence selected from the group consisting of SEQ ID NO 1-558 and/or a compound which comprises a contiguous sequence of nucleobases of between 8 and 30 nucleobases in length, wherein the nucleobase sequence of the contiguous sequence corresponds to a contiguous nucleic acid sequence present in said SEQ ID selected from the group consisting of SEQ ID 1-558.

In one embodiment the contiguous nucleobase sequence (which may be a nuclei acid sequence) is complementary to the (corresponding) region of said SEQ ID.

In one embodiment the sequence of nucleobases of the contiguous nucleobase sequence (which may be a nuclei acid sequence) is found within the (corresponding) region of said SEQ ID.

As in the above embodiments, and with reference to the list of embodiments herein and below, the term "corresponding to" may refer to a complementary sequence (preferably 100% complementary) or that the sequence is found within said sequence (i.e. homologous, preferably 100% homologus).

In one embodiment the SEQ ID is a mature miRNA sequence, i.e. selected from the odd numbered SEQ IDs present in the group consisting of SEQ IDs No 1-407 and/or column 1 of table 3.

In one embodiment the SEQ ID is a mature miRNA sequence, i.e. selected from the group of miRNAs present in the group consisting of the mature miRNAs listed in Table 5.

In one embodiment the SEQ ID is a premature miRNA sequence, i.e. selected from the group of pre-miRNAs listed in Table 4.

In one embodiment the SEQ ID is a pre-mature miRNA sequence, i.e. selected from the even numbered SEQ IDs present in the group consisting of SEQ IDs No 2-408 and/or column 2 of table 3.

In one embodiment, the invention provides for a nucleic acid or nucleobase sequence SEQ ID No 1 or 2 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 3 or 4 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 5 or 6 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 7 or 8 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 9 or 10 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 11 or 12 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 13 or 14 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 15 or 16 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 17 or 18 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 19 or 20 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 21 or 22 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 23 or 24 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 25 or 26 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 27 or 28 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 29 or 30 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 31 or 32 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 33 or 34 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 35 or 36 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 37 or 38 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 39 or 40 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 41 or 42 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 43 or 44 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 45 or 46 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 47 or 48 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 49 or 50 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 51 or 52 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 53 or 54 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 55 or 56 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 57 or 58 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 59 or 60 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 61 or 62 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 63 or 64 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 65 or 66 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 67 or 68 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 69 or 70 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 71 or 72 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 73 or 74 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 75 or 76 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 77 or 78 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 79 or 80 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 81 or 82 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 83 or 84 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 85 or 86 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 87 or 88 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 89 or 90 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 91 or 92 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 93 or 94 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 95 or 96 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 97 or 98 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 99 or 100 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 101 or 102 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 103 or 104 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 105 or 106 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 107 or 108 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 109 or 110 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 111 or 112 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 113 or 114 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 115 or 116 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 117 or 118 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 119 or 120 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 121 or 122 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 123 or 124 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 125 or 126 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 127 or 128 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 129 or 130 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 131 or 132 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 133 or 134 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 135 or 136 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 137 or 138 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 139 or 140 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 141 or 142 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 143 or 144 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 145 or 146 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 147 or 148 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 149 or 150 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 151 or 152 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 153 or 154 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 155 or 156 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 157 or 158 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 159 or 160 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 161 or 162 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 163 or 164 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 165 or 166 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 167 or 168 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 169 or 170 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 171 or 172 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 173 or 174 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 175 or 176 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 177 or 178 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 179 or 180 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 181 or 182 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 183 or 184 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 185 or 186 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 187 or 188 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 189 or 190 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 191 or 192 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 193 or 194 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 195 or 196 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 197 or 198 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 199 or 200 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 201 or 202 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 203 or 204 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 205 or 206 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 207 or 208 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 209 or 210 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 211 or 212 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 213 or 214 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 215 or 216 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 217 or 218 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 219 or 220 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 221 or 222 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 223 or 224 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 225 or 226 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 227 or 228 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 229 or 230 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 231 or 232 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 233 or 234 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 235 or 236 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 237 or 238 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 239 or 240 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 241 or 242 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 243 or 244 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 245 or 246 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 247 or 248 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 249 or 250 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 251 or 252 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 253 or 254 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 255 or 256 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 257 or 258 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 259 or 260 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 261 or 262 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 263 or 264 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 265 or 266 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 267 or 268 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 269 or 270 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 271 or 272 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 273 or 274 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 275 or 276 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 277 or 278 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 279 or 280 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 281 or 282 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 283 or 284 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 285 or 286 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 287 or 288 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 289 or 290 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 291 or 292 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 293 or 294 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 295 or 296 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 297 or 298 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 299 or 300 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 301 or 302 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 303 or 304 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 305 or 306 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 307 or 308 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 309 or 310 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 311 or 312 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 313 or 314 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 315 or 316 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 317 or 318 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 319 or 320 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 321 or 322 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 323 or 324 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 325 or 326 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 327 or 328 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 329 or 330 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 331 or 332 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 333 or 334 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 335 or 336 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 337 or 338 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 339 or 340 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 341 or 342 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 343 or 344 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 345 or 346 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 347 or 348 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 349 or 350 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 351 or 352 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 353 or 354 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 355 or 356 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 357 or 358 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 359 or 360 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 361 or 362 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 363 or 364 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 365 or 366 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 367 or 368 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 369 or 370 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 371 or 372 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 373 or 374 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 375 or 376 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 377 or 378 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 379 or 380 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 381 or 382 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 383 or 384 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 385 or 386 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 387 or 388 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 389 or 390 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 391 or 392 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 393 or 394 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 395 or 396 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 397 or 398 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 399 or 400 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 401 or 402 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 403 or 404 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 405 or 406 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 407 or 408 and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 411 and/or 412, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 413, 414 and/or 415, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 416 and/or 417, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 418, 420, 421 and/or 419, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 422 and/or 423, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 424 and/or 425, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 426, 428 and/or 427, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 429, 430, 431, 432 and/or 433, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 434 and/or 435, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 436 and/or 437, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 438 and/or 439, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 440 and/or 441, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 442 and/or 443, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 444, 445 and/or 446, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 447 and/or 448, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 449, 451 and/or 450, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 452 and/or 453, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 454 and/or 455, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 456 and/or 457, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 458 and/or 459, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 460 and/or 461, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 462 and/or 463, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No. 464 and/or 465, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 466, 468 and/or 467, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 469, 471, 472 and/or 470, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 473 and/or 474, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 475, 477 and/or 476, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 478 and/or 479, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 480 and/or 481, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 482 and/or 483, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 484 and/or 485, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 486 and/or 487, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 488 and/or 489, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 490, 492, 493 494, and/or 491, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 495, 497, 498, 499, 501, 496 and/or 500, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 502 and/or 503, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 504, 505 and/or 506, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 507 and/or 508, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 509 and/or 510, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 511 and/or 512, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 513 and/or 514, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 515, 517, and/or 516, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 518 and/or 519, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 520 and/or 521, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 522 and/or 523, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 524 and/or 525, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 526 and/or 527, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 528 and/or 529, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 530 and/or 531, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 532 and/or 533, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 534 and/or 535, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 536 and/or 537, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 538, 540 and/or 539, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 541, 543 and/or 542, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 544 and/or 545, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 546 and/or 547, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 548, 551, 552, 553, and/or 554, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 549, 552, 553 and/or 554, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 550, 553 and/or 554, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 555 and/or 556, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

In one embodiment, the invention provides for a nucleic acid or nucleobase sequence SEQ ID No 557 and/or 558, and/or a compound which comprises a contiguous sequence of nucleobases of between 8 and 30 nucleobases in length, wherein the nucleobase sequence of the contiguous sequence corresponds to a contiguous nucleic acid or nucleobases sequence present in said SEQ IDs.

A Compound

In a preferred embodiment, in the compound of the invention, the contiguous sequence of nucleobases is in the form of, or comprises an oligonucleotide.

The oligonucleotide may comprise nucleotide nucleobases and/or nucleotide analogue nucleobases.

The oligonucleotide (compound) of the invention may, for example be used in antisense therapy or as a research tool or diagnostic for a disease.

The oligonucleotide (compound) of the invention may comprises at least one nucleotide analogue, such as a LNA.

The oligonucleotide (compound) of the invention may comprises between 8 to 30 nucleobases, such as 9, 10, 11, 12, 13, 14, 15, 16, 17, 18, 19, 20, 21, 22, 23, 24, 25, 26, 27, 28, or 29 nucleobases, such as between 14 to 24 nucleobases, such as between 16 and 22 nucleobases, such as between 8 to 14 nucleobases, such as between 12 and 20 nucleobases.

The oligonucleotide (compound) of the invention may comprise other oligonucleotide analogues in combination with or without LNA. Such analogues may be selected from the group consisting of phosphorothioates or 2'-O-protected nucleotides or combinations thereof. Suitable nucleotide analogues include those selected from the group consisting of Locked Nucleic Acid (LNA) units; 2'-O-alkyl-RNA units, 2'-OMe-RNA units, 2'-amino-DNA units, 2'-fluoro-DNA units, PNA units, HNA units, and INA units.

In one embodiment. the compound according to the invention comprises a duplex formed between the contiguous sequence of nucleobases and a further nucleobase sequence which is complementary to the contiguous sequence of nucleobases.

In one embodiment. the compound according to the invention is in the form of a siRNA or miRNA.

In one embodiment the compound of the invention is in the form of a miRNA mimic which can be introduced into a cell to repress the expression of one or more mRNA target(s) present in the cell (such as one or more of the mRNA targets listed in Table 11). miRNA mimics are typically fully complementary to the full length miRNA sequence.

The invention therefore provides a method of inducing or enhancing miRNA mediated repression of a mRNA target in a cell, said method comprising the step of introducing the compound of the invention into said cell, so as to repress the mRNA target. miRNA mimics are compounds comprising a contiguous nucleobase sequence which are homologous to a corresponding region of one, or more, of the miRNA sequences provided herein (i.e. sense compounds).

In one embodiment the compound of the invention is an anti-miR which can be introduced into a cell to deactivate miRNA alleviating the miRNA-induced repression of the mRNA target (i.e de-repression).

The invention therefore provides a method of reducing or deactivating a miRNA in a cell, said method comprising the step of introducing the compound of the invention into said cell, so as to reduce or deactivate said miRNA in the cell. AntimiR compounds comprise a contiguous nucleobase sequence which is complementary to a corresponding region of one, or more, of the miRNA sequences provided herein (i.e. antisense compounds).

Numerous examples of the application of miRNA micmics and antimiRs are known in the art (Guimaraes-Sternberg et al., Leukemia Research 30(5): 583-595, 2006). For example, WO2007/112754, which is hereby incorporated by reference, provides suitable designs for antimiR compounds according to the invention.

Conjugates

The invention also provides for a conjugate comprising the compound according to the invention and at least one non-nucleobase moiety covalently attached thereto. Suitable conjugates for use with oligonucleotides/oligonucleobases are known in the art, such as those disclosed in US 2006154888.

Pharmaceutical Composition

The invention also provides for a pharmaceutical composition comprising a compound according to the invention, or the conjugate according to the invention, and at least one pharmaceutically acceptable diluent, carrier, salt or adjuvant. Suitable pharmaceutically acceptable diluent, carrier, salt or adjuvant are known in the art, such as those disclosed in US 2006154888.

The compound may be formulated as a prodrug, which is activated once it enters into the cell (such as the prodrug formulations disclosed in US 2006154888).

First Medical Indication

The invention also provides for the use of a compound according to the invention or the conjugate according to the invention or the pharmaceutical composition according to the invention as a medicament, such as for the treatment of a disease or medical condition selected from the group consisting of: cancer, such as a form of cancer selected from the group consisting of; breast cancer, adrenal gland cancer, bladder cancer, colon cancer, Cervical cancer, cancer of the duodenum, cancer of the esophagus, cancer of the kidney, liver cancer, lung cancer, ovarian cancer, prostate cancer, rectal cancer, stomach cancer and uterine cancer.

In one embodiment, the type of said cancer may be selected from the group consisting of the following: A solid tumor; ovarian cancer, breast cancer, non-small cell lung cancer, renal cell cancer, bladder cancer, esophagus cancer, stomach cancer, prostate cancer, pancreatic cancer, lung cancer, cervical cancer, colon cancer, colorectal cancer, renal cell cancer;

The type of cancer may be selected from the group consisting of: A carcinoma, such as a carcinoma selected from the group consisting of ovarian carcinoma, breast carcinoma, non-small cell lung cancer, renal cell carcinoma, bladder carcinoma, recurrent superficial bladder cancer, stomach carcinoma, prostatic carcinoma, pancreatic carcinoma, lung carcinoma, cervical carcinoma, cervical dysplasia, laryngeal papillomatosis, colon carcinoma, colorectal carcinoma, carcinoid tumors, renal cell carcinoma, A basal cell carcinoma; A malignant melanoma, such as a malignant melanoma selected from the group consisting of superficial spreading melanoma, nodular melanoma, lentigo maligna melanoma, acral melagnoma, amelanotic melanoma and desmoplastic melanoma; A sarcoma, such as a sarcoma selected from the group consisting of osteosarcoma, Ewing's sarcoma, chondrosarcoma, malignant fibrous histiocytoma, fibrosarcoma and Kaposi's sarcoma; and a glioma.

In one embodiment the type of cancer is a teratoma.

Second Medical Indication

The invention also provides for the use of a compound according to the invention or the conjugate according to the invention or the pharmaceutical composition according to the invention, in the manufacture of a medicament for the treatment of a disease or medical condition selected from the group consisting of cancer, such as breast cancer, or one of the above listed forms of cancer.

Method of Treatment

The invention also provides for a method of performing therapy comprising administering the compound according to the invention or the conjugate according to the invention or the pharmaceutical composition according to the invention to a patient in need of therapy, such as a patient suffering from, or susceptible to be suffering from cancer, such as breast cancer, or a cancer selected from one of the above listed forms of cancer.

miRNA Seed—Method of Identifying Genes Regulated by miRNAs

The invention also provides for a method of identifying a target to an miRNA in an organism, comprising acts of: providing a conserved miRNA sequence selected from the group consisting of SEQ ID No 1-558 or natural allelic variants thereof; providing a genome of an organism; defining at least 6 nucleotides (such as between 6 and 30 nucleotides, such as at least 10, 12, 14 or at least 16 nucleotides) of the conserved miRNA sequence as an miRNA seed; identifying a conserved UTR of a gene within the genome of the organism; and identifying the gene as a target of the miRNA by determining whether the conserved UTR comprises a segment having perfect complementarity with the miRNA seed. Table 11 provides a list of human genes whose mRNA are targeted by the miRNAs of the invention.

Method of Modulating Gene Expression

A method according of modulating the expression of a gene associated with a disease or medical condition, comprising administering the compound according to the invention or the conjugate according to the invention or the pharmaceutical composition according to the invention to a cell so as to modulate the expression of the gene associated with the disease or medical condition. Table 11 provides a list of possible human genes whose mRNA are targeted by the miRNAs of the invention. As described above, the use of miRNA mimics or antimiRs can be used to (optionally) further repress the mRNA targets, or to silence (down-regulate) the miRNA, thereby inhibiting the function of the endogenous miRNA, causing de-repression and increased expression of the mRNA target.

Detection/Oligonucleotide Probes

Detection Probe and Recognition Sequence

Typically, an oligonucleotide probe (detection probe) of the invention includes a plurality of nucleotide analogue monomers and hybridizes to a miRNA or miRNA precursor. In one embodiment, the nucleotide analogue is LNA, such as alpha and/or xylo LNA monomers. In one embodiment, the oligonucleotide probe hybridizes to the loop sequence of a miRNA precursor, e.g., to 5 nucleotides of the miRNA precursor loop sequence or to the center of the miRNA precursor loop sequence. The oligonucleotide probe may or may not also hybridize to the stem sequence of the miRNA precursor. The oligonucleotide probe may have a number of nucleotide analogue monomers corresponding to 20% to 40% of the probe oligonucleotides. The probes may also have a spacing between nucleotide analogue monomers such that two of the plurality of nucleotide analogue monomers are disposed 3 or 4 nucleotides apart, or a combination thereof. Alternatively, each nucleotide analogue monomer in a probe may be spaced 3 or 4 nucleotides from the closest nucleotide analogue monomer. Typically, when nucleotide analogue monomers are spaced apart, only naturally-occurring nucleotides are disposed between the nucleotide analogue monomers. Alternatively, two, three, four, or more nucleotide analogue monomers may be disposed adjacent to one another. The adjacent nucleotide analogue monomers may or may not be disposed at the 3' or 5' end of the oligonucleotide probe or so that one of the nucleotide analogue monomers hybridizes to the center of the loop sequence of the miRNA precursor. The probe may include none or at most one mismatched base, deletion, or addition. Desirably, the probe hybridizes to the miRNA or precursor thereof under stringent conditions or high stringency conditions. Desirably, the melting point of the duplex formed between the probe and the miRNA precursor is at least 1° C. higher, e.g., at least 5° C., than the melting point of the duplex formed between the miRNA precursor and a nucleic acid sequence not having a nucleotide analogue monomer, or any modified backbone. The probe may include at least 70% DNA; at least 10% nucleotide analogue monomers; and/or at most 30% nucleotide analogue monomers.

The probe may further include a 5' or 3' amino group and/or a 5' or 3' label, e.g., a fluorescent (such as fluorescein) label, a radioactive label, or a label that is a complex including an enzyme (such as a complex containing digoxigenin (DIG). The probe is for example 8 nucleotides to 30 nucleotides long, e.g., 12 nucleotides long or 15 nucleotides long. Other potential modifications of probes are described herein.

The probe when hybridized to the miRNA or precursor thereof may or may not provide a substrate for RNase H.

Preferably, the probes of the invention exhibit increased binding affinity for the target sequence by at least two-fold, e.g., at least 5-fold or 10-fold, compared to probes of the same sequence without nucleotide analogue monomers, under the same conditions for hybridization, e.g., stringent conditions or high stringency conditions.

The invention features a computer code for a preferred software program of the invention for the design and selection of the oligonucleotide probes. The invention provides a method, system, and computer program embedded in a computer readable medium ("a computer program product") for designing oligonucleotide probes having at least one stabilizing nucleobase, e.g., such as LNA. The method includes querying a database of target sequences (listed herein) and designing oligonucleotide probes which: i) have sufficient binding stability to bind their respective target sequence under stringent hybridization conditions, ii) have limited propensity to self-anneal, and iii) are capable of binding to and detecting/quantifying at least about 60%, at least about 70%, at least about 80%, at least about 90% or at least about 95% of their target sequences in the given database of miRNAs, miRNA precursors, or other RNA sequences.

The method further entails calculating stability based on the assumption that the oligonucleotide probes have at least one stabilizing nucleotide, such as an LNA monomer. In some cases, the calculated stability is used to eliminate oligonucleotide probe candidates with inadequate stability from the database of possible oligonucleotide probes prior to the query against the database to identify optimal sequences for the oligonucleotide probe.

In one embodiment, oligonucleotide probes were designed as reverse complementary sequences to the loop-region of the pre-miRNA. A stretch of 25 nucleotides were identified centered around the loop-region and a capture probe was designed for this 25-mer sequence using the same design rules as for capture probes for the mature miRNAs. This design process takes into account predictions of Tm of the capture probe, self-hybridization of the capture probe to itself and intra-molecular secondary structures and the difference between Tm and self-hybridization Tm. Further criteria to the capture probe design, includes that, in one embodiment, LNA-residues are not allowed in the 3'-end to enhance synthesis yield. Inter-probe comparison of capture probes against different miRNAs ensure that capture probes are designed against regions of the miRNAs that differ the most from other miRNAs in order to optimize the discrimination between different miRNAs.

The compound of the invention may form a detection probe, such as oligonucleotide probes, including detection probe pairs, which are independently capable of detecting one of each of the herein listed (miRNA or pre-miRNA) nucleic acids.

Therefore the invention also provides for detection probes.

Each detection probe comprises a recognition sequence consisting of nucleobases or equivalent molecular entities.

The recognition sequence typically comprises of the contiguous sequence of nucleobases present in the compound of the invention, although in one embodiment, for use in a detection probe, the recognition sequence may be as short as 6 nucleotides, such as 6 or 7 nucleobases.

The recognition sequence of the diagnostic probe according to the invention corresponds to the target nucleotide sequence or sequences as referred to herein.

The target sequences with odd SEQ IDs (from SEQ ID NO 1 to 407) or in column 1 of table 3, or as shown in Table 5, represent mature miRNA sequences which are associated with cancer such as breast cancer. Therefore in one embodiment, the detection probe(s) according to the invention comprise a contiguous sequence of nucleobases of at least 6 nucleobases, wherein the contiguous sequence corresponds (i.e. is homolgous to or complementary) to a contiguous nucleotide sequence present in the odd numbered SEQ IDs NO 1 to 407 and/or the SEQ IDs listed in column 1 of table 3, or in Table 5.

The target sequences with even SEQ IDs (from SEQ ID NO 2 to 408) or in column 2 of table 3, or as shown in Table 4, represent pre-mature miRNA sequences which are associated with cancer such as breast cancer. Therefore in one embodiment, the detection probe(s) according to the invention comprise a contiguous sequence of nucleobases of at least 6 nucleobases, wherein the contiguous sequence corresponds to a contiguous nucleotide sequence present in the even numbered SEQ IDs NO 2 to 408 and/or the SEQ IDs listed in column 2 of table 3, or as shown in table 4.

In one embodiment, the detection probes are capable of specifically hybridizing to a target sequence selected from the group consisting of a nucleic acid sequence selected from the group consisting of SEQ ID No 1-558

In one embodiment, the detection probes are capable of specifically hybridizing to a target sequence selected from the group consisting of a nucleic acid sequence selected from the group shown in Table 5.

In one embodiment, the detection probes are capable of specifically hybridizing to a target sequence selected from the group consisting of a nucleic acid sequence selected from the group shown in Table 4.

In a preferred embodiment, detection probes which are capable of specifically hybridizing to a target sequence have a contiguous nucleobase sequence which is complementary to a corresponding region in the target sequence.

In one embodiment, the detection probes are capable of specifically hybridizing to a target sequence selected from the group consisting of a nucleic acid sequence selected from the group consisting of SEQ ID No 1-408 (odd and/or even SEQ IDs), and SEQ ID No 411-558 (i.e. the SEQ IDs listed in columns 1 and/or 2 of Table 3), and allelic variants thereof.

In one embodiment, the detection probes are capable of specifically hybridizing to a target sequence selected from the group consisting of a nucleic acid sequence selected from the group consisting of the even numbered SEQ IDs present in the group SEQ ID No 1-408, and/or the SEQ IDs listed in column 2 of table 3, and allelic variants thereof. These sequences are novel precursor miRNA sequences which are further processed to form mature non-coding RNAs.

In one embodiment, the detection probes are capable of specifically hybridizing to a target sequence selected from the group consisting of a nucleic acid sequence selected from the group consisting of the even numbered SEQ IDs present in the group SEQ ID No 1-408, and/or the SEQ IDs listed in column 1 of table 3, and allelic variants thereof. These sequences are novel mature miRNA.

In one embodiment, the detection probe or probes are capable of specifically hybridising to the precursor form of the non-coding RNA, but are not capable of specifically hybridising to the mature form of the non-coding RNA. Suitable detection probes are routinely designed and made utilising the sequence information available, e.g. by selecting a detection probe which at least partially hybridises to the loop structure which is cleaved during miRNA processing. It should be noted that several mature siRNAs may originate from more than one precursor, hence by designing specific probes for a particular precursor, highly specific detection probes for use in the invention may be used.

It will be understood that whilst in the preferred embodiment the target sequence are the miRNA or pre-miRNA precursors themselves, in one embodiment, the target sequence may be a further nucleotide or nucleobase sequence which retains the sequence information from the corresponding miRNA/pre-miRNA.

The detection element of the detection probes according to the invention may be single or double labeled (e.g. by comprising a label at each end of the probe, or an internal position). In one aspect, the detection probe comprises two labels capable of interacting with each other to produce a signal or to modify a signal, such that a signal or a change in a signal may be detected when the probe hybridizes to a target sequence. A particular aspect is when the two labels comprise a quencher and a reporter molecule.

A particular detection aspect of the invention referred to as a "molecular beacon with a stem region" is when the recognition segment is flanked by first and second complementary hairpin-forming sequences which may anneal to form a hairpin. A reporter label is attached to the end of one complementary sequence and a quenching moiety is attached to the end of the other complementary sequence. The stem formed when the first and second complementary sequences are hybridized (i.e., when the probe recognition segment is not hybridized to its target) keeps these two labels in close proximity to each other, causing a signal produced by the reporter to be quenched by fluorescence resonance energy transfer (FRET). The proximity of the two labels is reduced when the probe is hybridized to a target sequence and the change in proximity produces a change in the interaction between the labels. Hybridization of the probe thus results in a signal (e.g. fluorescence) being produced by the reporter molecule, which can be detected and/or quantified.

Preferably, the compound of the invention, such as the detection probes of the invention, are modified in order to increase the binding affinity of the probes for the target sequence by at least two-fold compared to probes of the same sequence without the modification, under the same conditions for hybridization or stringent hybridization conditions. The preferred modifications include, but are not limited to, inclusion of nucleobases, nucleosidic bases or nucleotides that have been modified by a chemical moiety or replaced by an analogue to increase the binding affinity. The preferred modifications may also include attachment of duplex-stabilizing agents e.g., such as minor-groove-binders (MGB) or intercalating nucleic acids (INA). Additionally, the preferred modifications may also include addition of non-discriminatory bases e.g., such as 5-nitroindole, which are capable of stabilizing duplex formation regardless of the nucleobase at the opposing position on the target strand. Finally, multi-probes composed of a non-sugar-phosphate backbone, e.g. such as PNA, that are capable of binding sequence specifically to a target sequence are also considered as a modification. All the different binding affinity-increasing modifications mentioned above will in the following be referred to as "the stabilizing modification(s)", and the tagging probes and the detection probes will in the following also be referred to as "modified oligonucleotide". More preferably the binding affinity of the modified oligonucleotide is at least about 3-fold, 4-fold, 5-fold, or 20-fold higher than the binding of a probe of the same sequence but without the stabilizing modification(s).

Most preferably, the stabilizing modification(s) is inclusion of one or more LNA nucleotide analogs. Probes from 8 to 30 nucleotides according to the invention may comprise from 1 to 8 stabilizing nucleotides, such as LNA nucleotides. When at least two LNA nucleotides are included, these may be consecutive or separated by one or more non-LNA nucleotides. In one aspect, LNA nucleotides are alpha-L-LNA and/or xylo LNA nucleotides as disclosed in PCT Publications No. WO 2000/66604 and WO 2000/56748.

In a preferable embodiment, each detection probe preferably comprises affinity enhancing nucleobase analogues, and wherein the recognition sequences exhibit a combination of high melting temperatures and low self-complementarity scores, said melting temperatures being the melting temperature of the duplex between the recognition sequence and its complementary DNA or RNA sequence.

This design provides for probes which are highly specific for their target sequences but which at the same time exhibits a very low risk of self-annealing (as evidenced by a low self-complementarity score)—self-annealing is, due to the presence of affinity enhancing nucleobases (such as LNA monomers) a problem which is more serious than when using conventional deoxyribonucleotide probes.

In one embodiment the recognition sequences exhibit a melting temperature (or a measure of melting temperature) corresponding to at least 5° C. higher than a melting temperature or a measure of melting temperature of the self-complementarity score under conditions where the probe hybridizes specifically to its complementary target sequence (alternatively, one can quantify the "risk of self-annealing" feature by requiring that the melting temperature of the probe-target duplex must be at least 5° C. higher than the melting temperature of duplexes between the probes or the probes internally).

In a preferred embodiment all of the detection probes include recognition sequences which exhibit a melting temperature or a measure of melting temperature corresponding to at least 5° C. higher than a melting temperature or a measure of melting temperature of the self-complementarity score under conditions where the probe hybridizes specifically to its complementary target sequence.

However, it is preferred that this temperature difference is higher, such as at least 10° C., such as at least 15, at least 20, at least 25, at least 30, at least 35, at least 40, at least 45, and at least 50° C. higher than a melting temperature or measure of melting temperature of the self-complementarity score.

In one embodiment, the affinity-enhancing nucleobase analogues are regularly spaced between the nucleobases in said detection probes. One reason for this is that the time needed for adding each nucleobase or analogue during synthesis of the probes of the invention is dependent on whether or not a nucleobase analogue is added. By using the "regular spacing strategy" considerable production benefits are achieved. Specifically for LNA nucleobases, the required coupling times for incorporating LNA amidites during synthesis may exceed that required for incorporating DNA amidites. Hence, in cases involving simultaneous parallel synthesis of multiple oligonucleotides on the same instrument, it is advantageous if the nucleotide analogues such as LNA are spaced evenly in the same pattern as derived from the 3'-end, to allow reduced cumulative coupling times for the synthesis. The affinity enhancing nucleobase analogues are conveniently regularly spaced as every $2^{nd}$, every $3^{rd}$, every $4^{th}$ or every $5^{th}$ nucleobase in the recognition sequence, and preferably as every $3^{rd}$ nucleobase. Alternatively, the affinity enhancing nucleobase analogues may be spaced at a mixture of, for example every $2^{nd}$, every $3^{rd}$, every $4^{th}$ nucleobase.

The presence of the affinity enhancing nucleobases in the recognition sequence preferably confers an increase in the binding affinity between a probe and its complementary target nucleotide sequence relative to the binding affinity exhibited by a corresponding probe, which only include nucleobases. Since LNA nucleobases/monomers have this ability, it is preferred that the affinity enhancing nucleobase analogues are LNA nucleobases.

In some embodiments, the 3' and 5' nucleobases are not substituted by affinity enhancing nucleobase analogues.

As detailed herein, one huge advantage of such probes for use in the method of the invention is their short lengths which surprisingly provides for high target specificity and advantages in detecting small RNAs and detecting nucleic acids in samples not normally suitable for hybridization detection strategies. It is, however, preferred that the probes comprise a recognition sequence is at least a 6-mer, such as at least a 7-mer, at least an 8-mer, at least a 9-mer, at least a 10-mer, at least an 11-mer, at least a 12-mer, at least a 13-mer, at least a 14-mer, at least a 15-mer, at least a 16-mer, at least a 17-mer, at least an 18-mer, at least a 19-mer, at least a 20-mer, at least a 21-mer, at least a 22-mer, at least a 23-mer, and at least a 24-mer. On the other hand, the recognition sequence is preferably at most a 25-mer, such as at most a 24-mer, at most a 23-mer, at most a 22-mer, at most a 21-mer, at most a 20-mer, at most a 19-mer, at most an 18-mer, at most a 17-mer, at most a 16-mer, at most a 15-mer, at most a 14-mer, at most a 13-mer, at most a 12-mer, at most an 11-mer, at most a 10-mer, at most a 9-mer, at most an 8-mer, at most a 7-mer, and at most a 6-mer.

The present invention provides oligonucleotide compositions and probe sequences for the use in detection, isolation, purification, amplification, identification, quantification, or capture of miRNAs, their target mRNAs, precursor RNAs, stem-loop precursor miRNAs, siRNAs, other non-coding RNAs, RNA-edited transcripts or alternative mRNA splice variants or single stranded DNA (e.g. viral DNA) characterized in that the probe sequences contain a number of nucleoside analogues.

In a preferred embodiment the number of nucleoside analogue corresponds to from 20 to 40% of the oligonucleotide of the invention.

In a preferred embodiment the probe sequences are substituted with a nucleoside analogue with regular spacing between the substitutions In another preferred embodiment the probe sequences are substituted with a nucleoside analogue with irregular spacing between the substitutions In a preferred embodiment the nucleoside analogue is LNA.

In a further preferred embodiment the detection probe sequences comprise a photochemically active group, a thermochemically active group, a chelating group, a reporter group, or a ligand that facilitates the direct of indirect detection of the probe or the immobilisation of the oligonucleotide probe onto a solid support.

In a further preferred embodiment:
(a) the photochemically active group, the thermochemically active group, the chelating group, the reporter group, or the ligand includes a spacer (K), said spacer comprising a chemically cleavable group; or
(b) the photochemically active group, the thermochemically active group, the chelating group, the reporter group, or the ligand is attached via the biradical of at least one of the LNA(s) of the oligonucleotide.

Methods for defining and preparing probes and probe collections are disclosed in PCT/DK2005/000838.

In another aspect the invention features detection probe sequences containing a ligand, which said ligand means something, which binds. Such ligand-containing detection probes of the invention are useful for isolating and/or detecting target RNA molecules from complex nucleic acid mixtures, such as miRNAs, or their cognate target mRNAs, for example as shown in Table 11.

The invention therefore also provides for detection probes, such as oligonucleotide compositions, which are ligands to the molecular markers according to the invention.

In another aspect, the invention features detection probes whose sequences have been furthermore modified by Selectively Binding Complementary (SBC) nucleobases, i.e. modified nucleobases that can make stable hydrogen bonds to their complementary nucleobases, but are unable to make stable hydrogen bonds to other SBC nucleobases. Such SBC monomer substitutions are especially useful when highly self-complementary detection probe sequences are employed. As an example, the SBC nucleobase A', can make a stable hydrogen bonded pair with its complementary unmodified nucleobase, T. Likewise, the SBC nucleobase T' can make a stable hydrogen bonded pair with its complementary unmodified nucleobase, A. However, the SBC nucleobases A' and T' will form an unstable hydrogen bonded pair as compared to the base pairs A'-T and A-T'. Likewise, a SBC nucleobase of C is designated C' and can make a stable hydrogen bonded pair with its complementary unmodified nucleobase G, and a SBC nucleobase of G is designated G' and can make a stable hydrogen bonded pair with its complementary unmodified nucleobase C, yet C' and G' will form an unstable hydrogen bonded pair as compared to the base pairs C'-G and C-G'. A stable hydrogen bonded pair is obtained when 2 or more hydrogen bonds are formed e.g. the pair between A' and T, A and T', C and G', and C' and G. An unstable hydrogen bonded pair is obtained when 1 or no hydrogen bonds is formed e.g. the pair between A' and T', and C' and G'. Especially interesting SBC nucleobases are 2,6-diaminopurine (A', also called D) together with 2-thio-uracil (U', also called 2SU)(2-thio-4-oxo-pyrimidine) and 2-thio-thymine (T', also called 2ST)(2-thio-4-oxo-5-methyl-pyrimidine).

In another aspect, the detection probe sequences of the invention are covalently bonded to a solid support by reaction of a nucleoside phosphoramidite with an activated solid support, and subsequent reaction of a nucleoside phosphoramide with an activated nucleotide or nucleic acid bound to the solid support. In some embodiments, the solid support or the detection probe sequences bound to the solid support are activated by illumination, a photogenerated acid, or electric current. In other embodiments the detection probe sequences contain a spacer, e.g. a randomized nucleotide sequence or a non-base sequence, such as hexaethylene glycol, between the reactive group and the recognition sequence. Such covalently bonded detection probe sequence populations are highly useful for large-scale detection and expression profiling of mature miRNAs, stem-loop precursor miRNAs, siRNAs, piRNAs, snRNAs and other non-coding RNAs.

The present oligonucleotide compositions and detection probe sequences of the invention are highly useful and applicable for detection of individual small RNA molecules in complex mixtures composed of hundreds of thousands of different nucleic acids, such as detecting mature miRNAs, their target mRNAs, piRNAs, snRNAs or siRNAs, by Northern blot analysis or for addressing the spatiotemporal expression patterns of miRNAs, siRNAs or other non-coding RNAs as well as mRNAs by in situ hybridization in whole-mount.

The oligonucleotide compositions and detection probe sequences are especially applicable for accurate, highly sensitive and specific detection and quantitation of microRNAs and other non-coding RNAs, which are useful as biomarkers for diagnostic purposes of human diseases, such as cancer, including breast cancer and other cancers referred to herein, as well as for antisense-based intervention, targeted against tumorigenic miRNAs and other non-coding RNAs.

The detection probes, detection probe pairs, and oligonucleotide compositions and probe sequences which hybridise to the molecular markers according to the invention are furthermore applicable for sensitive and specific detection and quantitation of microRNAs, which can be used as biomarkers for the identification of the primary site of metastatic tumors of unknown origin.

Known miRNA/Pre-miRNA Control Sequences

The detection probes of the invention may be used in conjunction with other control detection probes against known sequences which are, for example associated with cancer, or the characteristic of cancer being investigated (+ve control detection probes).

In one embodiment the control detection probes may be a non-coding RNA, such as a miRNA, siRNA, piRNA or snRNA.

Suitable target sequences of non coding RNAs may be identified from the literature, for example the following publications disclose non coding RNA sequences associates with the corresponding form of cancer: Breast cancer: Iorio et al Cancer Res 2005; 65: 7065. Lung cancer: Yanaihara et al Cell Science 2006; 9: 189-198. Chronic lymphocytic leukaemia (CLL): Galin et al PNAS, 2004 101(32):11755-11760. Colon cancer: Cummins et al PNAS 2006, 103 (10):3687-3692. Prostate cancer: Volinia et al PNAS 2006; 103: 2257). Cancer: Lu et al (Nature 2005; 435:834-838).

Preferred +ve control detection probes include detection probes which specifically hybridise to a noncoding RNA selected from the group consisting of hsa mIR 21, hsa-Let 71, hsa miR 101, hsa miR 145, hsa miR 9, hsa miR 122a, hsa miR 128b, hsa miR 149, hsa miR 125a, hsa miR 143, hsa miR 136, which may be up-regulated in cancer cells, and hsa-miR 205, which may be down-regulated in breast cancer cells. The detection probes may be designed against either the mature miRNA, the pre-miRNA, or both—e.g. may form a control detection probe pair.

Detection probes prepared against mRNA and DNA markers (target nucleic acids) associated with cancer may also be used as controls, for example markers prepared against the Her-2 gene or mRNA, which is associated with breast cancer.

Method for the Characterisation of Cancer

The invention provides a method for the characterisation of cancer. The data obtained by the method can be used to provide information on one or more features of cancer.

The at least one feature of the cancer which is characterised by the method according to the invention may be selected from one or more of the following:

Diagnosis of cancer, the signal data can be used to determine whether the test sample comprises cells that are cancerous (i.e. presence or absence of cancer), and/or whether such cancer is a malignant cancer or a benign cancer.

The prognosis of the cancer, such as the speed at which the cancer may develop and or metastasize (i.e. spread from one part of the body to another) or the life expectancy of the patient with said cancer (such as less than five years, or greater than five years). In one embodiment the prognosis may be that the life expectancy of the patient is less than 5 years, such as less than 4 years, less than 3 years, less than two years, less than 1 year, less than six months or less than 3 months.

The origin of said cancer, this may be the cause of the cancer, or in the case of secondary cancer, the origin of the primary cancer. The origin may for example be selected from the following lists of cancer types.

The type of said cancer, such as a cancer selected from the group consisting of the following: A solid tumor; ovarian cancer, breast cancer, non-small cell lung cancer, renal cell cancer, bladder cancer, oesophagus cancer, stomach cancer, prostate cancer, pancreatic cancer, lung cancer, cervical cancer, colon cancer, colorectal cancer, renal cell cancer;

In one embodiment the type of said cancer is selected from the group consisting of; breast cancer, adrenal gland cancer, bladder cancer, colon cancer, Cervical cancer, cancer of the duodenum, cancer of the esophagus, cancer of the kidney, liver cancer, lung cancer, ovarian cancer, prostate cancer, rectal cancer, stomach cancer and uterine cancer.

The type of cancer may be selected from the group consisting of: A carcinoma, such as a carcinoma selected from the group consisting of ovarian carcinoma, breast carcinoma, non-small cell lung cancer, renal cell carcinoma, bladder carcinoma, recurrent superficial bladder cancer, stomach carcinoma, prostatic carcinoma, pancreatic carcinoma, lung carcinoma, cervical carcinoma, cervical dysplasia, laryngeal papillomatosis, colon carcinoma, colorectal carcinoma, carcinoid tumors, renal cell carcinoma, A basal cell carcinoma; A malignant melanoma, such as a malignant melanoma selected from the group consisting superficial spreading melanoma, nodular melanoma, lentigo maligna melanoma, acral melagnoma, amelanotic melanoma and desmoplastic melanoma; A sarcoma, such as a sarcoma selected from the group consisting of osteosarcoma, Ewing's sarcoma, chondrosarcoma, malignant fibrous histiocytoma, fibrosarcoma and Kaposi's sarcoma; and a glioma.

The use of non-coding RNA markers for determining the origin of cells is disclosed in U.S. application Ser. No. 11/324, 177, which is hereby incorporated by reference.

Cancer of unknown primary site is a common clinical entity, accounting for 2% of all cancer diagnoses in the Surviellance, Epidemiology, and End Results (SEER) registries between 1973 and 1987 (C. Muir. Cancer of unknown primary site Cancer 1995. 75: 353-356). In spite of the frequency of this syndrome, relatively little attention has been given to this group of patients, and systematic study of the entity has lagged behind that of other areas in oncology. Widespread pessimism concerning the therapy and prognosis of these patients has been the major reason for the lack of effort in this area. The patient with carcinoma of unknown primary site is commonly stereotyped as an elderly, debilitated individual with metastases at multiple visceral sites. Early attempts at systemic therapy yielded low response rates and had a negligible effect on survival, thereby strengthening arguments for a nihilistic approach to these patients. The heterogeneity of this group has also made the design of therapeutic studies difficult; it is well recognized that cancers with different biologies from many primary sites are represented. In the past 10 years, substantial improvements have been made in the management and treatment of some patients with carcinoma of unknown primary site. The identification of treatable patients within this heterogeneous group has been made possible by the recognition of several clinical syndromes that predict chemotherapy responsiveness, and also by the development of specialized pathologic techniques that can aid in tumor characterization. Therefore, the optimal management of patients with cancer of unknown primary site now requires appropriate clinical and pathologic evaluation to identify treatable subgroups, followed by the administration of specific therapy. Many patients with adenocarcinoma of unknown primary site have widespread metastases and poor performance status at the time of diagnosis. The outlook for most of these patients is poor, with median survival of 4 to 6 months. However, subsets of patients with a much more favorable outlook are contained within this large group, and optimal initial evaluation enables the identification of these treatable subsets. In addition, empiric chemotherapy incorporating newer agents has produced higher response rates and probably improves the survival of patients with good performance status.

Fine-needle aspiration biopsy (FNA) provides adequate amounts of tissue for definitive diagnosis of poorly differentiated tumors, and identification of the primary source in about one fourth of cases (C. V. Reyes, K. S. Thompson, J. D. Jensen, and A. M. Chouelhury. Metastasis of unknown origin: the role of fine needle aspiration cytology *Diagn Cytopathol* 1998. 18: 319-322).

microRNAs have emerged as important non-coding RNAs, involved in a wide variety of regulatory functions during cell growth, development and differentiation. Some reports clearly indicate that microRNA expression may be indicative of cell differentiation state, which again is an indication of organ or tissue specification. Therefore a catalogue of mir tissue expression profiles may serve as the basis for a diagnostic tool determining the tissue origin of tumors of unknown origin. So, since it is possible to map miRNA in cells vs. the tissue origin of cell, the present invention presents a convenient means for detection of tissue origin of such tumors.

Hence, the present invention in general relates to a method for determining tissue origin of tumors comprising probing cells of the tumor with a collection of probes which is capable of mapping miRNA to a tissue origin.

miRNA typing according to the principles of the present example can be applied to RNA from a variety of normal tissues and tumor tissues (of known origin) and over time a database is build up, which consists of miRNA expression profiles from normal and tumor tissue. When subjecting RNA from a tumor tissue sample, the resulting miRNA profile can be analysed for its degree of identity with each of the profiles of the database—the closest matching profiles are those having the highest likelyhood of representing a tumor having the same origin (but also other characteristics of clinical significance, such as degree of malignancy, prognosis, optimum treatment regimen and predictition of treatment success). The miRNA profile may of course be combined with other tumor origin determination techniques, cf. e.g. Xiao-jun Ma et al., Arch Pathol Lab Med 130, 465-473, which demonstrates molecular classification of human cancers into 39 tumor classes using a microarray designed to detect RT-PCR amplified mRNA derived from expression of 92 tumor-related genes. The presently presented technology allows for an approach which is equivalent safe for the use of a miRNA detection assay instead of an mRNA detection assay.

The invention provides a method of characterising a tumor of unknown origin, such as a metastasis, or putative metastasis, wherein at least one mature miRNA species is detected in a sample of RNA from a tumor, (i.e. a first population of target molecules obtained from at least one test sample) thus providing a miRNA expression profile from the tumor, and subsequently comparing said miRNA expression profile with previously established miRNA expression profiles from normal tissue and/or tumor tissue.

In one embodiment the tumor may selected from the group consisting of; breast tumor, adrenal gland tumor, bladder tumor, colon tumor, Cervical tumor, tumor of the duodenum, tumor of the esophagus, tumor of the kidney, liver tumor, lung tumor, ovarian tumor, prostate tumor, rectal tumor, stomach tumor and a uterine tumor.

In one embodiment, the tumor may be a breast tumor, or it may be derived from a breast tumor.

The RNA may be total RNA isolated from the tumor, or a purified fraction thereof.

In one embodiment, the miRNA expression profile from the tumor and the previously established miRNA expression profiles provides for an indication of the origin of the tumor, the patient's prognosis, the optimum treatment regimen of the tumor and/or a prediction of the outcome of a given anti-tumor treatment.

The therapy outcome prediction, such as a prediction of the responsiveness of the cancer to chemotherapy and/or radiotherapy and/or the suitability of said cancer to hormone treatment, and such as the suitability of said cancer for removal by invasive surgery. In one embodiment, the therapy out come predication may be the prediction of the suitability of the treatment of the cancer to combined adjuvant therapy.

The therapy may be herceptin, which is frequently used for the treatment of oestrogen receptor positive cancers (such as breast cancer).

The Patient and Test Sample

Suitable samples may comprise a wide range of mammalian and human cells, including protoplasts; or other biological materials, which may harbour target nucleic acids. The methods are thus applicable to tissue culture mammalian cells, mammalian cells (e.g., blood, serum, plasma, reticulocytes, lymphocytes, urine, bone marrow tissue, cerebrospinal fluid or any product prepared from blood or lymph) or any type of tissue biopsy (e.g. a muscle biopsy, a liver biopsy, a kidney biopsy, a bladder biopsy, a bone biopsy, a cartilage biopsy, a skin biopsy, a pancreas biopsy, a biopsy of the intestinal tract, a thymus biopsy, a mammae biopsy, a uterus biopsy, a testicular biopsy, an eye biopsy or a brain biopsy, e.g., homogenized in lysis buffer), and archival tissue nucleic acids.

The test sample is typically obtained from a patient that has or is suspected of having cancer, such as breast cancer, or who is suspected of having a high risk of developing cancer. The method can, therefore be undertaken as a precautionary matter in the prevention of, or early diagnosis of cancer.

The patient (or organism) is a mammal, preferably a human being. The patient may be male or female, although this may depend on the type of tissue/cancer being investigated (e.g. ovarian cancer effects only women).

The test sample is typically obtained from the patient by biopsy or tissue sampling. When referring to the signal obtained from a test (or control) sample, it refers to the signal obtained from the hybridisation using the first (or further) population of molecules prepared from the test (or control) sample.

The Control Sample

In one embodiment, the control sample may be obtained from the same patient at the same time that the test sample is taken. In one embodiment, the control sample may be a sample taken previously, e.g. a sample of the same or a different cancer/tumor, the comparison of which may, for example, provide characterisation of the source of the new tumor, or progression of the development of an existing cancer, such as before, during or after treatment.

In one embodiment, the control sample may be taken from healthy tissue, for example tissue taken adjacent to the cancer, such as within 1 or 2 cm diameter from the external edge of said cancer. Alternatively the control sample may be taken from an equivalent position in the patients body, for example in the case of breast cancer, tissue may be taken from the breast which is not cancerous.

In one embodiment, the control sample may also be obtained from a different patient, e.g. it may be a control sample, or a collection of control samples, representing different types of cancer, for example those listed herein (i.e. cancer reference samples). Comparison of the test sample data with data obtained from such cancer reference samples may for example allow for the characterisation of the test cancer to a specific type and/or stage of cancer.

In one embodiment, at least one control sample is obtained, and a second population of nucleic acids from the at least one control sample is, in addition to the test sample, presented and hybridised against at least one detection probe.

The detection probe target for the test and control sample may be the same, the ratio of the signal obtained between the control and test sample being indicative of a differential quantification of the target.

In one embodiment, the control sample may be obtained from the same patient as the test sample.

In one embodiment, the control sample may be obtained from a non tumorous tissue, such as from tissue adjacent to said putative tumor, and/or from an equivalent position elsewhere in the body.

In one embodiment, the control sample may be obtained from a non tumorous (or cancerous) tissue selected from the group consisting; breast tissue, adrenal gland tissue, bladder tissue, colon tissue, Cervical tissue, tissue of the duodenum, tissue of the esophagus, tissue of the kidney, liver tissue, lung tissue, ovarian tissue, prostate tissue, rectal tissue, stomach tissue and uterine tissue.

In one embodiment, the control sample (or a further control sample) may be obtained from a tumorous (or cancerous) tissue selected from the group consisting; tumorous (or cancerous) breast tissue, tumorous (or cancerous) adrenal gland tissue, tumorous (or cancerous) bladder tissue, tumorous (or cancerous) colon tissue, tumorous (or cancerous) Cervical tissue, tumorous (or cancerous) tissue of the duodenum, tumorous (or cancerous) tissue of the esophagus, tumorous (or cancerous) tissue of the kidney, tumorous (or cancerous) liver tissue, tumorous (or cancerous) lung tissue, tumorous (or cancerous) ovarian tissue, tumorous (or cancerous) prostate tissue, tumorous (or cancerous) rectal tissue, tumorous (or cancerous) stomach tissue and tumorous (or cancerous) uterine tissue.

In one embodiment, the control sample may be obtained from a tumor tissue. In this embodiment, there may be one or more control samples, e.g. a panel of control samples which represent one or more tumor types. Thereby allowing comparison of the test sample, with on or more control samples which have a defined origin. Such control samples, such as a panel of control samples is particularly useful when determining the origin of a cancer (e.g. metastasis) of unknown origin. Such control samples may be selected from one or more of the following: A solid tumor; ovarian cancer, breast cancer, non-small cell lung cancer, renal cell cancer, bladder cancer, esophagus cancer, stomach cancer, prostate cancer, pancreatic cancer, lung cancer, cervical cancer, colon cancer, colorectal cancer, renal cell cancer; Such control samples may also be selected from one or more of the following: The type of cancer may be selected from the group consisting of: A carcinoma, such as a carcinoma selected from the group consisting of ovarian carcinoma, breast carcinoma, non-small cell lung cancer, renal cell carcinoma, bladder carcinoma, recurrent superficial bladder cancer, stomach carcinoma, prostatic carcinoma, pancreatic carcinoma, lung carcinoma, cervical carcinoma, cervical dysplasia, laryngeal papillomatosis, colon carcinoma, colorectal carcinoma, carcinoid tumors, renal cell carcinoma, A basal cell carcinoma; A malignant melanoma, such as a malignant melanoma selected from the group consisting superficial spreading melanoma, nodular melanoma, lentigo maligna melanoma, acral melagnoma, amelanotic melanoma and desmoplastic melanoma; A sarcoma, such as a sarcoma selected from the group consisting of osteosarcoma, Ewing's sarcoma, chondrosarcoma, malignant fibrous histiocytoma, fibrosarcoma and Kaposi's sarcoma; and a glioma.

Or, such control samples may be selected from one or more of the following: breast tumor, adrenal gland tumor, bladder tumor, colon tumor, Cervical tumor, tumor of the duodenum, tumor of the esophagus, tumor of the kidney, liver tumor, lung tumor, ovarian tumor, prostate tumor, rectal tumor, stomach tumor and a uterine tumor.

In one embodiment, the hybridisation signal obtained from the test sample is higher than the hybridisation signal obtained from the control sample.

In one embodiment, the hybridisation signal obtained from the test sample is lower than the hybridisation signal obtained from the control sample.

In one embodiment, at least two control samples are obtained, one control sample being obtained from said patient (see above), and at least one further control sample being obtained from a previously obtained sample of a cancer, such as a cancer of the same type as the test sample, or a different cancer such as those herein listed. The cancer may originate from the same patient or a different patient.

In one embodiment, the hybridisation signal obtained from the at least one further test sample is equivalent to or greater than the signal obtained from the either the signal obtained from the first control sample and/or the signal obtained from the test sample.

In one embodiment, the hybridisation signal obtained from the at least one further test sample is less than the signal obtained from the either the signal obtained from the first control sample and/or the signal obtained from the test sample.

In one embodiment, the test and control samples are hybridised to said at least one detection probe simultaneously, either in parallel hybridisations or in the same hybridisation experiment.

In one embodiment, the test and control sample or samples are hybridised to said at least one detection probe sequentially, either in the same hybridisation experiment, or different hybridisation experiments.

The RNA Fraction

In one embodiment, the RNA fraction may remain within the test sample, such as remain in the cells of the biopsy or tissue sample, for example for in situ hybridisation. The cells may still be living, or they may be dead. The cells may also be prepared for in situ hybridisation using methods known in the art, e.g. they may be treated with an agent to improve permeability of the cells; the cells may also be fixed or partially fixed.

The RNA fraction may be isolated from the test sample, such as a tissue sample.

The RNA fraction preferably comprises small RNAs such as those less than 100 bases in length. The RNA fraction preferably comprises miRNAs.

In one embodiment the RNA fraction may also comprise other RNA fractions such as mRNA, and/or in siRNAs and/or piRNAs.

In one embodiment, the RNA fraction comprises snRNAs.

The RNA fraction may also comprise other nucleic acids, for example the RNA fraction may be part of a total nucleic acid fraction which also comprises DNA, such as genomic and/or mitochondrial DNA. The RNA fraction may be purified. Care should be taken during RNA extraction to ensure at least a proportion of the non encoding RNAs, such as miRNA and siRNAs are retained during the extraction. Suitably, specific protocols for obtaining RNA fractions comprising or enriched with small RNAs, such as miRNAs may be used. The RNA fraction may undergo further purification to obtain an enriched RNA fraction, for example an RNA fraction enriched for non-coding RNAs. This can be achieved, for example, by removing mRNAs by use of affinity purification, e.g. using an oligodT column. RNA fractions enriched in miRNA and siRNA may be obtained using. In one embodiment the RNA fraction is not isolated from the test sample, for example when in situ hybridisation is performed, the RNA fraction remains in situ in the test sample, and the detection probes, typically labeled detection probes, are hybridised to a suitable prepared test sample.

In one embodiment the RNA fraction is used directly in the hybridisation with the at least one detection probe.

The RNA fraction may comprise the target molecule, e.g. the RNA fraction obtained from a test sample, the presence of the target molecule within the RNA fraction may indicate a particular feature of a cancer. Alternatively the RNA fraction may not comprise the target molecule, e.g. the RNA fraction obtained from a test sample, the absence of the target (complementary) molecule within the RNA fraction may indicate a particular feature of a cancer.

The RNA fraction comprises non coding RNA such as noncoding RNA selection from the group consisting of microRNA (miRNA), siRNA, piRNA and snRNA.

In one embodiment, prior to (or even during) said hybridisation, the RNA fraction may be used as a template to prepare a complement of the RNA present in the fraction, said compliment may be synthesised by template directed assembly of nucleoside, nucleotide and/or nucleotide analogue monomers, to produce, for example an oligonucleotides, such as a DNA oligonucleotide. The complement may be further copied and replicated. The compliment may represent the entire template RNA molecule, or may represent a population of fragments of template molecules, such as fragments than, preferably in average, retain at least 8 consecutive nucleoside units of said RNA template, such as at least 12 of said units or at least 14 of said units. It is preferred that at least 8 consecutive nucleoside units of said complementary target, such as at least 12 of said units or at least 14 of said units of said complementary target are retained. When the complementary target is a precursor RNA, or a molecule derived therefore, if is preferred that at least part of the loop structure of the precursor molecule is retained, as this will allow independent detection over the mature form of the non-coding RNA, or molecule derived there from.

Therefore, in one embodiment the RNA fraction itself is not used in the hybridisation, but a population of molecules, such as population of oligonucleotides which are derived from said RNA fraction, and retain sequence information contained within said RNA fraction, are used. It is envisaged that the population of molecules derived from said RNA fraction may be further manipulated or purified prior to the hybridisation step—for example they may be labeled, or a sub-fraction may be purified there from.

The target molecule (complementary target) may therefore be derived from RNA, but may actually comprise an alternative oligo backbone, for example DNA. The target molecule may, therefore also be a complement to the original RNA molecule, or part of the original RNA molecule from which it is derived.

In one embodiment, the RNA fraction is analysed and the population of target RNAs and optionally control nucleic acids are determined. For example the RNA fraction, or a nucleic acid fraction derived there from may be undergo quantitative analysis for specific target and control sequences, for example using oligonucleotide based sequencing, such as oligonucleotide micro-array hybridization. The data from the quantitative analysis may then be used in a virtual hybridisation with a detection probe sequence.

Hybridisation

Hybridisation refers to the bonding of two complementary single stranded nucleic acid polymers (such as oligonucleotides), such as RNA, DNA or polymers comprising or consisting of nucleotide analogues (such as LNA oligonucleotides). Hybridisation is highly specific, and may be controlled by regulation of the concentration of salts and temperature. Hybridisation occurs between complementary sequences, but may also occur between sequences which comprise some mismatches. The probes used in the methods of the present invention may, therefore be 100% complementary to the target molecule. Alternatively, in one embodiment the detection probes may comprise one or two mismatches. Typically a single mismatch will not unduly affect the specificity of binding, however two or more mismatches per 8 nucleotide/nucleotide residues usually prevents specific binding of the detection probe to the target species. The position of the mismatch may also be of importance, and as such the use of mismatches may be used to determine the specificity and strength of binding to target RNAs, or to allow binding to more than one allelic variant of mutation of a target species.

In one embodiment, the detection probe consists of no more than 1 mismatch.

In one embodiment, the detection probe consists of no more than 1 mismatch per 8 nucleotide/nucleotide analogue bases.

In one embodiment, hybridisation may also occur between a single stranded target molecule, such as a miRNA and a probe which comprises a complementary surface to the said target molecule, in this respect, it is the ability of the probe to form the specific bonding pattern with the target which is important.

Suitable methods for hybridisation include RNA in-situ hybridisation, dot blot hybridisation, reverse dot blot hybridisation, northern blot analysis, RNA protection assays, or expression profiling by microarrays. Such methods are standard in the art.

In one embodiment, the detection probe is capable of binding to the target non coding RNA sequence under stringent conditions, or under high stringency conditions.

Exiqon (Denmark) provide microarrays suitable for use in the methods of the invention (microRNA Expression Profiling with miRCURY™ LNA Array).

The detection probe, such as each member of a collection of detection probes, may be bound (such as conjugated) to a bead. Luminex (Texas, USA) provides multiplex technology to allow the use of multiple detection probes to be used in a single hybridisation experiment. See also Panomics Quanti-genePlex™ (http://www.panomics.com/pdf/qgplexbrochure.pdf).

Suitable techniques for performing in situ hybridisation are disclosed in PCT/DK2005/000838

PCR Hybridisation

Whilst it is recognised that many of the short noncoding RNAs which are targets for the detection probes are too short to be detected by amplification by standard PCR, methods of amplifying such short RNAs are disclosed in WO2005/098029. Therefore, the hybridisation may occur during PCR, such as RT-PCT or quantitative PCR (q-PCR).

However, in one embodiment, the hybridisation step does not comprise PCR such as RT-PCR or q-pCR.

The Target

The term the 'target' 'or complementary target' or 'target nucleic acid' refers to a (typically non-coding) polynucleotide sequence associated with cancer, preferably an RNA sequence such as a miRNA, or precursor sequence thereof, or a sequence derived there from which retains the sequence information present the non-coding RNA sequence.

The list of preferred target sequences is provided herein.

Preferably the target is a human miRNA or precursor thereof.

In one embodiment the target may be one or more of the miRNA targets i.e. the mRNA targeted by the miRNA (see table 11).

The Signal

In one embodiment the target is labeled with a signal. In this respect the population of nucleic acids are labeled with a signal which can be detected. The hybridisation or the target molecules to the detection probe, which may be fixed to a solid surface, and subsequent removal of the remaining nucleic acids from the population, and therefore allows the determination of the level of signal from those labeled target which is bound to the detection probe. This may be appropriate when screening immobilised probes, such as arrays of detection probes.

In one embodiment the detection probe is labeled with a signal. This may be appropriate, for example, when performing in situ hybridisation and northern blotting, where the population of nucleic acids are immobilised.

It is also envisaged that both population of nucleic acids and detection probes are labeled. For example they may be labeled with fluorescent probes, such as pairs of FRET probes (Fluorescence resonance energy transfer), so that when hybridisation occurs, the FRET pair is formed, which causes a shift in the wavelength of fluorescent light emitted. It is also envisaged that pairs of detection probes may be used designed to hybridise to adjacent regions of the target molecule, and each detection probe carrying one half of a FRET pair, so that when the probes hybridise to their respective positions on the target, the FRET pair is formed, allowing the shift in fluorescence to be detected.

Therefore, it is also envisaged that neither the population of nucleic acid molecules or the detection probe need be immobilised.

Once the appropriate target RNA sequences have been selected, probes, such as the preferred LNA substituted detection probes are preferably chemically synthesized using commercially available methods and equipment as described in the art (Tetrahedron 54: 3607-30, 1998). For example, the solid phase phosphoramidite method can be used to produce short LNA probes (Caruthers, et al., *Cold Spring Harbor Symp. Quant. Biol.* 47:411-418, 1982, Adams, et al., *J. Am. Chem. Soc.* 105: 661 (1983).

Detection probes, such as LNA-containing-probes, can be labeled during synthesis. The flexibility of the phosphoramidite synthesis approach furthermore facilitates the easy production of detection probes carrying all commercially available linkers, fluorophores and labelling-molecules available for this standard chemistry. Detection probes, such as LNA-modified probes, may also be labeled by enzymatic reactions e.g. by kinasing using T4 polynucleotide kinase and gamma-$^{32}$P-ATP or by using terminal deoxynucleotidyl transferase (TDT) and any given digoxygenin-conjugated nucleotide triphosphate (dNTP) or dideoxynucleotide triphosphate (ddNTP).

Detection probes according to the invention can comprise single labels or a plurality of labels. In one aspect, the plurality of labels comprise a pair of labels which interact with each other either to produce a signal or to produce a change in a signal when hybridization of the detection probe to a target sequence occurs.

In another aspect, the detection probe comprises a fluorophore moiety and a quencher moiety, positioned in such a way that the hybridized state of the probe can be distinguished from the unhybridized state of the probe by an increase in the fluorescent signal from the nucleotide. In one aspect, the detection probe comprises, in addition to the recognition element, first and second complementary sequences, which specifically hybridize to each other, when the probe is not hybridized to a recognition sequence in a target molecule, bringing the quencher molecule in sufficient proximity to said reporter molecule to quench fluorescence of the reporter molecule. Hybridization of the target molecule distances the quencher from the reporter molecule and results in a signal, which is proportional to the amount of hybridization.

In the present context, the term "label" means a reporter group, which is detectable either by itself or as a part of a detection series. Examples of functional parts of reporter groups are biotin, digoxigenin, fluorescent groups (groups which are able to absorb electromagnetic radiation, e.g. light or X-rays, of a certain wavelength, and which subsequently reemits the energy absorbed as radiation of longer wavelength; illustrative examples are DANSYL (5-dimethylamino)-1-naphthalenesulfonyl), DOXYL (N-oxyl-4,4-dimethyloxazolidine), PROXYL (N-oxyl-2,2,5,5-tetramethylpyrrolidine), TEMPO(N-oxyl-2,2,6,6-tetramethylpiperidine), dinitrophenyl, acridines, coumarins, Cy3 and Cy5 (trademarks for Biological Detection Systems, Inc.), erythrosine, coumaric acid, umbelliferone, Texas red, rhodamine, tetramethyl rhodamine, Rox, 7-nitrobenzo-2-oxa-1-diazole (NBD), pyrene, fluorescein, Europium, Ruthenium, Samarium, and other rare earth metals), radio isotopic labels, chemiluminescence labels (labels that are detectable via the emission of light during a chemical reaction), spin labels (a free radical (e.g. substituted organic nitroxides) or other paramagnetic probes (e.g. $Cu^{2+}$, $Mg^{2+}$) bound to a biological molecule being detectable by the use of electron spin resonance spectroscopy). Especially interesting examples are biotin, fluorescein, Texas Red, rhodamine, dinitrophenyl, digoxigenin, Ruthenium, Europium, Cy5, Cy3, etc.

Control Detection Probes

It is preferably in the method according to the invention that in addition to the detection probe for the target in question, at least one further detection probe is used, where the at least one further detection probe is capable of hybridising to a control nucleic acid (control target) present in said population of nucleic acids (such as the RNA fraction). The control nucleic acid is not the same as the target in question.

In one embodiment, the at least one further detection probe may be derived from or is capable of selectively hybridising with a molecule selected from the group consisting of: a pre-miRNA molecule; a pre-siRNA molecule; and a pre-piRNA molecule.

In another embodiment, the at least one further detection probe may be derived from or is capable of selectively hybridising with a molecule selected from the group consisting of a mature miRNA, a mature siRNA, a mature piRNA and a snRNA.

A preferred type of detection probe, which may be used with as a detection probe control and/or as a detection probe, is one which is capable of hybridising to the loop region of an immature miRNA, siRNA or piRNA. Recent research has shown that the processing of pre-microRNAs to mature microRNAs may be controlled in a cell specific manner (Obernosterer et al). In this respect the ratio between the immature and mature form can give valuable information which may be used to characterise the cancer test sample.

Detection Probes to Precursor Non-Coding RNAs

The present invention provides for detection probes for the detection of non coding RNA precursors, such as pre-miRNAs, pre-siRNAs and pre-piRNAs, and their targets. miRNAs are transcribed as mono- or poly-cistronic, long, primary precursor transcripts (pri-miRNAs) that are cleaved into ~70-nt precursor hairpins, known as microRNA precursors (pre-miRNAs), by the nuclear RNase III-like enzyme Drosha (Lee et al., Nature 425:415-419, 2003). MicroRNA precursors (pre-miRNAs) form hairpins having a loop region and a stem region containing a duplex of the opposite ends of the RNA strand. Subsequently pre-miRNA hairpins are exported to the cytoplasm by Exportin-5 (Yi et al., Genes & Dev., 17:3011-3016, 2003; Bohnsack et al., RNA, 10:185-191, 2004), where they are processed by a second RNase III-like enzyme, termed Dicer, into ~22-nt duplexes (Bernstein et al., Nature 409:363-366, 2001), followed by the asymmetric assembly of one of the two strands into a functional miRNP or miRISC (Khvorova et al., Cell 115:209-216, 2003). miRNAs can recognize regulatory targets while part of the miRNP complex and inhibit protein translation. Alternatively, the active RISC complex is guided to degrade the specific target mRNAs (Lipardi et al., Cell 107:297-307, 2001; Zhang et al., EMBO J. 21:5875-5885, 2002; Nykanen et al., Cell 107:309-321, 2001). There are several similarities between miRNP and the RNA-induced silencing complex, RISC, including similar sizes and both containing RNA helicase and the PPD proteins. It has therefore been proposed that miRNP and RISC are the same RNP with multiple functions (Ke et al., Curr. Opin. Chem. Biol. 7:516-523, 2003).

Most reports in the literature have described the processing of miRNAs to be complete, suggesting that intermediates like pri-miRNA and pre-miRNA rarely accumulate in cells and tissues. However, previous studies describing miRNA profiles of cells and tissues have only investigated size-fractionated RNAs pools. Consequently the presence of larger miRNA precursors has been overlooked.

Alterations in miRNA biogenesis resulting in different levels of mature miRNAs and their miRNA precursors could illuminate the mechanisms underlying many disease processes. For example, the 26 miRNA precursors were equally expressed in non-cancerous and cancerous colorectal tissues from patients, whereas the expression of ma-ture human miR143 and miR145 was greatly reduced in cancer tissues compared with non-cancer tissues, suggesting altered processing for specific miRNAs in human disease (Michael et al., Mol. Cancer Res. 1:882-891, 2003).

Connections between miRNAs, their precursors, and human diseases will only strengthen in parallel with the knowledge of miRNA, their precursors, and the gene networks that they control. Moreover, the understanding of the regulation of RNA-mediated gene expression is leading to the development of novel therapeutic approaches that will be likely to revolutionize the practice of medicine (Nelson et al., TIBS 28:534-540, 2003).

siRNAs and piRNAs are considered to undergo a similar processing from precursor molecules.

To this end, the invention provides oligonucleotide probes for precursors of non-coding RNAs, such as miRNA precursors, siRNA precursors, and piRNA precursors.

The detection probes for precursors may be a detection probe that hybridizes to a non-coding RNA precursor molecule, wherein at least part of said probe hybridizes to a portion of said precursor not present in the corresponding mature non coding RNA, e.g. the loop region.

Such oligonucleotide probes include a sequence complementary to the desired RNA sequence and preferably a substitution with nucleotide analogues, preferably high-affinity nucleotide analogues, e.g., LNA, to increase their sensitivity and specificity over conventional oligonucleotides, such as DNA oligonucleotides, for hybridization to the desired RNA sequences.

An exemplary oligonucleotide probe includes a plurality of nucleotide analogue monomers and hybridizes to a miRNA precursor. Desirably, the nucleotide analogue is LNA, wherein the LNA may be oxy-LNA, preferably beta-D-oxy-LNA, monomers. Desirably, the oligonucleotide probe will hybridize to part of the loop sequence of a miRNA precursor, e.g., to 5 nucleotides of the miRNA precursor loop sequence or to the center of the miRNA precursor loop sequence. In other embodiments, the oligonucleotide probe will hybridize to part of the stem sequence of a miRNA precursor.

The invention also features a method of measuring relative amounts of non coding RNAs, such as miRNa, piRNA and siRNA, and their precursors, such as pre-miRNAs, pre-siRNAs and pre-piRNAs.

This may be achieved by using a detection probe pair which comprises of i) a first detection probe that hybridizes to a non-coding RNA precursor molecule, wherein at least part of said probe hybridizes to a portion of said precursor not present in the corresponding mature non-coding RNA, and ii) a further detection probe that hybridizes to the mature non-coding RNA, but will not hybridise to the precursor non-coding RNA, e.g. by designing the detection probe to hybridise to the sequence which flanks the stem loop splice site of the precursor molecule. The ratio of signal of hybridisation thereby provides data which can provide said characterisation of said breast cancer.

Therefore, the invention further provides for a detection probe pair which consist of a detection probe which specifically hybridises to the pre-miRNA sequence and a further detection probe which specifically hybridises to the mature miRNA sequence. By designing, for example the pre-miRNA detection probe across the stem loop region, which is cleaved during the maturation process, the detection probe which specifically hybridises to the pre-mature miRNA does not specifically hybridise to the mature miRNA sequence. Therefore in a preferred embodiment, by comparing the signal obtained from each member of the detection probe pair it is possible to determine the comparative population of pre-miRNAs as compared to the corresponding mature miRNAs in a sample.

In one embodiment, the comparison is made by contacting a first probe that hybridizes to the mature noncoding RNA, such as mature miRNA, with the sample under a first condition that also allows the corresponding non-coding RNA precursor, such as miRNA precursor to hybridize; contacting the first probe or a second probe that hybridizes to mature non-coding RNA with the sample under a second condition that does not allow corresponding miRNA precursor to hybridize; comparing the amounts of the probes hybridized under the two conditions wherein the reduction in amount hybridized under the second condition compared to the first condition is indicative of the amount of the miRNA precursor in the sample.

Furthermore, the invention features a kit including a probe of the invention (or a detection probe pair according to the invention) and packaging and/or labeling indicative of the non-coding RNA and/or non-coding precursor (e.g. miRNA precursor), to which the probe (or probe pair) hybridizes and conditions under which the hybridization occurs. The kit provides for the isolation, purification, amplification, detection, identification, quantification, or capture of natural or synthetic nucleic acids. The probes are preferably immobilized onto a solid support, e.g., such as a bead or an array.

The invention also features a method of treating a disease or condition in a living organism using any combination of the probes and methods of the invention.

The invention further features a method of comparing relative amounts of miRNA and miRNA precursor in a sample by contacting the sample with a first probe that hybridizes to miRNA precursor and a second probe that hybridizes to miRNA; and detecting the amount of one or more signals indicative of the relative amounts of miRNA and miRNA precursor.

The invention also features a method of measuring relative amounts of miRNA and miRNA precursor in a sample by contacting a first probe that hybridizes to miRNA with the sample under conditions that also allow miRNA precursor to hybridize; contacting the first probe or a second probe that hybridizes to miRNA with the sample under conditions that do not allow miRNA precursor to hybridize; comparing the amounts of the probes hybridized under the two conditions wherein the reduction in amount hybridized under the second condition compared to the first condition is indicative of the amount of miRNA precursor in the sample.

The invention also features methods of using the probes of the invention as components of Northern blots, in situ hybridization, arrays, and various forms of PCR analysis including PCR, RT-PCR, and qPCR.

Any probe of the invention may be used in performing any method of the inven-ion. For example, any method of the invention may involve probes having labels. Furthermore, any method of the invention may also involve contacting a probe with miRNA precursor that is endogenously or exogenously produced. Such contacting may occur in vitro or in vivo, e.g., such as in the body of an animal, or within or without a cell, which may or may not naturally express the miRNA precursor.

Also, primarily with respect to miRNA precursors, nucleotide analogue containing probes, polynucleotides, and oligonucleotides are broadly applicable to antisense uses. To this end, the present invention provides a method for detection and functional analysis of non-coding antisense RNAs, as well as a method for detecting the overlapping regions between sense-antisense transcriptional units.

The oligonucleotide probes of invention are also useful for detecting, testing, diagnosing or quantifying miRNA precursors and their targets implicated in or connected to human disease, e.g., analyzing human samples for cancer diagnosis.

For example, pre-mir-138-2 is ubiquitously expressed, unlike its mature miRNA derivative. The presence of an unprocessed miRNA precursor in most tissues of the organism suggests miRNA precursors as possible diagnostic targets. We envision that miRNA precursor processing could be a more general feature of the regulation of miRNA expression and be used to identify underlying disease processes. One could also imagine that the unprocessed miRNA precursors might play a different role in the cell, irrespective of the function of the mature miRNA, providing further insights into underlying disease processes.

Imperfect processing of miRNA precursors to mature miRNA as detected by sample hybridization to oligonucleotide probes may provide diagnostic or prognostic in-formation. Specifically, the ratio between levels of mature and precursor transcripts of a given miRNA may hold prognostic or diagnostic information. Furthermore, specific spatial expression patterns of mature miRNA compared to miRNA precursor may likewise hold prognostic or diagnostic infor-mation. In addition, performing in situ hybridization using mature miRNA and/or miRNA precursor specific oligonucleotide probes could also detect abnormal expression levels. LNA-containing probes are particularly well-suited for these purposes.

The present invention enables discrimination between different polynucleotide transcripts and detects each variant in a nucleic acid sample, such as a sample derived from a patient, e.g., addressing the spatiotemporal expression patterns by RNA in situ hybridization. The methods are thus applicable to tissue culture animal cells, animal cells (e.g., blood, serum, plasma, reticulocytes, lymphocytes, urine, bone marrow tissue, cerebrospinal fluid or any product prepared from blood or lymph) or any type of tissue biopsy (e.g., a muscle biopsy, a liver biopsy, a kidney biopsy, a bladder biopsy, a bone biopsy, a cartilage biopsy, a skin biopsy, a pancreas biopsy, a biopsy of the intestinal tract, a thymus biopsy, a mammae biopsy, a uterus biopsy, a testicular biopsy, an eye biopsy or a brain biopsy, e.g., homogenized in lysis buffer), archival tissue nucleic acids such as formalin fixated paraffin embedded sections of the tissue and the like.

pre-mir-138-1 and pre-mir-138-2 and their shared mature miRNA derivative mir-138 differ in their expression levels across various tissues as detected by oligonucleotide probes. The differential expression of pre-mir-138-1 and pre-mir-138-2 and their derived mature miRNA mir-138. pre-mir-138-2 is expressed in all tissues, and mir-138 is expressed in a tissue-specific manner. Furthermore, the experiments suggest that an inhibitory factor is responsible for tissue-specific processing of pre-mir-138-2 into mir-138 and that this inhibitory factor is specific for certain miRNA precursors. This inhibitory factor acting on pre-138-2 may be capable of distinguishing pre-mir-138-1 from pre-mir-138-2 as well. pre-mir-138-1 and pre-mir-138-2 have different pre-mir sequences, particularly in the loop region, and thus the inhibitory factor may be capable of recognizing these sequence differences to achieve such specificity. It is hypothesized that recognition by an inhibitory factor is dependent on the differences in the loop sequence, e.g., the size of the loop sequence, between pre-mir-138-1 and pre-mir-138-2. It is therefore possible that an oligonucleotide probe capable of hybridizing specifically to the sequences that are different between pre-mir-138-1 and pre-mir-138-2, e.g. in the loop region, could be utilized to block the inhibitory effect of the inhibitory factor, thereby allowing the pre-mir-138-2 to be processed.

Signal Data

The signal data obtained from the hybridisation experiment may be a quantitative measurement of the level of signal detected.

The signal data obtained from the hybridisation experiment may be a qualitative measurement of the level of signal detected.

For example, in the case of non-coding RNAs whose presence of absence is indicative of the presence/or absence of a feature of the cancer, the detection of signal, i.e. positive signal data or negative signal data may be a direct indication of the feature in question.

In one embodiment the signal data may be used to obtain a ratio of the signals obtained between the test sample and a control sample, or a matrix between the signal between the control sample and more than one of the controls as herein provided. The ratio or matrix being indicative of the feature in question.

The signal data from numerous hybridisations, for example arrays of a collection of detection probes may provide signals from hybridisations with several different targets, and it is the differential pattern of targets which allows for one or more of the features in question to be determined. Typically, the determination of previously characterised cancers can provide a dataset which can subsequently be used for comparison with data obtained from samples from a patient, thereby allowing determination of the features.

Therefore, in one embodiment, the method of the invention comprises the hybridisation of the test sample and one or more control samples to both i) one or more target detection probes, such as a collection of detection probes, which may be in the form as listed above, such as an array such as a microarray, and ii) one or more control detection probes, such as at least one normalising control probe and at least one mRNA marker control probe, or at least one normalising control probe and at least one DNA marker control probe and optionally at least one mRNA marker control probe.

or at least one normalising control probe and at least one immature noncoding RNA, selected from immature miRNA, immature siRNA and immature piRNA, and optionally at least one DNA marker control probe and optionally at least one mRNA marker control probe.

Collection of Probes of the Invention

In one embodiment a collection of probes according to the present invention comprises at least 10 detection probes, 15 detection probes, such as at least 20, at least 25, at least 50, at least 75, at least 100, at least 200, at least 500, at least 1000, and at least 2000 members.

The collection of detection probes may comprise a majority of detection probes to the target as compared to the control probes.

In one embodiment, at least 10%, such as at least 20%, such as at least 30%, such as at least 40%, such as at least 50%, such at least 60%, such as at least 70%, such as at least 80%, such as at least 90 or 95% of the detection probes in the collection of detection probes may be capable of hybridizing to the respective population of target molecules (as opposed to control-targets).

The collection of detection probes preferably comprises at least one control detection probe, and may comprise a collection of control detection probes.

In one embodiment, the collection of probes according to the present invention consists of no more than 500 detection probes, such as no more than 200 detection probes, such as no more than 100 detection probes, such as no more than 75 detection probes, such as no more than 50 detection probes, such as no more that 50 detection probes, such as no more than 25 detection probes, such as no more than 20 detection probes.

In one embodiment, the collection of probes according to the present invention has between 3 and 100 detection probes, such as between 5 and 50 detection probes, such as between 10 and 25 detection probes.

In one embodiment, the collection of probes of the invention is capable of specifically detecting all or substantially all members of the transcriptome of an organism.

In another embodiment, the collection of probes is capable of specifically detecting all small non-coding RNAs of an organism, such as all miRNAs, piRNAs, snRNAs and/or siRNAs.

In a preferred embodiment, the collection of probes is capable of specifically detecting a subset of non-coding RNAs, preferably a subset which has been selected for their ability to act as markers for at least one type of cancer, and preferably appropriate control probes or collection of control probes.

In one embodiment, the affinity-enhancing nucleobase analogues are regularly spaced between the nucleobases in at least 80% of the members of said collection, such as in at least 90% or at least 95% of said collection (in one embodiment, all members of the collection contains regularly spaced affinity-enhancing nucleobase analogues).

In one embodiment of the collection of probes, all members contain affinity enhancing nucleobase analogues with the same regular spacing in the recognition sequences.

Also for production purposes, it is an advantage that a majority of the probes in a collection are of the same length. In preferred embodiments, the collection of probes of the invention is one wherein at least 80% of the members comprise recognition sequences of the same length, such as at least 90% or at least 95%.

As discussed above, it is advantageous, in order to avoid self-annealing, that at least one of the nucleobases in the recognition sequence is substituted with its corresponding selectively binding complementary (SBC) nucleobase.

Typically, the nucleobases in the sequence are selected from ribonucleotides and deoxyribonucleotides, preferably deoxyribonucleotides. It is preferred that the recognition sequence consists of affinity enhancing nucleobase analogues together with either ribonucleotides or deoxyribonucleotides.

In certain embodiments, each member of a collection is covalently bonded to a solid support. Such a solid support may be selected from a bead, a microarray, a chip, a strip, a chromatographic matrix, a microtiter plate, a fiber or any other convenient solid support generally accepted in the art.

The collection may be so constituted that at least 90% (such as at least 95%) of the recognition sequences exhibit a melting temperature or a measure of melting temperature corresponding to at least 5° C. higher than a melting temperature or a measure of melting temperature of the self-complementarity score under conditions where the probe hybridizes specifically to its complementary target sequence (or that at least the same percentages of probes exhibit a melting temperature of the probe-target duplex of at least 5° C. more than the melting temperature of duplexes between the probes or the probes internally).

As also detailed herein, each detection probe in a collection of the invention may include a detection moiety and/or a ligand, optionally placed in the recognition sequence but also placed outside the recognition sequence. The detection probe may thus include a photochemically active group, a thermochemically active group, a chelating group, a reporter group, or a ligand that facilitates the direct of indirect detection of the probe or the immobilisation of the oligonucleotide probe onto a solid support.

Methods/Uses of Probes and Probe Collections

Preferred methods/uses include: Specific isolation, purification, amplification, detection, identification, quantification, inhibition or capture of a target nucleotide sequence in a sample, wherein said target nucleotide sequence is associated with cancer, such as breast cancer, by contacting said sample with a member of a collection of probes or a probe defined herein under conditions that facilitate hybridization between said member/probe and said target nucleotide sequence. Since the probes are typically shorter than the complete molecule wherein they form part, the inventive methods/uses include isolation, purification, amplification, detection, identification, quantification, inhibition or capture of a molecule comprising the target nucleotide sequence.

Typically, the molecule which is isolated, purified, amplified, detected, identified, quantified, inhibited or captured is a small, non-coding RNA, e.g. a miRNA such as a mature miRNA. Typically the small, non-coding RNA has a length of at most 30 residues, such as at most 29, 28, 27, 26, 25, 24, 23, 22, 21, 20, 19, or 18 residues. The small non-coding RNA typically also has a length of at least 15 residues, such as at least 16, 17, 18, 19, 20, 21, 22, 23, 24, 25, 26, 27, 28, 29 or 30 residues.

As detailed in PCT/DK2005/000838, the specific hybridization between the short probes of the present invention to miRNA and the fact that miRNA can be mapped to various tissue origins, allows for an embodiment of the uses/methods of the present invention comprising identification of the primary site of metastatic tumors of unknown origin.

As also detailed in PCT/DK2005/000838, the short, but highly specific probes of the present invention allows hybridization assays to be performed on fixated embedded tissue sections, such as formalin fixated paraffin embedded sections. Hence, an embodiment of the uses/methods of the present invention are those where the molecule, which is isolated, purified, amplified, detected, identified, quantified, inhibited or captured, is DNA (single stranded such as viral DNA) or RNA present in a fixated, embedded sample such as a formalin fixated paraffin embedded sample.

The detection probes herein disclosed may also be used for detection and assessment of expression patterns for naturally occurring single stranded nucleic acids such as miRNAs, their target mRNAs, stem-loop precursor miRNAs, siRNAs, piRNAs, other non-coding RNAs, RNA-edited transcripts or alternative mRNA splice variants by RNA in-situ hybridisation, dot blot hybridisation, reverse dot blot hybridisation, or in Northern blot analysis or expression profiling by microarrays.

In one embodiment the hybridisation occurs in in situ hybridisation of a test sample, such as a biopsy, taken from a patient during an operation. The use of in situ hybridisation is preferred when the two dimensional location of the target molecule is to be used in determining the feature of the cancer. For example, cancers are often made up of vascular cells, connective tissue etc as well as cancerous cells, the use of in situ hybridisation therefore allows a morphological distinction to be made between hybridisation in non cancer cells and cancer cells within a sample. Typically the in situ hybridisation is performed using only a few detection probes, such as between 1 and three detection probes, such as two detection probes. One or two of the detection probes may be control probes. The in situ hybridisation may be performed during or subsequent to a method of therapy such as surgery for removal or biopsy of a cancer.

The detection probes herein disclosed may also be used for antisense-based intervention, targeted against tumorgenic single stranded nucleic acids such as miRNAs, their target mRNAs, stem-loop precursor miRNAs, siRNAs, piRNAs, other non-coding RNAs, RNA-edited transcripts or alternative mRNA splice variants or viral DNA in vivo in plants or animals, such as human, mouse, rat, by inhibiting their mode of action, e.g. the binding of mature miRNAs to their cognate target mRNAs.

Further embodiments includes the use of the detection probe as an aptamer in molecular diagnostics or (b) as an aptamer in RNA mediated catalytic processes or (c) as an aptamer in specific binding of antibiotics, drugs, amino acids, peptides, structural proteins, protein receptors, protein enzymes, saccharides, polysaccharides, biological cofactors, nucleic acids, or triphosphates or (d) as an aptamer in the separation of enantiomers from racemic mixtures by stereospecific binding or (e) for labelling cells or (f) to hybridise to non-protein coding cellular RNAs, miRNA (preferably) such as tRNA, rRNA, snRNA and scRNA, in vivo or in-vitro or (g) to hybridise to non-protein coding cellular RNAs, such as miRNA (preferably) tRNA, rRNA, snRNA and scRNA, in vivo or in-vitro or (h) in the construction of Taqman probes or Molecular Beacons.

The present invention also provides a kit for the isolation, purification, amplification, detection, identification, quantification, or capture of nucleic acids, wherein said nucleic acids are associated with cancer, such as the cancers herein disclosed, such as breast cancer, where the kit comprises a reaction body and one or more LNAs as defined herein. The LNAs are preferably immobilised onto said reactions body (e.g. by using the immobilising techniques described above).

For the kits according to the invention, the reaction body is preferably a solid support material, e.g. selected from borosilicate glass, soda-lime glass, polystyrene, polycarbonate, polypropylene, polyethylene, polyethyleneglycol terephthalate, polyvinylacetate, polyvinylpyrrolidinone, polymethylmethacrylate and polyvinylchloride, preferably polystyrene and polycarbonate. The reaction body may be in the form of a specimen tube, a vial, a slide, a sheet, a film, a bead, a pellet, a disc, a plate, a ring, a rod, a net, a filter, a tray, a microtitre plate, a stick, or a multi-bladed stick.

A written instruction sheet stating the optimal conditions for use of the kit typically accompanies the kits.

A preferred embodiment of the invention is a kit for the characterisation of cancer, such as the cancers listed herein. Such kits may allow the detection or quantification of target non-coding RNAs, such as miRNA (preferably), siRNAs, snRNAs, piRNAs, non-coding antisense transcripts or alternative splice variants.

The kit may comprise libraries of detection probes, which comprise one or more detection probes and optionally one or more control probes. The kit may also comprise detection probes for mRNAs (i.e. coding RNAs), and DNA, the presence or absence or level of which may also contribute to characterising the cancer. It is preferable that the kit comprises an array comprising a collection of detection probes, such as an oligonucleotide arrays or microarray.

The use of the kit therefore allows detection of non-coding RNAs which are associated with cancer, and whose level or presence or absence, may, either alone, or in conjunction with the level or presence or absence of other non-coding RNAs, and optionally coding RNAs, provide signal data which can be used to characterise said cancer.

In one aspect, the kit comprises in silico protocols for their use. The detection probes contained within these kits may have any or all of the characteristics described above. In one preferred aspect, a plurality of probes comprises at least one stabilizing nucleotide, such as an LNA nucleotide. In another aspect, the plurality of probes comprises a nucleotide coupled to or stably associated with at least one chemical moiety for increasing the stability of binding of the probe.

The invention therefore also provides for an array, such as a microarray which comprises one or more detection probe according to the invention, such as the collection of detection probes and optionally one or more control probe, preferably a collection of control probes. The array or microarray is particularly preferred for use in the method of the invention.

EXAMPLES

The invention will now be further illustrated with reference to the following examples. It will be appreciated that what follows is by way of example only and that modifications to detail may be made while still falling within the scope of the invention.

LNA-substituted probes may be prepared according to Example 1 of PCT/DK2005/000838.

Example 1

Identification of Novel miRNAs by 454 Pyrosequencing

Experimental Methods—Preparation of a cDNA-Pool from Human Breast Cancer Tissues for 454 Amplicon Sequencing
Tissue: Five different human breast cancer tissue samples (about 200 mg in total) were shipped in RNA later on dry ice to Vertis Biotechnologie AG for RNA purification and fractionation.

Figure 1:
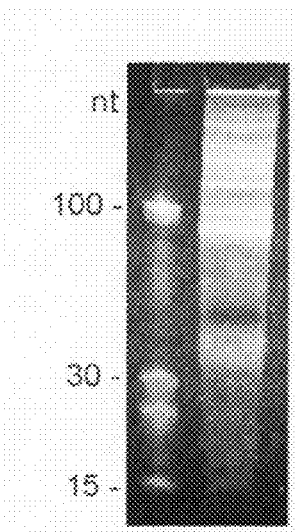
FIG. 1: Separation of small RNAs from human breast cancer tissues on a denaturing 12.5% polyacrylamide gel. miRNAs in the size range of 15-30 nt and 30-100 nt were extracted from the gel.

Preparation and gel purification of miRNAs: Tissues were ground under liquid nitrogen. RNA species smaller than 200 nt were enriched with the mirVana miRNA isolation kit (Ambion, Austin, Tex., USA). The small RNAs were then separated on a denaturing 12.5% polyacrylamide (PAA) gel. As molecular mass standard a mixture of oligonucleotides was used that range in size between 15 and 100 bases (see FIG. 1). The population of miRNAs with a length of 15-30 or 30-100 bases was obtained by passive elution of the RNAs from the gel. The miRNAs were then precipitated with ethanol and dissolved in water.

cDNA synthesis: For cDNA synthesis the miRNAs were first poly(A)-tailed using poly(A) polymerase followed by ligation of a RNA adapter to the 5'-phosphate of the miRNAs. First-strand cDNA synthesis was then performed using an oligo(dT)-linker primer and M-MLV-RNase H— reverse transcriptase. The resulting cDNAs were then PCR-amplified to about 20 ng/µl in cycle numbers indicated in Table 1 using Taq polymerase.

TABLE 1

Number of PCR cycles used for cDNA amplification, barcode sequences and size fraction of miRNA used for cDNA synthesis.

| Number | PCR cycles | 5'-TAG sequence | RNA size | cDNA size |
|--------|-----------|-----------------|----------|-----------|
| 1 | 20 | ATCG | 15-30 nt | 119-134 bp |
| 2 | 18 | CAGC | 30-100 nt | 135-205 bp |

The fusion primers used for PCR amplification were designed for amplicon sequencing according to the instructions of 454 Live Sciences. Barcode sequences for each cDNA species, which are attached to the 5'-ends of the cDNAs, are included in Table 1. The following adapter sequences flank the cDNA inserts:

5'-end (43 bases):
5'-<u>GCCTCCCTCGCGCCATCAG</u>CTNNNNGACCTTGGCTGTCACTCA-3'.        (SEQ ID NO 409)

3'-end (61 bases):
5'-<u>GCCTTGCCAGCCCGCTCAG</u>ACGAGACATCGCCCCGCTTTTTTTTTTTTTTTTTTTTTTT-3'.    (SEQ ID NO 410)

454 adapter sequences are underlined.

Figure 2:
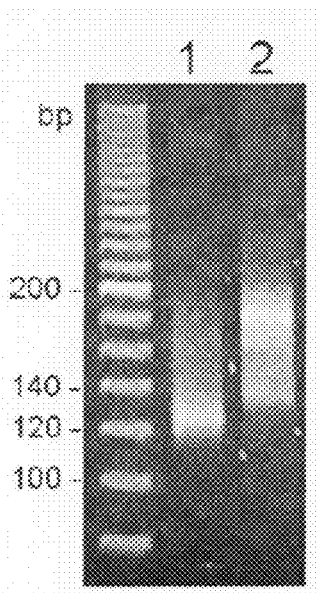
FIG. 2: PAGE analysis (6% PAA) of PCR-amplified cDNAs obtained from the 15-30 nt (lane 1) and the 30-100 nt (lane 2) miRNA fraction (100 ng each). The gel was stained with ethidiumbromide.

The combined length of the flanking sequences is 104 bases. Therefore, PCR-products containing miRNA cDNAs of 15-30 nt and 30-100 nt must have a total length of 119-134 bp and 135-205 bp. PAGE analysis of the 2 cDNAs revealed that the cDNAs were of the expected size (FIG. 2).

Figure 3:
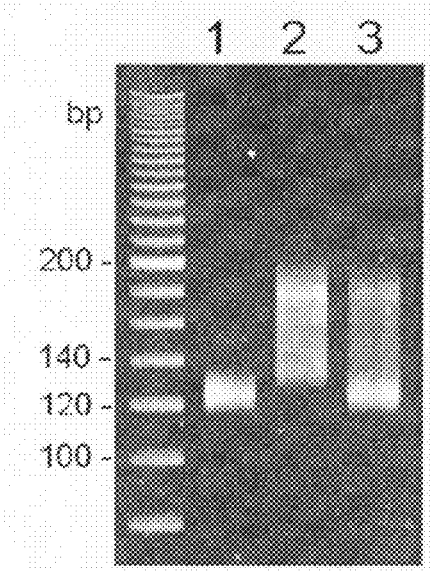
FIG. 3: PAA gel (6%) electrophoresis of the gel purified cDNA fractions containing miRNA cDNA inserts of 15-30 bp (lane 1, 20 ng) and 30-100 bp (lane 2, 40 ng) and the resulting cDNA pool (lane 3, 33 ng). The gel was stained with ethidiumbromide.

Pool formation: The correct size ranges of 119-134 bp and 135-205 bp of both cDNAs were obtained by separate purification on 6% PAA-gels. For pool formation the purified cDNAs shown in lane 1 (15-30 bp inserts) and 2 (30-100 bp inserts) of FIG. 3 were mixed in a molar ratio of 3+1. The concentration of the cDNA pool is 11 ng/µl dissolved in 25 µl water. 3 µl of the gel purified pool was analyzed on a 6% PAA gel (FIG. 3, lane 3).

Example 2

Molecular Classification of Breast Cancer by microRNA Signatures

Breast cancer is the most frequent form of cancer among women worldwide. Currently, treatment and prognosis is based on clinical and histo-pathological graduation, such as TNM classification (tumor size, lymph node and distant metastases status) and estrogen receptor status. To improve both the selection of therapy and the evaluation of treatment response, more accurate determinants for prognosis and response, such as molecular tumor markers, are needed. The primary aim of this study was to study the expression patterns of microRNAs (miRNAs) in tumors and normal breast tissue to identify new molecular markers of breast cancer.

Biopsies from primary tumors and from the proximal tissue (1 cm from the border zone of tumor) were collected from female patients (age 55-69) undergoing surgery for invasive ductal carcinoma. Total-RNA was extracted following the "Fast RNA GREEN" protocol from Bio101. Assessment of miRNA levels was carried out on miRCURY™ microarrays according to the manufacturers recommended protocol (Exiqon, Denmark).

The results from the miRNA analysis revealed numerous differentially expressed miRNAs, including those reported earlier to be associated with breast cancer, such as let-7a/d/f, miR-125a/b, miR-21, miR-32, and miR-136 [1]. In addition, we have identified several miRNAs that have not previously been connected with breast cancer.

RNA Extraction

Before use, all samples were kept at −80° C.

Two samples—ca. 100 mg of each—were used for RNA extraction:
PT (primary tumor)
1C (normal adjacent tissue, one cm from the primary tumor)

The samples were thawed on ice, and kept in RNAlater® (Cat#7020, Ambion) during disruption with a sterile scalpel into smaller ca. 1 mm wide slices.

To a FastPrep GREEN (Cat# 6040-600, Bio101) tube containing lysis matrix was added:
500 µL CRSR-GREEN
500 µL PAR
100 µL CIA
200 µL tissue The tubes were placed in the FastPrep FP120 cell disruptor (Bio101) and run for 40 seconds at speed 6. This procedure was repeated twice, before cooling on ice for 5 min. The tubes were centrifuged at 4° C. and at maximum speed in an Eppendorf microcentrifuge for 10 min to enable separation into organic and water phases. The upper phase from each vial was transferred to new Eppendorf 1.5 mL tubes while avoiding the interphase. 500 μl CIA was added, vortexed for 10 seconds, and spun at max speed for 2 min to separate the phases. Again, the top phase was transferred to new Eppendorf tubes, while the interphase was untouched. 500 μL DIPS was added, vortexed, and incubated at room temperature for 2 min. The tubes were centrifuged for 5 min at max speed to pellet the RNA. The pellet was washed twice with 250 μL SEWS and left at room temperature for 10 min to air dry. 50 μL SAFE was added to dissolve the pellet, which was stored at −80° C. until use. QC of the RNA was performed with the Agilent 2100 BioAnalyser using the Agilent RNA6000 Nano kit. RNA concentrations were measured in a Nanoprop ND-1000 spectrophotometer. The PT was only 71 ng/μL, so it was concentrated in a speedvac for 15 min to 342 ng/μL. The 1C was 230 ng/μL, and was used as is.

RNA Labelling and Hybridization

Essentially, the instructions detailed in the "miRCURY Array labelling kit Instruction Manual" were followed:

All kit reagents were thawed on ice for 15 min, vortexed and spun down for 10 min.

In a 0.6 mL Eppendorf tune, the following reagents were added:
2.5× labelling buffer, 8 μL
Fluorescent label, 2 μL
1 μg total-RNA (2.92 μL (PT) and 4.35 μL (1C))
Labeling enzyme, 2 μL
Nuclease-free water to 20 μL (5.08 μL (PT) and 3.65 μL (1C))

Each microcentrifuge tube was vortexed and spun for 10 min.

Incubation at 0° C. for 1 hour was followed by 15 min at 65° C., then the samples were kept on ice.

For hybridization, the 12-chamber TECAN HS4800Pro hybridization station was used.

25 μL 2× hybridization buffer was added to each sample, vortexed and spun.

Incubation at 95° C. for 3 min was followed by centrifugation for 2 min.

The hybridization chambers were primed with 1×Hyb buffer.

50 μl of the target preparation was injected into the Hyb station and incubated at 60° C. for 16 hours (overnight).

The slides were washed at 60° C. for 1 min with Buffer A twice, at 23° C. for 1 min with Buffer B twice, at 23° C. for 1 min with Buffer C twice, at 23° C. for 30 sec with Buffer C once.

The slides were dried for 5 min.

Scanning was performed in a ScanArray 4000XL (Packard Bioscience).

Results

Figure 4:
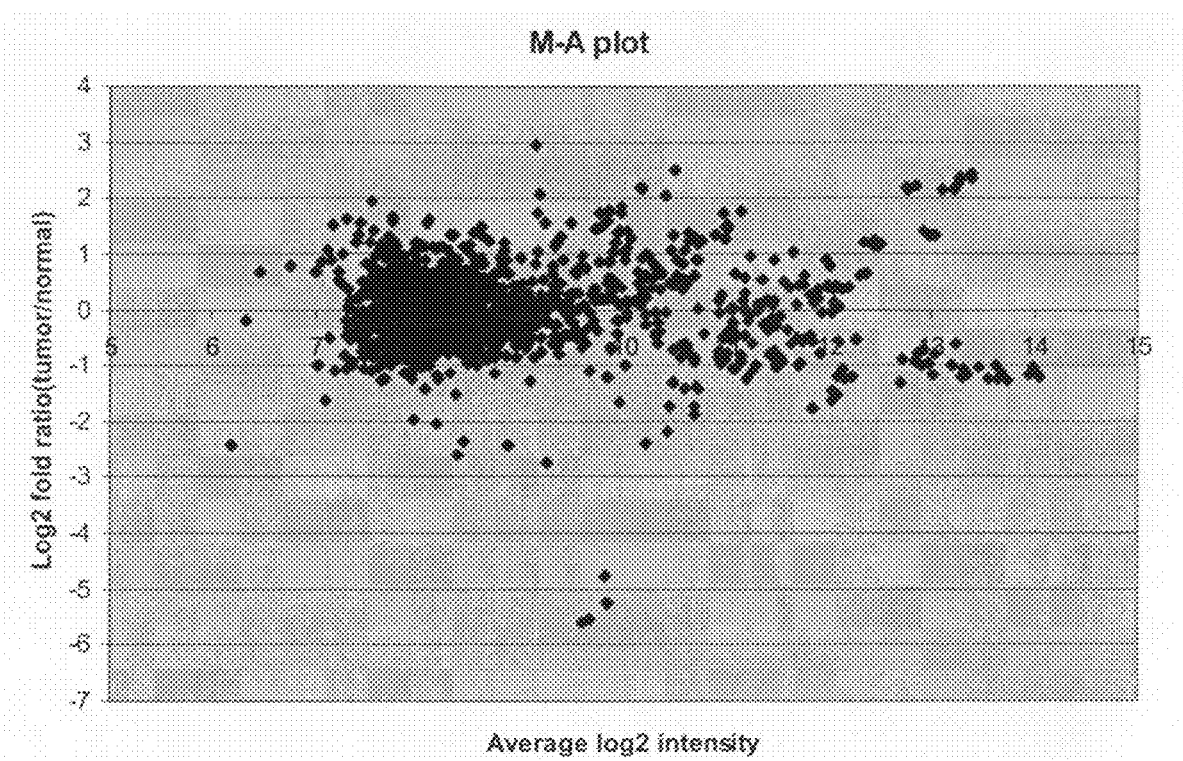
FIG. 4: M-A plot showing all miRNA signals before averaging.

The M-A plot (FIG. 4) shows the Log 2 fold ratio of tumor/normal (M) as a function of the Log 2

In this experiment, a total of 86 out of known 398 miRNAs were found to be differentially expressed between breast cancer and normal adjacent tissue.

Example 3

LNA-Substituted Detection Probes for Detection of microRNAs Associated with Breast Cancer in Humans LNA nucleotides are depicted by capital letters, DNA nucleotides by lowercase letters, mC denotes LNA methylcytosine. The detection probes can be used to detect and analyze conserved vertebrate miRNAs, such as human miRNAs by RNA in situ hybridization, Northern blot analysis and by silencing using the probes as miRNA inhibitors. The LNA-modified probes can be conjugated with a variety of haptens or fluorochromes for miRNA in situ hybridization using standard methods. 5'-end labeling using T4 polynucleotide kinase and gamma-32P-ATP can be carried out by standard methods for Northern blot analysis. In addition, the LNA-modified probe sequences can be used as capture sequences for expression profiling by LNA oligonucleotide microarrays. Covalent attachment to the solid surfaces of the capture probes can be accomplished by incorporating a $NH_2$—$C_6$- or a $NH_2$—$C_6$-hexaethylene glycol monomer or dimer group at the 5'-end or at the 3'-end of the probes during synthesis. As disclosed in PCT/DK2005/000838, It is possible to map miRNA in cells to determine the tissue origin of these cells, the present invention presents a convenient means for detection of tissue origin of tumors.

Hence, the present invention in general relates to a method for determining tissue origin of breast tumors comprising probing cells of the tumor with a collection of probes which is capable of mapping miRNA to a tissue origin. Example 4: Identification of further novel miRNAs Further microRNAs and pre-miRNAs were identified using similar experimental techniques as Examples 1-3. These are microRNAs and pre-miRNAs are shown in columns 1 and 2 of table 3, and in some cases they were found to be related to the microRNAs (and pre-miRNAs) identified from the previous examples (as shown in columns 3 and 4 of table 3). The pre-miRNA sequences and their corresponding SEQ ID number, pre-miR ID number, are provided in table 4. The corresponding miRNA sequences and their corresponding SEQ ID number are provided in table 5.

TABLE 3

| miRNA SEQ ID Column 1 | Pre-miRNA SEQ ID Column 2 | Related miRNAs SEQ IDs | Related pre-miRNAs SEQ IDs |
|---|---|---|---|
| 411 | 412 | | |
| 413 | 414 | 504 | 505 |
| | 415 | | |
| 416 | 417 | | |
| 418 | 419 | 147 | 148 |
| 420 | | 279 | 280 |
| 421 | | 447 | 448 |
| 422 | 423 | | |
| 424 | 425 | | |
| 426 | 427 | 480 | 481 |
| 428 | | | |
| 429 | 433 | 452 | 453 |
| 430 | | | |
| 431 | | | |
| 432 | | | |
| 434 | 435 | 502 | 503 |
| 436 | 437 | | |
| 438 | 439 | | |
| 440 | 441 | | |
| 442 | 443 | | |
| 444 | 445 | | |
| | 446 | | |
| 447 | 448 | 147 | 148 |
| | | 279 | 280 |
| | | 418 | 418 |
| | | 420 | |
| | | 421 | |
| 449 | 450 | 513 | 514 |
| 451 | | | |
| 452 | 453 | 429 | 433 |
| | | 430 | |
| | | 431 | |
| | | 432 | |
| 454 | 455 | | |
| 456 | 457 | | |
| 458 | 459 | | |
| 460 | 461 | | |
| 462 | 463 | | |

TABLE 3-continued

| miRNA SEQ ID Column 1 | Pre-miRNA SEQ ID Column 2 | Related miRNAs SEQ IDs | Related pre-miRNAs SEQ IDs |
|---|---|---|---|
| 464 | 465 | | |
| 466 | 467 | | |
| 468 | | | |
| 469 | 470 | 95 | 96 |
| 471 | | | |
| 472 | | | |
| 473 | 474 | | |
| 475 | 476 | | |
| 477 | | | |
| 478 | 479 | | |
| 480 | 481 | 426 | 427 |
| | | 428 | |
| 482 | 483 | | |
| 484 | 485 | | |
| 486 | 487 | | |
| 488 | 489 | | |
| 490 | 491 | | |
| 492 | | | |
| 493 | | | |
| 494 | | | |
| 495 | 496 | (429 et al. 1 mismatch) | (433 et al-1 mismatch) |
| 497 | 500 | | |
| 498 | | 541 | 542 |
| 499 | | 543 | |
| 501 | | | |
| 502 | 503 | 434 | 435 |
| 504 | 505 | | |
| | 506 | | |
| 507 | 508 | | |
| 509 | 510 | | |
| 511 | 512 | | |
| 513 | 514 | 449 | 450 |
| | | 451 | |
| | | 530 | 531 |
| | | 532 | 533 |
| 515 | 516 | | |
| 517 | | | |
| 518 | 519 | 228 | 229 |
| | | 245 | 246 |
| 520 | 521 | 239 | 240 |
| | | 273 | 274 |
| 522 | 523 | | |
| 524 | 525 | | |
| 526 | 527 | 187 | 188 |
| 528 | 529 | 245 | 246 |
| | | 518 | 519 |
| 530 | 531 | 513 | 514 |
| | | 532 | 533 |
| 532 | 533 | 513 | 514 |
| | | 530 | 531 |
| 534 | 535 | 371 | 372 |
| | | 391 | 392 |
| 536 | 537 | | |
| 538 | 539 | | |
| 540 | | | |
| 541 | 542 | 431 | 433 |
| 543 | | 432 | |
| | | 495 | 496 |
| | | 497 | |
| | | 498 | |
| | | 499 | |
| | | 500 | |
| | | 501 | |
| 544 | 545 | | |
| 546 | 547 | | |
| 548 | 551 | | |
| | 552 | | |
| | 553 | | |
| | 554 | | |
| 549 | 552 | 548 | 551 |
| | 553 | 550 | |
| | 554 | | |
| 550 | 553 | 548 | 551 |
| | 554 | 549 | 552 |
| 555 | 556 | | |
| 557 | 558 | 175 (mismatch) | 553 |
| | | 285 | 554 |
| | | 339 (mismatch) | |
| | | 548 | |
| | | 549 | |
| | | 550 | |

TABLE 4

Pre-miRNA Sequences

| Seq ID | premir id | name | PreMiR sequence |
|---|---|---|---|
| 2 | 9261 | premiR_09261 | ugaaaucaacgaaucaccuaccuaacuggguuagggcccuggcucc aucuccuuuaggaaaaccuucugugggagugggcuucgacccua acccaggugggcuguaacacugcuguguuuucuaaggggcagaguu uucuacuacuuuccgcuggcccag |
| 4 | 9252 | premiR_09252 | aggcagcucggcgggcggcgggcggcauucuggcgcggagcggagc ggcggcggcgcagcuagcgggucggccgcggagcggaggugcagc ucggcuuccccggcaccccuccccucgggcgccagcccaccccc uccgccggccgggccgaccc |
| 6 | 9183 | premiR_09183 | aucacccucugaucgccgaucaccucugagacccaacuugcucaua aacaaaacugcccaugucgguccucugcccuggaccugugacacuc uggacuauuucuguguuuauuugugcccgaguguaacaaccauaua auaaaucaccucuuccgcuguuuua |
| 8 | 9128 | premiR_09128 | auccugccuuggcuggaaaagccagccuuccacccagcgcccuaa aaugaucgggguugacuccaguuuuguuacgaaaggaggccgggcug cugagaggcucccugaguucccuucguggucgcccgucacauugcc cugcuguauacuuaauaa |
| 10 | 9242 | premiR_09242 | cagacaaagaggggcgugagggagcugccugcaggggaagaagccu uccguaucgagcuggcggcauuacacaggugcgcacagauaugg augaggaggggcgugagggagccacgugcaggggcagcaaguccucu auaucuugagcugggguggucauu |

TABLE 4-continued

Pre-miRNA Sequences

| Seq ID | premir id | name | PreMiR sequence |
|---|---|---|---|
| 12 | 9256 | premiR_09256 | accccaaagcucuccugccugcuucugugugauaugmuugauauu gguuguuaauuaggaaccaacuaaaugucaaacauauucuuaca gcagcaggugauucagcaccacccucuuucauacuucaaucucugg ggcuccugucucuuuuacugaa |
| 14 | 9147 | premiR_09147 | auugaguagggcaaauuuuaaaugggúauuauuuucaucuucaaa caggcagaccuguuauccuaaacuaggugagucagcuuuugguaca ugugaugauuuucaguguaaccaaugaugúaaugauucugccaaau gaaauauaaugauaucacuguaaaac |
| 16 | 9111 | premiR_09111 | uuggcaggaaguuuccauggccaugcagccgcagggucacccugag ugcuuuucaggguggcagggccuugccucagauggccacaagggca ccucuccuuggauacuuuaugauucugugacgccagcuacuugguu ugcuuuuguauuuuuaugcau |
| 18 | 9294 | premiR_09294 | ucuacaaaauuggugguauugguacuguuccuguuggccgaguga gacugguguucucaaaccuggugugguggucaccuuugcuccaguc aacauuacaacagaaguaaaaucugucgaaaugcaccaugaagcuu ugagugaagcucuuccuggggacaaug |
| 20 | 9192 | premiR_09192 | auagaaucaucuaaguauucagacacugcuuuccuaggaaauguua aacuccuugaggcaggcuggcuuccucaccaccuugugcacugcug cucccacaccacagugacuagcagcacauaaugguuugaauuaaag cugaaguaaaaaauauccagguucca |
| 22 | 9245 | premiR_09245 | uguagcuuaccuccucaaagcaauacacugaaaaugúuuagacggg cucacaucaccccauaaacaaauagguuugguccuagccuuucuau uagcucuuaguaagauuacacaugcaagcauccccguuccagugag uucacccucuaaaucaccacgau |
| 24 | 9237 | premiR_09237 | auuugagaaggaggcugcugagaugggaaagugucuccuucaaguau gccugggucuuggauaaacugaaagcugagcugaacaugguauca ccauugauaucucuuuguggaaauuugagaccagcaaguacuaugu gacuaucauugaugcccaggacaca |
| 26 | 9125 | premiR_09125 | ugccuaauacugacucagaugcacaauccaguuaacccagaugugu gagaucuuccggúuugaaagaacúguauuggcaaggcaaaaucaac cuauugúagaauauauuuauugúauaucagcauggggauuauuaau auugcuaauaaaaccauuauuuguaaa |
| 28 | 9234 | premiR_09234 | gggaaggauaaagggauggcaugguggggguuggaggcgugggúuu uagaaccuauccccuuucuagcccugagcaaugcuugccccagaagg aguuggggcuaggcccauuccaauccuuccagccuaagauccagac uccaaggcaugccccag |
| 30 | 9164 | premiR_09164 | ucaaucuggaggagcucagggguggccggcauucacaagaagguggc ccggaccaucggcauuucugugauccgaggaggcggaacaaguc cacggaguccocugcaggcgaacgugcagcggcugaaggaguaccgcu ccaaacucauccucuuccccagga |
| 32 | 9139 | premiR_09139 | accccauccaauuuaaucggguguuauuuaauuauacuacuauaau uguugúauuugcagguugacuguucucagggaacgcugaagguuc auaacaguagugauuugúaauugúgaggcuugagugúggaauugaa uuacuucauuagagaguaacc |
| 34 | 9290 | premiR_09290 | uggugúggccaaggccaacacugagucgaccugauggagagaagaa ggcaugúguccacuggcuccugaugaccaugcuuuggauguugcca acaaaauugggaucaucuaaucugagúccagcuugcuaauucuaaa gguauauaugúaucuuuucacca |
| 36 | 9154 | premiR_09154 | guuaaaaaaguaaaaggaacucggcaaaucuuaccccgccuguuu accaaaaacaucaccucuagcauucucaguauuagaggcaccgccu gcccagugacaugcguuuaacggccgcggúuacccuaacugugcaaa gguagcauaaucacuuguuccu |
| 38 | 9269 | premiR_09269 | gaagaucacuacaacaauuugucugccuccaaggúccucugaggca gcaggcucgggguuucgcugucccuuggaggúgúcuucugggu agagggaugggaaggaagggacccuuaccccggcucuucuccuga ccugccaauaaaaauuuaugguuca |
| 40 | 9296 | premiR_09296 | cacgcuuguggúgaaaucaggaauuuuuaggacucuuagcggúgga ucaaaaagaaaaagaaaacaggacagaguaaaaucuugcuccaaa gcuuguguucggcaaauaccgucugúgúucgaaugúgaaguugu uuccacuccucagagcccac |

TABLE 4-continued

Pre-miRNA Sequences

| Seq ID | premir id | name | PreMiR sequence |
|---|---|---|---|
| 42 | 9141 | premiR_09141 | ccgugaagaggcgggcaugacacagcaagacgagaagacccuaugg agcuuuaauuuauuaaugcaaacaguaccuaacaaacccacagguc cuaaacuaccaaaccugcauuaaaaauuucgguuggggcgaccucg gagcagaacccaaccuccgag |
| 44 | 9291 | premiR_09291 | cuuauuuacguuacuggcugaaagccugucugauaggauugacaug gagcacuaauuaaucaccuagggucuccucauuuacuaaucauauu gcacaaaacuucccugcugacugaggcucaagggcaaacugugggc uuccagccagcuuauuuuucauaa |
| 46 | 9263 | premiR_09263 | gauucaugaguagcagugacaaaccuaccgagccuggugauagcug guugccaagauagaaucuuagacaacucccuauaccagauccuc aauuaauuuuaauaaaggccuucuauuuauacuagccacaucaagc cuagccgucuacguacccacagaa |
| 48 | 9251 | premiR_09251 | gggcagaagucugagccagguguuucaucaucguucuugcucugccu cggucuguacaucugugaaaugggacucccucucuguuguggaggc ccuggggacagcggggaggacuggagggguggugggagguugugg uccuuauuagacauucagauacc |
| 50 | 9300 | premiR_09300 | ggcaagaacaaguaccuuacgaaagacagcaaaaagggagccaaga aguggcugauccauuucuuuuuucuuuuucuuuuuuugagac agcuugcucuauccccuggcuggaauacaauggugugaucucag cucacugcaaccuccgccuc |
| 52 | 9127 | premiR_09127 | caggccuuucugaaggaguuauucugcuaaaaauggucuuaguugu cugaaaagccagcucuugaacccuuucacaacaguaucaacacugg cuucucccgguucauuuuaugcgugcgagaagucagugguaacugc ugcagggcuuaauacauuagu |
| 54 | 9304 | premiR_09304 | ucacucgccaguaaccugucugcaugcaagacugggcagugacaag cacgaugugcucacugcccaagauuuugcuuugauuuuguuuuacu gcccaagaucugaacauuuuuugcaaacauagcagcuucucuaccu cugcugcauugacauauguuugaa |
| 56 | 9148 | premiR_09148 | auuuaaaacugugucuuucuguguccugaaauucucacacauggu acguuuucaaugacugauuuuguuucuccacucaaugcaguaauu gagcuucuuugguucagugcaugagugguucaguggucauugggc auccugguugagggaggggcu |
| 58 | 9159 | premiR_09159 | uuuaugguugcuacuguagguuuauaauuuguuuauaaauuuggccu aauuuccaucagccauacuaauauuggauuuuaaaaggaggcaacu uuuuuucuuuuugaaccaaaggaaugaguuagcuuugaaaacauaa uuugggauauuauaguaugga |
| 60 | 9205 | premiR_09205 | ccugcuggggguugaguucuuaaugaacauacaagugaauacacug aggcaaaaaaauuaaagcucuccaacugugggguauucauucuguu cacugugccagugguggaucaguacuggccacaccagguggccaa agagaacugcauucaucaugug |
| 62 | 9220 | premiR_09220 | ccucagccccuucagagagcgacuuucaaacucgcgcccgcgucgc ggcagcaccugggcagccccgcacgccgugcgcgucccgagcccgc ggggcagcuaccgcucggugagugucccugauucccucucucccc cucuuaucucccugcauuaggcug |
| 64 | 9182 | premiR_09182 | cugaaaaguuccagcauauuuugcgaguacucaacaccaacaucga uggggcagcggaaaauagccuuugccaucacugccauuaagggugug ggccgaagauaugcucaugguguugaggaaagcagacacugacc ucaccaagagggcgggagaacuc |
| 66 | 9121 | premiR_09121 | caugcuuuggguuuguuaccaaaauauacaguguggugaagguuga cugaagaaguccagugugguccaguuaaaacagaaauaaauuaaacu cuucaucaacaaagaccuguuuuugugacugccuugaguuuuauca gaauuauuggccuaguaauccuu |
| 68 | 9276 | premiR_09276 | augguuacuuauauggggaaggguggguaacaaggauuggacagggu uagauuagacccccucugaaggguaccuuguuuuuauaguuguaacuuuu uuuuuuuugagauggagucuugcucugucacccaggcuggagug caguggugcgaucucagcucacug |
| 70 | 9247 | premiR_09247 | cacacgauuaaccccaagucaauagaagccggcguaaagaguguuuu agaucacccccucccccaauaaagcuaaaacucaccugaguuguaaa aaacuccaguugacacaaaauagacuacgaaagugggcuuuaacaua ucugaacacacaauagcuaagacccaa |

TABLE 4-continued

Pre-miRNA Sequences

| Seq ID | premir id | name | PreMiR sequence |
|---|---|---|---|
| 72 | 9198 | premiR_09198 | ggcggcugccgaagauggcggaggugcaggucccaguccuccaugg ucgaggccaucuccugggccgccuggcggccaucguggcuaagcag guaauguugggcuggaaggugguggucguacgcugugagggcauca acauuucuggcaauuucuaca |
| 74 | 9123 | premiR_09123 | gcccaggacuccagcucaugcgccgaauaguagguacaguguucca augucuuugugguuuguagagaacaaucaacggucggcgaacauca guggggauaagguaaaauggcugagugaagcauuggacuguaaaucu aaagacaggggcuaagccucuuuu |
| 76 | 9146 | premiR_09146 | uguguagaggcggagaggagccaagaaacuaaaggugaaaaauac acuggaacucuggggcaagacaugucuaugguagcugagccaaaca cguaggauuuccguuuuaagguucacauggaaaagguuauagcuuu gccuugagauugacucauuaaa |
| 78 | 9137 | premiR_09137 | gacuaaaacuauuugaucuuuuaauauuuaauuaaugguucccccgu ggcguuuuauagucuguguucuauugugagcaacgagauuuuaau aagcagguucaggacuuuccauuguguagcaagaugucauugcuuc caugacacuaauuuggcuuucaua |
| 80 | 9186 | premiR_09186 | cacauacucaaggagcccuguuuuacagggcacuggagaacuaauu aauuugcaaugcagaaagaaugcagugacaucugaaauauuggccu cggguaucacaggucauuggaaauaguuugugacaaacuggggugg agggugggguggggaaggcaacucu |
| 82 | 9115 | premiR_09115 | gggggaggccugcgcggaggagcaccgcuuccucccgcgggaggg ggagucccgggcuccugcguccugucucccuccccggccgucgca ggagcacgaagggagugccuccucuucgucuccucggcuccccguaa cuucuccccucacuuccuccugg |
| 84 | 9203 | premiR_09203 | gucaaaagccccagagucuucacacaagccguguguaugaagcu gcauccucaggaccugggcuugggugguaggaggaauuggugcugg ucuuucauuuuggauuugacuccagccccacagccucagccaccc agccaauugucauaggagcugga |
| 86 | 9241 | premiR_09241 | gcgcggcggaggggggguggggccuuggggccgcgagugggagcg ggagcgguucugcggccuccucgggcuucuuggcccugggcggagu gggauugggugucccggcuguucgcaguggccgcgagugcggccgg accuggaguaguaccugagccgcu |
| 88 | 9156 | premiR_09156 | gagaacaugggucaccagcagggccugagaagagggagaaaauacg gaaaugugggauuggggucgcugagugcaggcauguaaguuaagug uuuggggaacagagcagugcuugacugaguguggcuggacgugagu acugagggggacaaaugagauugaucc |
| 90 | 9281 | premiR_09281 | ucgcgggucuguggcgcggggccccgguggucgugucgcguggggg gcgggugguugggcguccgguucgccgcgccccgccccggcccca ccggucccggccgccgccccgcgcccgcucgcucccucccguccg cccguccgcggcccguccgucc |
| 92 | 9124 | premiR_09124 | uuaggaagucugagaugauaaauauuucaaggucagugaagucuau caaucauucuccccuuccucaucagcaaugguagauagaaaugucc uaaacuuuucuaaauccuagugaugaggaugucugauauucaaca uaguccuuaaagugaaaacuga |
| 94 | 9171 | premiR_09171 | agcuacuuccuuucuucagccucuugcuuucuguucaaaucucagc uuuuaucacauucuuuucauggagagacaucucaaugucccuuuuc gccuaggagaagaauguuauugaguggggcucaggauuuaaaccca ggcagacuaauugguaugugag |
| 96 | 9155 | premiR_09155 | cacauacauuggcgaaaagaccaacaagucaugauuguucugaagu ucccuuuaucauguguccccuaaucucuacuaccaguaagccuuu guguuaucuuaggaugaggcaugggugguucaguguuauaauaag acgagucuaaaauggacaau |
| 98 | 9142 | premiR_09142 | uguuuaaugccugaaauccaagucuuccuccaugggaaaauacugu uauaccaaauaauucuagaugaguaacaaagaucuuuuuaggccuu cauuuuauguuuuucuuaacuguuauauuaugauugugacauaga uuauacuacuacuaauuuuuggaug |
| 100 | 9166 | premiR_09166 | cuuacggaaaaggaacagauuguuccuaaaccagaagaggagguug cccagaagaaaaagguaaauaaguaguugcucgguuuuguuuguga uaguagaaagauuuguggguugcugugaugacuaucuuaggacaccu uuggaauaacuaugaaagaaaacuau |

TABLE 4-continued

Pre-miRNA Sequences

| Seq ID | premir id | name | PreMiR sequence |
|---|---|---|---|
| 102 | 9149 | premiR_09149 | cuaggagugacucaugcagacucaagcagaaccuuggggcccaggg cagaagugugacuucaggucucacucagcacucaucagaacacuca cucaguaugcuuguaauuagaauugagugaucucauggaugaacug uacugggcuaacuugaagagcaca |
| 104 | 9118 | premiR_09118 | uaaaagcugaaaaucucaguuuaaaaaucaaaauguuaacacaaag cuaagauucaucagagcccacccuauucuaaggaaccacaauaacu uacucuggccccaguguuaaaacgaucuuucagauuuagagugacu auguaagaauuuaggauuuccucuuu |
| 106 | 9201 | premiR_09201 | ggccccgcggggcccguccgcuccuccagccgcugccucccgggcg gcgcucgccggcgcggcggcaaagacugagacagcuccgcugcccg cugaacuccauccucccggcggucgggcggcggcgcugcggucgg ucgcggcagcggcuccgcu |
| 108 | 9267 | premiR_09267 | ugccuggucaaaggcuucuaccccagcgacaucgccguggaguggg agagcagcgggcagccggagaacaacuacaacaccacgccucccau gcuggacuccgacggcuccuucuuccucuacagcaagcucaccgug gacaagagcagguggcagcaggg |
| 110 | 9200 | premiR_09200 | gugggaggucgaugaaugagugguuaauuaauuuuauuaggggu uaauuuugcguauuggggucauuggugucuuguaguugaaauaca acgaugguuuucauaucauuggucgugguuguaguccgugcgaga auaaugauguaugcuuuguu |
| 112 | 9193 | premiR_09193 | auucucaguauuggaucugcacauggagugutuuuucucucuagug uuacagaggaugaaugcauauugagauaaagaagugauuuuggtuc caaaggauuuuaaggaugaugagagaacaguggguacuucauugc caggucaugucuuugcaagaagaaa |
| 114 | 9292 | premiR_09292 | auucgugcugaaaaucucagacucauugaugauagcugccagugac aggaguaguguugccacuguaagauacgccaucuuuguuaguuacu cucaucuacucguuucuuguauucugccucuuggucaucuuugauu cucauuuaucugcaaauuuucuuggua |
| 116 | 9283 | premiR_09283 | aucaaaacacuuauccuauuaaacacagcauccaucggugaucccag ugacaaguaaaugaauguuaguucuggaguucuuuccuggggugaug gccuggagaagccucucuuuuaaggauuagauucagagguagaggu aaaugagaguugagcaccaggaagag |
| 118 | 9271 | premiR_09271 | gugcccgggagguggacuggggccuggguugugcuggaggccaggc ugaggccugccuuggutuuggggaggagaucccugcacuccggaac uccucuguggcccacggaggaucgcucugaacugccucagcguggc ggccaguggggguaggggguggagaga |
| 120 | 9136 | premiR_09136 | cuaccugaaguuuuaagagucuuggaaagucaggagugacuucugc uaaacacggggcuuuccagagucagagaagcuagcaagccuguggu uuggaccagguacuaaauauuugacaagaguaugccaggtuguaaug agcuacugucuauucccccuuuaaagc |
| 122 | 9284 | premiR_09284 | cucaccucgauccucccaggccuggguccagcaccagccuaggaa gagggugcccaugcugucuagcucuucuucgggauggggggcucc agguuccuugguauuuugcuuuggccuuuggagcccucgucaaaac ugaggaaaggugucauuuucacau |
| 124 | 9185 | premiR_09185 | uaguaaauguaggcaguuucuuuaggguuaaucaucuuucaaaggg ccuuaggaaugccuucaaacagaauauaaaugucaaagagaauau cucuuucguuugaaauuauuugggcagguugaaagaauuugauaa agggaaauucuauauuuaaucuuuc |
| 126 | 9270 | premiR_09270 | uguuguaaacaaacaaguuaagagcaagauucuugccaagagaauu aaugugcguauugagcacauuaagcacucugagagcugggauagu uccugaaauacauggagaaaaugaucagaaaaagaaagaagccaa agagaaaggguaccuggguucaacugaa |
| 128 | 9197 | premiR_09197 | ccugaagaggaagagaugacuguuggaaagcguuccccucccccau acggcagaacagcugcggcucccaggggaaagccccgcaggacag uccucgugggugugacggcuguuggguggagaagguuuggcgcccu auuuucuuaucugccuuucu |
| 130 | 9225 | premiR_09225 | gagaggaaaagucccagaccuaggacuaguuauggcaguuggagaga aagaacaucgggaugutuugaaaauaugccauugacuaucuuaacua cuguaauuuuaucauuuccaacgucaucuaacugggggacuagaaca aacugugaauucacuuucagcaac |

TABLE 4-continued

Pre-miRNA Sequences

| Seq ID | premir id | name | PreMiR sequence |
|---|---|---|---|
| 132 | 9112 | premiR_09112 | ucuuaaaaguuuuauuaaagggagggcaaauauuggcaauuagu uggcaguggccuguuacgguugggauuggugggugguuuagguaa auuguuuaguuuaugauugcagauaaacucaugccagagaacuuaa agucuuagaauggaaaaaguaaagaaa |
| 134 | 9307 | premiR_09307 | gaaggauugguuauucccgccuggagaucccacaguagggccuuugg agugauagacaucccaucucccuccacacccugcccuaccgcccc ccaaccccaaagcuucaacaaaggcuccuuuuuaaaguuuuccgg ugcccuuugcucuuuguuugccuu |
| 136 | 9295 | premiR_09295 | cuucaaguaugccugggucuuugcauaaacugaaagcugagcgugaa cguggauacaccauugauaucuccuuguggaaauuugagaccagca aguacuaugugacuaucauugaugcccaggacucagagacuucau caaaaacaugauuacagggacauc |
| 138 | 9120 | premiR_09120 | uggauuucgcccccgcucccucccggaaacuccuccuggugccugc gaccguucucacugagcaugugcagacggcggugcgcaugcucugu ugcggccgcuucgguuucuguucgggacccggggugucuccuag cgcaaccggaacuagccuucugg |
| 140 | 9153 | premiR_09153 | cacuguagcauaagcaagggcuuaguccugaacugaguuacagcu uuauuuucuuuugauucagcauguuuuuaaugauccauaaguuaa aagcugcugguguuuuauuaaagcugccauuuguuacuaaccagg cucugugugacuccuaaguggaa |
| 142 | 9116 | premiR_09116 | agccacaccccagcagugugcaagggaucagacacaaggguugaauc caucacaaaagcagaaucaccauggcaacugcauccuuugauucuu gagugugcccagcaaccugagcagaggcgauaguugaagugaacca aguucuccugagaaauggaggga |
| 144 | 9312 | premiR_09312 | aguccgugcgagaauaaugauguaugcuuuguuucuguugagugug gguuuaguaaugggguuugugggguuucuucuaagccuucccua uuuauggggguuuaguacugauuguuuagcggugugucggguguu uauuauucugaauuuuggggagguu |
| 146 | 9221 | premiR_09221 | aggaagggaaacucaacagcaggacuucagaaagggccuugugu uuauagcuuugucaaguaaauuggacgcagcuggagcacaggccc uguuuguuugcacauaauaaucuuguuuaucacuuuaaaaaauuca guaauaucucagcagucagg |
| 148 | 9151 | premiR_09151 | acucccugacagauaucucccucuuccauuucaucaagacccagcu gagucacugcacugccuaccaaucucgaccggaccucgaccggcu cgucuguguugccaaucgacucggcguggcgucggucgugguagau aggcggucaugcauacgaauuuucag |
| 150 | 9157 | premiR_09157 | agggacaaugccauauuuauccuucuagcccugacaccucacacaa ugcagagaacggaagggaguucaauaacugguagcaaagugccaac uccuugagaauagggccuguguuuagugaguauuuguuaagagaau gaauaaaugaugUacaguugua |
| 152 | 9305 | premiR_09305 | agcauuugaggugaugauggauucugugguuugagagcaacgcc auugccuacuaugugagcaaugaggagcugcggggaaguacuccag aggcagcagcccagguggugcagggugugagcuuugcugauuccga uauagugccccagccaguaccugg |
| 154 | 9309 | premiR_09309 | acaaggauggaagaggcccucgggccugacaacacgcauacgguua aggcauugccaccuacuucgugcaucuaaccaucguuuuuuuuuu uuuggguguuuguuuuuauuuuucuucagacggagucuuauucug ucgcccagacuggagugcaauggcgcg |
| 156 | 9239 | premiR_09239 | uuuuauaaccauagaguggagacagucaguaugaccaccaaaccca ggagccauauauuaaaaauacugauaaauuuaacuauauaaaaaaau uuugccggguggcgguggcucacaccugugauucuagcagaaaauc agaucaggagaucacagaagguc |
| 158 | 9177 | premiR_09177 | guccucccacuggccgcacucugugccccauggccuccucugcgccc cgcccggcgucccucacggccucgucugugcugagcuugggaa cucuuguucuuaccuccacagagucuguagaagaggcgacaccagg gcuuccaaaugaacaaccgaaa |
| 162 | 9122 | premiR_09122 | ucauuucgccacagucuuuuuuguugaagcaaguuagcaagcacu aagcacaucuacaaucaaggagaggggcaggcuuuaccuuuugaag gaagaaguaugaaagugaucacugacugaucaaguagagguaagc aguggaggacacucagaauaccuuuu |

TABLE 4-continued

Pre-miRNA Sequences

| Seq ID | premir id | name | PreMiR sequence |
|---|---|---|---|
| 164 | 9275 | premiR_09275 | acuaauaagcuacaaaacauuuaaaugacuagugucugugugugcu ugcuaguauuauuauaccaucagaaaguaaaaauggacauacaugu uaugcauuaaacccacaagagagaaaacuugaggacugauuaauuu aaguaguaaaugaauccaagaa |
| 166 | 9259 | premiR_09259 | ccuaaaauucucaauuaggcuauaaaugcaagaugagcugaaggga aauaggugauuuccauucuguagugu guauauaugagguuuuauuc ucaugacaagaaacagacuaugcaaaucucuuuaauuucuggcauu ucagcuuucuagaauua |
| 168 | 9248 | premiR_09248 | gggucaauaguacuugccgcaguacucuuaaaacuaggcggcuaug guauaaauacgccucacacucauucucaaccccccugacaaaacacau agccuaccccuuccuuguacuaucccuaugaggcauaauuauaaca agcuccaucugccuacgacaaa |
| 170 | 9191 | premiR_09191 | aaccagaacguggu uugccugaggcuguaacugagagaaagauucu ggggcuguguuaugaaaauauagacauucucacauaagcccaguuc aucaccauuccuccuuuaccuuucagugcaguuucuuuucacauu aggcuguuggu ucaaacuuuuggg |
| 172 | 9172 | premiR_09172 | gugugu guauauaugu auacauauaugu auguguauguguauauag agagagagcugagaguuauucuauuuauuccuuuucucuccuaauc ugaaaauggguguucuguauuuugggugg aagaggcauagaagggg augugu guugucucuuaagauu |
| 174 | 9199 | premiR_09199 | agacagaaaucaggacuaagu ccucugcuucaguuucauuguuaac gggccuuauucugaucucaccugucgcguagcucuaauauucacau aaacugaaauaaaggaaguggaaugaggagcuuugacauucaaauua ugugau guaauuuaucuucc |
| 176 | 9160 | premiR_09160 | uaugu guaagauagaaugaauauugagcaggaugcuuuaaaaguga ccaagcagauuugaaaaacauuaaaaaaguuggccuucucguccca guucuucccaaaguugagaaaagcugggu ugagaggaugaaaagaa aaaaaagaaaaauuuagugga |
| 178 | 9272 | premiR_09272 | gaaaauaaaggcaccugaaaagaaacuacuacuuuaacacugcugu gggaggccuuugcuuuauaagaaaaauauuauuagcuaugggaaag uaauguucuuuauguaaagacuuaaaaauagacuaauaguuuacag aguuauuauauaaaaauacgauguga |
| 180 | 9279 | premiR_09279 | aauccccuguuugcuucagggcgagaugu gugacagaggu ggcauca agcucuuacagucccaacccuccaacggaaaugggcgaagaucuca ggaauggcaucggucacaggaaaucgauaguggcuggcugcuagca uggccacuuggggcuuaggcag |
| 182 | 9236 | premiR_09236 | ggaaguuugggauaguaaaguuuguugccuuugugucuugugucuu uuuuccuuuucuuccuuucuuggggg agauagauagauagacagac agacagacagacagacacagagagagagagagagagagagagacag auaguguucauggauccugu |
| 184 | 9143 | premiR_09143 | guaaaaugaaaucacaguggu augggccucauggggguuaucgaaag aaugggcugaggcaugu gggccaugggcuuggu acaguccugag acauaaugaauacucaguucccuggu ggucuaguggu uagaaaaau aauaauaauaauaauaau |
| 186 | 9298 | premiR_09298 | uuuagaaguuucagucgcacacuccuacccgggu cggaguuagcuc aagcgguuaccuccucaugccggacuuucuaucuguccaucucugu gcuggggu ucgagacccgcggguguucacugacccuuuuaugcaau aaauucgguauaaaucugucacucuga |
| 188 | 9260 | premiR_09260 | gggcagccgug gggcguggaagccgcgcagaggccaaggcugcggg guucuucgucgucuacaggcuuucgcggcucagugu ggaaaacccg ccguuccucgcgccccacgu ccgacccaggccuccugggcaccu ucggggaggccgcgaucucgg |
| 190 | 9228 | premiR_09228 | guggcgucgcgugu gaggcgcgugcagggugagugugaguggacgc gugagugugugagu gugcgcgcuuggagcgcguguuaggcgagugcgu gcgcccacccgucgcccccuccucccgcuuacacuuugaucuuauu ugaucggaucgugaccccagccccgc |
| 192 | 9219 | premiR_09219 | gggcuagugu guuugugu uuccauucuaagauuugagucuggcaguc ccuguuuuuugcauggggu aacugcucuuugauuuuuuuaauu gcaguauuugu gugauugcaauaauaaaguuuggu uugguuuuuac agucaugcgcagggacgauccuug |

TABLE 4-continued

Pre-miRNA Sequences

| Seq ID | premir id | name | PreMiR sequence |
|---|---|---|---|
| 194 | 9244 | premiR_09244 | agcccagaaccccucucaccccagaaccuuccuugacuucugccag aguugagcagccggcccucgguaggcgcaugugaguggaugugg cacaugugggcccacuggaucugguggaugugucgcgucuggcccc cuggaucuggugggugugggc |
| 196 | 9180 | premiR_09180 | gugguauuugugauuugguuaaucuguauaaaaauuguaaguagaa agguuuauauuucaucuuaauucuuuugauguuguaaacguacuuu uuaaaagauggauuauuugaaguguuuauggcaccugacuuguaaaa aaaaaaaacuacaaaaaaaucc |
| 198 | 9288 | premiR_09288 | ugguaagaaacuggaagauggcccuaaauucuugaagucuggugau gcugccauuguugauacgguuccuggcaagcccuugugugguugaga gcuucucagacuauccaccuguggguucgcuuugcuguucaugaucu gagacagacaguugucguggguguugcau |
| 200 | 9306 | premiR_09306 | ccccgcucaccuccucuauccccacaguguacugcugcugcugcuu ggccaacguuucacugccuggcaucgggggcaccauuccugaguc aaaccuuucuucacgugaacguggcugacaucgagagccuggagg uagagguguccuaugugggccug |
| 202 | 9287 | premiR_09287 | aguugcgacaagacagaguuggagaauagaggagguucagaguugg aagaaaugggaguaggugauggcaacaccgaguugucagagugagc ugaggcaacauccucuacuuucagcucacugaugaaaauauccagg auagcgggucuggggguccagu |
| 204 | 9258 | premiR_09258 | cagaguggaccggcagcucccagacuugaggcggaggggccgcgg gccggagcucccugcagccgcuagccugggaagacuggagugcgcu gccaccgagggcugcgccgcgccggccgccccgggccgcuuugu gcgcgcccgcgcggucuguac |
| 206 | 9299 | premiR_09299 | cagaacccaccaaccagaacguggguuugccugaggcuguaacugag agaaagauucuggggcuguguaugaaaauauagacauucucacau aagcccaguucaucaccauuuccuccuuuaccuuucagugcaguuu cuuucacauuaggcuguuggguucaaa |
| 208 | 9285 | premiR_09285 | gcucuuucucuucccucucguuuaguuugccuggagcuugaaagg agaaagcacggggucgcccaaaccccuucugcuucugcccaucac aagugccacuaccgccaugggccucacuaucuccucccucuucucc cgacuauuuggcaagaagca |
| 212 | 9187 | premiR_09187 | acuuguucccuaaauagggacuuguacgaauugcuacacgagggu cagcugucucuuacuuuuaaucagugaaauugaccuaucugugaag aggugauauaaaaaauaagacgagaagacccuauggagcuuuaa uucauuaauacaaauaaaaacucaaac |
| 214 | 9194 | premiR_09194 | uggacacagaagaaacgagggagcccgggucuccuccgagugugca acaagcuggccuggggccccccgaaaggacgcuggagagaagccca ggaucacccagucuuugcagcagggugcaggcuggagucccccca agggcggcuagaaucagguccagg |
| 216 | 9204 | premiR_09204 | ugugucuuuuaaacuggaaaaucuucuagcauguuuggguuguuaca gaguauauuuugucugcagcuguuuugucccauccuaagagg aguuuauccauccugacuuguagcugugugacuucuugcagugccc ccaccccauccccccgggagag |
| 218 | 9212 | premiR_09212 | cagaagugacuuuacuuucucaaguuugauacugaguugacuguuc ccuuaucccucaccccuucccuucccuuuuccuaaggcaauagugca caacuuagguuauuuuugcuuccgaauuugaaugaaaaacuuaaug ccauggauuuuuucuuuugca |
| 220 | 9303 | premiR_09303 | cguucuccgcacuccugcuccgcgagggccccuucgaggcggcuga gacccgagugccgacucccgccgcuggagcggggcucggguucgg cagccggaaggaggugugcccccggggcgcuugggggcgccugagg ucccgaggggaggcaagauggga |
| 222 | 9218 | premiR_09218 | agaagaaaacaaguuaauuugaagagagucagaaagcgugagugu cagagccuacugagcccuggaagucacggauaaaaacaagaaguga agucaacacucucggugagaaagggagcgguacugacaaacuucua ccaucccagugugcccgguugcuccc |
| 224 | 9144 | premiR_09144 | cccuccggcgcgguggguggcgccucagcggguggcagcaugg ggcggggaggguguccccuccgcgccguu~aaaugaaacucuagug gcuggagucccggcagagcuugagggcaguuggugcggucggguug guucuuacaccccggcgggagc |

TABLE 4-continued

Pre-miRNA Sequences

| Seq ID | premir id | name | PreMiR sequence |
|---|---|---|---|
| 226 | 9262 | premiR_09262 | aagauucaugaguagcagugacaaaccuaccgagccuggugauagc ugguugugccaagauagaaucuuagacaacucccuauaccagauccu cuaauuaauuuuaauaaaggccuucuauuuauacuagccacaucaa gccuagccgucuacguacccacagaau |
| 228 | 9211 | premiR_09211 | gccuguugagaaagaccucggggcccguuggagauggcuggcag aaugguucucuugaugagcuucaugauaaagcagacuugccaauaa uaccaagagagaagacuggcucuacucuccaaaggaguccagggac agagagucagacagaugacaucagaag |
| 230 | 9301 | premiR_09301 | cggcccuguccugcggggguccggucgcggaggcggcggagggggcg cggggacacucccaccuccacugucgcccgucggccccggugc cuuuucucgccucgcgcacagcuccccgccgcagggcugagagag agaguggccgucuggugc |
| 232 | 9231 | premiR_09231 | agaaauaauaaugcaggguuucuucaaaauaugguucuggacagug gauuauaguuaccuggagagcuugguguuaaaauaucugaggaugau uccaaguaccagggcuuauacacaggaauacuugagaaccacugca cucaagcauuuaaaauuuuccu |
| 234 | 9240 | premiR_09240 | uccuagggcuuugacaccaaaaucuacuaugaugagucaggcuagg cuauaaacuugcaaggacuuagagcccagaaagugacaagcccaac uagccugccucuuggaggaaaaaagaagaauagcucaaaacacuua agaagguaaggaguccaagc |
| 236 | 9190 | preiniR_09190 | gggaggguggacaguccuuaacugcucugcaggyccaggauguuaa aaggggcagggacaacaaaugggugaccccaaccucaaccugcug cuucucucuccagucccaugugagagcagcagaggcggucuucaa cauccugccagccccacacagcua |
| 238 | 9145 | premiR_09145 | uaggucuguuauuuucacauacacuugguaacucagacuggucuga auauaaaguagaaauagcuaagaaccauuuguaaugaaugcaacuc uuauuuguuuuuaaugguguuuuaaggacuuaagggguauuagaacu gacaacaguuuauucaguuaagc |
| 240 | 9255 | premiR_09255 | accccaaagcucuccugccugcuucuguguauauguuugauauu ggguuguuuaauuaggaaccaacuaaaugucaaacauaauucuuaca gcagcaggugauucagcaccaccccucuuucauacuucaaucucugg ggcuccugucucuuuuacugaaccuc |
| 242 | 9131 | premiR_09131 | auccguuuuggaaccugcgucuggggcuccagucgcugcucuugcu ggcguccaucgccgcucggacggccgugcauuuucucgucucacg caguucgaggaggacccuagaaagccaggagcugugauugacagua gcuguagguuaccagacggcaac |
| 244 | 9129 | premiR_09129 | uacauuuuagggugguagagcuacuccuuacuuuaaaugcuaccua cucacugugacacuguuuaauaaaugguuauugacuagagaaguag ggaucucugucaccuagcauucaagucagucagucaucaguuuuu guagguuaucucagaagcaauag |
| 246 | 9208 | premiR_09208 | uucuucuucagcaaacauuaggagaguaucuucucuguuuuggcca uguguguacucacagccccucacacauggccgaaacagagaaguua cuuuccuaauauuugccuccuuggagugucucaaguccuggaagca agagauaauaagcaauuaauauaca |
| 248 | 9232 | premiR_09232 | cccgacagaucgacuauguugaucuaacuuuucuaagccaguuucu gucugauaugccaguugagcagcuccuuugcccagcuccccugg gcaucuagcugaugggagcucauuuuucuguuuuuucauuucaggu uuauuguuggccaaaaccaggcuuu |
| 250 | 9109 | premiR_09109 | gggucauggaccagcgccucagugcauuagucauucgcuuuuccuu acagacaaaucagauaacucuucccagugauugucaaaugauga auguaucucuguaaaugugguuuugacaugucacuguuacugaagg agaguauggaaucccacagga |
| 252 | 9179 | premiR_09179 | ggugaggcccgcgcugugguccggcugcggucggccgcgcucga ggggucccguggcgucccuucccgccggccgccuuucucgcgc cuucccgucgccccggccucgcccgggucucucgucuucucccg gcccgcucuuccgaaccgggucgg |
| 254 | 9308 | premiR_09308 | gccagcacccucugucucuuuaugcaaucagugccaggugggag ggaugcauucuguccaaugacaugcaggcacuuuagagggcuugca uucauucccaagccagcggcacacuuuauacauccuuggcugguc auugaggggaacaccggag |

TABLE 4-continued

Pre-miRNA Sequences

| Seq ID | premir id | name | PreMiR sequence |
|---|---|---|---|
| 256 | 9249 | premiR_09249 | accgcaacucccuuccccacuuucccaaacgggaggcgcuagccauggaacauggcacauccagggcuaccuccucccaaguuaccagaggucauguguacaagcagcaauucuaacaacagucccucaggcgugagcggcauuuuacaguuugcaa |
| 258 | 9246 | premiR_09246 | cuuaccuccucaaagcaauacacugaaaauguuuagacgggcucacaucaccccauaaacaaauaggguuggguccuagccuuucuauuagcucuuaguaagauuacacaugcaagcaucccgcguuccagugagaguucacccucuaaaucaccacgauca |
| 260 | 9226 | premiR_09226 | cagagcaacuggcuccuggcagcugugcuugucguuccugucagagugaucccagguuuccuccuggcccgucccauggucccuccacaggagugugagaggauggggaagcacugugggaagaccaccaaagauggcuggacaguggagagagcacguu |
| 262 | 9282 | premiR_09282 | caggacggccgccaucuugcgcgcagcuggagucggugccugagguugcagccgagagugugcgccagcccgcggcccagccgaagcucuuucccgccgcucuccgcgccucgcccagguucagcuccgccugacccuccgcuuggcacggucccug |
| 264 | 9184 | premiR_09184 | guuggcuuuuccagggccagcgugagugguggaggccagcucucucagugaccaucagagacaaggccuuggccagucccaggggcuuggggcuccacuuuucugaauuaugaaauguugagguguuuacccgucaauauauauacauuuauauauuuuuuugu |
| 266 | 9264 | premiR_09264 | agauucaugaguagcagugacaaaccuaccgagccuggugauagcuggugguccaagauagaaucuuagacaacucccuauaccagauccucuaauuaauuuuaauaaaggccuucuauuuauacuagccacaucaagccuagccgucuacguaccca |
| 268 | 9162 | premiR_09162 | gaagcccaaguuugaauugggaaggcucauggagcuucauggugaaggcaguaguucuggaaaagccacggggaugagacaggugcuaaaguuggacgagcugauggauaugaaccaccaguccaagaaucuguuaaaguucagacuucaaauaguggcaa |
| 270 | 9227 | premiR_09227 | cucucagcucugcagcugucugcgguggggggaaggguuggggggugucuggaggcauguccccucaccaccccgugggucucagggaggccgggugugaccucaucuuucucauggugcuauccuggugcuauugggguggggagcucccuccc |
| 272 | 9206 | premiR_09206 | auccuuuagcacguuuggauaaaguuggccuucuagguuguggcauuucaacugguuauggccugcugugaacacugccaagcuggagccuggcucuguuugugccaucuuuggccugggaggauuuggaucgggguuaccaugggcuguaaagug |
| 274 | 9254 | premiR_09254 | ucucuaauuagcuuucccaguauacuucuuagaaaguccaaguguucaggacuuuuauaccuguuauacuuuggcuuggguuuccaugauucuuacuuuauuagccuaguuuauaccaauaauacuugacggaaggcucaguaauuaguuaugaauaugg |
| 276 | 9134 | premiR_09134 | cauuaauuagguaauauuuuccucauuucuuuacugcugccauuuuccuuaccaguauuccagagauggucauagcucauuacucuaccaccaagaaccuaaaaggaauuagaauacagcagaauuggccucagugaagagcuuaaaauuguucuccucgua |
| 278 | 9289 | premiR_09289 | ugauauuacucaccauugauaccucuguuuggaaauuugagaccagcaagugacuaucgcuguugccuuaggccacagagacuuuaucaaaacgugauuacagggacauaucaggugggcuguguugccugauuaugcugcuggguuggcaacuuug |
| 280 | 9152 | premiR_09152 | acucccugacagauaucucccucuuccauuucaucaagacccagcugaguccacugcacugccuaccaaucucgaccggaccucgaccggcucgucuguuugccaaucgacucggcguggcgucggucgugguagauaggcggucaugcauacgaauuuuc |
| 282 | 9238 | premiR_09238 | auauaaaaacauuaggucaagguacagccuaugagguggcaagaaaugggcuacauuuucuauauccggcaaaucucacaacaaccuuuaugaaaucuaagggcucaaggaggauuuaguaguaaaccaagcgcagagugcuugguugaauaaggccaugaa |
| 284 | 9158 | premiR_09158 | uuucauuucugugauuauuuuaaauuagcuucuguguaaacucacuaacuuguccacaugacaauuuauagcaguccaaagauuuuuuauagccaugguuguuauaauuugacgaugcucaaggcuguuguuugcauuguucuucagaauuucaucuu |

TABLE 4-continued

Pre-miRNA Sequences

| Seq ID | premir id | name | PreMiR sequence |
|---|---|---|---|
| 286 | 9168 | premiR_09168 | cauuacacuccagccugggcaacaagagcaaaacucugucucaaaa aaaugaaaagaaaagaaaauaccuccauggggccuucucuucccag uucuuccuggagucggggaaaagcuggguugagaaggugaaaagaa aaaacaaaccuugacugggc |
| 288 | 9175 | premiR_09175 | ggaguagcuguaacauuauguggaaagcaaguggggagaaucaugaa aaaaaauaaucccauagauggagaagaauagaaagaaggaaaggag cauugccuaguguugguuauugaugguuaagcucagcuuuuauuua uucaauaggccugcagauguagacu |
| 290 | 9216 | premiR_09216 | uguaggauuuuuuguuuuuguagcuaacuuauggauugagauguga ucaaaggcuuuauuaaaauuuguacuucagcauauggcugcguu cugcauuucauuccgccauaugccuggaccguucacacuugggguau cugggcuuagggagcauguaggcuuc |
| 292 | 9117 | premiR_09117 | ucuagcucuguuauaaagaaaacauuuaggaaauucucucuuucuc ucuuucaccuauccuacuuuuugugugucccuuuguaguuuugcacc aucauuccuaacgaauuuauuuggcauuuggaagauagguuagcaa aaauuuuacuauauuugaaaggcua |
| 294 | 9167 | premiR_09167 | ggucaccaggcugagaaagcaggagaugcuacugcugaggaacugu cacuugucauuucaagguccacuccuccacccucuggcagcaugag ucgcucugaaagauuuugaagcugggacaggagaggugagugagg ugaggccuccgcaugccagguuuuc |
| 296 | 9126 | premiR_09126 | auucaucucugguuuucuugccaccucugggagucccauccau uuucauccugagcccaaccaggcccugccauuggccucuugucccu uggcacacuuguacccacaggugaggggcaggaccugaagguauug gccuguucaacaaucaucaugg |
| 298 | 9274 | premiR_09274 | uuuuacauaaguagacacaggugggaaacuguuuagacgggcucac aucaccccauaaacaaauagguuuggguccuagccuuucuauuagcu cuuaguaagauuacacaugcaagcaucccccauuccagugaguucac ccucuaaaucaccacgauga |
| 300 | 9140 | premiR_09140 | acuguuuauaagucgguguuguaaaucugaugugaauuuuguuuc uuuuucuuagauuuuugccuuuaugacgacagcuugucauugguug caguuugggucuggcuuuacgaagauggcgaccguaacacuccuua gaaacuggcagucguauguuag |
| 302 | 9135 | premiR_09135 | aguaggcaacugaggacugauuucucagggugauuagaaaggaaag gguggcggccuccuuucauacuucggaaagucuuguucccaucagc cuuccucaugguugccauaacuggaauggcggcaaggucccucuuuc cugugccugucuuaaguuucugg |
| 304 | 9176 | premiR_09176 | gcgccccaaagugucccuccugcugugacuuucuagccaagaaga cauuucucccauggccaagugaucucugauagauccuguaggacca cugaagucagacaggacaaguugagcaggggccugugugugccagug cgcagcaugcuuggggagugaca |
| 306 | 9178 | premiR_09178 | uaacgcaugcgcggggagggcggagcugggcguugccguggcuacu gggaacgcauuucacgggggcggggcguggcuuccggggcggggcgc ggccgccggaagugcguggccgcccggggccauggcgacacucagc uucgucuuccugcugcugggg |
| 308 | 9207 | premiR_09207 | ucgauggguguucuuuuaaaaauacgguucuaagucuaagucuaaca uucgguguaucuaaccgaauguuaauugauggagacaaggugauac ggguucagaaaauagaauucagaaaagaaaaggaagaauuggcaaa auucagaaaucaauuuuuaagaaaaau |
| 310 | 9163 | premiR_09163 | cccacggauucgccccgccgcgccucuccgcgcguagauuggccgg agcgaggcgaacgggcccggccuuggguagccgccgaccgagcgcug gcugcccuggaaccuaggcggcggcgggagcccggggcgccucgcggca cggaagagcggcgagaug |
| 312 | 9161 | premiR_09161 | ccuguucccccaaaacccaaggacacucucaugaucucccggacc ccugaggucacgugcguggugguggacgugagccaggaagaccccg aggucccaguucaacugguacgugguggcguggaggugcauaaugc caagacaaagccgcgggaggagc |
| 314 | 9273 | premiR_09273 | cuccgugcuaccaucacaccacguccuaaaaguaaggucagcuaaa uaagcugucaggcccauaccccaaaaauguuggguuacauccuuccu guacuaauuaaccuauuagcucagcuuaucaucuacuuuacuauuu cuacagguacccuuaucacaaugc |

TABLE 4-continued

Pre-miRNA Sequences

| Seq ID | premir id | name | PreMiR sequence |
|---|---|---|---|
| 316 | 9133 | premiR_09133 | uggaaaucacagcaacccauugaaaacugcccuccccaccagaacgugcuacguucuuucuucaugccuaugugugcuccauuccucauuucuacuuggcucaagaaaacauuucugcagucaggugagacuuuuacaaaagaggagaaaaucaaugccuc |
| 318 | 9210 | premiR_09210 | cugaucauaguauucugucagauaaugccuaagaaugaccgcugaagaacguugacccauuugaguacccggucucagucgucauuuuaaguccagugagcauugugguaguuguucuuagauugcaguuucuuauguuuugaguuugaaguugauuuuca |
| 320 | 9113 | premiR_09113 | aaagucuuagaauggaaaaguaaagaaauaucaacuuccaaguuggcaaguaacucccaaugauuuaguuuuuucccccccaguuugaauugggaagcugggggaaguuaaauaugagccacuggguguaccagugcauuaauuugggcaaggaaagug |
| 322 | 9268 | premiR_09268 | cuccaggucaucaucagugugguauuaucuaugagaacuugagcgacagaguauuccuugaugaauuuauagaucauuugagauguugaguuacuuuuguuuuguuucaaauagguagagacuauuaauguaaaaaaacaagaaaggaaaaugaaaugugc |
| 324 | 9114 | premiR_09114 | cacccccgugccuuuugaucuagcacagacccuucaccccucaccucgaugcagccaguagcuuggauccuugugggcaugauccauaaucgguuucaagguaacgauggugucgaggucuuugguggguugaacuauguuagaaaaggccauuaauuugcc |
| 326 | 9189 | premiR_09189 | cccucuggcaugguucauuagggccaauuaauguggcuggguuauuugcaacuuaaacuggggauaaugucgcuugagggagcguuucguuuuaggaaauauuguuuugguucggguuugaaggcagcugucaaaaagcggcauggaaauucauugg |
| 328 | 9181 | premiR_09181 | gagcuaguaccuucuccccuuagcaacuuccucauucuaaaauggggguggcagaaccauuguuuggcuccaguuguccucagaaagguggcuuccagaugccagugacugcuggugagugcaggcugcuucaguauuuccuggccagcugacaagguguua |
| 330 | 9278 | premiR_09278 | acauaaaaucuuaucuaugugcagcaugacucucuccaggugacagaaagggcucuagacagcugagaggaccugaucauguagggagggacggggaggggagccaggacccaggagcugcauggcuguaagaggaagguccuuggaggguaucagcagucuca |
| 332 | 9188 | premiR_09188 | ggaaccugcuuggacaagucuuucuggcucgaccucgacaugcuccaucggaugaauuguugguguuuagcccugcggccccacgcaccaggguaagagagacucucgcuuccugcccuggcccgagggaccgacuggcugggccugccuucugcccagcucacc |
| 334 | 9280 | premiR_09280 | cuucaggaguugguguguugacugggagugaauugacggaagggaccaugggaauuuauauaucauuuugaaacuuaugaaaccuuuugucaaaguuucacuuucugacucaggcucaguccaggacauuguucaaucccccuggguguaggcauca |
| 336 | 9233 | premiR_09233 | ggucaacaaggugagucuggaugaggggcagggaugccaggcaagugagcaggucugggagucaggccuugcucaggcccuguucuuccccuugcagcuucugucuggccccaaagagaccccugcugcccagagccccaccagaggccccucugacaccaaga |
| 338 | 9224 | premiR_09224 | cuguguuguguccugacaccuccaaguucuagggccgucaggacacgggaggguuuggggacagaguguccuuccucuguccucucaucccaguccugauggccguuggugagugucuggugcccugguggccugccccagcucucuuggcuuucugagcag |
| 340 | 9130 | premiR_09130 | uuacaaugguucuaugaggacguggccccacaguaaguugaggagcacuggguauguaugaauaaaauggcaugacaggccuucucuuuccaguucuucccagaauugggaaaagcuggguugagaggguaagaaaagaaaaacaaauaaauuuuuuaaa |
| 342 | 9195 | premiR_09195 | gcgagacucuuuuuucuccaggaccugcggagcagccaggcuucaugaguuaaaugcagaucugaaccauacccaguugggauuggguacacacucuacuccucugaaaacuagcuagggguucgaacuuggugagagggagagugggacagagc |
| 344 | 9213 | premiR_09213 | aaguucugagaguccaggaggcagaggcugggguugggggaugucagagggcaaaucggggcuuggggggcccaggaagcagagaugaagguuuuagagucuccagagaacaaaucugguacuuuuaaggcccaggaagcggaggcuggggucuugggaaa |

TABLE 4-continued

Pre-miRNA Sequences

| Seq ID | premir id | name | PreMiR sequence |
|---|---|---|---|
| 346 | 9173 | premiR_09173 | aauuugaaaauccauauaaagguacguccacauuuauguuauuaug aguagucauauuggugaagucaggacaauggccugucauuagauc uuugauucuuguuugcagugaagggagaugugaagaagccauguuc ucugaacgugcugcuuggaggacu |
| 348 | 9253 | premiR_09253 | cggguguuuccggccgccgucgcgucccagggaggcugaggcgagag guagcuguccgggugggagcccgcacuaccuucuuccucuuccuc cuccuccucccgggugagggagcgaagguuggggguccccgagccc auggaccaggaggaggcgga |
| 350 | 9214 | premiR_09214 | uuuuuuuuuuaacaccuauauaucacccauugaacggguauuuuac ugaacacaguacaguagacuguuuaaaacucacauccugguaacuu ucacuacuugaaauuacaaagugcuuuuguuaauugcauauuuuug cucagccaucuuagaauugu |
| 352 | 9223 | premiR_09223 | aagcuggcccuggcuggagauggcuagccccugagacaugcacuuc ugguuuugaaaugacucugucuguggggcagcagaaacuagagaag gcaaguggcugcccaccccaaggcgugaccaggaggaacagccug cagcucacuccaugccacacggg |
| 354 | 9217 | premiR_09217 | uugguggugugauaagaaugauuucuugcuaauugaggauguguga gguuuaaggcuguggagcugaucuuugaaaaauaguuuccuguuucu aaagugacauuacccaguauuugcuuacugcuuuguccuuaucuc ccgcuuucuuuuuaguauuucug |
| 356 | 9265 | premiR_09265 | gaaagagaaagccaagauccacuaccggaagaagaaacagcucaug aggcuacggaaacaggccgagaagaacguggagaagaaaauugaca aauacacagagguccucaagacccacggacuccuggucugagccca auaaagacuguuaauuccucaaa |
| 358 | 9235 | premiR_09235 | ugggcgucuacaacggcaagaccuucaaccagguggagaucaagcc cgagaugaucgaccacuaccuggggcgaguucccaucaccuacaag cccauaaagcacggcgggcccggcaucggggccagccacuccuccc gcuucaucccucucaagcaguggcuca |
| 360 | 9174 | premiR_09174 | guagcccacauggauagcacaguugucagacaagauuccuucagau uccgaguugccuaccgguuguuuucguuguuguuguugugguuuuu cuuuucuuuuuuuuuugaagacagcaauaaccacaguacauauu acuguaguucucuauaguuuuac |
| 362 | 9311 | premiR_09311 | ggcggcgggagaaguagauugaagccaguugauuagggugcuuagc uguuaacuaaguguuuguggguuuaaguccauuggucuaguaagg gcuuagcuuaauuaaaguggcugauuugcguucaguugaugcagag uggggguuugcaguccuuagcuguug |
| 364 | 9266 | premiR_09266 | ucauucugaggucacauaacacauaaaaauuaguuucuaugagugua uaccauuuaaagaauuuuuuucaguaaaagggaauauuacaaug uuggaggagagauaaguuauagggagcuggauuucaaaacgugguc caagauucaaaaauccuauugauagu |
| 366 | 9132 | premiR_09132 | guaagaugguuaucgauaguguaaaugauggaugaagugcacuga ggcucuuaaaagauacuuaggauuuuugacuuuacucuguagguuc uaaaguaaacauauaugaggguuuuaauuucucagauacuauaccu gcagcucuuuuugcugacucaagau |
| 368 | 9293 | premiR_09293 | agcacaaguacacacauaaaaacauuaggucaagguguagcccaug agguggcacgaaaugggcuacauuuucuaugccagaaaaucucac aacauccuuuaggaaaucuaagggcucaaggaggauuuagcaguaa accaagagcagagugcuuggungaa |
| 370 | 9138 | premiR_09138 | gucacucaggacagacuucuugaaguagguggcccuucaacugagc ugaaggaagagaagggcauugcaggcugagggaugauccaggu gccccccagaucuaaagugugagucugucaucgaggugcguagcc ucuccagaggugucacuguguuccau |
| 372 | 9169 | premiR_09169 | cugcaaacagccuuuccacugacgcagugccuuggggcucugcca agcgaccccuagaauggggauuguggggggucgcucuaggcaccgc agcacugugcggggauguugcagcugccugggagugacuucacac aguccucucugccuccagggucaccc |
| 374 | 9165 | premiR_09165 | guggauaugagugaagacggggcaggcaggccacaucucuuagaag aggaaggugauugccacgucuccuuccuccaugcugauggcaaggc gugcggggcuguguucucuugcagccagcgucccaugcucggugcc ccagaaaagucagugaguguaggccu |

TABLE 4-continued

Pre-miRNA Sequences

| Seq ID | premir id | name | PreMiR sequence |
|---|---|---|---|
| 376 | 9196 | premiR_09196 | aggaaacacaagaagaaacgccuggugcagagccccaauuccuacu ucauggaugugaaaugcccaagaugcuauaaaaucaccacggucuu uagccaugcacaaacgguaguuuugugguguuggcugcuccacuguc cucugccagccuauaggag |
| 378 | 9209 | premiR_09209 | cauagauauguauucagcuugucuucaaauacggccaagcagaaaa uguuuuauauuuuauaaaucaucuuuugacucuguauuuaaauucu augauacugaaaauaaaggcauucuggaaaaauacugacugauuuu ggugcagaaguuuugaguaucaag |
| 380 | 9310 | premiR_09310 | aauuaaaguggcugauuugcguucaguugaugcagaguggggguuuu gcaguccuuagcuguugcagaaauuaaguauugcaacuuacugagg gcuuugaaggcucuuggucuguauuuaaccuaaauuucuauaagau uauuaguauaaaaggggagauagguag |
| 382 | 9302 | premiR_09302 | ccaggagaggaaaaggaaaugggaccucagaaguagaagccucagg gaaggaguaaaguagaaaucagaagaaaagaagcuucacuugauag uaauaaggguuuuaacuucaaguaccuucagaaaaugugauuuuga uaagaggaaagggcaaauuuag |
| 384 | 9222 | premiR_09222 | agccugugaccccucgggacugccggugcaggugguggcagcugg agggacccaugcagcaccaggucagagcagacccuccccugccgg ccugcgccagcuggaccugaugggccccuguggcgccuugaccugc ugggccaggcugcccugggacucuc |
| 386 | 9150 | premiR_09150 | ggccccgcauccgcguucgucuaggcgcucuugucaccucgccaug ccggagccaucgcgggcggcuccggcuucuaaaaagggcuccaaga aggccauuaccaaggcgcagaagaaggacggcaagaagcgcaagcg cggccgcaaggagagcuauucuauc |
| 388 | 9119 | premiR_09119 | gaaacaucuuaaugcacagccacaaguuacaaugcaacagccugcu gcucauguacaaggucaggaaccuuugacugcuuccauguugguau cugcccaugcucaagagcaaaagcaaaauguugggugaacggcuguu uccucuuauucaagccaugcaccuu |
| 390 | 9257 | premiR_09257 | ugaaacuaacuagauuuauuggauaucaguacuuugagaguuagaa augguuacugauugucaucuuuucagugaaggguucuauaguugag uaaaaauuugucuaacuuuguaaguauaguuuauauuguagaaau ugcuuccaauuuuguuggauaacuucau |
| 392 | 9170 | premiR_09170 | cugcaaacagccuuuccacugacgcagugccuuggggggcucugcca agcgaccccuagaauggggauugugggggggucgcucuaggcaccgc agcacugugcuggggauguugcagcugccugggagugacuucacac aguccucucugccuccagggu |
| 394 | 9277 | premiR_09277 | cccagggugggcauaggagaaaaaggugcugaaggcacagcuggaaa ugauggugcaagaguaagugaaaguauuccuuuucuagcugggcua ggaaccaacauuacaguaucauaugaguuucccugaaccuuccaaa auaaagucagucauguuuccuuggua |
| 396 | 9250 | premiR_09250 | acaugcagggugaaauccucacuauuuuuaugaaacagcaucugau cuugaacuuuuaugacucaccucagucacuucaccuguauuuuggc ccugucagaucaugucuuuauuuaaacuuuugauauuuuauucuuu auauguuuuugcauuaguuuuuauuuu |
| 398 | 9202 | premiR_09202 | aaacaauaaaaaacuggcugcuaucgaagcccuaaaaugauggugaa cuccagaaagccauugacuuauucacagaugccaucaagcugaauc cucacuuggcccuuuuguaugccaagagggccagugucuucgucaa auuacagaagccaaauacugccau |
| 400 | 9230 | premiR_09230 | cugguuauaucaggauaaauucauaaagggguuuugugugugugu guuuuguguguguguuguuuagggguuuuuuuuuuuuaaacagggu ugcuuguugcccaggaugaaaugcaaucacacacaaucauggcuc auugcaucacuaucuauguauuca |
| 402 | 9215 | premiR_09215 | ucaguuaagccaauacauuuaaaguuuugcaugaggaacacugacu uuauuaagcauuucagauguggugguuguauuuuugccccaagaa guguuuggauaaccacacaaaagcaugaugaaaaggcuucuuguag ucccauaauuucuugugaacuaauguu |
| 404 | 9297 | premiR_09297 | uucugaagggauauuugcauguucauuauuaaucugagugagaggu uagugcuauaaaguacaagauuuccugaucacuuaaaauuuuc uuguagucagagauuugacucugaaucgucacuucaaaaauuuguc uuuucagguacuauguaaagagaacu |

TABLE 4-continued

Pre-miRNA Sequences

| Seq ID | premir id | name | PreMiR sequence |
|---|---|---|---|
| 406 | 9286 | premiR_09286 | cacuacggccucuggccaugcaccaguugudaguuuugugguguuggc ugcuccacuguuguducugccagcccacaggagggaaagugaggcucc uggaaggacgcuccuucagaugdaagcagcacuggaagagcccaa guugaggugcaugggacacaaacu |
| 408 | 9110 | premiR_09110 | auaaugaguaaaaauguucaucuuuaauaaagcaaaaauagagcaa cccaccaaauaguuaacacuugccuggagagauuuaggaacaccag uauuccacugagauugcugagaguducucaggaaagaaaggucuaacu uaaauugyauuuuaccauuucugag |
| 412 | 9313 | premiR_09313 | gcaaagaaagaagaaucugaggagucugaugaugacaugggcuuug gucuuuugacuaaaccucuuuuauaaugyguucaauaaaagcug aacuuuaaaaaaagauuggggguuuaucaugdaauuguuucauuuu guugdauducugugduaagauuucuaa |
| 414 | 9314 | premiR_09314 | ccggccgcugggcgcacccguccguucgucccoggacguugcucu cuaccccgggaacgucgagacuggagcgcccgaacugagccaccuu cgcg |
| 415 | 9315 | premiR_09315 | ucucggaagcuaagcagggucgggccugguuaguacuuggacggga gaccgccugggaauaccgggugcuguaggcuuuuucuuuggcuuuu ug |
| 417 | 9316 | premiR_09316 | ucuuggaagcuaagcagggucgggccugguuaguacuuggauggga gaccaccugggaauaccgggugcuguaggcuuuggccgggcguggu gg |
| 419 | 9317 | premiR_09317 | ggcguaggggggccggccugcugugaugacauuccaauuaaagcac guguuagacugcugacgcgggugaugcgaacuggagucugagccug cccgagcggagc |
| 419 | 9318 | premiR_09318 | cacugucacugccuaccaaucucgaccggaccucgaccggcucguc uguguugccaaucgacucggcguggcgucggucguggduagauaggc ggu |
| 419 | 9319 | premiR_09319 | cacugucacugccuaccaaucucgaccggaccucgaccggcucguc uguguugccaaucgacucggcguggcgucggucguggduagauaggc ggu |
| 423 | 9320 | premiR_09320 | cacugucacugccuaccaaucucgaccggaccucgaccggcucguc uguguugccaaucgacucggcguggcgucggucguggduagauaggc ggu |
| 425 | 9321 | premiR_09321 | ugcugcaggguguuggagagcagugugguguugccuggggacugugug gacugguaucacccagacagcuugcacugacuccagacccugccgu caug |
| 427 | 9322 | premiR_09322 | cgccccgggccgcggcuccugauugduccaaacgcaauucucgaguc uauggcuccggccgagaguuagucuggacgucccgagccgccgcc cccaa |
| 427 | 9323 | premiR_09323 | aguaccaagaaguuaucauuuccauaugacugucauugcuuaaaac uagcuaguaugagcaggacggduggccauggaagucgaaaucgcua ag |
| 433 | 9324 | premiR_09324 | aguaccaagaaguuaucauuuccauaugacugucauugcuuaaaac uagcuaguaugagcaggacggduggccauggaagucgaaaucgcua ag |
| 433 | 9325 | premiR_09325 | gggauugacagauugacagcucuuucucgauucugugggugguggu gcauggccauucuuaguuggduggaguga uuugucugguuaauucug auaa |
| 433 | 9326 | premiR_09326 | gggauugacagauugacagcucuuucucgauucugugggugguggu gcauggccauucuuaguuggduggaguga uuugucugguuaauucug auaa |
| 433 | 9327 | premiR_09327 | gggauugacagauugacagcucuuucucgauucugugggugguggu gcauggccauucuuaguuggduggaguga uuugucugguuaauucug auaa |
| 435 | 9328 | premiR_09328 | gggauugacagauugacagcucuuucucgauucugugggugguggu gcauggccauucuuaguuggduggaguga uuugucugguuaauucug auaa |

TABLE 4-continued

Pre-miRNA Sequences

| Seq ID | premir id | name | PreMiR sequence |
|---|---|---|---|
| 437 | 9329 | premiR_09329 | ugcaacugccgucagccauugaugaucguucuucucuccguauugg<br>ggagugagagggagagaacgcggucugaguggutuuuccuucuuga<br>ug |
| 439 | 9330 | premiR_09330 | auacguguaauugugaugaggauggauagcaaggaagccgcuccca<br>ccugacccucacggccuccguguuaccuguccucuaggugggacgc<br>uc |
| 441 | 9331 | premiR_09331 | gggugugagaagccggauccuguggugacccaguggccuaauggau<br>aaggcaucagccuccggagcuggggauugugggu ucgaguc ccauc<br>ugg |
| 443 | 9332 | premiR_09332 | ccgggagcggggaggcggcggcuccagggaccuggcggccgccgau<br>cggggcugcgaggccccauggcgccgccccagcccgcuccuggc<br>gccga |
| 445 | 9333 | premiR_09333 | gggccgggaaugccgcggcggggacggcgauuggu ccguaugugug<br>gugccaccggccgccggcuccgccccggccccgccccacacgccg<br>cau |
| 446 | 9334 | premiR_09334 | uggugggggagccgcggggaucgccgagggccggucggccgcccc<br>gggugccgcgcggugccgccggcggcggugaggccccgcgcgugug<br>ucccggcugcgg |
| 448 | 9335 | premiR_09335 | ggggaggagacggu uccggggaccggccgcgacgcggcggcggu<br>ggugggggagccgcggggaucgccgagggccggucggccgccccg<br>ggugccgcgcgg |
| 450 | 9336 | premiR_09336 | acugucacugccuaccaaucucgaccggaccucgaccggcucgucu<br>guguugccaaucgacucggcguggcgucggucgugguagauaggcg<br>gucaug |
| 453 | 9338 | premiR_09338 | aaugcagugugauuucugcccagugcucugaaugucaaagugaaga<br>aauucagagaagccuggguagccgggcgugguggcucacaccugua<br>aucccagcac |
| 455 | 9339 | premiR_09339 | augaauuguuggguguuagcccugcggccccacgcaccagggu aaga<br>gagacucucgcuuccugcccuggcccgagggaccgacuggcugggc<br>cugccuu |
| 457 | 9340 | premiR_09340 | cuucuccccagccagaggu ggagccaagugguccagcgucacucca<br>gugcucagcugu ggcuggaggagcuggccuguggcacagcccugag<br>u |
| 459 | 9341 | premiR_09341 | gcacccagaucagugcuuggcaccuagcaagcacucaguaaauauu<br>uguugagugccugcuaugugccaggcauugugcugagggcuuugug<br>ggga |
| 461 | 9342 | premiR_09342 | aguuggu agagggcagagggaugagggggaaaguucuauaguccug<br>agaucuaauuacaggacuauagaacuuccccc ucaucccucuacc<br>cuua |
| 463 | 9343 | premiR_09343 | gugcugcaggu guggagagcagugugugu ugccuggggacugugu<br>ggacugguaucacccagacagcuugcacugacuccagacccugccg<br>ucaug |
| 465 | 9344 | premiR_09344 | gagggcgggagacaaaaucucgcaauucugaccugccuuuggacau<br>aauugaggcuuuaugaggaagguggggaugcgggagu ggcgauccc |
| 465 | 9345 | premiR_09345 | ggcguugcuuggcugcaacugccgucagccauugaugaucguucuu<br>cucuccguauuggggagugagagggagagaacgcggucugaguggu<br>uuuuccuucuuga |
| 465 | 9346 | premiR_09346 | ggcguugcuuggcugcaacugccgucagccauugaugaucguucuu<br>cucuccguauuggggagugagagggagagaacgcggucugaguggu<br>uuuuccuucuuga |
| 465 | 9347 | premiR_09347 | ggcguugcuuggcugcaacugccgucagccauugaugaucguucuu<br>cucuccguauuggggagugagagggagagaacgcggucugaguggu<br>uuuuccuucuuga |
| 465 | 9348 | premiR_09348 | ggcguugcuuggcugcaacugccgucagccauugaugaucguucuu<br>cucuccguauuggggagugagagggagagaacgcggucugaguggu<br>uuuuccuucuuga |

TABLE 4-continued

Pre-miRNA Sequences

| Seq ID | premir id | name | PreMiR sequence |
|---|---|---|---|
| 467 | 9349 | premiR_09349 | ggcguugcuuggcugcaacugccgucagccauugaugaucguucuu cucuccguauuggggagugagagggagagaacgcggucugaguggu uuuuccuucuuga |
| 467 | 9350 | premiR_09350 | ugugagacgaauuuuugagcggguaaaggucgcccucaaggugacc cgccuacuuugcgggaugccugggaguugcgaucugcccgaccuua uuca |
| 470 | 9351 | premiR_09351 | ugugagacgaauuuuugagcggguaaaggucgcccucaaggugacc cgccuacuuugcgggaugccugggaguugcgaucugcccgaccuua uuca |
| 470 | 9352 | premiR_09352 | gugaacggcggcuggguggcgaguuccgcugugccagcuuccguugg cguuugccaucggugcaugggugguucagugguagaauucucgccu g |
| 470 | 9353 | premiR_09353 | gugaacggcggcuggguggcgaguuccgcugugccagcuuccguugg cguuugccaucggugcaugggugguucagugguagaauucucgccu g |
| 470 | 9354 | premiR_09354 | gugaacggcggcuggguggcgaguuccgcugugccagcuuccguugg cguuugccaucggugcaugggugguucagugguagaauucucgccu g |
| 474 | 9363 | premiR_09363 | gugaacggcggcuggguggcgaguuccgcugugccagcuuccguugg cguuugccaucggugcaugggugguucagugguagaauucucgccu gccacgcgggaggc |
| 476 | 9364 | premiR_09364 | ccaucaccacugugaaucagagcaacaaaacagcuggaggcagaac agcacucagcuggagcauuggugguucagugguagaauucucgccu gc |
| 476 | 9365 | premiR_09365 | cgaggaaguagugaccugccacuggccaccugcggaaccagaguuc cccacuggagggccgcguuggugguauaguggugagcauagcugcc uu |
| 479 | 9367 | premiR_09367 | cgaggaaguagugaccugccacuggccaccugcggaaccagaguuc cccacuggagggccgcguuggugguauaguggugagcauagcugcc uuccag |
| 481 | 9368 | premiR_09368 | ccgacccgggccugggcuguggcugugacuggcgcugccgugggcg ccgcagcccucgcgggagccggacgcgguaaugccccagcggcgca gc |
| 483 | 9369 | premiR_09369 | guaccaagaaguuaucauuuccauaugacugucauugcuuaaaacu agcuaguaugagcaggacggguggccauggaagucgaaauucgcuaa gg |
| 483 | 9370 | premiR_09370 | cugcugagaguaggugggggauguagcucaguggguagagcgcaugcu uugcauguaugaggccccgggguucgauccccggcaucuccagugua gu |
| 485 | 9373 | premiR_09373 | cugcugagaguaggugggggauguagcucaguggguagagcgcaugcu uugcauguaugaggccccgggguucgauccccggcaucuccagugua gu |
| 487 | 9374 | premiR_09374 | cugcugagaguaggugggggauguagcucaguggguagagcgcaugcu uugcauguaugaggccccgggguucgauccccggcaucuccagugua gu |
| 489 | 9375 | premiR_09375 | cugcugagaguaggugggggauguagcucaguggguagagcgcaugcu uugcauguaugaggccccgggguucgauccccggcaucuccagugua gu |
| 491 | 9376 | premiR_09376 | gccgacagccagcuggaucuccugucccgagcccuggguacugggg gugcccugaguugggguucccucagaccuggugaucgggcccugga g |
| 491 | 9377 | premiR_09377 | cucccucuccuccccgggguucggugcgcggccggggccggaguu cgcugcaagucggcggaaaguuuggcugcgcggguuccccgaagu ucaggugcg |
| 491 | 9378 | premiR_09378 | gucugaucucagaagcuaagcaaggucggguucuaguuaguacuugg auggggagacugccuggaauaccgggugcuguaggcuuuuggccuau cguucccu |

TABLE 4-continued

Pre-miRNA Sequences

| Seq ID | premir id | name | PreMiR sequence |
|---|---|---|---|
| 491 | 9379 | premiR_09379 | agagagccccggggugcagauccuugggagcccuguuagacucugg<br>auuuuacacuuggagugaacgggcgccaucccgaggcuuugcacag<br>gggcaa |
| 496 | 9380 | premiR_09380 | agagagccccggggugcagauccuugggagcccuguuagacucugg<br>auuuuacacuuggagugaacgggcgccaucccgaggcuuugcacag<br>gggcaa |
| 496 | 9381 | premiR_09381 | agagagccccggggugcagauccuugggagcccuguuagacucugg<br>auuuuacacuuggagugaacgggcgccaucccgaggcuuugcacag<br>gggcaa |
| 496 | 9382 | premiR_09382 | agagagccccggggugcagauccuugggagcccuguuagacucugg<br>auuuuacacuuggagugaacgggcgccaucccgaggcuuugcacag<br>gggcaa |
| 500 | 9383 | premiR_09383 | ggauugacagauugauagcucuuucucgauuccgugggguggug<br>cauggccguucuuaguuggugagcgauuugucugguuaauuccga<br>uaac |
| 500 | 9384 | premiR_09384 | ggauugacagauugauagcucuuucucgauuccgugggguggug<br>cauggccguucuuaguuggugagcgauuugucugguuaauuccga<br>uaac |
| 503 | 9385 | premiR_09385 | ggauugacagauugauagcucuuucucgauuccgugggguggug<br>cauggccguucuuaguuggugagcgauuugucugguuaauuccga<br>uaac |
| 503 | 9386 | premiR_09386 | ggauugacagauugacagcucuuucucgauucgugggguggug<br>cauggccauucuuaguuggugagugauuugucugguuaauucuga<br>uaa |
| 503 | 9387 | premiR_09387 | ggauugacagauugacagcucuuucucgauucgugggguggug<br>cauggccauucuuaguuggugagugauuugucugguuaauucuga<br>uaa |
| 503 | 9388 | premiR_09388 | gcaacugccgucagccauugaugaucguucuucucuccguauggg<br>gagugagagggagagaacgcggucugaguggguuuuuccuucuugau<br>g |
| 503 | 9389 | premiR_09389 | gcaacugccgucagccauugaugaucguucuucucuccguauggg<br>gagugagagggagagaacgcggucugaguggguuuuuccuucuugau<br>g |
| 505 | 9390 | premiR_09390 | gcaacugccgucagccauugaugaucguucuucucuccguauggg<br>gagugagagggagagaacgcggucugaguggguuuuuccuucuugau<br>g |
| 506 | 9391 | premiR_09391 | gcaacugccgucagccauugaugaucguucuucucuccguauggg<br>gagugagagggagagaacgcggucugaguggguuuuuccuucuugau<br>g |
| 508 | 9392 | premiR_09392 | gcaacugccgucagccauugaugaucguucuucucuccguauggg<br>gagugagagggagagaacgcggucugaguggguuuuuccuucuugau<br>g |
| 510 | 9393 | premiR_09393 | aucuuggaagcuaagcagggucgggccugguuaguacuuggauggg<br>agaccaccugggaauaccgggugcuguaggcuuuggccgggcgugg<br>ugg |
| 512 | 9394 | premiR_09394 | aucucggaagcuaagcagggucgggccugguuaguacuuggacggg<br>agaccgccugggaauaccgggugcuguaggcuuuucuuuggcuuu<br>uug |
| 514 | 9395 | premiR_09395 | auccucccuggggcauccuguacugagcugccccgaggcccuucau<br>gcugcccagcucggggcagcucaguacaggauacucgggguggag<br>uca |
| 516 | 9396 | premiR_09396 | acaucaagugacugugcuuggcuguggggcuaccaagaugaagaag<br>gaaugcuccugcccucgaggagcucacagucuagugggagggaaca<br>augc |
| 516 | 9397 | premiR_09397 | ggggcucgcggacccggcccagagggcggc-gguggcggcagcuacu<br>uuucuggucagggcucggacaccggcgcgucucucaagcucgccuc<br>uuc |

TABLE 4-continued

Pre-miRNA Sequences

| Seq ID | premir id | premir name | PreMiR sequence |
|---|---|---|---|
| 519 | 9398 | premiR_09398 | uaaugcagugugauuucugcccagugcucugaaugucaaagugaagaaauucagagaagccuggguagccgggcgugguggcucacaccuguaa |
| 521 | 9399 | premiR_09399 | guuccuuguguucuuccagaccgcccucugucaccuugcagacggcuuucucuccgaaugucugcaagugucagaggcgaggaguggcagcugcau |
| 523 | 9400 | premiR_09400 | guuccuuguguucuuccaguccgcccucugucaccuugcagacggcuuucucuccgaaugucugcaagugucagaggcgaggaguggcagcugcau |
| 523 | 9401 | premiR_09401 | aacauuaggagaguaucuucucuguuuuggccaugugguguacucacagcccucacacauggccgaaacagagaaguuacuuuccuaauauuugccu |
| 525 | 9402 | premiR_09402 | cugccugcuucugugugauauguuugauauugggguuguuuaauuaggaaccaacuaaaugucaaacauauucuuacagcagcaggugauucagcacc |
| 527 | 9403 | premiR_09403 | ccgggccgcggcuccugauugoccaaacgcaauucucgagucuauggcuccggccgagaguugagucuggacgucccgagccgccgcccccaaaccuc |
| 529 | 9404 | premiR_09404 | ccgggccgcggcuccugauugoccaaacgcaauucucgagucuauggcuccggccgagaguugagucuggacgucccgagccgccgcccccaaaccuc |
| 531 | 9405 | premiR_09405 | guugugcuguccaggugcuggaucagugguucgagucugagccuuuaaaagccacucuagccacagaugcagugauuggagccaugacaagucccca |
| 533 | 9406 | premiR_09406 | accuaccuaacuggguuaggggcccuggcuccaucuccuuuaggaaaaccuucuguggggagugggggcuucgacccuaacccaggugggcuguaac |
| 535 | 9407 | premiR_09407 | cauuaggagaguaucuucucuguuuuggccaugugguguacucacagcccucacacauggccgaaacagagaaguuacuuuccuaauauuugccucc |
| 537 | 9408 | premiR_09408 | uaccuccagcuguguucugcccagugcucugcugacuggacgccucuguguccuuagaccaugugcagggccugaugcaggaaagagcuga |
| 537 | 9409 | premiR_09409 | uuaaugcagugugauuucugcccagugcucugaaugucaaagugaagaaauucagagaagccuggguagccgggcgugguggcucacaccuguaa |
| 539 | 9410 | premiR_09410 | accccuagaauggggauugugggggggucgcucuaggcaccgcagcacugugcugggggauguugcagcugccugggagugacuucacacagucucucug |
| 539 | 9411 | premiR_09411 | ucguccagcgagggcgcgcuggcccugggcagcguguggcugaaggucaccauguucuccuuggccauggggcugcgcggggccagcaggucacg |
| 542 | 9412 | premiR_09412 | ucguccagcgagggcgcgcuggcccugggcagcguguggcugaaggucaccauguucuccuuggccauggggcugcgcggggccagcaggucacg |
| 545 | 9414 | premiR_09414 | cagcuccgcagggguuggggaaacggccgcugagugaggcgucggcuguguuucuaccgcggucuuuuccucccacucuuggcugguuggacc |
| 547 | 9415 | premiR_09415 | gauugacagauugauagcucuuucucgauuccgugggugguggugcauggccguucuuaguugguggagcgauuugucugguuaauuccgauaa |
| 551 | 9416 | premiR_09416 | gauugacagauugauagcucuuucucgauuccgugggugguggugcauggccguucuuaguugguggagcgauuugucugguuaauuccgauaac |
| 552 | 9417 | premiR_09417 | ccggcggggcgaagcccgcggcugcuggacccacccggccgggaauagugcuccugguuguuccggcucgcguggguguucggcggcggggcc |

TABLE 4-continued

Pre-miRNA Sequences

| Seq ID | premir id | name | PreMiR sequence |
|---|---|---|---|
| 553 | 9418 | premiR_09418 | ccugagcaaggucacaaagcugggugagaggggcugggauucacau ucaagcacuguguuccuaggccccuugacccccuggcaucuguggg |
| 554 | 9419 | premiR_09419 | cugaaaugucuucaaauguaucaauaagccuucucuucccaguucu ucuuggagucaggaaaagcuggguugagaggagcagaaaagaaaaa |
| 556 | 9423 | premiR_09423 | ucuucuaccuaagaauucugucucuuaggcuuucucuucccagauu ucccaaaguuggggaaaagcuggguugagagggcaaaaggaaaaaaa a |

TABLE 5 miRNA Sequences

| Seq ID | MiR name | mature_sequence |
|---|---|---|
| 1 | miR_1966 | CGAGCCUGGUGAUAGCUGGUUGUCCAAG |
| 3 | miR_1967 | GAGGCUGAGGCGAGAGGU |
| 5 | miR_1968 | AUUUGUGGCCGAGUGUAACAACC |
| 7 | miR_1969 | UCCCUUCGUGGUCGCC |
| 9 | miR_1970 | GCAGGGGAAGAAGCCUUCCGU |
| 11 | miR_1971 | ACUUUGAGAGUUAGAAAUGGUUACU |
| 13 | miR_1972 | AACCAAUGAUGUAAUGAUUCUGCC |
| 15 | miR_1973 | AUGAUUCUGUGACGCCAGCU |
| 17 | miR_1974 | GAAAGCUGAGCGUGAACGUGGU |
| 19 | miR_1975 | UAGCAGCACAUAAUGGUUUGAAU |
| 21 | miR_1976 | UGUUUAGACGGGCUCACAU |
| 23 | miR_1977 | GGAAAUUUGAGACCAGCAAGUACU |
| 25 | miR_1978 | AUUGUAUAUCAGCAUGGGGAUUAUU |
| 27 | miR_1979 | UUGGAGGCGUGGGUU |
| 29 | miR_1980 | AACGUGCAGCGGCUGAAGGAGU |
| 31 | miR_1981 | AAUUGUGAGGCUUGAGUGU |
| 33 | miR_1982 | UGAUAGGAUUGACAUGGAGCAC |
| 35 | miR_1983 | AACGGCCGCGGUACCCUAAC |
| 37 | miR_1984 | UCUUGCCAAGAGAAUUAAUGUGCGU |
| 39 | miR_1985 | AAUCUGAGUGAGAGGUUAGUUGCU |
| 41 | miR_1986 | AUUAAAAAUUUCGGUUGGG |
| 43 | miR_1987 | GAUAGCUGCCAGUGACAGGAGUAGU |
| 45 | miR_1988 | GAGCCUGGUGAUAGCUGG |
| 47 | miR_1989 | UGGCGCGGAGCGGAGCGG |
| 49 | miR_1990 | AGGCGGCGGAGGGGCG |
| 51 | miR_1991 | AUGCGUGCGAGAAGUCAGUGG |
| 53 | miR_1992 | UGUGUUUGAGAGCAACGCCAUUGCCU |
| 55 | miR_1993 | GCAUGAGUGGUUCAGUGGU |
| 57 | miR_1994 | AAGGAAUGAGUUAGCUUUG |
| 59 | miR_1995 | ACAAGUGAAUACACUGAGGC |
| 61 | miR_1996 | CUCGCGCCCGCGUCGCGGCAGC |
| 63 | miR_1997 | GUGGUGUUGAGGAAAGCAGAC |
| 65 | miR_1998 | GUUUUUGUGACUGCCUUGAGU |
| 67 | miR_1999 | AAGGCACAGCUGGAAAUGAUGGUG |
| 69 | miR_2000 | AACUAGGCGGCUAUGGUAU |
| 71 | miR_2001 | GUGGUGGUCGUACGCUGUG |
| 73 | miR_2002 | GCUGAUGAAGCAUUGGACUGU |
| 75 | miR_2003 | AGGUUCACAUGGAAAAGGUU |
| 77 | miR_2004 | CCAUUGUGUAGCAAGAUGUCAU |
| 79 | miR_2005 | GGAAAUAGUUUGUGACAAACUGGG |
| 81 | miR_2006 | CUCCUCUUCGUCUCCUCGGUC |
| 83 | miR_2007 | ACUCCAGCCCCACAGCCUCAG |
| 85 | miR_2008 | GCCGCGAGUGGGAGCGGGAGCG |
| 87 | miR_2009 | GCUUGACUGAGUGUGGCUGGACGUG |
| 89 | miR_2010 | AGUCGGUGCCUGAGGUUGC |
| 91 | miR_2011 | AGUGAUGAGGAUGUGCUGAU |
| 93 | miR_2012 | AUUGAGUGGGGCUCAGGAUU |
| 95 | miR_2013 | GCAUGGGUGGUUCAGUGU |
| 97 | miR_2014 | AACUGUUAUAUUAUGAUUGUGAC |
| 99 | miR_2015 | UUGCUGUGAUGACUAUCUUAGGAC |
| 101 | miR_2016 | AGAAUUGAGUGAUCUCAUGGAU |
| 103 | miR_2017 | AAAACGAUCUUUCAGAUUUAGAGU |
| 105 | miR_2018 | GCGGUCGGGCGGCGGCG |
| 107 | miR_2019 | AUGAGAACUUGAGCGACAGAGU |

TABLE 5-continued miRNA Sequences

| Seq ID | MiR name | mature_sequence |
|---|---|---|
| 109 | miR_2020 | AUUGGUCGUGGUUGUAGU |
| 111 | miR_2021 | GAUGAGAGAACAGUGGGUACUUC |
| 113 | miR_2022 | CAAGGUGUAGCCCAUGAGGUGGC |
| 115 | miR_2023 | AGCACCAGCCUAGGAAGAGGGU |
| 117 | miR_2024 | ACUUUAACACUGCUGUGGAAGGC |
| 119 | miR_2025 | AUUUGACAAGAGUAUGCCAGGUGU |
| 121 | miR_2026 | CUGGGAGCUUGAAAGGAG |
| 123 | miR_2027 | AUUUGGGCAGGUUGAAAGAAUUU |
| 125 | miR_2028 | GUGCUGGAGGCCAGGCUGAGGCCC |
| 127 | miR_2029 | GCUGUUGGUGGAGAAGGU |
| 129 | miR_2030 | AUGGCAGUUGGAGAGAAAGAAC |
| 131 | miR_2031 | GCAGAUAAACUCAUGCCAGAGAACU |
| 133 | miR_2032 | AGUGCCAGGUGGGGAGG |
| 135 | miR_2033 | GACUCUUAGCGGUGGAUC |
| 137 | miR_2034 | CUGUUGCGGGACCCGGGGUGU |
| 139 | miR_2035 | UUAAAGCUGCCAUUUGUUACU |
| 141 | miR_2036 | GAGCAGAGGCGAUAGUUGAAGU |
| 143 | miR_2037 | GAUGACAUGGGCUUUGGUCUUUUU |
| 145 | miR_2038 | AGAAAGGGCCUUGUGUUU |
| 147 | miR_2039 | ACUCGGCGUGGCGUCGGUCGUGGUAG |
| 149 | miR_2040 | GUGUUUAGUGAGUAUUUGUU |
| 151 | miR_2041 | ACUGCUGCUGCUGCUUGGCC |
| 153 | miR_2042 | UGCAGAGUGGGGUUUUGCAGUCCUU |
| 155 | miR_2043 | AUGACCACCAAACCCAGGAGC |
| 157 | miR_2044 | CAGAGUCUGUAGAAGAGGCG |
| 159 | miR_2045 | CCUUGACUUCUGCCAGAGU |
| 161 | miR_2046 | AUCACUGACUGAUCAAGUAGAGGU |
| 163 | miR_2047 | AAGGAUUGGACAGGGUUAGAUU |
| 165 | miR_2048 | AGGCCAAGGCUGCGGGGUU |
| 167 | miR_2049 | AACGGGAGGCGCUAGCCAUGG |
| 169 | miR_2050 | ACCUUCAGUGCAGUUUCUUUU |
| 171 | miR_2051 | AUUUUGGGUGGAAGAGGCAU |
| 173 | miR_2052 | GGAAUGAGGAGCUUUGAC |
| 175 | miR_2053 | AAAAGCUGGGUUGAGAGGAU |
| 177 | miR_2054 | AGUAAGGUCAGCUAAAUAAGCU |
| 179 | miR_2055 | GAAUUGACGGAAGGGAC |
| 181 | miR_2056 | UUGUGUCUUGUGUCUUUU |
| 183 | miR_2057 | UCCCUGGUGGUCUAGU |
| 185 | miR_2058 | UGAGGCUGUAACUGAGAGAAAGAUU |
| 187 | miR_2059 | UUAGGGCCCUGGCUCCAUCUCCU |
| 189 | miR_2060 | GAGUGUGAGUGGACGCGUGAGUGU |
| 191 | miR_2061 | AUUGAGUCUGGCAGUCCCUGUU |
| 193 | miR_2062 | AAAAUGUUUAGACGGGCUCAC |
| 195 | miR_2063 | GAAUGUUUAUGGCACCUGAC |
| 197 | miR_2064 | GGAAAUUUGAGACCAGCAAGU |
| 199 | miR_2065 | ACAGUAGGGCCUUUGGAGUGAU |
| 201 | miR_2066 | CUUGAAGUCUGGUGAUGCUGCCAUU |
| 203 | miR_2067 | AGAUGAGCUGAAGGG |
| 205 | miR_2068 | AAAAAGGGAGCCAAGAAG |
| 207 | miR_2069 | AGUUUGUGUGUUGGCUGCUCC |
| 209 | miR_2070 | GGUUUAGUGAGCAGAGUU |
| 211 | miR_2071 | AAGACGAGAAGACCCUAUGGAGCUU |
| 213 | miR_2072 | AGCAGGGUGCAGGCUUGGAGUC |
| 215 | miR_2073 | AUGUUGGGUUGUUACAGAGU |
| 217 | miR_2074 | ACUGAGUUGACUGUUCCCUU |
| 219 | miR_2075 | ACUGGGCAGUGACAAGCACGAU |
| 221 | miR_2076 | AGAAAGCGUGAGUGUCCAGAGCCU |
| 223 | miR_2077 | GCUUGAGGGCAGUUGGUGCGG |
| 225 | miR_2078 | CCGAGCCUGGUGAUAGCUGGUUGUC |
| 227 | miR_2079 | UGGAGAUGGCUGGCAGAAUGGUUCU |
| 229 | miR_2080 | AAGUAGAAGCCUCAGGGAAG |
| 231 | miR_2081 | AUGGUUCUGGACAGUGGAUU |
| 233 | miR_2082 | GAUGAGUCAGGCUAGGCU |
| 235 | miR_2083 | AUGUGAGAGCAGCAGAGGCGGU |
| 237 | miR_2084 | GUUUUAAGGACUUAAGGGUAU |
| 239 | miR_2085 | UGAUAUGUUUGAUAUUGGGU |
| 241 | miR_2086 | AGAAAGCCAGGAGCUGUGAUU |
| 243 | miR_2087 | AUUCUAAGUCAGUCAGUCAUC |
| 245 | miR_2088 | UUCUCUGUUUUGGCCAUGUGUGU |
| 247 | miR_2090 | UUCUAAGCCAGUUUCUGUCGAU |
| 249 | miR_2091 | GGUUUUGACAUGUCACUGUU |
| 251 | miR_2092 | CUCGCCCGUGGUCUCUCGUCUU |
| 253 | miR_2093 | AACACGCAUACGGUUAAGGCAUUGC |
| 255 | miR_2094 | UGAAACAGCAUCUGAUCUUGAACUU |
| 257 | miR_2095 | GCGUAAAGAGUGUUUUAGAUCACCC |

TABLE 5-continued miRNA Sequences

| Seq ID | MiR name | mature_sequence |
|---|---|---|
| 259 | miR_2096 | GUCCGUUUCCUGUCAGAGUGAUCC |
| 261 | miR_2097 | CCAUCGGUGAUCCCAGUGACAAGU |
| 263 | miR_2098 | GAAAUGUUGAGUGUUUACCCUGU |
| 265 | miR_2099 | GAAGAAACAGCUCAUGAGGCU |
| 267 | miR_2100 | AUGAACCACCAGUCCAAGAAUCU |
| 269 | miR_2101 | GGAAGGUUGGGGGUGU |
| 271 | miR_2102 | UUCUAGGUUGUGGCAUUU |
| 273 | miR_2103 | UGAUAUGUUUGAUAUUGGGUUGUU |
| 275 | miR_2104 | AGAAUACAGCAGAAUUGGCCUC |
| 277 | miR_2105 | CUGAUGGAGAGAAGAAGGCAU |
| 279 | miR_2106 | ACUCGGCGUGGCGUCGGUCGUG |
| 281 | miR_2107 | AUGAGGUGGCAAGAAAUGGGCU |
| 283 | miR_2108 | AAUUUUGACAGAUGCUCAAGGCUGU |
| 285 | miR_2109 | AAAAGCUGGGUUGAGAAG |
| 287 | miR_2110 | AUUGAUGGUUAAGCUCAGCUUUU |
| 289 | miR_2111 | AUGGAUUGAGAUGUGAUCAAAGGC |
| 291 | miR_2113 | AUUUGGCAUUUGGAAGAUAGGUU |
| 293 | miR_2114 | ACUGCUGAGGAACUGUCACUUGU |
| 295 | miR_2115 | AGGUGAGGGCAGGACCUGAAGGU |
| 297 | miR_2116 | AGUGUCUGUGUGUGCUUGCU |
| 299 | miR_2117 | ACGAAGAUGGCGACCGUAAC |
| 301 | miR_2118 | AACUGGAAUGGCGGCAAGGUCCU |
| 303 | miR_2119 | AGUUGAGUCAGGGCCUGUGUG |
| 305 | miR_2120 | GCCGCCCGGGGCCAUGGCG |
| 307 | miR_2121 | AAGUCUAAGUCUAACAUUCGGUGU |
| 309 | miR_2122 | CGGCGGGAGCCCGGGG |
| 311 | miR_2123 | ACGUGGAUGGCGUGGAGGUGC |
| 313 | miR_2124 | GUUUAGACGGGCUCACAU |
| 315 | miR_2125 | AUUUCUGCAGUCAGGUGAGAC |
| 317 | miR_2126 | AAGAAUGACCGCUGAAGAACGU |
| 319 | miR_2127 | AAAUAUGAGCCACUGGGUGU |
| 321 | miR_2128 | AAGGUCCUCUGAGGCAGCAGGCU |
| 323 | miR_2129 | GUCGAGGUCUUUGGUGGGUUG |
| 325 | miR_2130 | GGUUUCGGGUUUGAAGGCAGC |
| 327 | miR_2131 | GCUGGUGAGUGCAGGCUGCUUC |
| 329 | miR_2132 | GACAGAGGUGGCAUCAAGCU |
| 331 | miR_2133 | CUGCCCUGGCCCGAGGGACCGAC |
| 333 | miR_2134 | UCGUGUCGCGUGGGGGGCGG |
| 335 | miR_2135 | GGGAUGCCAGGCAAGUGAGCAGGUC |
| 337 | miR_2136 | AGGGCCGUCAGGACACGGGAGGGUU |
| 339 | miR_2137 | GAAAAGCUGGGUUGAGAGGGU |
| 341 | miR_2138 | AACUAGCUAGGGGUUCG |
| 343 | miR_2139 | GGGUUUGGGGGAUGUCAGAGGGC |
| 345 | miR_2140 | UGAAGGGAGAUGUGAAGAAGCC |
| 347 | miR_2141 | AGAAAGUCCAAGUGUUCAGG |
| 349 | miR_2142 | UGAACGGGUAUUUUACUG |
| 351 | miR_2143 | CUGAGACAUGCACUUCUGGUU |
| 353 | miR_2144 | AAUUGAGGAUGUGUGAGGUUU |
| 355 | miR_2145 | AGUUUCUAUGAGUGUAUACCAUUU |
| 357 | miR_2146 | AGGUGGAGAUCAAGCCCGAGAUGAU |
| 359 | miR_2147 | GAAGACAGCAAUAACCACAGU |
| 361 | miR_2148 | GUUUCUGUUGAGUGUGGGUUUAGU |
| 363 | miR_2149 | AUCGCCGUGGAGUGGGAGAGC |
| 365 | miR_2150 | GGAUGAAGUGCACUGAGGCUCUU |
| 367 | miR_2151 | UCCUGUUGGCCGAGUGGAGACUGGUGU |
| 369 | miR_2152 | GUGGAGUCUGUCAUCGAGGUGCGU |
| 371 | miR_2153 | UUGCAGCUGCCUGGGAGUGACUUC |
| 373 | miR_2154 | UGCAGCCAGCGUCCCAUGCUCG |
| 375 | miR_2155 | AGUUUUGUGUGUUGGCU |
| 377 | miR_2156 | ACGGCCAAGCAGAAAAUGUUUU |
| 379 | miR_2157 | GAUUAGGGUGCUUAGCUGUUAACU |
| 381 | miR_2158 | CCUUCGAGGCGGCUGAGACCC |
| 383 | miR_2159 | AGGUGGUGGCAGCUGGAGGGACC |
| 385 | miR_2160 | AGAAGAAGGACGGCAAGAAGCGC |
| 387 | miR_2161 | AAAAGCAAAUGUUGGGUGAACGG |
| 389 | miR_2162 | GGCGGAGGGGCCGCGGGCC |
| 391 | miR_2163 | UUGCAGCUGCCUGGGAGUG |
| 393 | miR_2164 | UCUCUCCAGGUGACAGAAAGGGCU |
| 395 | miR_2165 | CGUUCUUGCUCUGCCUCGGUC |
| 397 | miR_2166 | AUGCCAAGAGGGCCAGUGUCUU |
| 399 | miR_2167 | UUUUGUGUGUGUGUUUGUUUUU |
| 401 | miR_2168 | AUGAGGAACACUGACUUUAUUAAGC |
| 403 | miR_2169 | GGGUCGGAGUUAGCUCAAGCGGUU |
| 405 | miR_2170 | GGAGGUUCAGAGUUGGAAG |
| 407 | miR_2171 | GAGAGUCUCAGGAAAGAAAGGUC |

TABLE 5-continued miRNA Sequences

| Seq ID | MiR name | mature_sequence |
|---|---|---|
| 411 | miR_2364 | ACCCGUCCCGUUCGUCCCCGG |
| 413 | miR_2365 | ACCGGGUGCUGUAGGCUUU |
| 416 | miR_2366 | ACGCGGGUGAUGCGAACUGGAGUCUGAGC |
| 418 | miR_2367 | ACUCGGCGUGGCGUCGGUCG |
| 420 | miR_2368 | ACUCGGCGUGGCGUCGGUCGU |
| 421 | miR_2369 | ACUCGGCGUGGCGUCGGUCGUGGU |
| 422 | miR_2370 | AGAGCAGUGUGUGUUGCCUGG |
| 424 | miR_2371 | AGAGUUGAGUCUGGACGUCCCG |
| 426 | miR_2372 | AGGACGGUGGCCAUGGAAG |
| 428 | miR_2373 | AGGACGGUGGCCAUGGAAGU |
| 429 | miR_2374 | AGUUGGUGGAGUGAUUUGUCU |
| 430 | miR_2375 | AGUUGGUGGAGUGAUUUGUCUG |
| 431 | miR_2376 | AGUUGGUGGAGUGAUUUGUCUGG |
| 432 | miR_2377 | AGUUGGUGGAGUGAUUUGUCUGGU |
| 434 | miR_2378 | AGAACGCGGUCUGAGUGGU |
| 436 | miR_2379 | AUGAGGAUGGAUAGCAAGG |
| 438 | miR_2380 | CGGAGCUGGGGAUUGUGGGU |
| 440 | miR_2381 | CGGCGGCUCCAGGGACCGGCG |
| 442 | miR_2382 | CGGCGGGGACGGCGAUUGGU |
| 444 | miR_2383 | CGGGGAUCGCCGAGGGCCGGUCGGCCGCC |
| 447 | miR_2384 | CUCGGCGUGGCGUCGGUCGUGGU |
| 449 | miR_2385 | CUGCCCAGUGCUCUGAAUG |
| 451 | miR_2386 | CUGCCCAGUGCUCUGAAUGUCAAAGUG |
| 452 | miR_2387 | CUGCCCUGGCCCGAGGGACCGACU |
| 454 | miR_2388 | CUGGAGGAGCUGGCCUGU |
| 456 | miR_2389 | CUUGGCACCUAGCAAGCACUC |
| 458 | miR_2390 | GACUAUAGAACUUUCCCCCUC |
| 460 | miR_2391 | GAGAGCAGUGUGUGUUGCCUGG |
| 462 | miR_2392 | GAGGAAGGUGGGGAUGC |
| 464 | miR_2393 | GAGUGAGAGGGAGAGAACGCGGUCUGAGUG |
| 466 | miR_2394 | GAUGCCUGGGAGUUGCGAUCU |
| 468 | miR_2395 | GAUGCCUGGGAGUUGCGAUCGC |
| 469 | miR_2396 | GCAUGGGUGGUUCAGUGG |
| 471 | miR_2397 | GCAUGGGUGGUUCAGUGGU |
| 472 | miR_2398 | GCAUGGGUGGUUCAGUGGUAGAAUUCUCGCC |
| 473 | miR_2399 | GCAUUGGUGGUUCAGUGGU |
| 475 | miR_2400 | GCGUUGGUGGUAUAGUGGU |
| 477 | miR_2402 | GCGUUGGUGGUAUAGUGGUGAGC |
| 478 | miR_2403 | GCUGUGGCUGUGACUGGCG |
| 480 | miR_2404 | GGACGGUGGCCAUGGAAGU |
| 482 | miR_2405 | GGGGAUGUAGCUCAGUGGU |
| 484 | miR_2406 | GGUUCCCUCAGACCUGGU |
| 486 | miR_2407 | GGAAAGUUUGGCUGCGCGGGUUCCCC |
| 488 | miR_2408 | GGAAUACCGGGUGCUGUAGGCUUUU |
| 490 | miR_2409 | GUGAACGGGCGCCAUCCCGAGGC |
| 492 | miR_2410 | GUGAACGGGCGCCAUCCCGAGGCU |
| 493 | miR_2411 | GUGAACGGGCGCCAUCCCGAGGCUU |
| 494 | miR_2412 | GUGAACGGGCGCCAUCCCGAGGCUUU |
| 495 | miR_2413 | GUUGGUGGAGCGAUUUGUCUG |
| 497 | miR_2414 | GUUGGUGGAGCGAUUUGUCUGG |
| 498 | miR_2415 | GUUGGUGGAGCGAUUUGUCUGGU |
| 499 | miR_2416 | GUUGGUGGAGUGAUUUGUCU |
| 501 | miR_2417 | GUUGGUGGAGUGAUUUGUCUG |
| 502 | miR_2418 | GAACGCGGUCUGAGUGGU |
| 504 | miR_2419 | UACCGGGUGCUGUAGGCUUU |
| 507 | miR_2420 | UCCUGUACUGAGCUGCCCCG |
| 509 | miR_1120 | UCGAGGAGCUCACAGUCUAGU |
| 511 | miR_2422 | UCGGACACCGGCGCGUCUCU |
| 513 | miR_2423 | UCUGCCCAGUGCUCUGAAU |
| 515 | miR_2424 | UCUGCAAGUGUCAGAGGCGAG |
| 517 | miR_2425 | UCUGCAAGUGUCAGAGGCGAGG |
| 518 | miR_2426 | UCUUCUCUGUUUUGGCCAUGUG |
| 520 | miR_2427 | UGAUAUGUUUGAUAUUGGGUUG |
| 522 | miR_2428 | UGAUUGUCCAAACGCAAUUCUCG |
| 524 | miR_2429 | UGCUGGAUCAGUGGUUCGAGUC |
| 526 | miR_2430 | UUAGGGCCCUGGCUCCAUCU |
| 528 | miR_2431 | UUCUCUGUUUUGGCCAUGUG |
| 530 | miR_2432 | UUCUGCCCAGUGCUCUG |
| 532 | miR_2433 | UUCUGCCCAGUGCUCUGAAU |
| 534 | miR_2435 | UUGGCCAUGGGGCUGCGGGG |
| 536 | miR_2436 | UUGGCCAUGGGGCUGCGCGGG |
| 538 | miR_2437 | UUGGGGAAACGGCCGCUGAG |
| 540 | miR_2438 | UUGGGGAAACGGCCGCUGAGU |
| 541 | miR_2439 | UUGGUGGAGCGAUUUGUCU |
| 543 | miR_2440 | UUGGUGGAGCGAUUUGUCUG |

TABLE 5-continued miRNA Sequences

| Seq ID | MiR name | mature_sequence |
|---|---|---|
| 544 | miR_2441 | UUUCCGGCUCGCGUGGGUGU |
| 546 | miR_2442 | AAAGCUGGGUGAGAGGG |
| 548 | miR_2443 | AAAGCUGGGUUGAGAGG |
| 549 | miR_2444 | AAAGCUGGGUUGAGAGGG |
| 550 | miR_2445 | AAAGCUGGGUUGAGAGGGC |
| 555 | miR_2446 | AACCUUGGAGAGCUGAGC |
| 557 | miR_2447 | AAGCUGGGUUGAGAGGGC |

Example 5

Expression Data

Array Design

The array contains LNA spiked capture probes for detection of the microRNAs listed herein Sample Collection Samples were collected and frozen to −80° C., before treatment with RNAlater ICE (Cat#7030, Ambion) according to manual.

RNA Extraction

Samples from RNAlater® ICE (Ambion) were disrupted and homogenized using the TissueRuptor (Qiagen) in Trizol reagent (Invitrogen). Total RNA was extracted from the samples using the protocol provided with the Trizol reagent.

Quality Control (QC) of the total RNA samples were performed with the Agilent 2100 BioAnalyzer using the Agilent RNA6000 Nano kit. RNA concentrations were measured in a NanoDrop ND-1000 spectrophotometer.

RNA Labelling and Hybridization

Essentially, the instructions detailed in the "miRCURY™ LNA microRNA, Hy3™/Hy5™ Power labeling kit" were followed.

All kit reagents were thawed on ice for 15 min, vortexed and spun down for 10 min.

For hybridization, the 12-chamber TECAN HS4800Pro hybridization station was used. 25 µL 2× hybridization buffer was added to each sample, vortexed and spun.

Samples were incubated at 95° C. for 3 min before injection into the hybridization chamber. The hybridization chambers were primed with 100 ul of 1× Hybridization buffer. 50 µl of the target preparation was injected into the Hybridization station and incubated at 56° C. for 16 hours (overnight).

The slides were washed at 60° C. for 1 min with Buffer A twice, at 23° C. for 1 min with Buffer B twice, at 23° C. for 1 min with Buffer C twice, at 23° C. for 30 sec with Buffer C once. The slides were dried for 5 min.

Slides were scanned using the DNA Microarray Scanner (Agilent) at 1000% PMT setting.

Image Analysis and Data Processing

Image analysis and spot identification was done using Imagene 7.0.0 software (Biodiscovery). Tumor and normal adjacent tissue were paired and normalized with Lowess smooth fitting using Genesight 4.1.6 Lite edition software (Biodiscovery).

Ratios of tumor/normal were calculated and log 2 transformed from the Lowess normalized data sets. Raw values (Lowess normalized values) were further treated and median scaled for comparison between samples. To illustrate the tissue specificity of the individually microRNAs, an index was calculated as a ratio between the median scaled signal and an average of signal across tissues. This ratio was log 2 transformed and stated as the tissue specificity index.

Results

Differential expression of microRNAs between tumor and normal adjacent tissue can be identified using the log 2 ratios in Table 6 (ratios_454miRs) and in Table 7 (ratios_454premiRs). E.g. seq ID 113 are downregulated in tumor samples compared to normal adjacent tissue by $2^{(-1.61)} \approx 3$ fold. This could indicate a function of this microRNA in the regulation of normal tissue, which is impaired in the tumor cells. This observation could lead to the development of a cancer biomarker useful for identification of special phenotypes important for treatment of for instance adrenal cancers.

TABLE 6 table ratios_454miRs: Contains ratio data generated on tumor versus normal adjacent tissues from a variety of tissues.

| Tissue MiR name | Adrenal gland | | Bladder | | | | Colon | | Cervix | Duodenum | | Esophagus |
|---|---|---|---|---|---|---|---|---|---|---|---|---|
| | T/N-30 | T/N-30 | T/N-34 | T/N-46 | T/N-74 | T/N-ambion | T/N-47 | T/N-47 | T/N-ambion | T/N-79 | T/N-79 | T/N-ambion |
| miR_1966-miR_1988-miR_2078 | 1.35 | 1.18 | −0.28 | −0.34 | ND | 0.45 | −1.16 | −2.30 | 0.10 | −0.88 | −1.36 | −0.70 |
| miR_1967 | 0.01 | −0.17 | 0.21 | −0.83 | −0.63 | −0.06 | 0.04 | −0.12 | 0.15 | −0.52 | −0.80 | 0.14 |
| miR_1968 | 0.89 | 1.14 | −0.24 | 0.81 | 0.53 | −1.07 | 0.56 | 0.34 | −0.02 | 1.33 | 1.10 | 0.29 |
| miR_1969 | 0.75 | 1.11 | 0.30 | −0.57 | 1.15 | −0.63 | 0.61 | 0.33 | −1.68 | −0.70 | 0.25 | 0.47 |
| miR_1970 | −1.61 | −2.26 | 0.74 | −0.18 | −0.13 | −0.08 | −0.23 | ND | 0.16 | 0.78 | 0.27 | −0.36 |
| miR_1971 | 0.03 | 0.21 | −0.02 | −0.08 | −0.27 | 0.25 | −0.05 | 0.07 | 0.12 | −0.09 | 0.14 | 0.29 |
| miR_1972 | 0.61 | 0.81 | −1.88 | 0.19 | 5.03 | −1.09 | 1.11 | 0.74 | −0.56 | 2.67 | 1.62 | 0.04 |
| miR_1973 | 0.02 | 0.26 | 0.01 | −0.09 | −0.49 | 0.26 | 0.10 | 0.18 | 0.21 | ND | 0.18 | 0.33 |
| miR_1974 | −0.14 | −0.14 | 0.62 | 0.57 | 0.38 | −0.17 | −1.11 | ND | 0.27 | −0.80 | −1.08 | 0.09 |
| miR_1975 | 0.46 | 0.58 | ND | 1.12 | 4.93 | 0.16 | 0.64 | 0.39 | −0.62 | 2.28 | 1.23 | −0.95 |
| miR_1976-miR_2124 | 0.16 | 0.27 | −0.75 | 1.53 | 2.44 | −0.32 | 0.05 | ND | 0.17 | 0.59 | 0.59 | −0.14 |
| miR_1977-miR_2064 | −0.28 | −0.38 | 0.47 | 0.39 | −0.21 | −0.36 | −1.06 | −1.16 | 0.25 | −0.98 | −0.89 | 0.18 |
| miR_1978 | −1.04 | −0.28 | 0.29 | −0.45 | −1.05 | 0.19 | 0.04 | −0.05 | 0.12 | −2.37 | −1.79 | 0.16 |
| miR_1979 | 0.22 | 0.39 | −0.70 | −0.93 | 0.29 | −0.79 | 0.91 | 0.25 | 0.04 | 0.51 | 0.32 | 0.49 |

TABLE 6-continued table ratios_454miRs: Contains ratio data generated on tumor versus normal adjacent tissues from a variety of tissues.

| miR | | | | | | | | | | | | |
|---|---|---|---|---|---|---|---|---|---|---|---|---|
| miR_1980 | 0.16 | −0.07 | 0.46 | 0.44 | −0.37 | −0.21 | −0.66 | ND | 0.01 | −1.27 | −1.07 | 0.22 |
| miR_1981 | 0.25 | −0.03 | 0.39 | −0.09 | −0.41 | −0.28 | −0.67 | −0.56 | −0.14 | −1.68 | −1.76 | 0.28 |
| miR_1982 | 0.24 | 0.37 | 0.23 | −0.05 | −0.12 | 0.18 | −0.05 | 0.11 | −0.02 | 0.08 | 0.12 | −0.07 |
| miR_1983 | 0.06 | −0.09 | 0.16 | −0.04 | −0.16 | −0.07 | −1.69 | −1.36 | −0.02 | −0.52 | −0.41 | 0.53 |
| miR_1984 | 0.31 | 0.35 | −0.01 | −0.11 | 0.55 | −0.74 | −0.82 | ND | −0.12 | 1.57 | 1.11 | 0.15 |
| miR_1985 | 2.29 | 1.15 | 0.85 | 2.19 | ND | −0.21 | 0.68 | 0.22 | −1.57 | 1.04 | 0.52 | 0.09 |
| miR_1986 | 0.85 | 0.74 | 0.28 | −0.36 | ND | −0.46 | −1.71 | −2.76 | −0.12 | 0.80 | 0.29 | 0.05 |
| miR_1987 | −0.11 | −0.25 | 0.28 | 0.04 | −0.33 | −0.11 | −0.30 | −0.31 | −0.18 | −0.35 | −0.40 | 0.00 |
| miR_1989 | −0.83 | −0.88 | −0.64 | −0.25 | −0.62 | 0.83 | −0.21 | ND | 0.69 | 0.13 | 0.09 | 0.40 |
| miR_1990 | −0.55 | −1.25 | −0.45 | −0.10 | 0.10 | 0.42 | −0.35 | −0.20 | 1.29 | 0.07 | −1.21 | 0.25 |
| miR_1991 | 0.14 | −0.13 | 0.01 | 0.01 | −0.42 | −0.14 | −0.29 | −0.36 | −0.28 | −0.15 | −0.22 | −0.02 |
| miR_1992 | −0.16 | −0.28 | 0.40 | 0.50 | 0.30 | −0.25 | −0.09 | −0.02 | 0.01 | 0.23 | 0.24 | −0.03 |
| miR_1993 | 0.34 | 0.91 | −0.12 | 1.11 | 1.81 | ND | 0.28 | ND | −0.32 | 0.83 | 1.07 | 0.58 |
| miR_1994 | 0.29 | −0.15 | ND | −0.24 | 1.02 | 0.07 | −0.06 | −0.26 | 0.09 | −0.84 | −1.06 | 0.17 |
| miR_1995 | 1.13 | 0.66 | 0.15 | 0.12 | 1.34 | 0.32 | 0.14 | 0.18 | −0.04 | −0.41 | −0.26 | 0.07 |
| miR_1996 | −1.02 | −0.47 | 0.23 | −0.11 | −1.14 | 0.51 | −0.45 | 0.28 | 0.44 | −0.26 | −0.10 | 0.30 |
| miR_1997 | −0.25 | −0.45 | 0.39 | 0.42 | −0.18 | −0.43 | −0.55 | ND | 0.00 | 0.83 | 0.52 | 0.06 |
| miR_1998 | ND | −0.19 | ND | 0.12 | 0.03 | −0.23 | 0.56 | −0.51 | −0.26 | 0.00 | −0.16 | −0.15 |
| miR_1999 | −0.04 | −0.05 | 1.22 | 1.31 | −0.37 | −0.43 | −0.97 | −0.39 | −0.11 | −0.62 | −0.42 | −0.60 |
| miR_2000 | −0.78 | −0.93 | 0.01 | 0.11 | 0.00 | 0.53 | −0.54 | −0.18 | 1.38 | 0.15 | −1.07 | 0.22 |
| miR_2001 | ND | −0.50 | −0.19 | −0.12 | 0.07 | −0.45 | 0.04 | ND | −0.57 | ND | −0.47 | −0.50 |
| miR_2002 | 0.39 | 0.13 | −1.16 | 0.94 | ND | −0.79 | 0.10 | −0.44 | −1.93 | 1.21 | 0.53 | −0.29 |
| miR_2003 | ND | 1.28 | 0.02 | ND | −0.09 | −0.14 | −0.03 | −0.33 | −0.26 | ND | −0.10 | −0.09 |
| miR_2004 | 0.10 | −0.02 | −0.16 | −0.16 | 0.12 | −0.05 | 0.07 | −0.12 | −0.07 | −0.09 | −0.11 | 0.03 |
| miR_2005 | 0.06 | −0.41 | −0.10 | ND | 0.08 | −0.43 | 0.14 | ND | −0.48 | −0.05 | −0.39 | −0.35 |
| miR_2006 | −0.44 | −0.17 | −0.08 | −1.06 | −1.17 | 0.63 | −0.21 | −0.14 | 0.27 | −0.13 | 0.22 | 0.37 |
| miR_2008 | 0.21 | −0.28 | 0.45 | 0.30 | −0.26 | 0.16 | −0.56 | −0.43 | 0.47 | 0.11 | −0.27 | 0.26 |
| miR_2009 | −0.05 | −0.31 | 0.03 | 0.20 | −0.19 | −0.32 | −0.06 | −0.45 | −0.31 | −0.12 | −0.49 | 0.08 |
| miR_2010 | −0.14 | −0.37 | 0.23 | 0.09 | −0.68 | −0.39 | 0.14 | ND | −0.44 | 0.04 | −0.01 | −0.14 |
| miR_2011 | 0.63 | 0.08 | ND | −0.08 | −0.37 | 0.06 | 0.13 | 0.06 | −0.40 | −0.73 | −0.58 | −0.13 |
| miR_2012 | −0.49 | −0.89 | 0.54 | −0.18 | −0.29 | 0.46 | −0.11 | 0.30 | 0.78 | −0.16 | −0.33 | 0.14 |
| miR_2013- miR_2396- miR_2397- miR_2398 | 0.18 | 0.82 | ND | 0.70 | 1.14 | ND | 0.40 | 0.80 | −0.48 | 0.54 | 1.28 | 0.78 |
| miR_2014 | 0.07 | 0.00 | −0.15 | −0.04 | 0.12 | 0.04 | 0.07 | −0.15 | −0.03 | ND | −0.06 | 0.13 |
| miR_2015 | 1.61 | 1.35 | −1.50 | 0.58 | ND | −0.89 | 1.24 | 0.80 | −0.31 | 2.44 | 1.20 | −0.13 |
| miR_2016 | ND | −0.03 | −0.14 | 0.00 | 0.00 | −0.11 | 0.03 | −0.29 | −0.19 | −0.07 | −0.05 | −0.01 |
| miR_2017 | ND | 0.03 | 1.24 | ND | 0.07 | −0.01 | 0.05 | −0.19 | −0.09 | ND | ND | 0.07 |
| miR_2018 | −0.29 | −1.34 | −0.12 | −0.16 | 0.18 | 0.79 | −0.03 | −0.13 | 1.56 | 0.20 | −0.69 | 0.30 |
| miR_2019 | 1.04 | 0.88 | 0.59 | 0.50 | ND | −1.39 | −0.91 | ND | 0.28 | −0.03 | −0.63 | 0.67 |
| miR_2020 | 0.44 | 0.69 | −0.42 | −0.35 | 5.39 | −0.18 | 0.47 | 0.05 | −1.72 | 1.18 | 0.76 | −0.26 |
| miR_2021 | 1.72 | 0.48 | 0.28 | 0.61 | 3.63 | 0.09 | −0.59 | −0.26 | −0.76 | −0.21 | −0.53 | −0.07 |
| miR_2022 | −1.18 | −1.61 | 0.77 | −1.32 | −0.65 | −0.09 | −0.95 | −0.94 | −0.03 | −1.80 | −2.91 | 0.34 |
| miR_2023 | 0.00 | 0.20 | 0.34 | 0.16 | −0.18 | 0.12 | −0.54 | ND | 0.36 | −0.26 | −0.23 | −0.19 |
| miR_2024 | −1.54 | −2.18 | 0.42 | −0.61 | −1.18 | −0.56 | 0.49 | 0.33 | 0.51 | 0.35 | 0.29 | −0.16 |
| miR_2025 | −0.72 | −0.78 | 0.19 | −0.47 | −1.37 | 0.02 | −0.12 | −0.19 | −0.08 | −0.68 | −0.48 | 0.07 |
| miR_2026 | −0.08 | −0.27 | 0.04 | 0.41 | −0.13 | 0.00 | −0.48 | −0.10 | 0.28 | −0.06 | −0.33 | 0.03 |
| miR_2027 | −0.05 | −0.32 | 0.29 | −0.09 | −0.33 | 0.31 | −0.35 | ND | 0.39 | −0.07 | −0.56 | 0.14 |
| miR_2028 | −0.16 | −0.33 | ND | −0.14 | −0.58 | −0.19 | −0.03 | −0.30 | −0.30 | −0.23 | −0.07 | −0.15 |
| miR_2029 | −0.71 | −1.11 | 0.57 | −0.42 | −1.08 | 0.20 | −0.03 | −0.08 | 0.01 | −0.44 | −0.28 | −0.13 |
| miR_2030 | −0.24 | −0.44 | 0.71 | 0.30 | −0.03 | −0.12 | −0.13 | −0.14 | 0.24 | −0.01 | −0.45 | 0.01 |
| miR_2031 | −0.44 | −0.60 | 0.44 | −0.16 | −0.56 | −0.19 | 0.21 | 0.18 | 0.18 | −0.14 | −0.37 | 0.06 |
| miR_2032 | −2.07 | −3.88 | 0.02 | 0.12 | −0.84 | 0.27 | 0.93 | 0.61 | 0.30 | 0.34 | −1.50 | 0.01 |
| miR_2033 | 0.22 | 0.70 | −0.78 | −0.94 | −0.09 | −0.60 | 0.26 | 0.25 | 1.35 | 1.32 | 0.95 | −0.14 |
| miR_2034 | −1.51 | −1.82 | 0.53 | 0.19 | −0.99 | −0.36 | −0.25 | −0.18 | 0.74 | 0.32 | 0.20 | 0.54 |
| miR_2035 | 0.45 | 0.62 | −0.91 | −0.16 | 0.24 | −0.27 | 0.13 | ND | −0.18 | 1.64 | 1.20 | −0.11 |
| miR_2036 | −0.40 | 0.04 | 0.03 | 0.17 | −0.50 | −0.17 | −0.15 | −0.17 | 0.37 | −0.33 | −0.37 | 0.25 |
| miR_2037 | 0.05 | −0.12 | 0.07 | 0.03 | −0.47 | −0.40 | −0.32 | −0.15 | 0.05 | 0.55 | 0.34 | 0.20 |
| miR_2038 | −0.70 | −0.62 | 0.25 | −0.40 | −1.45 | 0.02 | 0.04 | 0.03 | −0.23 | 0.18 | 0.43 | −0.08 |
| miR_2040 | ND | −0.11 | −0.10 | −0.04 | 0.02 | −0.06 | −0.14 | ND | −0.14 | −0.03 | −0.07 | 0.00 |
| miR_2041 | −0.48 | 0.00 | 0.62 | 0.03 | −0.26 | 0.04 | −0.38 | −0.05 | 0.24 | −0.22 | −0.33 | 0.23 |
| miR_2042 | 0.48 | 0.56 | −0.89 | 0.17 | −0.02 | 0.08 | 0.13 | −0.05 | −0.80 | 1.06 | 0.56 | −0.70 |
| miR_2043 | 1.40 | 1.22 | −0.57 | 0.16 | 1.13 | 0.41 | −1.31 | −1.56 | 0.10 | 0.08 | 0.04 | −0.61 |
| miR_2044 | −0.19 | −0.25 | 0.14 | 0.00 | −0.62 | −0.13 | 0.13 | ND | −0.13 | −0.10 | −0.24 | −0.07 |
| miR_2045 | ND | −0.22 | ND | 0.00 | 0.10 | −0.55 | 0.06 | −0.42 | −0.41 | −0.01 | −0.30 | −0.40 |
| miR_2046 | ND | −0.25 | −0.11 | −0.06 | 0.12 | −0.22 | 0.04 | −0.44 | −0.32 | ND | −0.23 | −0.19 |
| miR_2047 | −0.37 | −0.19 | 0.19 | 0.60 | −0.65 | 0.04 | −0.01 | −0.22 | −0.39 | −0.70 | −0.64 | 0.04 |
| miR_2048 | −0.90 | −0.82 | −0.34 | 0.88 | −1.02 | 0.14 | −0.97 | −0.70 | 0.13 | −0.26 | −0.61 | 0.15 |
| miR_2049 | 0.08 | −0.02 | 0.06 | −0.91 | −0.79 | 0.43 | 0.71 | 0.61 | 0.43 | 0.66 | 0.67 | 0.16 |
| miR_2050 | 0.09 | −0.21 | −0.07 | 0.03 | −0.04 | −0.25 | −0.03 | −0.37 | 0.06 | −0.04 | −0.17 | −0.35 |
| miR_2051 | −0.03 | −0.32 | 0.51 | 0.25 | −0.54 | −0.15 | −0.51 | −0.57 | 0.33 | −0.40 | −0.45 | 0.00 |
| miR_2052 | −0.17 | −0.41 | 0.42 | 0.52 | −1.04 | 0.07 | −0.35 | ND | 0.16 | −0.38 | −0.21 | 0.01 |

TABLE 6-continued table ratios_454miRs: Contains ratio data generated on tumor versus normal adjacent tissues from a variety of tissues.

| | | | | | | | | | | | | |
|---|---|---|---|---|---|---|---|---|---|---|---|---|
| miR_2053-miR_2137-miR_2443-miR_2444-miR_2445-320 | 0.57 | 0.66 | −0.04 | 0.19 | 0.52 | 0.67 | 0.80 | 0.56 | 0.08 | −0.25 | −0.15 | −0.53 |
| miR_2054 | 0.01 | 0.33 | −0.97 | 1.10 | ND | −0.78 | −0.06 | −1.24 | 0.74 | 2.07 | 1.13 | −0.27 |
| miR_2055 | −1.80 | −2.60 | 0.36 | −0.33 | −0.70 | 0.31 | −0.24 | 0.48 | 0.16 | −0.62 | −1.08 | −0.18 |
| miR_2056 | ND | −0.16 | −0.04 | ND | 0.07 | −0.14 | −0.18 | −0.38 | −0.21 | −0.12 | −0.41 | −0.28 |
| miR_2057 | 0.08 | 0.54 | −0.10 | 0.28 | 1.29 | −0.61 | 0.18 | ND | 1.74 | 1.48 | 0.83 | 0.14 |
| miR_2058 | 0.88 | 0.01 | 0.96 | 1.18 | 0.86 | −1.01 | −0.28 | −0.11 | 0.08 | −0.16 | −0.33 | −0.37 |
| miR_2060 | −0.41 | −0.54 | 0.84 | −1.25 | −0.77 | −0.03 | 0.75 | 0.07 | 0.45 | −1.85 | −0.70 | 0.48 |
| miR_2061 | −0.38 | −0.41 | 0.26 | 0.03 | −0.95 | −0.11 | −0.34 | −0.30 | −0.09 | −0.81 | −0.59 | 0.30 |
| miR_2062 | 0.08 | 0.21 | −0.80 | 1.25 | 1.06 | −0.47 | 0.00 | ND | 0.25 | −0.07 | 0.73 | −0.26 |
| miR_2063 | 0.00 | 0.24 | ND | −0.07 | −0.18 | 0.16 | 0.16 | −0.06 | 0.15 | −0.07 | 0.20 | 0.29 |
| miR_2065 | −0.27 | −0.33 | 0.24 | −0.33 | −1.39 | 0.00 | 0.08 | −0.12 | −0.25 | 0.20 | 0.22 | −0.22 |
| miR_2066 | −0.29 | −0.28 | 0.76 | 0.81 | −0.14 | −0.40 | −0.87 | −0.75 | 0.17 | −0.70 | −0.45 | −0.11 |
| miR_2067 | −0.37 | −0.76 | 0.74 | 0.33 | −0.92 | −0.26 | −0.38 | −0.18 | 0.20 | −0.31 | −0.26 | −0.01 |
| miR_2068 | 0.01 | −0.40 | 0.05 | −0.10 | 0.43 | −0.03 | 0.11 | −0.15 | 0.66 | −0.18 | −0.03 | −0.07 |
| miR_2069-miR_2155 | −0.10 | −0.07 | −0.02 | 0.13 | −0.44 | 0.04 | −0.30 | ND | −0.19 | −0.50 | −0.37 | −0.07 |
| miR_2070 | −0.29 | −0.41 | 0.26 | 0.17 | −0.61 | −0.04 | −0.49 | −0.41 | −0.10 | −0.58 | −0.72 | 0.02 |
| miR_2071 | 0.37 | 0.62 | 0.03 | 0.03 | −0.65 | 0.09 | −0.92 | ND | 0.18 | −0.68 | −2.48 | −0.46 |
| miR_2072 | 0.10 | −0.02 | ND | 0.96 | 0.51 | −0.09 | −0.51 | −0.25 | −0.09 | −0.40 | −0.28 | 0.32 |
| miR_2073 | 0.16 | −0.15 | −0.04 | −0.02 | 0.04 | −0.09 | 0.02 | −0.25 | −0.19 | −0.07 | −0.13 | −0.07 |
| miR_2074 | 0.04 | 0.06 | −0.07 | −0.10 | 0.02 | 0.13 | 0.04 | 0.03 | 0.05 | −0.02 | 0.02 | 0.28 |
| miR_2075 | 0.44 | −0.06 | 0.20 | 0.06 | 0.42 | −0.07 | −0.29 | ND | −0.21 | 0.01 | −0.12 | −0.04 |
| miR_2076 | 0.35 | 0.17 | 0.32 | 0.14 | −0.19 | 0.30 | −0.02 | 0.07 | 0.25 | 0.24 | −0.47 | 0.42 |
| miR_2077 | −0.34 | −0.39 | 0.11 | −0.16 | −0.74 | 0.00 | −0.82 | −0.25 | 0.14 | −0.04 | −0.07 | 0.05 |
| miR_2079 | −0.17 | −0.22 | 0.23 | −0.22 | −1.02 | −0.27 | 0.44 | ND | 0.22 | −0.91 | −0.33 | 0.06 |
| miR_2080 | −0.60 | −0.13 | ND | 0.06 | −1.28 | −0.14 | −0.28 | −0.29 | −0.24 | −0.06 | −0.15 | −0.10 |
| miR_2081 | ND | −0.12 | −0.10 | −0.03 | −0.11 | −0.12 | 0.02 | −0.32 | −0.32 | ND | −0.14 | −0.04 |
| miR_2082 | −0.27 | −0.09 | 0.46 | −0.91 | −1.22 | 0.13 | 1.26 | 0.49 | 0.08 | −0.38 | −0.43 | −0.17 |
| miR_2083 | −0.01 | −0.16 | 0.47 | 0.55 | −0.49 | −0.15 | −0.62 | −0.45 | 0.40 | −0.68 | −0.77 | −0.15 |
| miR_2084 | ND | −0.38 | 0.05 | ND | −0.40 | −0.39 | −0.21 | −0.43 | −0.31 | 0.05 | −0.17 | −0.35 |
| miR_2086 | −0.03 | 0.03 | 0.43 | 0.16 | −0.70 | −0.16 | −0.33 | −0.24 | −0.02 | −0.59 | −0.58 | 0.06 |
| miR_2087 | −1.54 | −1.04 | 0.29 | −0.42 | −1.65 | 0.31 | 0.35 | 0.27 | 0.14 | −0.51 | −0.19 | −0.10 |
| miR_2088-miR_2431 | 0.12 | 0.05 | −0.13 | 0.01 | 0.12 | 0.04 | 0.09 | −0.01 | −0.03 | ND | 0.27 | 0.13 |
| miR_2090 | 2.26 | 1.57 | 0.26 | 2.23 | ND | −1.79 | 0.74 | ND | −1.87 | 2.06 | 0.96 | −0.05 |
| miR_2091 | 0.00 | −0.45 | ND | ND | 0.15 | −0.41 | 0.20 | −0.59 | −0.35 | −0.02 | −0.43 | −0.32 |
| miR_2092 | −0.87 | −0.38 | −0.11 | −0.34 | −1.10 | 0.02 | 0.23 | 0.13 | −0.05 | 0.34 | 0.24 | 0.09 |
| miR_2093 | 1.34 | 1.27 | −0.51 | 0.80 | 5.42 | −0.37 | 1.26 | 0.94 | −1.46 | 2.07 | 1.34 | −0.55 |
| miR_2094 | 0.12 | 0.28 | −0.06 | −0.15 | 0.01 | 0.21 | 0.08 | ND | 0.22 | ND | 0.10 | 0.28 |
| miR_2095 | 1.03 | 0.98 | −0.88 | −0.52 | 4.18 | 0.36 | −1.18 | −1.28 | 0.01 | 2.12 | 1.34 | −0.34 |
| miR_2096 | 0.01 | 0.31 | −0.04 | −0.03 | −0.02 | 0.33 | ND | 0.24 | 0.28 | −0.27 | 0.28 | 0.41 |
| miR_2097 | 0.00 | 0.26 | −0.05 | −0.13 | 0.05 | 0.24 | −0.01 | 0.12 | 0.10 | ND | 0.11 | 0.30 |
| miR_2098 | 0.08 | −0.19 | −0.13 | −0.17 | 0.08 | −0.25 | 0.04 | ND | −0.33 | ND | −0.34 | −0.21 |
| miR_2099 | −0.01 | 0.19 | ND | ND | 0.24 | −0.34 | −0.15 | −0.24 | −0.28 | 0.25 | 0.30 | −0.20 |
| miR_2100 | 0.91 | 0.76 | 0.27 | 0.33 | 1.40 | −0.60 | 0.09 | 0.14 | 0.01 | 0.22 | 0.39 | −0.22 |
| miR_2101 | 0.11 | 0.06 | 0.19 | 0.39 | −0.68 | −0.27 | −0.55 | −0.19 | −0.70 | 0.35 | 0.26 | 0.02 |
| miR_2102 | −0.04 | −0.34 | −0.09 | −0.01 | −0.03 | −0.40 | −0.06 | −0.55 | −0.34 | −0.07 | −0.33 | −0.36 |
| miR_2104 | −0.29 | −0.17 | 0.27 | −0.16 | −0.68 | 0.09 | −0.02 | −0.08 | 0.06 | −0.01 | 0.09 | 0.04 |
| miR_2105 | −0.20 | −0.76 | 0.55 | −0.09 | −0.22 | −0.28 | −0.53 | −0.41 | −0.19 | 0.00 | −0.13 | −0.12 |
| miR_2107 | 1.21 | 0.80 | 0.27 | −0.13 | 1.44 | −0.32 | −1.57 | −2.21 | −0.21 | 0.17 | −0.11 | 0.12 |
| miR_2108 | 0.14 | −0.05 | −0.06 | −0.08 | 0.02 | −0.18 | −0.01 | ND | −0.13 | ND | −0.11 | −0.16 |
| miR_2109 | 0.17 | 0.35 | ND | −0.59 | −0.25 | 0.54 | 0.72 | 0.28 | 0.13 | −0.92 | −0.73 | −0.07 |
| miR_2110 | 0.01 | −0.25 | −0.10 | −0.03 | 0.02 | −0.24 | 0.08 | −0.33 | −0.34 | ND | −0.13 | −0.17 |
| miR_2111 | 0.40 | 0.33 | 0.02 | 0.03 | 0.14 | 0.21 | 0.10 | 0.22 | 0.13 | 0.19 | 0.32 | 0.24 |
| miR_2113 | −0.11 | −0.03 | 0.18 | 0.01 | −0.48 | 0.02 | −0.32 | −0.16 | −0.12 | ND | −0.07 | −0.03 |
| miR_2114 | 1.09 | 0.78 | 0.33 | 1.08 | 4.54 | −0.60 | −0.16 | 0.00 | −0.93 | −0.35 | −0.64 | 0.05 |
| miR_2115 | −0.79 | −0.87 | 0.09 | 0.05 | −0.74 | 0.04 | −0.53 | −0.37 | 0.13 | −0.13 | −0.16 | 0.03 |
| miR_2116 | 0.01 | −0.11 | −0.10 | −0.03 | −0.11 | −0.03 | 0.00 | ND | −0.10 | −0.23 | −0.41 | 0.14 |
| miR_2117 | −0.58 | 0.39 | ND | −0.31 | −0.91 | 0.17 | 0.25 | 0.28 | 0.25 | ND | 0.66 | 0.36 |
| miR_2118 | −0.67 | −0.89 | 0.10 | −0.08 | −0.01 | 0.47 | −0.55 | −0.22 | 1.30 | 0.13 | −1.16 | 0.23 |
| miR_2119 | −1.04 | −0.83 | −0.68 | −0.88 | −1.09 | 0.57 | −0.19 | 0.07 | 0.90 | −0.34 | −0.06 | 0.19 |
| miR_2120 | −1.16 | −0.81 | 0.19 | −0.94 | −0.81 | 0.05 | −0.14 | 0.08 | 0.27 | −0.07 | 0.26 | 0.58 |
| miR_2121 | 0.01 | 0.07 | −0.19 | −0.09 | 0.09 | 0.12 | 1.66 | −0.22 | −0.02 | −0.01 | 0.02 | 0.14 |
| miR_2122 | −0.22 | −0.54 | 0.41 | 0.44 | 0.65 | −0.33 | −0.23 | −0.09 | 0.75 | 0.03 | 0.16 | 0.36 |
| miR_2123 | −0.99 | −0.93 | 0.47 | 0.20 | −1.29 | 0.10 | −0.72 | −0.12 | 0.02 | −2.34 | −2.30 | 0.33 |
| miR_2125 | 0.25 | 0.02 | ND | −0.14 | 0.84 | 0.10 | −0.68 | −0.40 | 0.07 | −0.38 | −0.30 | 0.27 |
| miR_2126 | −0.07 | 0.19 | 0.14 | 0.07 | −0.33 | 0.27 | −0.30 | 0.09 | 0.19 | −0.14 | −0.05 | 0.31 |
| miR_2127 | −0.49 | −0.29 | 0.33 | 0.58 | −0.81 | −0.28 | −0.99 | −0.97 | −0.04 | −2.13 | −2.09 | 0.38 |
| miR_2128 | −0.68 | −0.84 | 0.24 | −0.50 | −0.80 | 0.20 | 0.20 | ND | 0.25 | −1.02 | −1.34 | 0.03 |
| miR_2129 | −0.30 | −0.54 | 0.36 | 0.16 | −0.64 | −0.12 | −0.69 | −0.68 | 0.12 | −0.79 | −0.90 | 0.14 |
| miR_2130 | −0.78 | −0.50 | 0.98 | −0.82 | −0.67 | 0.55 | 0.62 | 0.29 | 0.10 | −3.36 | −3.10 | 0.45 |
| miR_2131 | 0.02 | 0.11 | 0.06 | 0.50 | −0.20 | −0.05 | −0.15 | −0.15 | −0.14 | −0.21 | −0.26 | 0.04 |

TABLE 6-continued table ratios_454miRs: Contains ratio data generated on tumor versus normal adjacent tissues from a variety of tissues.

| miR | | | | | | | | | | | | |
|---|---|---|---|---|---|---|---|---|---|---|---|---|
| miR_2132 | −0.10 | 0.23 | 0.24 | 0.08 | −0.22 | 0.10 | −0.26 | ND | 0.25 | −0.26 | −0.07 | 0.36 |
| miR_2134 | 0.03 | −0.02 | ND | 0.00 | −0.83 | −0.11 | −0.39 | −0.03 | −0.07 | 0.12 | −0.03 | 0.16 |
| miR_2135 | −0.11 | −0.49 | 0.22 | 0.19 | −0.83 | −0.05 | −0.29 | −0.38 | −0.07 | −0.80 | −1.05 | 0.02 |
| miR_2136 | 0.18 | 0.19 | 0.11 | −0.90 | −0.94 | 0.53 | −0.04 | −0.05 | 0.02 | 0.10 | 0.16 | −0.01 |
| miR_2137-miR_2444-miR_2445-miR_2447-320 | 0.39 | 0.71 | 0.23 | 0.34 | −0.07 | 0.69 | 0.82 | 0.35 | −0.09 | −0.58 | −0.45 | −0.46 |
| miR_2138 | 0.97 | 0.81 | −0.58 | 0.42 | 1.46 | −0.27 | 0.28 | 0.06 | −2.09 | 0.74 | 0.43 | 0.00 |
| miR_2139 | −1.04 | −1.38 | 0.40 | −0.02 | −0.76 | −0.16 | −0.18 | −0.01 | −0.14 | −0.12 | −0.34 | −0.28 |
| miR_2140 | −0.72 | −0.88 | 0.63 | 0.85 | −1.07 | −0.11 | −0.42 | −0.49 | 0.19 | −0.92 | −1.15 | 0.01 |
| miR_2141 | −0.04 | 0.08 | −0.11 | 0.13 | 0.14 | 0.09 | −0.16 | −0.14 | 0.05 | 0.19 | ND | 0.08 |
| miR_2142 | −1.31 | −1.10 | 0.29 | −0.51 | −1.43 | 0.28 | −0.26 | ND | 0.02 | −1.17 | −1.22 | 0.07 |
| miR_2143 | 0.08 | −0.17 | ND | −0.15 | 0.13 | −0.24 | 0.07 | −0.18 | −0.17 | −0.06 | −0.20 | −0.11 |
| miR_2144 | −0.03 | −0.15 | 0.58 | 1.77 | −0.88 | −0.24 | −2.17 | −0.41 | 0.00 | 0.11 | −0.58 | 0.54 |
| miR_2145 | 0.21 | −0.20 | −0.09 | −0.08 | −0.52 | −0.19 | 0.05 | −0.28 | −0.16 | 0.01 | −0.13 | −0.07 |
| miR_2146 | −0.76 | −0.45 | 0.48 | 0.42 | −1.13 | 0.15 | −0.43 | −0.31 | 0.34 | −0.77 | −0.39 | 0.23 |
| miR_2147 | −0.07 | 0.24 | 0.20 | 0.17 | −0.11 | 0.20 | −0.42 | 0.04 | 0.20 | ND | 0.16 | 0.51 |
| miR_2148 | 0.07 | −0.28 | −0.01 | 0.01 | −0.32 | −0.18 | −0.66 | −0.77 | −0.35 | 0.53 | 0.40 | −0.18 |
| miR_2149 | 0.41 | 0.17 | 0.55 | 1.84 | 1.36 | −0.32 | 0.41 | −0.37 | −0.40 | 0.20 | −0.35 | 0.04 |
| miR_2150 | 1.40 | 1.20 | 0.30 | 0.59 | 2.57 | −0.21 | 0.76 | ND | −0.32 | 0.34 | 0.58 | 0.19 |
| miR_2151 | −0.36 | −0.36 | 0.71 | 0.57 | −0.54 | −0.23 | −0.84 | −0.83 | −0.15 | −0.70 | −0.63 | 0.20 |
| miR_2152 | ND | 0.10 | ND | 0.24 | 1.68 | 0.00 | −0.26 | −0.11 | 0.21 | −0.01 | ND | 0.29 |
| miR_2153-miR_2163 | 0.15 | 0.22 | 0.19 | 0.68 | −0.42 | −0.26 | 0.16 | 0.17 | −0.31 | −0.23 | −0.10 | −0.12 |
| miR_2154 | 0.23 | 0.28 | −0.21 | 0.05 | 0.21 | 0.19 | 0.14 | 0.11 | 0.00 | 0.26 | 0.28 | 0.24 |
| miR_2156 | −0.03 | 0.08 | −3.46 | −0.12 | −0.23 | 0.08 | −0.03 | −0.10 | 0.04 | −0.03 | 0.08 | 0.19 |
| miR_2157 | 0.55 | 0.31 | −1.43 | 0.52 | 3.35 | −1.07 | −0.24 | −0.61 | −3.96 | 1.17 | 0.64 | −0.32 |
| miR_2158 | −0.67 | −0.72 | 0.26 | 0.28 | −0.34 | −0.15 | −0.87 | −0.52 | 0.87 | −1.17 | −1.66 | −0.01 |
| miR_2159 | −0.02 | 0.06 | 0.73 | 0.61 | 0.01 | −0.18 | 0.32 | ND | −0.02 | −0.17 | 0.03 | −0.35 |
| miR_2160 | −1.11 | −0.98 | ND | 0.23 | −0.82 | −0.05 | −0.75 | 0.03 | 0.22 | 0.11 | −0.56 | −0.01 |
| miR_2161 | −0.37 | −0.36 | 0.62 | 0.49 | −0.77 | −0.29 | −0.50 | −0.43 | −0.12 | −0.17 | −0.28 | 0.16 |
| miR_2162 | −1.20 | −1.75 | −0.02 | −0.50 | −0.59 | 0.37 | 0.02 | 0.13 | 0.68 | −0.03 | −0.01 | 0.11 |
| miR_2164 | −0.45 | −0.64 | 0.59 | −0.64 | −0.87 | 0.32 | 0.00 | 0.16 | 0.25 | −1.19 | −1.33 | −0.01 |
| miR_2165 | −0.21 | −0.03 | −0.18 | −0.12 | −0.83 | −0.03 | −0.25 | 0.00 | 0.20 | −0.73 | −0.43 | 0.34 |
| miR_2166 | −0.61 | −0.81 | 0.58 | −0.63 | −1.02 | 0.25 | −0.02 | 0.22 | 0.15 | −0.42 | −0.01 | 0.13 |
| miR_2167 | −0.04 | 0.00 | 0.24 | 0.05 | −0.68 | 0.07 | −0.51 | ND | 0.26 | −2.81 | −2.69 | −0.01 |
| miR_2168 | 1.34 | 1.02 | 0.18 | 0.62 | ND | −0.66 | −0.36 | −0.30 | −0.60 | −0.71 | −0.64 | −0.02 |
| miR_2169 | −0.47 | −0.37 | −0.47 | 0.16 | 1.01 | −0.60 | 1.64 | 1.16 | −0.05 | 2.04 | 1.40 | 0.08 |
| miR_2170 | 0.18 | −0.02 | 0.05 | 0.38 | −0.85 | 0.07 | −0.23 | −0.06 | −0.18 | −0.04 | −0.20 | 0.10 |
| miR_2171 | −1.25 | −1.59 | 1.06 | −0.84 | −0.99 | 0.31 | 0.21 | ND | −0.07 | 0.70 | 0.36 | −0.64 |
| miR_2364 | −0.04 | 0.14 | ND | −0.32 | −0.68 | 0.18 | 0.04 | 0.00 | 0.11 | −0.08 | 0.20 | 0.15 |
| miR_2365-miR_2408-miR_2419 | 0.10 | 1.07 | −0.26 | −0.26 | 0.84 | −0.14 | 0.11 | 0.49 | −1.29 | −0.71 | 0.20 | 0.35 |
| miR_2366 | 1.52 | 1.30 | 0.20 | 0.90 | ND | 0.01 | 0.48 | 0.30 | 0.08 | −1.19 | −1.09 | −0.28 |
| miR_2370-miR_2391 | 0.04 | 0.18 | −0.04 | −0.09 | −0.29 | 0.18 | −0.13 | −0.08 | 0.12 | −0.25 | 0.01 | 0.21 |
| miR_2371 | −0.06 | −0.34 | −0.04 | ND | −0.31 | −0.32 | 0.04 | ND | −0.39 | ND | −0.28 | −0.22 |
| miR_2372-miR_2373-miR_2404 | −0.30 | −0.18 | −0.02 | −0.87 | −0.91 | 0.25 | 0.40 | 0.35 | 0.17 | −0.17 | −0.61 | 0.15 |
| miR_2374-miR_2375-miR_2376-miR_2377 | 0.12 | −0.20 | 0.69 | −1.92 | −0.51 | 0.33 | 0.74 | ND | −0.12 | ND | ND | 0.13 |
| miR_2374-miR_2375-miR_2376-miR_2377-miR_2416-miR_2417 | 0.54 | 0.20 | 0.24 | −1.86 | −0.52 | 0.14 | 0.47 | 0.16 | −0.13 | −2.45 | −1.98 | 0.10 |
| miR_2378-miR_2418 | 1.16 | 1.09 | 0.79 | 0.71 | ND | −0.33 | 0.06 | 0.43 | −1.61 | −0.78 | −0.04 | −0.03 |
| miR_2379 | 0.38 | 0.06 | ND | 0.44 | −0.22 | −0.23 | −0.73 | −0.99 | 0.28 | −0.93 | −1.03 | −0.08 |
| miR_2380 | −0.16 | 0.28 | −0.13 | 0.18 | 0.40 | −0.22 | 0.03 | −0.06 | 0.67 | −0.95 | −1.83 | 0.59 |
| miR_2381 | −2.50 | −6.54 | 0.76 | −0.35 | −0.80 | −0.84 | 0.72 | 0.83 | 0.99 | 0.39 | 0.48 | −0.50 |
| miR_2383 | −1.78 | −2.66 | 2.24 | −0.93 | 0.05 | 1.44 | −0.20 | −0.10 | 0.79 | ND | ND | −0.27 |
| miR_2385-miR_2386-miR_2423-miR_2433 | −1.19 | −1.16 | 0.25 | −1.99 | −0.96 | 0.97 | 0.43 | 0.32 | 0.46 | −1.79 | −3.33 | 0.12 |
| miR_2387 | −0.81 | −0.59 | 0.14 | −0.86 | −0.78 | 0.79 | 0.35 | 0.63 | 0.56 | −0.40 | −0.50 | −0.10 |
| miR_2388 | −0.67 | −0.29 | 0.15 | 0.40 | −1.30 | 0.16 | −1.97 | −0.66 | 0.20 | −1.74 | −0.61 | 0.51 |
| miR_2389 | 0.21 | 0.25 | −0.14 | −0.14 | −0.53 | 0.22 | 0.01 | 0.11 | 0.15 | −0.07 | 0.11 | 0.16 |
| miR_2390 | −0.30 | −0.28 | −0.14 | −0.26 | −0.64 | 0.13 | 0.37 | ND | 0.11 | 0.39 | 0.42 | −0.09 |

TABLE 6-continued table ratios_454miRs: Contains ratio data generated on tumor versus normal adjacent tissues from a variety of tissues.

| miR | | | | | | | | | | | | |
|---|---|---|---|---|---|---|---|---|---|---|---|---|
| miR_2392 | −0.26 | −0.26 | −0.18 | −0.74 | −1.14 | −0.22 | 1.51 | 0.77 | 0.35 | 1.32 | 1.12 | −0.17 |
| miR_2393 | 0.41 | 0.56 | 0.69 | 0.76 | 0.43 | −0.38 | 0.24 | 0.36 | −1.18 | −0.02 | −0.03 | −0.31 |
| miR_2394-miR_2395 | 1.55 | 1.57 | 0.20 | 0.80 | 2.60 | −0.57 | 0.16 | ND | −1.55 | −1.18 | −0.52 | −0.27 |
| miR_2396-miR_2397-miR_2398 | 0.34 | 0.90 | −0.97 | 0.30 | 1.11 | ND | 0.28 | 0.60 | −0.65 | 0.74 | 1.11 | 0.61 |
| miR_2399 | 0.58 | 0.76 | −0.43 | 0.87 | 1.54 | −1.02 | −0.02 | 0.08 | −1.11 | 0.55 | 0.68 | 0.12 |
| miR_2400-miR_2401-miR_2402 | 0.61 | 1.21 | −0.83 | 0.66 | 1.23 | −0.89 | 0.18 | ND | 0.25 | 0.42 | 1.10 | −0.18 |
| miR_2403 | 0.10 | −0.03 | ND | −0.10 | −0.08 | −0.35 | −0.18 | −0.33 | −0.05 | −0.65 | −0.56 | 0.24 |
| miR_2405 | 0.27 | 0.97 | −0.60 | 0.44 | −0.13 | −0.85 | 0.09 | 0.17 | −0.03 | 0.43 | 0.71 | 0.12 |
| miR_2406 | −0.08 | 0.11 | 0.52 | −0.27 | −0.01 | 0.31 | 0.32 | 0.22 | 0.22 | −0.14 | 0.06 | 0.05 |
| miR_2407 | ND | 0.11 | ND | ND | −0.01 | 0.09 | −0.15 | −0.03 | 0.06 | ND | 0.09 | 0.19 |
| miR_2409-miR_2410-miR_2411-miR_2412 | −1.10 | −0.16 | 0.18 | −0.81 | −1.58 | 0.35 | 0.61 | 0.45 | 0.30 | 0.26 | 0.38 | 0.09 |
| miR_2413-miR_2414-miR_2415-miR_2439-miR_2440 | −0.21 | −0.42 | 0.06 | −0.73 | −0.83 | 0.04 | −0.50 | 0.37 | 0.11 | −3.27 | ND | 0.05 |
| miR_2422 | −0.84 | 0.04 | 0.00 | −0.42 | −1.49 | 0.37 | 0.39 | ND | 0.20 | 0.37 | 0.55 | 0.28 |
| miR_2424-miR_2425 | −1.07 | −1.92 | 0.07 | 0.03 | −0.71 | −0.52 | −0.33 | −0.13 | 0.43 | 0.09 | −0.51 | −0.08 |
| miR_2426 | 0.05 | −0.19 | −0.15 | −0.04 | 0.14 | −0.18 | 0.14 | −0.36 | −0.24 | 0.07 | −0.08 | −0.08 |
| miR_2428 | 0.87 | 0.97 | −0.25 | 0.02 | 0.59 | 0.03 | 0.30 | ND | −0.06 | 0.81 | 0.85 | 0.12 |
| miR_2429 | 0.42 | 0.31 | ND | 0.12 | 0.47 | −0.01 | 0.16 | 0.15 | −0.04 | 0.43 | 0.49 | 0.04 |
| miR_2432-miR_2433 | −1.44 | −2.19 | 0.26 | −2.04 | −1.05 | 0.88 | 0.47 | 0.33 | 0.21 | −2.21 | −4.44 | 0.12 |
| miR_2435-miR_2436 | 1.09 | 0.56 | −0.86 | 0.68 | 0.93 | −0.48 | −0.06 | −0.23 | −1.99 | 0.84 | 0.46 | 0.23 |
| miR_2442 | −0.12 | −0.07 | 0.14 | −0.45 | −1.11 | 0.51 | 0.69 | 0.46 | 0.13 | 0.25 | 0.13 | −0.52 |
| miR_2446 | 1.69 | 1.26 | 0.08 | 1.49 | ND | −0.26 | 0.14 | −0.02 | −0.36 | 0.02 | −0.42 | −0.05 |

| Tissue MiR name | Kidney | | | | | | | | | | |
|---|---|---|---|---|---|---|---|---|---|---|---|
| | T/N-48 | T/N-55 | T/N-55 | T/N-57 | T/N-57 | T/N-60 | T/N-61 | T/N-66 | T/N-73 | T/N-76 | T/N-81 |
| miR_1966-miR_1988-miR_2078 | −2.43 | −4.15 | ND | −1.02 | −1.00 | 0.20 | −2.63 | −0.25 | 0.31 | 0.38 | 0.49 |
| miR_1967 | 0.79 | 0.03 | 0.03 | −0.53 | −0.53 | −0.79 | 0.81 | −0.49 | 0.18 | −1.29 | 0.10 |
| miR_1968 | −0.27 | −0.43 | 0.32 | 0.80 | 0.49 | 0.56 | 0.35 | −0.12 | 0.96 | 0.99 | 0.55 |
| miR_1969 | −0.43 | −0.99 | −0.12 | −0.12 | −0.24 | −0.07 | −0.14 | −0.50 | 0.27 | −0.23 | −0.41 |
| miR_1970 | 0.17 | 0.24 | 0.11 | −0.80 | −0.88 | −0.75 | −0.16 | 0.13 | −0.84 | −1.17 | 0.08 |
| miR_1971 | 0.05 | 0.00 | 0.19 | −0.18 | −0.03 | 0.20 | 0.09 | −0.03 | −0.27 | 0.03 | 0.14 |
| miR_1972 | −0.14 | −0.19 | −0.01 | 0.32 | 0.09 | 0.54 | −0.83 | 0.35 | 1.36 | ND | 1.43 |
| miR_1973 | −0.09 | −0.03 | 0.21 | −0.10 | −0.01 | 0.14 | 0.19 | −0.04 | −0.09 | −0.03 | −0.85 |
| miR_1974 | −0.08 | −0.02 | −0.22 | −0.49 | −0.53 | −0.63 | −0.23 | −1.16 | −0.19 | −1.24 | 0.85 |
| miR_1975 | −1.34 | −0.13 | 0.50 | 1.57 | 0.51 | 1.70 | −1.31 | 1.08 | 3.53 | 3.16 | 1.06 |
| miR_1976-miR_2124 | −1.01 | −0.90 | −1.88 | −0.11 | −0.43 | −0.81 | 0.82 | −0.15 | −1.05 | −1.29 | 0.36 |
| miR_1977-miR_2064 | −0.19 | −0.32 | −0.39 | −0.58 | −0.62 | 0.10 | −0.33 | −0.34 | 0.24 | −0.49 | 0.86 |
| miR_1978 | 0.65 | 0.27 | 0.18 | −0.57 | −0.42 | −0.38 | −0.16 | −0.60 | −0.56 | −1.50 | −0.35 |
| miR_1979 | −0.44 | −0.53 | 0.31 | 1.22 | 1.16 | 1.35 | 0.39 | 0.26 | 2.76 | 0.96 | −0.65 |
| miR_1980 | 1.13 | 0.82 | 0.39 | −0.52 | −0.49 | −0.91 | −0.23 | 0.13 | −0.29 | −0.81 | −0.10 |
| miR_1981 | 0.72 | 0.63 | −0.11 | −0.51 | −0.50 | −1.00 | 0.36 | −0.06 | −0.35 | −0.67 | −0.34 |
| miR_1982 | −0.13 | 0.14 | 0.07 | −0.39 | −0.09 | 0.02 | −0.11 | −0.18 | 0.23 | 0.10 | 0.22 |
| miR_1983 | −1.07 | −0.86 | −0.82 | −0.53 | −0.30 | −0.64 | −0.42 | 0.29 | −0.87 | −0.59 | −0.10 |
| miR_1984 | −0.08 | −0.13 | −0.22 | 0.12 | 0.05 | 0.26 | −0.12 | −0.25 | 0.16 | 0.21 | 0.11 |
| miR_1985 | −0.46 | 0.49 | −0.13 | 1.09 | 0.74 | −0.47 | −0.99 | 0.82 | −2.26 | 2.42 | 2.07 |
| miR_1986 | −2.18 | −2.39 | −3.19 | 0.29 | 0.15 | −0.27 | −1.48 | −0.37 | −1.82 | 1.65 | 0.53 |
| miR_1987 | ND | −0.11 | −0.30 | −0.52 | −0.22 | −0.34 | 0.02 | 0.05 | 0.20 | −0.11 | 0.05 |
| miR_1989 | 0.58 | 1.07 | 0.93 | 1.02 | 1.01 | −0.18 | 0.11 | 0.89 | −0.20 | 0.97 | −0.04 |
| miR_1990 | 0.09 | 0.44 | 0.35 | 0.14 | 0.28 | 0.69 | −0.25 | 0.10 | −0.16 | 1.15 | −0.01 |
| miR_1991 | −0.17 | 0.07 | −0.14 | −0.29 | −0.05 | −0.58 | −0.11 | −0.16 | −1.02 | −0.22 | −0.04 |
| miR_1992 | 0.06 | 0.14 | 0.01 | −0.27 | −0.11 | −0.19 | −0.13 | −0.04 | 0.14 | 0.28 | 0.60 |
| miR_1993 | −0.30 | −0.48 | 0.31 | 1.18 | 1.00 | 1.33 | 0.84 | −0.39 | 1.36 | 0.78 | −0.26 |
| miR_1994 | 0.25 | 0.53 | 0.13 | −0.54 | −0.58 | −0.61 | −0.22 | −0.07 | −1.94 | −0.31 | 0.91 |
| miR_1995 | 0.82 | 0.44 | 0.55 | 0.14 | 0.05 | 0.11 | 0.41 | −0.06 | −0.39 | 0.00 | 1.32 |
| miR_1996 | 0.76 | 1.05 | 0.91 | −0.16 | −0.22 | −0.23 | −0.66 | 0.68 | −0.31 | −0.21 | −1.01 |
| miR_1997 | 0.20 | 0.16 | 0.07 | −0.38 | −0.44 | −0.29 | −0.33 | 0.03 | −0.02 | −0.77 | 1.66 |

TABLE 6-continued table ratios_454miRs: Contains ratio data generated on tumor versus normal adjacent tissues from a variety of tissues.

| | | | | | | | | | | | |
|---|---|---|---|---|---|---|---|---|---|---|---|
| miR_1998 | 0.06 | −0.03 | −0.26 | −0.29 | −0.06 | 0.26 | 0.15 | −0.03 | −0.05 | −0.03 | 0.24 |
| miR_1999 | ND | 0.11 | −0.03 | −0.77 | −0.30 | −0.46 | 0.03 | −0.25 | 0.00 | −0.32 | 0.03 |
| miR_2000 | 0.38 | 0.74 | 0.43 | 0.08 | 0.41 | 0.56 | −0.76 | 0.33 | 0.16 | 1.77 | −0.10 |
| miR_2001 | −0.07 | −0.40 | −0.55 | 0.25 | 0.05 | 0.36 | 0.17 | 0.06 | −0.01 | 0.01 | −0.08 |
| miR_2002 | −2.40 | −4.15 | −6.48 | −0.84 | −0.77 | −1.03 | −2.02 | −0.14 | −0.54 | −0.20 | −0.33 |
| miR_2003 | ND | ND | −0.23 | −0.05 | 0.03 | 0.34 | 0.15 | 0.02 | 0.00 | −0.07 | −0.07 |
| miR_2004 | 0.04 | −0.11 | −0.01 | 0.24 | 0.10 | 0.36 | 0.20 | −0.01 | −0.04 | 0.00 | −0.10 |
| miR_2005 | ND | −0.28 | −0.44 | 0.23 | 0.06 | 0.24 | 0.20 | −0.04 | −0.06 | 0.03 | −0.13 |
| miR_2006 | 0.18 | 0.22 | 0.26 | −0.21 | −0.16 | 0.26 | −0.34 | 1.05 | 0.03 | −0.32 | −0.87 |
| miR_2008 | 0.27 | 0.43 | 0.42 | 0.11 | 0.18 | 0.55 | 0.34 | 0.07 | 0.17 | −0.18 | 0.16 |
| miR_2009 | 0.08 | 0.03 | −0.39 | −0.12 | −0.03 | −0.05 | 0.25 | 0.01 | −0.13 | 0.01 | 0.21 |
| miR_2010 | −0.06 | 0.00 | −0.27 | −0.48 | −0.31 | −0.44 | 0.01 | 0.01 | −0.12 | −0.32 | 0.27 |
| miR_2011 | 0.74 | 0.30 | 0.50 | −0.59 | −0.55 | −0.45 | 1.15 | −0.87 | −1.33 | −1.58 | 0.89 |
| miR_2012 | 0.51 | 0.19 | 0.12 | −0.15 | −0.02 | −0.14 | −0.17 | 0.97 | −0.21 | 0.84 | 0.56 |
| miR_2013-miR_2396-miR_2397-miR_2398 | −0.26 | −0.55 | 0.50 | 1.46 | 1.21 | 1.66 | 1.16 | −0.49 | 1.36 | 1.12 | −0.36 |
| miR_2014 | −0.06 | −0.16 | −0.04 | 0.16 | 0.04 | 0.50 | 0.08 | 0.03 | −0.04 | 0.16 | −0.07 |
| miR_2015 | −0.53 | −0.47 | −0.05 | 0.28 | 0.09 | 0.77 | −1.16 | 1.29 | 2.18 | 2.46 | 0.77 |
| miR_2016 | 0.01 | ND | −0.14 | ND | ND | 0.44 | 0.18 | 0.02 | −0.05 | ND | −0.06 |
| miR_2017 | ND | −0.14 | −0.01 | ND | 0.05 | 0.48 | 0.13 | 0.02 | −0.02 | ND | −0.12 |
| miR_2018 | 0.07 | 0.13 | 0.34 | 0.30 | 0.72 | 1.04 | −0.01 | 0.04 | −0.14 | 1.38 | 0.06 |
| miR_2019 | 0.20 | 0.20 | 0.43 | 1.13 | 1.30 | 1.72 | −0.31 | −1.42 | 1.86 | 1.41 | 0.18 |
| miR_2020 | −1.97 | −1.91 | −3.81 | −0.85 | −0.76 | −1.23 | −0.49 | −0.30 | 0.48 | −0.29 | −0.53 |
| miR_2021 | 0.83 | 0.18 | 0.14 | 0.24 | 0.11 | 1.42 | −0.49 | 0.18 | 0.30 | 1.22 | 0.17 |
| miR_2022 | −0.55 | −0.87 | −1.54 | −1.12 | −1.07 | −1.15 | −1.45 | −1.00 | −1.99 | −1.89 | −0.91 |
| miR_2023 | 0.07 | −0.30 | 0.06 | −0.61 | −0.28 | −0.10 | −0.03 | 0.15 | 0.63 | −0.07 | −0.06 |
| miR_2024 | 0.53 | 0.34 | 0.53 | −0.61 | −0.65 | −0.35 | 0.34 | 0.33 | −0.57 | −1.74 | 0.37 |
| miR_2025 | 0.12 | 0.03 | −0.14 | −0.43 | −0.27 | −0.44 | 0.15 | 0.38 | 0.37 | −0.99 | −0.52 |
| miR_2026 | 0.15 | −0.01 | 0.25 | −0.06 | 0.02 | 0.91 | 0.32 | −0.08 | −0.85 | −0.41 | 0.19 |
| miR_2027 | 0.36 | 0.57 | 0.31 | 0.78 | 0.71 | 1.27 | −0.29 | 0.73 | −0.51 | 0.72 | 0.30 |
| miR_2028 | 0.03 | −0.12 | −0.09 | −0.11 | −0.03 | 0.15 | 0.15 | −0.04 | −0.13 | −0.16 | 0.13 |
| miR_2029 | 0.43 | 0.11 | 0.22 | −0.66 | −0.70 | −0.52 | 0.29 | 0.71 | −0.62 | −2.03 | 0.04 |
| miR_2030 | −0.26 | 0.27 | −0.15 | −1.01 | −0.96 | −0.91 | −0.52 | −0.48 | −1.56 | 0.60 | 1.56 |
| miR_2031 | −0.08 | −0.09 | −0.21 | −0.52 | −0.34 | 0.04 | −0.15 | 0.43 | 0.49 | 0.38 | 0.36 |
| miR_2032 | 1.59 | 0.09 | −0.37 | 0.17 | 0.26 | −0.66 | 0.47 | 1.28 | 1.60 | −2.01 | −0.26 |
| miR_2033 | −1.04 | −1.35 | −0.85 | −0.66 | −0.65 | −0.58 | −1.49 | 0.10 | 1.62 | −0.56 | −0.58 |
| miR_2034 | 0.69 | 0.12 | 0.71 | −0.31 | −0.31 | −0.30 | 0.98 | 0.14 | −0.82 | −0.29 | 0.18 |
| miR_2035 | −0.59 | −0.64 | −0.73 | −0.10 | −0.04 | −0.19 | −0.86 | 0.57 | −0.27 | 0.25 | 0.01 |
| miR_2036 | 0.53 | 0.58 | 0.27 | 0.03 | 0.01 | 0.56 | −0.10 | 0.45 | −0.68 | 0.08 | 0.16 |
| miR_2037 | 0.04 | 0.03 | −0.13 | −0.22 | −0.06 | −0.08 | 0.22 | 0.29 | −0.06 | 0.07 | 0.00 |
| miR_2038 | 0.16 | 0.00 | 0.09 | −0.48 | −0.24 | −0.57 | 0.12 | 0.54 | −0.29 | −0.98 | −0.18 |
| miR_2040 | ND | −0.40 | −0.14 | −0.43 | −0.13 | −0.11 | 0.02 | −0.12 | −0.14 | 0.00 | −0.08 |
| miR_2041 | 0.34 | 0.11 | 0.12 | −0.37 | −0.24 | −0.19 | 0.04 | 0.01 | 0.16 | −0.04 | −0.24 |
| miR_2042 | −1.96 | −1.52 | −2.74 | −0.03 | −0.01 | −0.97 | 0.14 | 0.16 | 0.65 | 0.02 | −0.66 |
| miR_2043 | −1.52 | −1.87 | −0.96 | −0.59 | −0.40 | −0.28 | −1.33 | 1.18 | 0.55 | 0.26 | 0.15 |
| miR_2044 | 0.00 | −0.09 | −0.16 | −0.47 | −0.23 | −0.60 | 0.16 | 0.05 | −0.20 | −0.01 | −0.03 |
| miR_2045 | −0.14 | −0.12 | −0.42 | 0.44 | 0.15 | 0.23 | 0.16 | 0.02 | −0.28 | 0.10 | 0.13 |
| miR_2046 | −0.02 | −0.14 | −0.30 | 0.20 | 0.07 | 0.50 | 0.17 | 0.02 | −0.06 | −0.01 | −0.16 |
| miR_2047 | 0.50 | −0.20 | −0.20 | −0.13 | −0.14 | 0.16 | −0.38 | 0.11 | −0.30 | −0.02 | 0.03 |
| miR_2048 | 0.33 | 1.39 | 0.58 | 0.49 | 0.39 | −0.09 | 0.18 | 0.94 | −1.58 | −0.10 | 0.38 |
| miR_2049 | 0.55 | 0.50 | 0.80 | 0.63 | 0.38 | 0.12 | 0.63 | 0.56 | −0.54 | 0.14 | 0.40 |
| miR_2050 | −0.02 | ND | −0.16 | 0.07 | ND | 0.53 | 0.17 | 0.03 | −0.02 | 0.04 | −0.10 |
| miR_2051 | 0.30 | 0.12 | 0.14 | −1.13 | −1.08 | −0.55 | 0.18 | −0.08 | −0.89 | −1.31 | 0.31 |
| miR_2052 | 0.04 | 0.32 | 0.15 | −0.63 | −0.62 | −0.70 | −0.05 | −0.32 | −0.42 | −1.06 | 0.26 |
| miR_2053-miR_2137-miR_2443-miR_2444-miR_2445-320 | 0.08 | 1.53 | 0.50 | 0.59 | 0.29 | 0.25 | −0.69 | −0.40 | 0.47 | 0.15 | 0.75 |
| miR_2054 | −4.80 | ND | −7.05 | 0.12 | −0.04 | 0.55 | −2.65 | 0.52 | 1.63 | 3.94 | 0.66 |
| miR_2055 | 1.04 | −0.21 | 0.07 | −0.37 | −0.31 | −0.39 | 0.43 | −0.35 | −0.67 | −1.97 | −0.18 |
| miR_2056 | ND | −0.12 | −0.23 | 0.02 | 0.04 | 0.20 | 0.07 | −0.06 | 0.27 | −0.05 | −0.14 |
| miR_2057 | −0.94 | −1.36 | 0.03 | 0.50 | 0.49 | 0.83 | −0.01 | 0.26 | 3.55 | 0.79 | −0.57 |
| miR_2058 | 0.73 | 0.35 | 0.33 | −0.30 | −0.24 | 0.64 | −0.30 | 0.06 | −0.06 | 0.56 | 0.11 |
| miR_2060 | 0.96 | 1.06 | 0.45 | −0.81 | −0.77 | −0.41 | 0.23 | −0.06 | 0.08 | −0.28 | −1.06 |
| miR_2061 | 0.09 | 0.02 | 0.07 | −0.52 | −0.32 | −0.37 | 0.04 | 0.09 | −0.15 | −0.87 | −0.39 |
| miR_2062 | −0.13 | −0.01 | −1.62 | 0.12 | 0.02 | −0.59 | 0.62 | −0.33 | −1.34 | −1.05 | −0.04 |
| miR_2063 | −0.09 | ND | 0.18 | 0.22 | 0.04 | 0.34 | 0.14 | −0.02 | −0.03 | −0.06 | 0.09 |
| miR_2065 | 0.07 | 0.03 | 0.01 | −0.27 | −0.10 | −0.15 | 0.19 | 0.67 | −0.20 | −0.34 | −0.16 |
| miR_2066 | 0.39 | 0.37 | 0.07 | −0.54 | −0.57 | −0.58 | 0.06 | −0.42 | 0.11 | −0.87 | 0.16 |
| miR_2067 | 0.17 | 0.08 | 0.07 | −0.57 | −0.62 | −0.51 | 0.17 | −0.03 | −0.54 | −1.52 | 0.12 |
| miR_2068 | −0.04 | −0.20 | −0.14 | 0.11 | 0.18 | 0.42 | 0.14 | −0.23 | 0.41 | 0.02 | −0.17 |
| miR_2069-miR_2155 | 0.02 | −0.01 | ND | −0.84 | −0.39 | −0.82 | 0.23 | −0.25 | 0.44 | −0.35 | −0.12 |

TABLE 6-continued table ratios__454miRs: Contains ratio data generated on tumor versus normal adjacent tissues from a variety of tissues.

| | | | | | | | | | | | |
|---|---|---|---|---|---|---|---|---|---|---|---|
| miR_2070 | 0.04 | −0.01 | −0.18 | −0.73 | −0.44 | −0.42 | −0.17 | −0.12 | 0.08 | −0.53 | 0.15 |
| miR_2071 | −1.84 | −2.66 | ND | −1.03 | −0.90 | −1.05 | −1.31 | −0.50 | −0.84 | −1.38 | −0.17 |
| miR_2072 | 0.50 | −0.14 | 0.02 | −0.70 | −0.47 | 0.35 | 0.40 | −0.74 | −0.06 | −0.18 | 0.04 |
| miR_2073 | 0.11 | −0.09 | −0.22 | 0.04 | 0.05 | 0.24 | 0.13 | 0.00 | 0.07 | 0.04 | −0.08 |
| miR_2074 | 0.37 | −0.09 | 0.11 | 0.09 | 0.05 | 0.34 | 0.20 | 0.04 | −0.05 | 0.01 | −0.03 |
| miR_2075 | −0.13 | −0.39 | −0.21 | −0.13 | −0.06 | 0.07 | −0.23 | 0.35 | 0.05 | 0.07 | 0.30 |
| miR_2076 | 0.75 | 0.71 | 0.52 | −0.48 | −0.46 | −0.30 | 0.75 | −0.11 | −0.53 | 0.07 | 0.66 |
| miR_2077 | 0.31 | 0.23 | −0.06 | −0.51 | −0.54 | −0.22 | 0.19 | 0.02 | −0.50 | −0.88 | −0.04 |
| miR_2079 | 0.22 | −0.35 | 0.08 | −0.25 | −0.25 | −0.23 | 1.68 | −0.15 | −0.72 | −0.71 | −0.02 |
| miR_2080 | 0.08 | −0.06 | −0.22 | −0.55 | −0.37 | −0.32 | −0.04 | 0.20 | −0.13 | −0.73 | 0.19 |
| miR_2081 | ND | ND | −0.10 | −0.05 | 0.02 | 0.35 | 0.13 | 0.01 | −0.01 | ND | −0.04 |
| miR_2082 | ND | 0.69 | 0.17 | −0.32 | −0.16 | 0.17 | −0.06 | 0.92 | 0.21 | 0.02 | −0.39 |
| miR_2083 | 0.13 | 0.23 | 0.04 | −0.55 | −0.55 | −0.38 | −0.20 | 0.15 | 0.23 | −0.22 | −0.08 |
| miR_2084 | ND | −0.13 | −0.32 | 0.10 | 0.04 | 0.17 | 0.18 | 0.00 | −0.07 | −0.09 | −0.02 |
| miR_2086 | 0.15 | 0.07 | 0.05 | −0.70 | −0.46 | −0.31 | −0.03 | −0.14 | −0.01 | −0.43 | 0.49 |
| miR_2087 | 0.04 | −0.25 | 0.14 | −0.44 | −0.23 | −0.81 | −0.04 | −0.25 | 0.14 | −1.05 | −0.57 |
| miR_2088-miR_2431 | 0.09 | −0.05 | 0.03 | 0.25 | 0.08 | 0.31 | 0.17 | 0.04 | 0.04 | 0.14 | −0.08 |
| miR_2090 | −1.73 | −0.55 | −0.13 | 5.88 | 2.46 | 1.84 | −1.23 | −0.12 | 2.82 | 4.76 | 1.15 |
| miR_2091 | 0.02 | −0.13 | −0.44 | 0.46 | 0.11 | 0.35 | 0.23 | −0.15 | −0.04 | −0.07 | −0.13 |
| miR_2092 | 0.05 | 0.33 | 0.00 | −0.22 | −0.08 | 0.16 | 0.22 | 0.99 | −0.02 | −0.11 | −0.20 |
| miR_2093 | −1.28 | −0.03 | 0.37 | 0.15 | 0.10 | 0.29 | −0.80 | 0.83 | 0.19 | 1.25 | 0.96 |
| miR_2094 | −0.04 | −0.25 | 0.21 | 0.16 | 0.04 | 0.26 | 0.06 | −0.03 | 0.00 | 0.00 | −0.08 |
| miR_2095 | −1.88 | −2.13 | −2.15 | 0.02 | 0.01 | 0.30 | −1.46 | 1.96 | 2.24 | 1.96 | 0.12 |
| miR_2096 | ND | ND | 0.32 | ND | 0.03 | 0.42 | 0.14 | 0.02 | −0.01 | ND | −0.11 |
| miR_2097 | ND | −0.22 | 0.17 | −0.02 | 0.03 | 0.30 | 0.01 | −0.02 | −0.06 | 0.02 | −0.05 |
| miR_2098 | −0.05 | −0.40 | −0.31 | 0.19 | 0.04 | 0.32 | 0.18 | 0.01 | 0.02 | 0.05 | −0.13 |
| miR_2099 | 0.00 | −0.20 | −0.33 | 0.39 | 0.07 | 0.24 | 0.09 | −0.05 | 0.05 | −0.05 | 0.35 |
| miR_2100 | −0.01 | −0.16 | 0.28 | 0.78 | 0.47 | 0.74 | 1.08 | −0.36 | −0.02 | 0.67 | 0.56 |
| miR_2101 | −1.35 | −0.13 | −0.93 | −0.22 | −0.22 | −0.42 | −0.46 | 0.07 | −1.42 | 0.38 | 0.13 |
| miR_2102 | 0.11 | −0.16 | −0.35 | −0.16 | −0.05 | 0.26 | 0.01 | 0.05 | 0.00 | −0.02 | −0.01 |
| miR_2104 | 0.05 | −0.18 | −0.01 | −0.17 | −0.05 | −0.18 | 0.10 | −0.10 | 0.15 | −0.53 | −0.16 |
| miR_2105 | 0.11 | 0.18 | −0.07 | −0.66 | −0.68 | −0.24 | −0.56 | −0.01 | −0.38 | −1.42 | 0.52 |
| miR_2107 | −2.57 | −3.26 | −4.43 | −1.16 | −1.12 | −0.90 | −1.75 | −0.41 | −0.82 | −1.56 | 0.36 |
| miR_2108 | −0.10 | −0.37 | −0.09 | 0.08 | 0.04 | 0.32 | 0.16 | −0.03 | −0.09 | −0.01 | −0.08 |
| miR_2109 | 0.37 | 0.81 | 0.40 | 0.37 | 0.25 | 1.35 | −0.63 | 0.41 | 0.75 | 0.82 | 0.09 |
| miR_2110 | ND | −0.16 | −0.28 | 0.15 | 0.06 | 0.34 | 0.17 | 0.03 | −0.07 | ND | −0.12 |
| miR_2111 | −0.06 | 0.11 | 0.23 | −0.02 | 0.02 | 0.10 | 0.02 | −0.05 | 0.02 | 0.14 | 0.15 |
| miR_2113 | ND | −0.03 | −0.11 | −0.36 | −0.10 | −0.21 | 0.17 | −0.11 | 0.00 | −0.15 | −0.03 |
| miR_2114 | 0.45 | 0.24 | 0.23 | −0.12 | 0.10 | 0.22 | −1.18 | −0.34 | 0.80 | 1.49 | 0.54 |
| miR_2115 | −0.10 | 1.05 | 0.36 | −0.44 | −0.45 | −0.28 | 0.21 | 0.45 | −1.02 | −1.06 | 0.36 |
| miR_2116 | 0.04 | −0.10 | −0.14 | −0.58 | −0.15 | −0.18 | −0.04 | −0.37 | 0.57 | 0.02 | 0.10 |
| miR_2117 | 0.20 | 0.39 | 0.35 | −0.35 | −0.27 | −0.27 | 0.12 | 0.37 | −0.34 | −0.65 | −0.15 |
| miR_2118 | 0.36 | 0.67 | 0.33 | −0.13 | 0.12 | 0.58 | −0.70 | 0.41 | 0.14 | 1.36 | −0.13 |
| miR_2119 | 0.65 | 0.10 | 0.64 | 0.22 | 0.01 | −0.32 | 0.63 | 0.14 | −0.19 | −0.40 | −0.91 |
| miR_2120 | 0.32 | 0.25 | 0.80 | −0.02 | −0.03 | 0.10 | 1.80 | 0.88 | 0.36 | 1.51 | −0.31 |
| miR_2121 | ND | ND | 0.01 | −0.19 | ND | 0.49 | 0.20 | −0.21 | −0.07 | ND | −0.04 |
| miR_2122 | 0.00 | −0.27 | 0.39 | 0.01 | 0.00 | 0.46 | 0.28 | −0.32 | 0.08 | −0.22 | −0.04 |
| miR_2123 | 0.83 | −0.01 | −0.20 | 0.05 | −0.07 | −0.79 | 0.96 | −0.31 | −0.15 | −2.32 | −0.94 |
| miR_2125 | 0.18 | 0.54 | 0.48 | 0.10 | 0.02 | 0.15 | 0.73 | 0.40 | −0.71 | 0.01 | 0.88 |
| miR_2126 | ND | 0.11 | 0.20 | −0.51 | −0.15 | −0.28 | 0.16 | −0.18 | −0.22 | −0.27 | 0.29 |
| miR_2127 | 0.25 | 0.20 | −0.17 | −0.89 | −0.88 | −0.18 | −0.24 | 0.10 | −0.17 | −0.49 | −0.41 |
| miR_2128 | 1.12 | −0.16 | −0.10 | −0.20 | −0.20 | −0.24 | 0.23 | −0.67 | −0.02 | −2.18 | −0.39 |
| miR_2129 | −0.18 | 0.16 | −0.53 | −0.54 | −0.57 | −0.31 | 0.10 | 0.32 | −1.10 | −0.37 | 0.41 |
| miR_2130 | 1.46 | −0.22 | 0.35 | −1.04 | −1.03 | −0.66 | −0.28 | −1.20 | 0.31 | −1.75 | −0.24 |
| miR_2131 | 0.12 | 0.00 | −0.09 | −0.60 | −0.33 | −0.11 | 0.20 | −0.14 | 0.03 | −0.12 | 0.02 |
| miR_2132 | −0.05 | −0.02 | 0.17 | −0.55 | −0.29 | −0.66 | 0.01 | 0.30 | −0.19 | −0.39 | 0.06 |
| miR_2134 | 0.02 | 0.30 | 0.02 | 0.08 | −0.07 | −0.17 | 0.31 | 0.48 | −0.50 | −0.44 | −0.06 |
| miR_2135 | 0.18 | 0.46 | −0.33 | −0.52 | −0.38 | −0.77 | −0.02 | −0.09 | 0.39 | −1.10 | −0.10 |
| miR_2136 | 0.37 | 0.64 | 0.49 | 0.08 | −0.07 | −0.01 | 0.38 | 1.17 | −0.74 | −0.58 | −0.26 |
| miR_2137-miR_2444-miR_2445-miR_2447-320 | 0.34 | 1.50 | 0.26 | 0.37 | 0.27 | 0.18 | −0.67 | −0.55 | 0.18 | −0.14 | 0.65 |
| miR_2138 | −1.84 | −1.93 | −1.77 | 1.25 | 0.99 | 1.36 | −0.92 | −0.59 | 0.36 | 1.58 | −0.32 |
| miR_2139 | −0.16 | 0.07 | −0.04 | −0.53 | −0.43 | −0.34 | 0.13 | 0.18 | −1.32 | −1.47 | 0.02 |
| miR_2140 | 0.34 | 0.58 | 0.25 | −1.03 | −1.03 | −1.05 | 0.50 | −0.41 | −0.97 | −3.64 | −0.33 |
| miR_2141 | −0.06 | −0.10 | 0.11 | −0.02 | 0.02 | 0.44 | 0.08 | −0.01 | −0.01 | ND | −0.08 |
| miR_2142 | 0.95 | −0.60 | −0.04 | −0.47 | −0.48 | −0.47 | 0.40 | −1.00 | −1.39 | −1.93 | −0.59 |
| miR_2143 | 0.04 | −0.17 | −0.20 | 0.48 | 0.08 | 0.36 | 0.30 | 0.03 | −0.05 | −0.14 | −0.09 |
| miR_2144 | −0.99 | 0.80 | 0.20 | −0.42 | −0.46 | −0.32 | 0.09 | 1.11 | −2.81 | −0.21 | 0.05 |
| miR_2145 | −0.03 | −0.18 | −0.18 | 0.24 | 0.08 | 0.25 | 0.18 | 0.04 | −0.02 | 0.00 | −0.09 |
| miR_2146 | 0.12 | 0.22 | 0.21 | −0.81 | −0.81 | −0.97 | 0.37 | −0.22 | −1.40 | −1.79 | −0.16 |
| miR_2147 | 0.00 | −0.08 | 0.20 | 0.02 | 0.03 | 0.23 | 0.13 | 0.16 | 0.15 | ND | −0.19 |
| miR_2148 | ND | −0.36 | −0.66 | −0.66 | −0.33 | −0.63 | −0.26 | −0.24 | −0.74 | −0.17 | −0.08 |
| miR_2149 | −0.19 | 0.84 | −0.17 | 0.43 | 0.48 | −0.71 | −0.71 | 0.47 | −2.04 | 1.10 | 1.55 |

TABLE 6-continued table ratios__454miRs: Contains ratio data generated on tumor versus normal adjacent tissues from a variety of tissues.

| | | | | | | | | | | | |
|---|---|---|---|---|---|---|---|---|---|---|---|
| miR_2150 | 0.76 | 0.14 | 0.63 | −0.17 | −0.26 | −0.23 | 0.20 | −0.29 | 0.87 | 0.97 | 1.07 |
| miR_2151 | 0.15 | 0.40 | 0.02 | −0.48 | −0.49 | −0.53 | −0.09 | −0.46 | −0.33 | −1.51 | 0.25 |
| miR_2152 | ND | ND | 0.09 | −0.34 | −0.04 | 0.29 | 0.04 | −0.02 | −0.01 | ND | 0.56 |
| miR_2153-<br>miR_2163 | 0.41 | 0.30 | 0.11 | −0.03 | −0.13 | −0.57 | 1.35 | −0.21 | −1.04 | −0.79 | 0.50 |
| miR_2154 | −0.11 | 0.28 | 0.17 | 0.09 | 0.06 | −0.06 | −0.14 | 0.12 | −0.47 | 0.37 | 0.74 |
| miR_2156 | −0.03 | −0.05 | 0.05 | 0.09 | 0.01 | 0.39 | 0.13 | −0.12 | 0.11 | 0.04 | 0.15 |
| miR_2157 | −1.55 | −1.98 | −3.36 | −0.28 | −0.26 | −0.98 | −1.35 | −0.34 | −1.30 | −0.48 | −0.33 |
| miR_2158 | 0.43 | 0.63 | 0.22 | −1.33 | −1.42 | −0.05 | −0.85 | 0.39 | −0.15 | −0.87 | −0.78 |
| miR_2159 | 1.00 | 0.85 | 0.60 | 0.46 | 0.37 | −0.10 | 1.18 | 0.29 | −0.34 | 0.36 | 0.74 |
| miR_2160 | −0.04 | 0.22 | 0.22 | −0.20 | −0.11 | −0.60 | 0.31 | 0.21 | −0.79 | −1.80 | −0.41 |
| miR_2161 | 0.07 | 0.08 | −0.16 | −0.26 | −0.08 | −0.23 | 0.19 | 0.03 | −0.17 | −0.17 | 0.38 |
| miR_2162 | 0.72 | 0.61 | 0.70 | 0.35 | 0.38 | 0.41 | 0.21 | 0.58 | −0.23 | 0.92 | −0.25 |
| miR_2164 | 0.98 | 0.68 | 0.17 | −0.09 | −0.19 | −0.01 | −0.18 | 0.33 | −0.34 | −0.63 | −0.24 |
| miR_2165 | 0.05 | −0.09 | 0.16 | −0.70 | −0.39 | −0.22 | −0.03 | −0.34 | 0.12 | −0.37 | −0.10 |
| miR_2166 | 0.60 | 0.10 | 0.41 | −0.90 | −0.83 | −0.41 | 0.29 | 0.24 | −0.08 | −1.77 | −0.55 |
| miR_2167 | 0.36 | −0.47 | −0.73 | −1.50 | −1.46 | −0.87 | −0.34 | −0.88 | 1.17 | −2.09 | −0.34 |
| miR_2168 | 0.49 | −0.25 | 0.39 | −0.35 | −0.41 | 1.09 | −1.04 | −0.84 | 0.71 | 2.01 | 0.29 |
| miR_2169 | −0.01 | 1.46 | 0.95 | 2.27 | 0.89 | 1.97 | 0.59 | 0.26 | −0.38 | 1.38 | −0.05 |
| miR_2170 | −0.08 | 0.48 | −0.11 | −0.62 | −0.39 | −0.67 | −0.20 | 0.31 | −0.58 | −0.02 | 0.32 |
| miR_2171 | −0.06 | 0.77 | 0.58 | −0.66 | −0.60 | −0.69 | 0.38 | 1.33 | −1.14 | −2.09 | −0.30 |
| miR_2364 | 0.03 | 0.06 | 0.11 | 0.29 | 0.09 | 0.46 | 0.13 | 0.00 | −0.03 | −0.04 | −0.06 |
| miR_2365-<br>miR_2408-<br>miR_2419 | 0.09 | −0.46 | −0.69 | 0.25 | 0.72 | 0.46 | 0.10 | −0.36 | 0.41 | 1.30 | −0.34 |
| miR_2366 | 1.05 | 0.92 | 0.60 | 0.25 | 0.26 | 0.25 | 0.65 | −0.89 | 1.46 | 1.79 | 0.91 |
| miR_2370-<br>miR_2391 | 0.04 | ND | 0.17 | ND | −0.06 | 0.07 | 0.10 | −0.11 | 0.16 | −0.04 | −0.10 |
| miR_2371 | ND | −0.25 | −0.31 | −0.16 | −0.04 | 0.21 | 0.11 | −0.04 | −0.05 | −0.01 | −0.03 |
| miR_2372-<br>miR_2373-<br>miR_2404 | 0.36 | −0.42 | 0.00 | −0.33 | −0.34 | −0.71 | 0.68 | 0.24 | 0.29 | −0.87 | −0.71 |
| miR_2374-<br>miR_2375-<br>miR_2376-<br>miR_2377 | 2.27 | 0.15 | 0.43 | −0.87 | −0.81 | −0.23 | −0.27 | −2.50 | 0.51 | −0.81 | −1.08 |
| miR_2374-<br>miR_2375-<br>miR_2376-<br>miR_2377-<br>miR_2416-<br>miR_2417 | 1.34 | −0.34 | 0.07 | −0.43 | −0.49 | −0.25 | −0.41 | −1.09 | 0.86 | −1.18 | −0.67 |
| miR_2378-<br>miR_2418 | −0.38 | 0.26 | −0.55 | −0.27 | −0.04 | −0.96 | −1.12 | 0.09 | −0.55 | 0.23 | −0.08 |
| miR_2379 | 0.11 | −0.34 | −0.33 | −0.93 | −0.87 | −0.28 | −0.35 | −0.63 | −0.22 | −1.08 | 0.28 |
| miR_2380 | 0.02 | −0.54 | −0.03 | 0.05 | 0.20 | 0.33 | 0.52 | −0.46 | 0.67 | −0.40 | −0.11 |
| miR_2381 | 0.81 | −0.05 | 0.50 | −0.77 | −0.63 | −1.13 | 0.60 | 0.20 | −0.14 | −0.63 | −0.35 |
| miR_2383 | 2.11 | −0.26 | 0.02 | −0.99 | −1.49 | 0.08 | −0.99 | −1.71 | 0.02 | −1.00 | −0.42 |
| miR_2385-<br>miR_2386-<br>miR_2423-<br>miR_2433 | 1.34 | −0.90 | −0.47 | −0.19 | −0.16 | −0.60 | 0.48 | −1.46 | 3.82 | −1.02 | −1.16 |
| miR_2387 | 0.46 | −0.26 | 0.26 | −0.78 | −0.68 | −0.68 | −0.22 | −1.31 | 0.27 | −0.81 | −0.83 |
| miR_2388 | 0.39 | 0.34 | 0.34 | −0.72 | −0.69 | −0.72 | 0.11 | −0.18 | −0.53 | −1.53 | −0.43 |
| miR_2389 | 0.06 | 0.23 | 0.18 | 0.14 | 0.11 | −0.18 | 0.10 | −0.26 | 0.18 | 0.36 | −0.14 |
| miR_2390 | −0.15 | −0.33 | 0.21 | 0.70 | 0.33 | 0.04 | 1.87 | 0.91 | −0.66 | −0.19 | 0.15 |
| miR_2392 | 0.12 | 0.57 | −0.20 | −0.03 | −0.14 | −0.40 | 1.30 | 0.35 | −0.68 | −1.54 | −0.01 |
| miR_2393 | −0.08 | −0.04 | −0.26 | 0.10 | 0.11 | −0.85 | −0.83 | 0.19 | −0.96 | 0.02 | 0.09 |
| miR_2394-<br>miR_2395 | 0.10 | 0.39 | 0.20 | 0.86 | 0.97 | −0.47 | 0.21 | −0.73 | −0.29 | −0.01 | −0.42 |
| miR_2396-<br>miR_2397-<br>miR_2398 | −0.27 | −0.74 | 0.33 | 1.43 | 1.15 | 1.42 | 0.70 | −0.24 | 1.66 | 1.20 | −0.29 |
| miR_2399 | −0.25 | −0.97 | −0.32 | 0.91 | 0.87 | 1.07 | −0.03 | −0.14 | 1.94 | 0.58 | −0.04 |
| miR_2400-<br>miR_2401-<br>miR_2402 | −1.30 | −0.95 | 0.22 | 2.00 | 1.66 | 1.26 | −0.41 | −0.48 | 2.70 | 1.57 | −0.46 |
| miR_2403 | 0.03 | −0.16 | −0.27 | −0.46 | −0.36 | −0.34 | 0.07 | −0.29 | −0.10 | −0.52 | 0.14 |
| miR_2405 | −0.98 | −0.63 | 0.22 | 1.15 | 1.05 | 1.35 | −0.02 | −0.31 | 2.14 | 1.28 | −0.32 |
| miR_2406 | 0.01 | −0.22 | 0.21 | −0.14 | −0.01 | 0.00 | 0.11 | 0.25 | 1.15 | −0.02 | −0.33 |
| miR_2407 | ND | 0.08 | 0.07 | 0.04 | 0.05 | 0.07 | 0.09 | 0.06 | −0.05 | 0.03 | 0.00 |
| miR_2409-<br>miR_2410-<br>miR_2411-<br>miR_2412 | 0.14 | 0.17 | 0.25 | −0.24 | −0.07 | −0.36 | 0.32 | 0.13 | 0.00 | −0.15 | −0.42 |

TABLE 6-continued table ratios_454miRs: Contains ratio data generated on tumor versus normal adjacent tissues from a variety of tissues.

| | | | | | | | | | | | |
|---|---|---|---|---|---|---|---|---|---|---|---|
| miR_2413-<br>miR_2414-<br>miR_2415-<br>miR_2439-<br>miR_2440 | 1.06 | −0.04 | −0.18 | −0.09 | −0.05 | −0.30 | 0.09 | −1.54 | −0.44 | −2.14 | −1.20 |
| miR_2422 | −0.07 | 0.06 | 0.34 | −0.08 | −0.02 | −0.38 | 0.19 | 0.27 | −0.18 | 0.10 | −0.07 |
| miR_2424-<br>miR_2425 | 0.27 | 0.69 | 0.43 | −0.27 | −0.24 | −0.08 | −0.11 | 0.47 | −1.04 | −1.49 | 0.12 |
| miR_2426 | −0.04 | −0.15 | −0.21 | 0.24 | 0.06 | 0.60 | 0.13 | 0.06 | −0.03 | 0.01 | −0.10 |
| miR_2428 | −0.14 | −0.34 | 0.06 | 0.12 | 0.04 | 0.54 | −0.01 | −0.07 | 0.24 | 0.61 | 0.25 |
| miR_2429 | 0.02 | −0.07 | −0.04 | 0.12 | 0.05 | −0.23 | 0.30 | −0.31 | −0.25 | 0.18 | 0.36 |
| miR_2432-<br>miR_2433 | 1.38 | −0.63 | −0.56 | −0.45 | −0.36 | −0.74 | 0.69 | −1.51 | 3.24 | −1.49 | −0.99 |
| miR_2435-<br>miR_2436 | −2.70 | −2.35 | −2.55 | 0.18 | 0.04 | −0.14 | −1.78 | −0.77 | −0.24 | 1.71 | −0.11 |
| miR_2442 | 0.12 | 1.07 | 0.38 | 0.10 | −0.06 | −0.14 | −0.26 | −0.04 | −0.20 | −0.25 | 0.54 |
| miR_2446 | 0.83 | 0.91 | 0.48 | −0.12 | −0.08 | 0.71 | 0.02 | −0.40 | 0.76 | 0.91 | 0.86 |

| Tissue<br>MiR<br>Name | Liver<br>T/N-<br>ambion | Lung<br>T/N-<br>ambion | Mamma | | | | | | | Ovary<br>T/N-<br>ambion |
|---|---|---|---|---|---|---|---|---|---|---|
| | | | T/N-32 | T/N-41 | T/N-43 | T/N-44 | T/N-45 | T/N-52 | T/N-53 | T/N-ambion | |
| miR_1966-<br>miR_1988-<br>miR_2078 | −0.83 | −0.41 | −0.90 | 0.40 | 0.59 | 1.01 | 0.51 | 1.54 | −1.71 | 0.48 | −0.17 |
| miR_1967 | −0.04 | 0.04 | 0.52 | 0.23 | −0.08 | −0.42 | −0.74 | 0.27 | 0.42 | −0.42 | −0.01 |
| miR_1968 | 0.21 | 0.39 | −0.01 | 0.99 | 0.64 | 0.66 | 0.46 | 0.95 | −0.01 | 0.77 | −0.11 |
| miR_1969 | 0.77 | 0.42 | 0.14 | 0.10 | 1.36 | 0.45 | 0.19 | 1.36 | 1.45 | 1.19 | 1.06 |
| miR_1970 | 0.23 | 0.03 | 0.82 | −0.07 | −0.42 | −0.23 | −0.33 | −1.09 | 0.32 | −1.82 | 0.33 |
| miR_1971 | 0.24 | 0.26 | 0.10 | 0.07 | 0.00 | 0.14 | 0.03 | −0.08 | 0.30 | 0.24 | 0.22 |
| miR_1972 | 0.45 | 0.82 | −0.30 | 2.29 | 0.06 | 0.43 | 1.48 | 0.75 | −1.37 | 1.61 | 0.04 |
| miR_1973 | 0.25 | 0.21 | 0.09 | 0.04 | −0.07 | −0.05 | −0.02 | −0.15 | 0.25 | 0.26 | 0.19 |
| miR_1974 | 0.42 | 0.10 | −0.25 | 0.03 | −0.55 | −0.23 | 0.79 | −0.26 | 0.38 | 0.66 | 0.88 |
| miR_1975 | 0.76 | −1.43 | −0.43 | 2.05 | 0.37 | 0.97 | 1.94 | 1.42 | 0.01 | 0.77 | 0.59 |
| miR_1976-<br>miR_2124 | −0.19 | −0.04 | −0.62 | 0.44 | 1.35 | 0.96 | 1.29 | 6.08 | 0.68 | 1.36 | 0.71 |
| miR_1977-<br>miR_2064 | 0.33 | 0.10 | −0.19 | 0.35 | −0.29 | −0.49 | 0.04 | 0.21 | 0.58 | 0.73 | 0.88 |
| miR_1978 | 0.09 | 0.12 | −0.02 | −1.12 | 0.03 | −1.25 | −0.49 | −0.24 | 0.22 | 0.08 | −0.03 |
| miR_1979 | −0.25 | 0.31 | 0.70 | 1.14 | −0.49 | −0.25 | 0.44 | 1.35 | 0.25 | −0.08 | 0.27 |
| miR_1980 | 0.24 | 0.05 | 0.13 | −0.45 | 0.45 | 0.15 | −0.23 | 0.37 | 0.69 | 0.12 | 0.42 |
| miR_1981 | −0.20 | −0.22 | 0.98 | −0.36 | 1.09 | 0.14 | −0.75 | 0.22 | 0.35 | −0.09 | −0.09 |
| miR_1982 | 0.16 | −0.08 | 0.16 | −0.46 | 0.04 | 0.02 | 0.07 | −0.10 | 0.26 | −0.54 | 0.06 |
| miR_1983 | −0.04 | −0.03 | −0.33 | −0.17 | 0.10 | 0.11 | −0.16 | 0.11 | −0.05 | 0.05 | −0.01 |
| miR_1984 | 0.04 | 0.00 | −0.11 | 0.00 | −0.07 | −0.15 | 0.15 | −0.06 | 0.04 | 0.89 | 0.32 |
| miR_1985 | 0.60 | 0.66 | −1.18 | −3.21 | 2.20 | 1.13 | 0.45 | 0.68 | 0.51 | 1.21 | 0.62 |
| miR_1986 | −0.32 | 0.71 | −0.29 | −0.28 | −0.15 | 0.16 | −0.59 | −0.06 | −0.24 | 0.10 | 0.10 |
| miR_1987 | −0.69 | −0.25 | −0.02 | −0.01 | −0.03 | −0.18 | −0.06 | −0.03 | 0.00 | −0.05 | −0.12 |
| miR_1989 | −0.27 | −0.75 | −0.52 | −0.92 | 0.16 | 0.31 | −0.01 | −0.71 | 0.17 | −0.24 | 0.04 |
| miR_1990 | 0.18 | −1.08 | 0.18 | 0.08 | −0.06 | −0.19 | 0.03 | −0.90 | 0.29 | −0.31 | −0.01 |
| miR_1991 | −0.25 | −0.26 | 0.09 | 0.20 | −0.02 | −0.06 | −0.03 | −0.28 | −0.06 | −0.16 | −0.25 |
| miR_1992 | 0.17 | 0.28 | −0.29 | −0.30 | 0.27 | 0.12 | 0.37 | 0.12 | 0.26 | 0.31 | 0.45 |
| miR_1993 | 0.83 | 0.97 | 0.35 | 1.37 | 2.11 | 0.73 | 0.98 | 2.68 | 0.86 | 0.09 | 1.22 |
| miR_1994 | 0.02 | 0.11 | 0.03 | −0.96 | −0.30 | −0.22 | −0.65 | 0.37 | 0.25 | −0.24 | 0.24 |
| miR_1995 | −0.05 | 0.09 | −0.60 | −0.45 | 1.13 | 0.38 | −0.21 | 0.04 | −0.10 | −0.01 | 0.07 |
| miR_1996 | 0.05 | −0.58 | −0.14 | −0.14 | −0.49 | −0.37 | 0.15 | −0.74 | 0.08 | 0.34 | −0.14 |
| miR_1997 | 0.44 | 0.19 | 0.07 | 0.05 | −0.01 | 0.02 | 0.71 | −0.13 | 0.66 | 0.37 | 0.54 |
| miR_1998 | −0.26 | −0.18 | ND | −0.12 | −0.07 | −0.12 | −0.01 | −0.19 | −0.02 | −0.11 | −0.18 |
| miR_1999 | 0.04 | 0.09 | −0.01 | −0.60 | 0.08 | −0.10 | 0.23 | −0.08 | 0.18 | −0.06 | 0.09 |
| miR_2000 | 0.19 | −1.24 | −0.11 | −0.02 | −0.41 | 0.20 | −0.03 | −0.64 | 0.30 | −0.20 | 0.02 |
| miR_2001 | −0.55 | −0.50 | 0.23 | 0.21 | −0.08 | −0.28 | −0.07 | −0.23 | −0.43 | −0.44 | −0.53 |
| miR_2002 | −0.19 | 0.14 | −0.81 | 0.81 | 0.89 | 1.21 | 0.95 | 3.74 | −0.44 | 1.73 | −0.33 |
| miR_2003 | −0.22 | −0.13 | ND | 0.14 | ND | −0.10 | ND | −0.14 | ND | −0.05 | −0.20 |
| miR_2004 | −0.09 | −0.11 | 0.26 | 0.10 | −0.02 | −0.16 | −0.04 | −0.26 | −0.06 | −0.03 | −0.20 |
| miR_2005 | −0.45 | −0.43 | 0.16 | ND | −0.14 | −0.13 | ND | −0.23 | −0.27 | −0.36 | −0.38 |
| miR_2006 | 0.12 | −0.14 | 0.46 | 0.31 | −0.76 | 0.00 | −0.41 | −0.16 | 0.05 | 0.34 | 0.07 |
| miR_2008 | 0.10 | 0.02 | 0.32 | −0.36 | 0.35 | 0.29 | 0.24 | −0.17 | −0.23 | −0.44 | 0.20 |
| miR_2009 | −0.32 | −0.36 | 0.12 | 0.18 | −0.10 | −0.27 | 0.01 | −0.21 | −0.22 | −0.37 | −0.32 |
| miR_2010 | −0.39 | −0.21 | 0.06 | −0.01 | 0.02 | −0.05 | −0.21 | −0.05 | −0.17 | −0.38 | −0.36 |
| miR_2011 | 0.01 | −0.10 | 0.13 | −0.16 | 0.38 | −0.28 | −0.10 | −0.01 | −0.32 | −0.39 | −0.10 |
| miR_2012 | −0.09 | −0.09 | 0.13 | −0.92 | −0.13 | 0.73 | −0.20 | −0.61 | 0.76 | −0.56 | 0.00 |
| miR_2013-<br>miR_2396-<br>miR_2397-<br>miR_2398 | 0.65 | 0.90 | 0.55 | 1.28 | 1.66 | 0.49 | 0.39 | 1.47 | 0.73 | −0.50 | 1.27 |

TABLE 6-continued table ratios_454miRs: Contains ratio data generated on tumor versus normal adjacent tissues from a variety of tissues.

| | | | | | | | | | | | |
|---|---|---|---|---|---|---|---|---|---|---|---|
| miR_2014 | 0.08 | 0.05 | 0.09 | 0.12 | 0.01 | −0.14 | 0.01 | −0.23 | 0.17 | 0.12 | 0.03 |
| miR_2015 | 0.73 | 1.43 | −0.26 | 2.50 | 0.19 | 0.51 | 1.55 | 1.16 | −0.83 | 2.10 | −0.37 |
| miR_2016 | −0.10 | −0.05 | 0.07 | 0.09 | 0.04 | 0.17 | ND | −0.21 | 0.10 | 0.03 | −0.12 |
| miR_2017 | −0.08 | −0.02 | ND | 0.09 | ND | −0.09 | ND | −0.21 | 0.06 | 0.06 | −0.02 |
| miR_2018 | 0.06 | −1.27 | −0.10 | −0.06 | −0.24 | −0.74 | −0.10 | −0.78 | −0.28 | −0.37 | −0.13 |
| miR_2019 | 0.11 | 0.04 | −0.74 | 0.37 | 2.21 | 1.23 | −0.14 | 1.56 | −0.18 | 0.73 | 1.25 |
| miR_2020 | −0.32 | 0.39 | −0.31 | 1.28 | 0.74 | 0.85 | 0.62 | 3.68 | 0.11 | 1.56 | 0.03 |
| miR_2021 | −0.13 | 0.10 | −0.69 | −1.42 | 1.32 | 0.22 | 0.26 | 0.29 | −0.54 | 0.35 | −0.13 |
| miR_2022 | −0.11 | 0.41 | −0.13 | −0.68 | −0.83 | −2.15 | −1.53 | −0.29 | 0.08 | −0.97 | 0.03 |
| miR_2023 | 0.22 | 0.12 | 0.17 | 0.31 | −0.08 | −0.03 | −0.01 | 0.30 | 0.34 | 0.52 | 0.27 |
| miR_2024 | 0.06 | 0.12 | 0.38 | −0.31 | −0.52 | −0.75 | −0.64 | −0.61 | 0.41 | −1.16 | 0.03 |
| miR_2025 | −0.18 | −0.06 | 0.20 | 0.07 | −0.65 | −0.40 | −0.68 | −0.10 | −0.06 | −0.43 | −0.23 |
| miR_2026 | 0.23 | 0.08 | 0.38 | −0.15 | 0.24 | 0.40 | 0.12 | −0.63 | 0.32 | −0.36 | 0.24 |
| miR_2027 | 0.07 | −0.01 | 0.96 | −0.25 | 0.15 | −0.12 | −0.15 | −1.74 | 0.69 | 0.05 | −0.45 |
| miR_2028 | −0.30 | −0.25 | −0.09 | 0.12 | 0.02 | 0.12 | 0.01 | −0.16 | −0.05 | −0.19 | −0.20 |
| miR_2029 | −0.59 | −0.31 | 0.85 | −0.08 | −0.72 | −0.14 | −0.77 | −1.01 | −0.08 | −1.16 | −0.49 |
| miR_2030 | 0.21 | 0.07 | 0.10 | −1.37 | 0.32 | 0.24 | 0.12 | −0.23 | 0.61 | −0.48 | 0.44 |
| miR_2031 | 0.29 | 0.25 | −0.63 | 0.41 | 0.22 | 0.27 | 0.69 | 0.45 | 0.31 | 0.38 | 0.23 |
| miR_2032 | 0.00 | 0.23 | 0.69 | −0.49 | −0.17 | −0.60 | −0.16 | −0.85 | −0.11 | −1.67 | −0.65 |
| miR_2033 | −0.37 | 0.39 | 0.06 | 0.97 | 0.23 | −0.47 | 0.56 | 1.26 | −0.58 | 0.20 | −0.55 |
| miR_2034 | 0.17 | 0.48 | −0.40 | −0.73 | 0.20 | 0.32 | −0.09 | −0.22 | 0.55 | 0.03 | 0.90 |
| miR_2035 | 0.00 | 0.17 | 0.06 | 0.88 | −0.08 | 0.00 | 0.42 | 0.40 | −0.21 | 0.26 | 0.77 |
| miR_2036 | 0.14 | −0.05 | 0.66 | −0.12 | 0.31 | −0.63 | −0.16 | −0.43 | 0.45 | 0.24 | 0.23 |
| miR_2037 | 0.18 | 0.53 | 0.24 | 0.37 | 0.08 | −0.19 | −0.04 | −0.09 | −0.11 | 0.58 | −0.26 |
| miR_2038 | −0.18 | −0.11 | 0.25 | 0.09 | −0.36 | 0.12 | −0.48 | −0.46 | −0.02 | −0.86 | −0.11 |
| miR_2040 | −0.03 | −0.07 | 0.10 | 0.17 | ND | −0.12 | ND | −0.19 | 0.04 | −0.07 | 0.01 |
| miR_2041 | 0.09 | −0.03 | 0.18 | 0.22 | −0.11 | −0.17 | −0.23 | −0.04 | 0.23 | 0.26 | 0.03 |
| miR_2042 | −0.68 | 0.06 | −0.18 | 1.15 | 0.03 | 0.48 | 0.33 | 1.03 | −1.05 | 1.53 | −0.88 |
| miR_2043 | −0.19 | 0.08 | −0.14 | 0.68 | 0.14 | 0.12 | 0.53 | 1.48 | −1.08 | 0.55 | 0.10 |
| miR_2044 | −0.12 | −0.18 | 0.11 | 0.05 | −0.16 | −0.21 | −0.11 | −0.15 | −0.07 | −0.28 | −0.22 |
| miR_2045 | −0.47 | −0.38 | ND | 0.09 | 0.04 | −0.02 | −0.05 | −0.14 | −0.38 | −0.39 | −0.43 |
| miR_2046 | −0.30 | −0.23 | ND | 0.08 | −0.07 | −0.14 | 0.17 | −0.18 | −0.14 | −0.19 | −0.22 |
| miR_2047 | −0.27 | −0.14 | 0.43 | −0.46 | 0.51 | −0.30 | −0.59 | 0.17 | 0.27 | −0.10 | −0.16 |
| miR_2048 | −0.11 | −0.19 | 0.41 | −0.39 | 0.07 | −0.11 | 0.63 | −1.36 | 0.15 | 0.06 | −0.03 |
| miR_2049 | 0.10 | 0.28 | −0.22 | −0.55 | 0.29 | 0.13 | 0.03 | −0.49 | 0.28 | −0.68 | 0.29 |
| miR_2050 | −0.16 | −0.09 | 0.08 | 0.11 | −0.06 | −0.15 | 0.04 | −0.27 | 0.05 | −0.18 | −0.24 |
| miR_2051 | 0.11 | −0.14 | 0.08 | −0.32 | −0.21 | 0.02 | 0.06 | −0.43 | 0.71 | −0.52 | 0.33 |
| miR_2052 | 0.11 | 0.05 | 0.03 | −0.20 | −0.11 | −0.07 | −0.17 | −0.17 | 0.38 | −0.13 | 0.13 |
| miR_2053-miR_2137-miR_2443-miR_2444-miR_2445-320 | 0.22 | −0.14 | −0.69 | −0.82 | −0.37 | −0.67 | 0.25 | −0.05 | −2.93 | −0.42 | −1.13 |
| miR_2054 | −0.63 | 0.05 | −0.05 | 1.81 | 1.61 | 1.23 | 1.48 | 4.81 | −0.30 | 1.02 | −0.13 |
| miR_2055 | −0.23 | 0.11 | 0.15 | −0.91 | −0.40 | −0.62 | −0.58 | −0.10 | 0.05 | −1.15 | −0.10 |
| miR_2056 | −0.12 | −0.19 | 0.23 | 0.03 | −0.05 | ND | ND | −0.13 | −0.02 | −0.36 | 0.03 |
| miR_2057 | −0.17 | 0.24 | 0.42 | 1.35 | 1.02 | 0.52 | 1.30 | 1.05 | −0.37 | −0.01 | −0.16 |
| miR_2058 | 0.21 | 0.43 | −0.32 | −1.02 | 1.04 | −0.13 | 0.51 | 0.19 | 0.23 | −0.33 | 0.06 |
| miR_2060 | −0.49 | −0.10 | 0.34 | −0.56 | −0.55 | −0.44 | −0.97 | −0.10 | 0.56 | −0.06 | 0.13 |
| miR_2061 | −0.05 | −0.17 | 0.04 | 0.09 | −0.13 | −0.03 | −0.20 | −0.08 | 0.08 | 0.10 | −0.11 |
| miR_2062 | −0.30 | −0.28 | −0.56 | 0.41 | 0.85 | 0.39 | 0.81 | 4.55 | 0.51 | 1.19 | 0.58 |
| miR_2063 | 0.18 | 0.20 | 0.08 | 0.18 | 0.02 | 0.74 | ND | −0.06 | 0.26 | 0.29 | 0.21 |
| miR_2065 | −0.17 | −0.21 | 0.41 | −0.19 | −0.08 | 0.01 | −0.11 | −0.45 | 0.03 | −0.71 | −0.17 |
| miR_2066 | 0.22 | 0.17 | −0.12 | −0.21 | −0.10 | −0.26 | 0.25 | 0.27 | 0.10 | 0.32 | 0.40 |
| miR_2067 | 0.06 | −0.16 | 0.38 | −0.10 | −0.42 | −0.37 | −0.34 | −0.31 | 0.19 | −0.90 | −0.05 |
| miR_2068 | 0.48 | −0.22 | −0.08 | 0.12 | −0.05 | −0.37 | −0.12 | −0.17 | −0.04 | −0.10 | 0.55 |
| miR_2069-miR_2155 | −0.04 | −0.15 | −0.16 | −0.54 | −0.07 | −0.02 | −0.10 | −0.12 | ND | −0.22 | −0.06 |
| miR_2070 | −0.01 | −0.15 | 0.06 | 0.01 | −0.13 | −0.07 | 0.02 | 0.09 | 0.22 | −0.03 | −0.05 |
| miR_2071 | −0.50 | −0.07 | −0.53 | −0.09 | −0.53 | −0.36 | −0.55 | 1.50 | −1.33 | 0.20 | 0.07 |
| miR_2072 | −0.07 | −0.07 | −0.04 | 0.53 | 0.13 | 0.01 | 0.36 | −0.03 | 0.12 | 0.39 | 0.14 |
| miR_2073 | −0.15 | −0.12 | 0.10 | ND | 0.01 | −0.15 | 0.05 | −0.16 | 0.02 | −0.07 | −0.11 |
| miR_2074 | 0.10 | 0.08 | −0.02 | 0.04 | −0.05 | 0.00 | ND | −0.22 | 0.11 | 0.13 | 0.02 |
| miR_2075 | 0.05 | −0.05 | −0.11 | 0.01 | −0.05 | −0.04 | −0.08 | −0.07 | 0.03 | −0.15 | −0.06 |
| miR_2076 | 0.24 | 0.18 | −0.11 | −0.01 | 0.08 | 0.20 | −0.16 | 0.16 | 0.27 | 0.06 | 0.12 |
| miR_2077 | −0.09 | −0.07 | 0.02 | 0.05 | −0.24 | −0.57 | −0.26 | −0.04 | 0.25 | −0.12 | 0.08 |
| miR_2079 | 0.02 | 0.25 | 0.19 | −0.13 | −0.02 | −0.51 | −0.49 | −0.07 | 0.37 | 0.85 | −0.05 |
| miR_2080 | −0.16 | −0.15 | 0.14 | 0.04 | −0.07 | 0.07 | −0.07 | −0.09 | 0.15 | −0.30 | 0.03 |
| miR_2081 | −0.16 | −0.12 | −0.08 | 0.04 | 0.02 | −0.04 | 0.01 | −0.21 | ND | −0.07 | −0.24 |
| miR_2082 | 0.15 | 0.25 | 0.13 | −0.35 | −0.35 | −0.20 | −0.60 | −0.44 | 0.22 | 0.60 | −0.08 |
| miR_2083 | 0.17 | −0.11 | 0.10 | 0.22 | −0.09 | −0.09 | 0.28 | 0.31 | 0.47 | 0.39 | 0.40 |
| miR_2084 | −0.41 | −0.34 | −0.22 | 0.10 | ND | 0.15 | 0.01 | −0.13 | −0.15 | −0.39 | −0.28 |
| miR_2086 | 0.13 | −0.06 | 0.11 | −0.17 | 0.17 | −0.16 | 0.12 | 0.05 | 0.39 | 0.32 | 0.13 |
| miR_2087 | 0.17 | 0.02 | 0.07 | −0.59 | −0.25 | −0.50 | −0.61 | −0.18 | 0.11 | −0.24 | −0.10 |
| miR_2088-miR_2431 | 0.01 | 0.07 | 0.06 | 0.22 | 0.02 | −0.04 | ND | −0.19 | 0.07 | 0.05 | 0.03 |

TABLE 6-continued table ratios_454miRs: Contains ratio data generated on tumor versus normal adjacent tissues from a variety of tissues.

| | | | | | | | | | | | |
|---|---|---|---|---|---|---|---|---|---|---|---|
| miR_2090 | 1.15 | 1.41 | −1.50 | 0.77 | 2.70 | 1.18 | 1.78 | 3.41 | 0.67 | 2.62 | 0.34 |
| miR_2091 | −0.20 | −0.37 | −0.06 | 0.24 | −0.05 | −0.07 | ND | −0.11 | −0.35 | −0.37 | −0.37 |
| miR_2092 | −0.05 | 0.00 | 0.32 | −0.42 | −0.18 | −0.27 | −0.15 | −0.02 | −0.10 | −0.21 | −0.14 |
| miR_2093 | 0.54 | 0.45 | −0.15 | 0.35 | 0.45 | 0.75 | 0.91 | 0.67 | 0.55 | 1.58 | −0.11 |
| miR_2094 | 0.21 | 0.20 | 0.20 | 0.14 | −0.05 | −0.13 | −0.13 | −0.22 | 0.17 | 0.25 | 0.12 |
| miR_2095 | −0.50 | 0.15 | −0.02 | 4.16 | ND | 0.55 | 1.15 | 2.67 | −0.39 | 0.63 | 0.39 |
| miR_2096 | 0.28 | 0.31 | −0.03 | ND | −0.03 | 0.00 | ND | −0.22 | 0.28 | 0.37 | 0.28 |
| miR_2097 | 0.25 | 0.19 | 0.05 | 0.14 | −0.03 | −0.06 | −0.17 | −0.20 | ND | 0.24 | 0.13 |
| miR_2098 | −0.25 | −0.18 | 0.14 | 0.11 | −0.16 | −0.22 | −0.06 | −0.22 | −0.20 | −0.18 | −0.19 |
| miR_2099 | −0.01 | −0.05 | −0.24 | 0.22 | 0.02 | 0.01 | 0.09 | −0.04 | 0.04 | 0.37 | −0.08 |
| miR_2100 | 0.45 | 0.65 | −0.38 | −0.15 | 1.02 | 0.46 | 0.22 | 0.59 | 0.16 | 0.66 | 0.12 |
| miR_2101 | −0.35 | −0.07 | 0.06 | −0.20 | −0.54 | 0.15 | 0.17 | −1.52 | −0.20 | −1.06 | −0.01 |
| miR_2102 | −0.32 | −0.40 | 0.13 | ND | −0.09 | −0.12 | −0.10 | −0.27 | −0.14 | −0.30 | 0.06 |
| miR_2104 | 0.10 | 0.03 | 0.22 | −0.11 | −0.09 | −0.09 | −0.20 | −0.04 | 0.12 | −0.08 | 0.01 |
| miR_2105 | 0.02 | −0.11 | 0.05 | −0.74 | −0.04 | −0.17 | −0.12 | −0.58 | −0.02 | −0.64 | 0.21 |
| miR_2107 | −0.08 | 0.35 | −0.57 | −0.07 | 0.38 | 0.12 | −0.41 | 1.48 | −0.08 | 0.18 | 0.27 |
| miR_2108 | −0.08 | −0.04 | 0.18 | 0.02 | −0.01 | −0.18 | −0.05 | −0.27 | 0.00 | −0.03 | −0.17 |
| miR_2109 | 0.40 | 0.11 | 0.54 | −0.54 | −0.51 | 0.32 | −0.41 | −1.14 | −0.66 | −0.07 | −0.92 |
| miR_2110 | −0.23 | −0.20 | 0.04 | 0.20 | −0.08 | −0.17 | 0.00 | −0.15 | −0.06 | −0.15 | −0.22 |
| miR_2111 | 0.25 | 0.23 | 0.03 | 0.14 | 0.01 | 0.12 | 0.06 | −0.17 | ND | 0.28 | 0.24 |
| miR_2113 | 0.07 | −0.02 | 0.07 | −0.13 | 0.03 | −0.07 | ND | −0.16 | 0.14 | −0.17 | 0.03 |
| miR_2114 | 0.09 | 0.76 | −0.88 | −0.27 | 1.31 | 0.99 | −0.21 | 2.36 | −0.42 | 1.02 | 0.20 |
| miR_2115 | −0.03 | −0.11 | 0.53 | 0.07 | −0.36 | −0.01 | 0.31 | −1.13 | 0.23 | −0.79 | 0.09 |
| miR_2116 | −0.06 | −0.17 | 0.02 | −0.30 | −0.12 | −0.06 | 0.03 | −0.11 | 0.14 | −0.22 | −0.02 |
| miR_2117 | 0.22 | 0.14 | 0.24 | −0.62 | −0.05 | 0.19 | −0.28 | −0.09 | 0.21 | 0.08 | 0.24 |
| miR_2118 | 0.23 | −1.29 | 0.05 | −0.07 | −0.34 | 0.05 | −0.01 | −0.90 | 0.23 | −0.38 | −0.06 |
| miR_2119 | −0.83 | −0.67 | −0.51 | −1.65 | 0.48 | 0.23 | −0.26 | −0.59 | −0.19 | −0.52 | 0.45 |
| miR_2120 | 0.05 | 0.47 | 0.17 | 0.06 | −0.47 | −0.30 | −0.18 | −0.78 | 0.65 | −0.18 | 0.86 |
| miR_2121 | −0.01 | 0.08 | 0.08 | 0.17 | 0.01 | 0.18 | 0.01 | −0.25 | 0.15 | 0.14 | −0.10 |
| miR_2122 | −0.09 | 0.33 | −0.07 | −0.90 | 0.86 | 0.60 | 0.24 | 0.38 | 0.31 | −0.73 | 0.94 |
| miR_2123 | −0.09 | 0.29 | 0.12 | −1.10 | −0.72 | −1.81 | −0.78 | −0.36 | 0.03 | −0.58 | −0.55 |
| miR_2125 | 0.23 | 0.24 | −0.31 | −1.09 | 0.29 | 0.09 | −0.21 | 0.10 | 0.36 | 0.11 | 0.09 |
| miR_2126 | 0.24 | 0.26 | 0.07 | 0.06 | −0.04 | 0.01 | 0.02 | −0.16 | 0.28 | 0.23 | 0.25 |
| miR_2127 | 0.10 | −0.22 | −0.38 | 0.21 | −0.47 | −0.22 | 0.04 | 0.08 | 0.25 | 0.25 | 0.29 |
| miR_2128 | −0.09 | −0.13 | 0.28 | 0.10 | −0.35 | −0.95 | −0.45 | 0.50 | 0.28 | −0.73 | −0.25 |
| miR_2129 | −0.06 | −0.18 | −0.04 | 0.03 | −0.19 | 0.11 | −0.05 | 0.05 | 0.38 | −0.10 | 0.21 |
| miR_2130 | −0.07 | −0.05 | −0.03 | −1.44 | −0.07 | −0.71 | −1.00 | 0.27 | 0.09 | −0.48 | −0.09 |
| miR_2131 | −0.08 | −0.17 | 0.07 | 0.11 | −0.01 | −0.14 | 0.08 | −0.19 | −0.03 | −0.11 | −0.13 |
| miR_2132 | 0.21 | 0.20 | 0.01 | −0.13 | −0.15 | −0.12 | −0.04 | −0.03 | 0.36 | −0.02 | 0.25 |
| miR_2134 | −0.21 | −0.03 | 0.11 | 0.39 | 0.03 | −0.09 | 0.18 | −0.11 | 0.19 | 0.16 | 0.00 |
| miR_2135 | −0.25 | −0.18 | 0.16 | 0.00 | 0.21 | −0.55 | 0.33 | 0.05 | 0.01 | 0.00 | −0.06 |
| miR_2136 | −0.21 | −0.40 | 0.02 | −0.58 | −0.16 | 0.37 | −0.06 | −0.70 | −0.52 | −1.12 | −0.12 |
| miR_2137-miR_2444-miR_2445-miR_2447-320 | 0.35 | 0.00 | −0.69 | −0.35 | −0.58 | 0.54 | −0.01 | −0.32 | −2.98 | −0.55 | −1.10 |
| miR_2138 | −0.34 | 0.36 | −0.48 | 0.78 | 1.57 | 0.79 | 0.25 | 1.30 | −0.49 | 1.05 | −0.11 |
| miR_2139 | −0.17 | −0.24 | 0.60 | 0.36 | −0.45 | −0.18 | −0.50 | −1.20 | −0.16 | −1.28 | −0.02 |
| miR_2140 | −0.05 | −0.16 | 0.87 | −0.47 | 0.22 | −0.70 | −0.32 | −0.82 | 0.37 | −0.88 | 0.30 |
| miR_2141 | 0.12 | 0.13 | 0.16 | 0.03 | 0.04 | −0.10 | 0.04 | −0.18 | 0.25 | 0.13 | 0.15 |
| miR_2142 | 0.10 | 0.03 | 0.82 | −1.24 | 0.49 | −1.00 | −1.21 | −0.38 | 0.04 | −0.40 | 0.05 |
| miR_2143 | −0.37 | −0.22 | 0.08 | 0.34 | −0.02 | −0.33 | −0.08 | −0.18 | −0.19 | −0.18 | −0.31 |
| miR_2144 | −0.01 | 0.04 | 0.31 | 0.06 | −0.61 | 0.37 | 0.04 | −0.88 | 0.45 | 0.06 | 0.37 |
| miR_2145 | −0.17 | −0.20 | 0.11 | 0.16 | 0.00 | −0.22 | 0.00 | −0.19 | −0.13 | −0.13 | −0.15 |
| miR_2146 | 0.20 | 0.19 | 0.06 | −0.31 | 0.00 | −0.22 | 0.02 | −0.24 | 0.46 | −0.17 | 0.19 |
| miR_2147 | 0.41 | 0.37 | 0.18 | 0.05 | ND | 0.11 | 0.29 | 0.23 | 0.22 | 0.17 | 0.24 |
| miR_2148 | −0.27 | −0.13 | 0.06 | 0.15 | −0.05 | −0.19 | 0.07 | −0.10 | −0.06 | −0.18 | −0.01 |
| miR_2149 | 0.56 | 0.38 | −0.36 | −1.78 | 0.94 | 0.92 | 0.51 | 0.47 | 0.45 | −0.15 | 0.48 |
| miR_2150 | −0.25 | 0.79 | −0.97 | −0.19 | 1.36 | 0.55 | −0.10 | 0.56 | −0.75 | 0.66 | 0.32 |
| miR_2151 | 0.13 | −0.08 | 0.22 | −0.12 | 0.03 | −0.22 | 0.37 | −0.04 | 0.35 | 0.33 | 0.31 |
| miR_2152 | 0.19 | 0.30 | ND | −0.75 | 0.00 | 0.07 | 0.09 | −0.15 | 0.29 | 0.25 | 0.09 |
| miR_2153-miR_2163 | −0.23 | −0.06 | −0.47 | −0.28 | 0.43 | 0.21 | 0.25 | 0.13 | −0.06 | 0.18 | −0.31 |
| miR_2154 | 0.21 | 0.16 | 0.13 | −0.19 | −0.06 | 0.06 | −0.01 | −0.30 | 0.22 | 0.23 | 0.03 |
| miR_2156 | 0.07 | 0.08 | 0.11 | 0.17 | ND | 0.24 | 0.00 | −0.10 | 0.17 | 0.07 | 0.06 |
| miR_2157 | −0.11 | 0.07 | −0.30 | 0.87 | 0.21 | 0.75 | 0.25 | 2.21 | −0.07 | 1.46 | −0.13 |
| miR_2158 | 0.39 | −0.72 | 0.43 | 0.18 | −1.00 | −0.43 | 0.10 | −0.88 | 0.38 | −0.48 | 0.37 |
| miR_2159 | 0.08 | 0.44 | −0.83 | −1.40 | 0.83 | 0.67 | 0.19 | 0.11 | 0.46 | −0.61 | 0.59 |
| miR_2160 | 0.11 | 0.07 | 0.62 | 0.01 | −0.34 | −0.62 | −0.20 | −0.74 | 0.20 | −0.45 | 0.18 |
| miR_2161 | −0.04 | 0.04 | 0.04 | −0.10 | 0.00 | −0.38 | 0.05 | −0.07 | 0.22 | 0.11 | 0.10 |
| miR_2162 | 0.29 | −0.55 | −0.24 | −0.92 | 0.01 | 0.25 | −0.12 | −0.58 | −0.12 | −0.59 | 0.18 |
| miR_2164 | 0.05 | 0.08 | 0.14 | 0.28 | −0.58 | 0.04 | −0.39 | −0.91 | 0.46 | −0.09 | −0.16 |
| miR_2165 | 0.06 | −0.16 | 0.26 | 0.08 | −0.17 | −0.27 | −0.14 | 0.09 | 0.24 | 0.28 | 0.17 |
| miR_2166 | 0.00 | 0.16 | 0.38 | −0.42 | −0.65 | 0.12 | −0.36 | −0.87 | 0.24 | −1.05 | 0.15 |
| miR_2167 | −0.05 | −0.02 | −0.45 | 0.07 | −0.99 | −0.80 | −0.15 | 1.20 | 0.47 | −0.02 | 0.48 |
| miR_2168 | −0.60 | 0.60 | −0.96 | −1.10 | 1.62 | 0.40 | −0.25 | 0.79 | −0.80 | 1.12 | −0.12 |

TABLE 6-continued table ratios_454miRs: Contains ratio data generated on tumor versus normal adjacent tissues from a variety of tissues.

| | | | | | | | | | | | |
|---|---|---|---|---|---|---|---|---|---|---|---|
| miR_2169 | 0.53 | 0.06 | −0.33 | −1.00 | 0.01 | 0.18 | −0.07 | 0.18 | −0.96 | −0.83 | 0.37 |
| miR_2170 | 0.06 | 0.04 | 0.06 | −0.77 | 0.01 | −0.02 | 0.22 | −0.25 | 0.30 | −0.21 | 0.05 |
| miR_2171 | 0.17 | −0.17 | 1.65 | −0.31 | −0.43 | 0.38 | −0.64 | −1.45 | −0.42 | −1.93 | 0.30 |
| miR_2364 | 0.00 | 0.17 | ND | ND | ND | 0.69 | ND | −0.11 | −0.03 | 0.10 | −0.04 |
| miR_2365-miR_2408-miR_2419 | 0.21 | 0.45 | −0.09 | −0.14 | 0.22 | −0.52 | 0.12 | 0.18 | 0.21 | 0.89 | 0.49 |
| miR_2366 | −1.35 | −0.20 | −1.33 | 0.07 | 1.17 | 1.29 | −0.21 | 3.41 | −3.70 | 1.36 | −0.47 |
| miR_2370-miR_2391 | 0.18 | 0.24 | 0.05 | 0.00 | 0.00 | 0.25 | 0.01 | −0.05 | 0.32 | 0.22 | 0.19 |
| miR_2371 | −0.31 | −0.31 | 0.08 | 0.03 | −0.04 | ND | ND | −0.15 | −0.09 | −0.26 | −0.36 |
| miR_2372-miR_2373-miR_2404 | −0.44 | −0.55 | 0.62 | −0.37 | −1.17 | −1.20 | −0.87 | −0.41 | −0.31 | −0.56 | −0.75 |
| miR_2374-miR_2375-miR_2376-miR_2377 | −0.51 | 0.01 | −0.01 | −1.68 | −0.37 | −2.32 | −1.86 | 0.21 | −0.83 | −0.39 | −0.46 |
| miR_2374-miR_2375-miR_2376-miR_2377-miR_2416-miR_2417 | −0.78 | −0.13 | 0.18 | −0.58 | −0.46 | −1.30 | −0.96 | 0.57 | −0.90 | −0.47 | −0.52 |
| miR_2378-miR_2418 | 0.90 | 0.78 | −1.23 | −0.56 | 1.68 | 1.15 | 0.20 | 2.80 | 0.84 | 1.21 | 0.89 |
| miR_2379 | 0.09 | 0.03 | 0.42 | −0.02 | −0.17 | −0.38 | −0.06 | 0.19 | 0.70 | 0.17 | 0.55 |
| miR_2380 | −0.24 | 0.27 | 0.44 | 0.20 | −0.19 | −0.71 | −0.04 | 0.76 | 0.40 | −0.25 | 0.46 |
| miR_2381 | −0.01 | 0.88 | −0.40 | −1.88 | −0.95 | 0.07 | −0.46 | 0.11 | 0.95 | −1.72 | 0.38 |
| miR_2383 | −0.62 | 0.46 | −0.80 | −2.97 | −0.25 | −2.15 | −1.68 | 0.89 | 0.27 | −0.55 | 0.76 |
| miR_2385-miR_2386-miR_2423-miR_2433 | −1.22 | 0.17 | −0.11 | 0.25 | −0.71 | −0.85 | −0.66 | 0.67 | −1.25 | −0.26 | −1.02 |
| miR_2387 | −0.58 | 0.09 | −0.50 | −0.35 | −0.06 | −0.60 | −0.64 | 0.35 | −0.55 | −0.50 | −0.70 |
| miR_2388 | 0.19 | 0.06 | −0.23 | 0.09 | −0.55 | −0.12 | −0.89 | −0.08 | 0.36 | 0.14 | 0.05 |
| miR_2389 | 0.14 | 0.15 | 0.07 | −0.01 | −0.14 | −0.22 | 0.02 | −0.25 | 0.01 | 0.10 | −0.12 |
| miR_2390 | −0.09 | 0.00 | 0.21 | −0.56 | 0.11 | 0.53 | −0.18 | −0.87 | −0.07 | −0.40 | −0.12 |
| miR_2392 | −0.09 | −0.37 | 0.46 | −0.51 | −0.57 | −0.97 | −0.28 | −0.89 | −0.22 | −0.82 | −0.56 |
| miR_2393 | 0.78 | 0.60 | −0.90 | −0.03 | 0.94 | 1.11 | 0.26 | 0.73 | 0.57 | 0.22 | 0.66 |
| miR_2394-miR_2395 | 0.92 | 0.26 | −0.70 | −0.27 | 1.57 | 0.98 | 0.61 | 2.44 | 1.12 | 1.22 | 1.07 |
| miR_2396-miR_2397-miR_2398 | 0.55 | 0.67 | 0.73 | 1.45 | 1.09 | 0.09 | 1.11 | 0.81 | 0.56 | −0.44 | 1.11 |
| miR_2399 | 0.12 | 0.38 | 0.32 | 1.53 | 1.31 | 0.48 | 1.02 | 1.38 | 0.13 | 0.49 | 0.48 |
| miR_2400-miR_2401-miR_2402 | 0.12 | 0.43 | 0.43 | 1.00 | 1.26 | 0.46 | 0.85 | 0.88 | 0.66 | 0.98 | 0.74 |
| miR_2403 | −0.09 | −0.07 | 0.28 | −0.08 | −0.23 | −0.42 | −0.26 | 0.07 | 0.21 | 0.08 | 0.04 |
| miR_2405 | 0.38 | 0.38 | 0.94 | 1.58 | 0.76 | −0.21 | 0.70 | 0.66 | 0.62 | −0.62 | 0.41 |
| miR_2406 | −0.16 | 0.20 | 0.26 | 0.05 | −0.08 | ND | −0.41 | −0.15 | −0.11 | −0.34 | 0.19 |
| miR_2407 | 0.29 | 0.11 | ND | ND | ND | ND | ND | −0.08 | 0.25 | 0.20 | −0.03 |
| miR_2409-miR_2410-miR_2411-miR_2412 | 0.13 | 0.07 | 0.06 | 0.03 | −0.22 | 0.06 | −0.31 | −0.30 | 0.01 | −0.22 | 0.08 |
| miR_2413-miR_2414-miR_2415-miR_2439-miR_2440 | −0.75 | −0.06 | 0.52 | −0.26 | −0.43 | −3.62 | −0.87 | 0.02 | −0.82 | −0.56 | −0.26 |
| miR_2422 | 0.26 | 0.32 | 0.04 | −0.19 | −0.06 | 0.02 | −0.19 | −0.79 | 0.27 | 0.15 | 0.17 |
| miR_2424-miR_2425 | −0.19 | 0.12 | 0.34 | −0.35 | −0.31 | −0.05 | −0.17 | −0.84 | 0.20 | −1.06 | −0.17 |
| miR_2426 | −0.23 | −0.26 | 0.12 | 0.09 | −0.04 | −0.29 | −0.02 | −0.31 | −0.09 | −0.17 | −0.28 |
| miR_2428 | 0.12 | 0.09 | −0.09 | 0.04 | −0.04 | −0.04 | 0.11 | −0.12 | 0.11 | 0.17 | 0.01 |
| miR_2429 | 0.03 | −0.02 | 0.03 | 0.00 | 0.21 | 0.22 | −0.01 | 0.02 | 0.07 | −0.03 | −0.06 |
| miR_2432-miR_2433 | −1.29 | 0.06 | −0.13 | 0.37 | −1.02 | −1.07 | −0.81 | 0.41 | −1.28 | −0.43 | −1.15 |
| miR_2435-miR_2436 | −0.43 | 0.37 | −0.36 | 1.26 | 1.39 | 0.90 | 0.04 | 1.01 | −0.73 | 1.36 | −0.14 |
| miR_2442 | 0.21 | −0.19 | −0.08 | −1.00 | −0.71 | −0.06 | −0.44 | −0.85 | −2.52 | −1.10 | −1.08 |
| miR_2446 | 0.29 | 0.68 | −1.34 | −0.74 | 1.13 | 1.03 | 0.08 | 1.52 | −1.31 | 1.21 | −0.15 |

TABLE 6-continued table ratios_454miRs: Contains ratio data generated on tumor versus normal adjacent tissues from a variety of tissues.

| Tissue<br>MiR name | Prostate<br>T/N-ambion | T/N-31 | T/N-50 | Rectal<br>T/N-62 | T/N-68 | T/N-69 | T/N-71 | T/N-85 | Stomach<br>T/N-ambion | Uterus<br>T/N-38 | T/N-ambion |
|---|---|---|---|---|---|---|---|---|---|---|---|
| miR_1966-miR_1988-miR_2078 | 0.44 | 0.05 | −1.15 | 1.13 | 0.64 | −2.42 | −3.01 | 0.04 | −0.20 | 0.37 | −1.71 |
| miR_1967 | −0.05 | −0.06 | 0.51 | 0.96 | 0.25 | 0.26 | 0.11 | 0.49 | −0.87 | 0.18 | 0.42 |
| miR_1968 | 0.39 | 0.99 | 0.23 | 0.75 | 0.69 | 0.51 | −0.11 | 0.56 | −0.01 | 0.02 | −0.01 |
| miR_1969 | 0.26 | 0.01 | −0.56 | −0.14 | −0.08 | −0.37 | −0.75 | −0.45 | 0.03 | 0.26 | 1.45 |
| miR_1970 | −0.30 | −0.55 | 0.41 | −0.05 | −0.55 | 0.12 | 0.68 | −0.16 | 0.26 | 1.05 | 0.32 |
| miR_1971 | 0.24 | −0.11 | 0.05 | 0.06 | −0.03 | 0.28 | −0.10 | −0.09 | 0.27 | −0.41 | 0.30 |
| miR_1972 | 0.26 | 1.64 | 1.67 | 2.07 | 5.42 | 1.81 | 0.53 | 1.01 | 0.31 | −1.30 | −1.37 |
| miR_1973 | 0.24 | −0.05 | −0.06 | −0.30 | −0.05 | 0.14 | −0.13 | −0.10 | 0.29 | −0.43 | 0.25 |
| miR_1974 | 0.59 | 0.86 | 0.28 | 0.28 | 0.26 | 0.97 | 0.75 | 0.57 | −0.21 | 1.02 | 0.38 |
| miR_1975 | −0.90 | 1.51 | 0.82 | 2.36 | 1.59 | 0.45 | −1.14 | 1.53 | 0.91 | −0.32 | 0.01 |
| miR_1976-miR_2124 | 0.14 | 0.63 | 0.59 | 0.81 | 2.60 | 0.19 | −0.27 | 0.19 | 0.33 | 0.62 | 0.68 |
| miR_1977-miR_2064 | 0.47 | 0.48 | 0.42 | 0.57 | 0.54 | 0.59 | 0.70 | 0.45 | −0.30 | 0.90 | 0.58 |
| miR_1978 | 0.20 | −0.58 | −0.80 | −0.86 | −1.04 | −0.25 | −0.13 | −0.94 | 0.17 | −0.45 | 0.22 |
| miR_1979 | 0.34 | 0.86 | −0.21 | 1.80 | 1.44 | 0.13 | −1.06 | 0.70 | −0.81 | −1.37 | 0.25 |
| miR_1980 | 0.14 | −0.21 | 0.18 | −0.83 | −0.19 | 0.06 | 0.66 | −0.09 | −1.01 | 0.69 | 0.69 |
| miR_1981 | −0.04 | −0.62 | −0.11 | −0.16 | −0.06 | −0.61 | −0.13 | −0.55 | −1.14 | 0.56 | 0.35 |
| miR_1982 | 0.06 | −0.37 | −0.15 | 0.22 | −0.05 | −0.23 | −0.01 | 0.41 | 0.05 | 0.59 | 0.26 |
| miR_1983 | 0.17 | 0.11 | 0.45 | 0.68 | −0.19 | −0.03 | 0.21 | −0.09 | 0.02 | 0.66 | −0.05 |
| miR_1984 | 0.34 | 0.54 | 0.01 | 0.49 | 0.06 | 0.24 | 0.40 | 0.12 | 0.13 | 0.69 | 0.04 |
| miR_1985 | 0.18 | −1.15 | −0.61 | −1.52 | 0.60 | 1.40 | 1.22 | 1.01 | 1.32 | 1.36 | 0.51 |
| miR_1986 | 0.46 | −0.76 | 0.18 | −0.02 | 0.58 | 1.04 | 0.51 | 0.66 | 1.15 | 1.14 | −0.24 |
| miR_1987 | −0.04 | −0.10 | 0.11 | 0.38 | 0.06 | −0.11 | 0.10 | −0.02 | −0.29 | 0.35 | 0.00 |
| miR_1989 | −0.22 | −0.53 | −0.86 | −1.54 | −1.55 | −0.25 | 0.49 | 0.02 | 0.12 | −0.75 | 0.17 |
| miR_1990 | 0.09 | −0.45 | −0.02 | −0.49 | −0.28 | 0.22 | 0.47 | −0.16 | −1.49 | −0.38 | 0.29 |
| miR_1991 | −0.08 | 0.18 | 0.17 | −0.22 | 0.01 | 0.16 | 0.28 | −0.18 | −0.25 | −0.19 | −0.06 |
| miR_1992 | 0.26 | 0.19 | 0.24 | 0.26 | 0.29 | 0.59 | 0.59 | 0.74 | −0.01 | 0.54 | 0.26 |
| miR_1993 | 0.05 | 1.63 | 0.70 | 1.19 | 1.97 | 1.15 | −0.48 | 0.63 | −0.84 | 0.01 | 0.86 |
| miR_1994 | 0.19 | −0.36 | 0.19 | −0.82 | −0.09 | 0.95 | 0.97 | −0.40 | −0.22 | 0.58 | 0.25 |
| miR_1995 | 0.12 | −0.36 | −0.29 | −0.96 | −0.68 | −0.22 | 0.46 | 0.32 | 0.00 | 0.43 | −0.10 |
| miR_1996 | 0.19 | −0.35 | −0.19 | −1.94 | −0.71 | −0.11 | 0.85 | −0.18 | −0.23 | −0.14 | 0.08 |
| miR_1997 | 0.30 | 0.83 | 0.96 | 1.39 | 0.56 | 0.96 | 0.90 | 1.30 | −0.01 | 0.60 | 0.66 |
| miR_1998 | −0.10 | 0.12 | 0.28 | 0.25 | 0.07 | 0.36 | 0.02 | −0.03 | −0.15 | −0.17 | −0.02 |
| miR_1999 | 0.01 | 0.02 | 0.31 | 0.03 | 0.24 | 0.41 | 0.35 | 0.17 | −0.17 | 0.57 | 0.18 |
| miR_2000 | 0.15 | −0.31 | −0.12 | −0.52 | −0.61 | −0.01 | 0.63 | −0.12 | −1.40 | 0.04 | 0.30 |
| miR_2001 | −0.46 | −0.13 | −0.03 | −0.18 | −0.09 | 0.24 | −0.18 | −0.09 | −0.51 | −0.80 | −0.43 |
| miR_2002 | 0.05 | 0.53 | 0.11 | 3.28 | 1.98 | 0.41 | 0.39 | 0.56 | −0.48 | 0.35 | −0.44 |
| miR_2003 | ND | −0.42 | −0.02 | −0.05 | 0.02 | 0.22 | −0.20 | −0.01 | −0.16 | −0.59 | ND |
| miR_2004 | −0.03 | −0.01 | −0.10 | −0.35 | −0.01 | 0.13 | −0.35 | −0.16 | 0.01 | −0.06 | −0.66 |
| miR_2005 | −0.34 | −0.08 | −0.08 | −0.26 | −0.03 | 0.14 | −0.32 | −0.13 | −0.33 | −0.66 | −0.27 |
| miR_2006 | 0.16 | −0.39 | −0.23 | 0.04 | −0.34 | −0.68 | −0.02 | 0.44 | −0.24 | −0.06 | 0.05 |
| miR_2008 | −0.21 | −0.43 | −0.55 | −0.65 | −0.98 | −0.13 | 0.37 | 0.23 | −0.48 | 0.79 | −0.23 |
| miR_2009 | −0.29 | 0.08 | 0.33 | −0.01 | 0.11 | 0.46 | 0.06 | 0.06 | −0.29 | −0.16 | −0.22 |
| miR_2010 | −0.32 | −0.04 | 0.62 | 0.34 | 0.38 | 0.85 | 0.33 | 0.92 | −0.40 | 0.12 | −0.17 |
| miR_2011 | −0.20 | −0.68 | −0.24 | −0.63 | −0.51 | 0.04 | 0.03 | 0.08 | 0.08 | 0.43 | −0.32 |
| miR_2012 | 0.12 | −0.33 | −0.60 | −0.89 | −0.98 | −0.52 | 0.61 | 0.28 | 0.22 | 0.62 | 0.76 |
| miR_2013-miR_2396-miR_2397-miR_2398 | −0.11 | 1.36 | 0.85 | 1.37 | 1.41 | 1.16 | −0.71 | 0.61 | −0.91 | −1.09 | 0.73 |
| miR_2014 | 0.09 | −0.03 | −0.14 | −0.18 | −0.04 | 0.34 | −0.19 | −0.10 | 0.18 | −0.41 | 0.17 |
| miR_2015 | 0.16 | 2.04 | 1.23 | 3.16 | 4.43 | 2.02 | 0.76 | 1.27 | 1.20 | −1.44 | −0.83 |
| miR_2016 | 0.00 | −0.04 | −0.02 | −0.17 | −0.07 | 0.21 | −0.18 | −0.05 | −0.01 | −0.61 | 0.10 |
| miR_2017 | ND | ND | −0.10 | −0.21 | 0.02 | 0.26 | −0.23 | −0.12 | −0.01 | −0.58 | 0.06 |
| miR_2018 | 0.05 | −0.21 | −0.18 | −0.29 | −0.71 | −0.13 | 0.10 | −0.16 | −1.21 | −0.56 | −0.28 |
| miR_2019 | 0.48 | 0.05 | −0.01 | 0.57 | −1.76 | −1.42 | −0.47 | 0.21 | −1.52 | 1.62 | −0.18 |
| miR_2020 | 0.17 | 0.64 | 0.29 | 1.90 | 1.41 | 0.14 | −0.43 | 1.32 | −0.23 | −0.11 | 0.11 |
| miR_2021 | −0.10 | −0.54 | −0.90 | −0.41 | −0.90 | −0.02 | 0.41 | 0.27 | −0.23 | 0.73 | −0.54 |
| miR_2022 | 0.37 | −0.44 | 1.39 | 0.63 | −0.56 | 0.86 | 0.70 | −0.19 | 0.56 | 0.76 | 0.08 |
| miR_2023 | 0.30 | 0.22 | 0.02 | 0.45 | 0.26 | 0.15 | 0.18 | 0.32 | 0.12 | 0.68 | 0.34 |
| miR_2024 | 0.20 | 0.21 | 0.51 | −0.14 | −0.25 | 0.66 | 0.82 | 0.67 | 0.77 | 0.29 | 0.41 |
| miR_2025 | 0.00 | −0.08 | 0.15 | 0.27 | 0.00 | −0.03 | 0.02 | −0.14 | −0.30 | 0.12 | −0.06 |
| miR_2026 | 0.02 | −0.38 | 0.38 | −1.27 | −1.19 | 0.55 | 0.62 | −0.07 | −0.50 | 0.65 | 0.32 |
| miR_2027 | 0.01 | −0.77 | −0.79 | −2.26 | −0.92 | −0.05 | 0.34 | −0.49 | −0.13 | 0.57 | 0.69 |
| miR_2028 | −0.19 | 0.00 | 0.28 | 0.06 | −0.14 | 0.18 | −0.04 | 0.02 | −0.26 | −0.51 | −0.05 |
| miR_2029 | −0.30 | −0.37 | 0.43 | −0.34 | −0.51 | −0.01 | 0.33 | 0.03 | −0.35 | 0.59 | −0.08 |
| miR_2030 | 0.12 | 0.04 | 0.69 | −0.10 | 0.30 | 1.01 | 1.08 | 0.45 | −0.14 | 0.75 | 0.61 |
| miR_2031 | 0.34 | 0.16 | 0.63 | 0.84 | 0.57 | 0.50 | 0.76 | 0.76 | 0.22 | 0.56 | 0.31 |

TABLE 6-continued table ratios__454miRs: Contains ratio data generated on tumor versus normal adjacent tissues from a variety of tissues.

| | | | | | | | | | | | |
|---|---|---|---|---|---|---|---|---|---|---|---|
| miR_2032 | −0.25 | −0.16 | 0.84 | 0.01 | −0.69 | −0.19 | 0.07 | 0.43 | −0.10 | 0.55 | −0.11 |
| miR_2033 | 0.04 | −0.14 | −0.81 | 1.31 | 1.28 | −0.33 | −1.20 | −0.30 | −0.04 | −0.20 | −0.58 |
| miR_2034 | 0.52 | 0.51 | 1.63 | 1.29 | 0.06 | 0.20 | 0.86 | 0.18 | −1.09 | 0.94 | 0.55 |
| miR_2035 | 0.15 | 0.84 | 0.63 | 1.02 | 1.40 | 0.62 | 0.48 | 0.48 | −0.18 | 0.44 | −0.21 |
| miR_2036 | 0.18 | −0.32 | −0.23 | −1.59 | −0.29 | 0.28 | 0.47 | 0.19 | −0.51 | 0.64 | 0.45 |
| miR_2037 | 0.05 | 0.26 | 0.27 | 0.29 | 0.59 | 0.13 | 0.34 | −0.29 | 0.10 | 0.19 | −0.11 |
| miR_2038 | −0.19 | −0.30 | 0.24 | −0.23 | −0.30 | −0.02 | 0.16 | −0.07 | 0.00 | −0.04 | −0.02 |
| miR_2040 | −0.04 | 0.03 | 0.19 | 0.08 | 0.08 | 0.19 | −0.19 | −0.07 | −0.03 | −0.43 | 0.04 |
| miR_2041 | 0.23 | 0.21 | 0.26 | 0.14 | 0.18 | 0.43 | 0.42 | 0.23 | −0.25 | −0.01 | 0.23 |
| miR_2042 | 0.03 | 0.70 | −0.07 | 1.34 | 1.54 | 0.17 | −0.25 | 0.35 | −0.71 | 0.01 | −1.05 |
| miR_2043 | 0.65 | 0.37 | −0.41 | 1.29 | 1.38 | −0.81 | −0.75 | −0.11 | 0.10 | 1.03 | −1.08 |
| miR_2044 | −0.13 | −0.09 | 0.36 | 0.03 | 0.15 | 0.32 | 0.20 | 0.11 | −0.17 | −0.63 | −0.07 |
| miR_2045 | −0.35 | −0.05 | −0.18 | −0.50 | −0.22 | 0.09 | −0.05 | −0.14 | −0.36 | −0.66 | −0.38 |
| miR_2046 | −0.21 | −0.07 | −0.10 | −0.26 | −0.12 | 0.17 | −0.20 | −0.11 | −0.22 | −0.49 | −0.14 |
| miR_2047 | −0.03 | −0.45 | −0.25 | −0.57 | −0.45 | 0.14 | 0.60 | 0.15 | −0.39 | 0.46 | 0.27 |
| miR_2048 | 0.01 | −1.08 | −0.84 | −3.48 | −1.16 | 0.18 | 0.98 | −0.21 | −0.44 | 0.46 | 0.15 |
| miR_2049 | 0.18 | −0.16 | 0.05 | −0.69 | −0.83 | 0.36 | 0.74 | 0.53 | 0.48 | 0.02 | 0.28 |
| miR_2050 | −0.02 | 0.06 | 0.14 | −0.08 | −0.11 | 0.27 | −0.15 | −0.13 | −0.09 | −0.56 | 0.05 |
| miR_2051 | −0.03 | 0.01 | 0.93 | 0.62 | 0.14 | 0.83 | 0.90 | 0.37 | −0.20 | 0.85 | 0.71 |
| miR_2052 | 0.00 | −0.05 | 0.45 | −0.04 | 0.04 | 0.33 | 0.63 | −0.10 | −0.04 | 0.65 | 0.38 |
| miR_2053-miR_2137-miR_2443-miR_2444-miR_2445-320 | −0.75 | −0.72 | −1.56 | −1.43 | −1.77 | −1.46 | −1.00 | −1.21 | 0.56 | −2.29 | −2.93 |
| miR_2054 | 0.19 | 1.61 | 1.21 | ND | 4.80 | 0.70 | 0.08 | 1.25 | −0.03 | 0.04 | −0.30 |
| miR_2055 | 0.02 | −0.52 | 0.62 | −0.35 | −0.88 | 0.71 | 0.86 | 0.29 | 0.37 | 0.72 | 0.05 |
| miR_2056 | −0.07 | 0.05 | 0.32 | 0.40 | 0.10 | 0.03 | −0.20 | −0.09 | −0.24 | −0.43 | −0.02 |
| miR_2057 | −0.13 | 0.67 | 0.01 | 1.84 | 1.34 | −0.19 | −1.42 | 0.22 | −0.46 | −0.40 | −0.37 |
| miR_2058 | 0.14 | −0.13 | −0.24 | −0.37 | −0.51 | 0.35 | 0.40 | −0.05 | 0.01 | 0.42 | 0.23 |
| miR_2060 | 0.08 | 0.05 | −0.05 | 0.70 | −0.07 | −0.70 | −0.10 | −0.96 | −0.86 | −0.24 | 0.56 |
| miR_2061 | −0.01 | −0.24 | 0.18 | 0.20 | 0.08 | −0.25 | 0.14 | −0.10 | −0.38 | 0.41 | 0.08 |
| miR_2062 | 0.01 | 0.72 | 0.92 | 0.37 | 2.02 | 0.32 | 0.12 | −0.48 | 0.05 | 0.59 | 0.51 |
| miR_2063 | 0.25 | −0.02 | −0.03 | −0.08 | −0.19 | 0.16 | −0.07 | −0.01 | 0.29 | −0.67 | 0.26 |
| miR_2065 | −0.14 | −0.32 | −0.12 | −0.61 | −0.42 | −0.32 | 0.13 | 0.00 | −0.13 | 0.00 | 0.03 |
| miR_2066 | 0.31 | 0.71 | 0.37 | 0.04 | 0.24 | 0.33 | 0.59 | −0.25 | −0.42 | 0.79 | 0.10 |
| miR_2067 | −0.02 | 0.08 | 0.52 | −0.03 | −0.21 | 0.39 | 0.58 | 0.48 | −0.22 | 0.69 | 0.19 |
| miR_2068 | 0.00 | −0.03 | −0.05 | 0.31 | 0.22 | −0.25 | −0.51 | −0.16 | −0.05 | −0.24 | −0.04 |
| miR_2069-miR_2155 | −0.02 | 0.07 | 0.38 | 0.59 | 0.16 | −0.21 | −0.08 | −0.46 | −0.38 | 0.36 | ND |
| miR_2070 | 0.00 | −0.10 | 0.44 | 0.41 | 0.32 | 0.25 | 0.30 | 0.14 | −0.41 | 0.52 | 0.22 |
| miR_2071 | 0.34 | 0.31 | 0.62 | 0.99 | 0.57 | −0.41 | −1.02 | 0.69 | −0.09 | 1.23 | −1.33 |
| miR_2072 | 0.04 | 0.54 | 0.83 | −0.10 | −0.21 | 0.38 | 0.36 | −0.72 | −0.36 | 0.36 | 0.12 |
| miR_2073 | −0.08 | ND | −0.27 | −0.20 | −0.03 | −0.02 | −0.21 | −0.05 | −0.10 | −0.57 | 0.02 |
| miR_2074 | 0.15 | −0.01 | 0.03 | −0.22 | −0.02 | 0.08 | −0.23 | −0.08 | 0.19 | −0.56 | 0.11 |
| miR_2075 | −0.01 | −0.08 | 0.98 | 0.57 | 0.35 | 0.07 | −0.07 | 0.05 | −0.01 | 0.36 | 0.03 |
| miR_2076 | 0.26 | −0.09 | 0.52 | 0.00 | 0.09 | 0.75 | 0.87 | 0.02 | 0.04 | 0.55 | 0.27 |
| miR_2077 | 0.12 | −0.43 | 0.21 | −0.16 | 0.09 | 0.25 | 0.51 | 0.07 | −0.52 | 0.35 | 0.25 |
| miR_2079 | 0.11 | 0.45 | 0.58 | −0.17 | 0.32 | 0.74 | 0.52 | −0.71 | −0.12 | 0.37 | 0.37 |
| miR_2080 | −0.20 | 0.05 | 0.45 | 0.36 | 0.10 | 0.50 | 0.33 | 0.31 | −0.30 | 0.10 | 0.15 |
| miR_2081 | −0.05 | −0.03 | 0.06 | 0.04 | −0.10 | 0.25 | −0.16 | 0.01 | −0.12 | −0.60 | ND |
| miR_2082 | 0.04 | −0.14 | 0.16 | −0.70 | −0.19 | −0.48 | 0.75 | −1.87 | 0.09 | 0.32 | 0.22 |
| miR_2083 | 0.22 | 0.15 | 0.32 | 0.44 | 0.33 | 0.15 | 0.45 | 0.17 | −0.31 | 0.61 | 0.47 |
| miR_2084 | −0.31 | ND | 0.05 | −0.08 | −0.07 | 0.09 | 0.03 | 0.06 | −0.37 | −0.32 | −0.15 |
| miR_2086 | −0.04 | 0.13 | 0.58 | 0.47 | 0.24 | 0.38 | 0.45 | 0.21 | −0.27 | 0.59 | 0.39 |
| miR_2087 | 0.21 | −0.21 | 0.02 | 0.50 | −0.23 | −0.25 | −0.01 | 0.20 | 0.18 | 0.36 | 0.11 |
| miR_2088-miR_2431 | 0.10 | −0.05 | −0.05 | −0.03 | −0.03 | 0.20 | −0.17 | 0.02 | 0.21 | −0.66 | 0.07 |
| miR_2090 | 0.40 | 1.66 | 0.57 | 3.81 | 4.37 | 1.47 | −1.27 | 2.08 | 1.50 | −0.13 | 0.67 |
| miR_2091 | −0.33 | ND | −0.18 | −0.26 | 0.03 | 0.09 | −0.33 | −0.21 | −0.29 | −0.78 | −0.35 |
| miR_2092 | −0.08 | 0.21 | 1.07 | 0.96 | 1.08 | 1.39 | 0.84 | 1.35 | 0.06 | −0.20 | −0.10 |
| miR_2093 | 0.21 | 1.34 | 0.36 | 0.98 | 1.85 | 1.39 | 1.08 | 1.07 | 1.27 | −0.39 | 0.55 |
| miR_2094 | 0.29 | −0.10 | −0.06 | −0.19 | −0.15 | 0.09 | −0.25 | −0.12 | 0.24 | −0.56 | 0.17 |
| miR_2095 | 0.13 | 2.60 | 0.74 | 3.62 | ND | −1.38 | −9.41 | 0.78 | −0.31 | 0.66 | −0.39 |
| miR_2096 | 0.34 | −0.05 | −0.03 | −0.11 | −0.02 | 0.23 | −0.11 | −0.09 | 0.38 | −0.59 | 0.28 |
| miR_2097 | ND | −0.08 | −0.01 | −0.06 | −0.03 | 0.20 | −0.23 | −0.08 | 0.26 | −0.40 | ND |
| miR_2098 | −0.28 | −0.01 | −0.01 | −0.14 | 0.08 | 0.22 | −0.30 | −0.16 | −0.25 | −0.55 | −0.20 |
| miR_2099 | 0.09 | 0.37 | 0.12 | 0.29 | 0.12 | 0.06 | 0.33 | 0.23 | −0.23 | −0.23 | 0.04 |
| miR_2100 | 0.37 | −0.24 | −0.79 | −0.62 | −0.41 | −0.03 | 0.12 | 0.31 | 0.04 | 0.49 | 0.16 |
| miR_2101 | −0.08 | −0.23 | 0.42 | −1.08 | −0.52 | 0.25 | 0.56 | 0.17 | −0.20 | 0.54 | −0.20 |
| miR_2102 | −0.24 | 0.19 | 0.29 | 0.16 | 0.08 | 0.30 | 0.00 | 0.01 | −0.36 | −0.48 | −0.14 |
| miR_2104 | 0.12 | −0.12 | 0.00 | 0.18 | −0.19 | 0.07 | −0.02 | 0.18 | 0.08 | −0.07 | 0.12 |
| miR_2105 | −0.13 | −0.26 | 0.53 | 0.33 | −0.22 | 0.40 | 0.67 | 0.55 | −0.33 | 0.67 | −0.02 |
| miR_2107 | 0.25 | 0.86 | 0.42 | 1.86 | 1.28 | 0.21 | 0.07 | 0.87 | 0.07 | 0.91 | −0.08 |
| miR_2108 | −0.06 | −0.01 | 0.03 | −0.08 | −0.01 | 0.39 | −0.07 | −0.09 | −0.07 | −0.30 | 0.00 |
| miR_2109 | −0.31 | −0.50 | −0.99 | −1.22 | −0.98 | −1.25 | −0.58 | −0.70 | 0.19 | −0.62 | −0.66 |

TABLE 6-continued table ratios_454miRs: Contains ratio data generated on tumor versus normal adjacent tissues from a variety of tissues.

| | | | | | | | | | | | |
|---|---|---|---|---|---|---|---|---|---|---|---|
| miR_2110 | −0.13 | −0.05 | −0.10 | −0.34 | −0.04 | 0.09 | −0.22 | −0.09 | −0.18 | −0.57 | −0.06 |
| miR_2111 | 0.23 | 0.02 | −0.02 | 0.02 | 0.12 | 0.07 | 0.08 | 0.12 | 0.26 | −0.23 | ND |
| miR_2113 | 0.06 | −0.39 | 0.30 | 0.26 | 0.09 | −0.20 | −0.01 | −0.08 | −0.05 | −0.01 | 0.14 |
| miR_2114 | 0.21 | −0.13 | −0.15 | 0.34 | −0.06 | −0.03 | 0.32 | 0.45 | 0.18 | 0.71 | −0.42 |
| miR_2115 | 0.01 | −0.50 | −0.10 | −0.41 | −0.34 | 0.18 | 0.71 | 0.48 | −0.55 | 0.53 | 0.23 |
| miR_2116 | −0.03 | −0.12 | 0.35 | 0.65 | 0.08 | −0.31 | −0.39 | −0.22 | −0.19 | −0.27 | 0.14 |
| miR_2117 | 0.31 | 0.29 | 0.06 | −0.71 | −0.30 | −0.29 | 0.24 | 0.23 | −0.35 | 0.55 | 0.21 |
| miR_2118 | 0.10 | −0.19 | −0.05 | −0.35 | −0.60 | 0.02 | 0.68 | −0.16 | −1.41 | −0.11 | 0.23 |
| miR_2119 | 0.07 | −0.71 | −0.81 | −0.66 | −1.79 | −0.43 | 0.43 | 0.10 | 0.28 | −0.35 | −0.19 |
| miR_2120 | 0.51 | 0.32 | 1.03 | 1.97 | 0.38 | 0.21 | 0.35 | 0.21 | −0.19 | 0.44 | 0.65 |
| miR_2121 | 0.17 | 0.01 | 0.05 | −0.20 | −0.12 | 0.25 | −0.15 | −0.11 | 0.11 | −0.58 | 0.15 |
| miR_2122 | 0.14 | −0.06 | 0.02 | 0.23 | −0.72 | −0.18 | 0.01 | −0.03 | −0.30 | 1.47 | 0.31 |
| miR_2123 | −0.16 | −0.48 | 0.39 | −0.58 | −1.16 | 0.51 | 0.44 | −0.27 | 0.85 | 0.53 | 0.03 |
| miR_2125 | 0.20 | −0.31 | 0.38 | −0.73 | −0.12 | 0.35 | 0.53 | 0.08 | 0.17 | 0.60 | 0.36 |
| miR_2126 | 0.29 | 0.00 | 0.37 | −0.01 | 0.08 | 0.16 | 0.23 | −0.19 | 0.20 | 0.06 | 0.28 |
| miR_2127 | 0.32 | −0.19 | 0.55 | 0.22 | −0.17 | −0.03 | 0.34 | −0.09 | −0.27 | 0.61 | 0.25 |
| miR_2128 | 0.25 | 0.29 | 0.90 | 0.26 | −0.05 | 0.60 | 0.63 | −0.34 | −0.31 | 0.95 | 0.28 |
| miR_2129 | 0.24 | −0.16 | 0.65 | 0.26 | 0.31 | 0.62 | 0.65 | 0.16 | −0.41 | 0.63 | 0.38 |
| miR_2130 | 0.26 | −0.75 | 0.40 | 0.89 | −0.55 | 0.00 | 0.16 | −0.58 | −0.09 | 0.43 | 0.09 |
| miR_2131 | −0.06 | 0.03 | 0.35 | −0.03 | −0.09 | 0.02 | 0.22 | −0.41 | −0.19 | 0.11 | −0.03 |
| miR_2132 | 0.25 | 0.09 | 0.32 | 0.14 | 0.06 | 0.44 | 0.42 | 0.17 | 0.06 | 0.24 | 0.36 |
| miR_2134 | −0.02 | −0.25 | 0.95 | 0.62 | 0.49 | 1.86 | 1.07 | 1.24 | −0.20 | −0.08 | 0.19 |
| miR_2135 | −0.09 | −0.10 | 0.04 | 0.31 | 0.03 | −0.03 | 0.02 | 0.06 | −0.38 | 0.38 | 0.01 |
| miR_2136 | −0.21 | −0.61 | −0.06 | −0.98 | −0.11 | −0.30 | 0.76 | 0.12 | −0.17 | 0.19 | −0.52 |
| miR_2137-miR_2444-miR_2445-miR_2447-320 | −0.61 | −0.45 | −1.08 | −1.21 | −1.54 | −0.98 | −0.78 | −1.07 | 0.60 | −2.70 | −2.98 |
| miR_2138 | 0.03 | 0.05 | −0.36 | 0.89 | 0.37 | −0.15 | −0.03 | 0.59 | −0.30 | 0.43 | −0.49 |
| miR_2139 | −0.29 | −0.24 | 0.31 | −0.29 | −0.30 | 0.47 | 0.76 | 0.05 | 0.02 | 0.90 | −0.16 |
| miR_2140 | −0.13 | −0.67 | 0.93 | 0.29 | −0.03 | 0.90 | 0.72 | 0.12 | −0.39 | 0.68 | 0.37 |
| miR_2141 | 0.13 | 0.06 | 0.24 | 0.06 | −0.03 | 0.26 | −0.03 | −0.02 | 0.09 | −0.18 | 0.25 |
| miR_2142 | −0.10 | −0.72 | −0.70 | −2.07 | −1.49 | 0.16 | 0.44 | −0.54 | 0.02 | 0.73 | 0.04 |
| miR_2143 | −0.16 | −0.06 | −0.23 | −0.38 | −0.23 | 0.07 | −0.31 | −0.20 | −0.11 | −0.79 | −0.19 |
| miR_2144 | 0.16 | −0.40 | 0.79 | −4.91 | −0.22 | −0.03 | 1.28 | 0.48 | −0.58 | 1.11 | 0.45 |
| miR_2145 | −0.11 | −0.07 | −0.13 | −0.27 | −0.05 | 0.11 | −0.29 | −0.12 | −0.07 | −0.62 | −0.13 |
| miR_2146 | 0.09 | −0.33 | 0.61 | −0.24 | −0.12 | 0.15 | 0.77 | −0.43 | −0.10 | 0.78 | 0.46 |
| miR_2147 | 0.25 | 0.41 | 0.52 | 0.47 | 0.21 | 0.13 | 0.06 | −0.11 | 0.21 | 0.14 | 0.22 |
| miR_2148 | −0.14 | 0.25 | 0.56 | 0.15 | 0.15 | 0.60 | 0.37 | 0.11 | −0.18 | 0.42 | −0.06 |
| miR_2149 | 0.08 | −0.63 | 0.86 | −0.93 | 0.09 | 1.17 | 1.17 | 0.58 | 0.47 | 0.34 | 0.45 |
| miR_2150 | 0.50 | 0.24 | −0.26 | 0.06 | 0.11 | −0.36 | 0.11 | 0.21 | 0.32 | 0.66 | −0.75 |
| miR_2151 | 0.10 | 0.23 | 0.56 | 0.14 | 0.35 | 0.77 | 0.79 | −0.39 | −0.35 | 0.67 | 0.35 |
| miR_2152 | ND | 0.18 | 0.37 | 0.44 | 0.14 | 0.33 | 0.11 | 0.26 | 0.05 | −0.03 | 0.29 |
| miR_2153-miR_2163 | −0.15 | −0.27 | −0.11 | −0.71 | −0.02 | 0.00 | 0.28 | −0.17 | 0.04 | 0.38 | −0.06 |
| miR_2154 | 0.20 | −0.18 | 0.07 | −0.33 | 0.01 | 0.33 | 0.22 | 0.25 | 0.29 | −0.28 | 0.22 |
| miR_2156 | 0.16 | 0.09 | 0.02 | 0.18 | −0.05 | 0.19 | −0.11 | 0.04 | 0.21 | −0.33 | 0.17 |
| miR_2157 | 0.06 | 1.15 | 0.96 | 2.83 | 3.34 | 1.36 | 0.75 | 0.21 | −0.34 | −0.01 | −0.07 |
| miR_2158 | 0.31 | −0.04 | 0.21 | 0.11 | −0.10 | −0.21 | 0.64 | −0.20 | −1.43 | 0.67 | 0.38 |
| miR_2159 | 0.20 | −0.04 | 0.60 | −0.08 | −0.31 | 0.43 | 0.83 | 0.79 | 0.45 | 0.49 | 0.46 |
| miR_2160 | −0.15 | −0.15 | 0.63 | −1.05 | −0.13 | 0.83 | 1.17 | 0.32 | −0.53 | 1.19 | 0.20 |
| miR_2161 | 0.04 | 0.81 | 0.69 | 0.27 | 0.12 | 0.56 | 0.51 | 0.49 | −0.12 | 0.33 | 0.22 |
| miR_2162 | −0.08 | 0.06 | 0.29 | 0.22 | −0.63 | −0.06 | 0.61 | 0.39 | −0.52 | −0.22 | −0.12 |
| miR_2164 | 0.16 | −0.47 | −0.81 | −1.97 | −1.24 | −0.17 | 0.30 | −0.42 | −0.11 | −0.37 | 0.46 |
| miR_2165 | 0.26 | 0.58 | 0.88 | 1.07 | 1.01 | 0.77 | 0.29 | 0.11 | −0.09 | 0.33 | 0.24 |
| miR_2166 | −0.01 | −0.53 | −0.03 | −0.29 | −0.79 | −0.60 | 0.17 | 0.28 | 0.03 | 0.54 | 0.24 |
| miR_2167 | 0.31 | 0.18 | 0.76 | 1.31 | −0.04 | −0.52 | −0.68 | −1.01 | −0.61 | 0.62 | 0.47 |
| miR_2168 | 0.27 | −0.35 | −0.70 | −0.07 | −0.42 | −0.87 | −0.36 | 0.10 | 0.27 | 1.00 | −0.80 |
| miR_2169 | −0.43 | 0.68 | −0.97 | 0.27 | 0.48 | 0.37 | 0.72 | −0.41 | −0.47 | −6.86 | −0.96 |
| miR_2170 | 0.02 | −0.13 | 0.57 | 0.33 | 0.52 | 0.55 | 0.59 | 0.03 | −0.16 | 0.39 | 0.30 |
| miR_2171 | −0.22 | −0.76 | 0.13 | −0.80 | −0.97 | −1.01 | 0.43 | 0.63 | 0.76 | 1.20 | −0.42 |
| miR_2364 | 0.19 | 0.08 | −0.19 | 0.00 | −0.13 | 0.00 | 0.03 | 0.03 | 0.20 | −0.45 | −0.03 |
| miR_2365-miR_2408-miR_2419 | 0.38 | −0.10 | −0.42 | −0.07 | 0.21 | 0.04 | −0.50 | −0.15 | 0.38 | 0.44 | 0.21 |
| miR_2366 | 0.27 | −0.34 | −0.94 | −0.09 | 0.51 | −1.62 | −0.88 | −0.26 | −0.37 | 0.20 | −3.70 |
| miR_2370-miR_2391 | 0.22 | −0.07 | 0.18 | 0.38 | −0.06 | 0.13 | −0.10 | −0.12 | 0.15 | −0.28 | 0.32 |
| miR_2371 | −0.26 | 0.01 | 0.15 | −0.01 | −0.03 | 0.23 | −0.07 | 0.09 | −0.30 | −0.48 | −0.09 |
| miR_2372-miR_2373-miR_2404 | 0.03 | −0.09 | −0.16 | 0.14 | −0.50 | −0.58 | 0.23 | −0.05 | −0.84 | −0.53 | −0.31 |
| miR_2374-miR_2375-miR_2376-miR_2377 | 0.24 | −1.30 | −1.53 | −0.75 | −1.80 | −1.22 | −2.34 | −3.17 | −1.06 | 0.23 | −0.83 |

TABLE 6-continued table ratios_454miRs: Contains ratio data generated on tumor versus normal adjacent tissues from a variety of tissues.

| | | | | | | | | | | | |
|---|---|---|---|---|---|---|---|---|---|---|---|
| miR_2374-<br>miR_2375-<br>miR_2376-<br>miR_2377-<br>miR_2416-<br>miR_2417 | 0.17 | −0.22 | −0.36 | 0.67 | −0.86 | −0.83 | −1.98 | −1.46 | −1.28 | 0.01 | −0.90 |
| miR_2378-<br>miR_2418 | 0.41 | −0.16 | 0.04 | 0.30 | 0.91 | 0.04 | 0.58 | 0.15 | 1.32 | 0.65 | 0.84 |
| miR_2379 | 0.24 | 0.20 | 0.81 | 0.28 | 0.56 | 1.24 | 0.78 | 0.49 | −0.43 | 1.01 | 0.70 |
| miR_2380 | −0.04 | 0.15 | −0.34 | −0.28 | 0.27 | 0.19 | −0.45 | −0.20 | −0.99 | 0.18 | 0.40 |
| miR_2381 | −0.19 | 0.23 | 0.49 | 1.39 | −0.70 | 0.16 | 0.13 | 0.47 | 2.03 | 1.20 | 0.95 |
| miR_2383 | 1.78 | −2.42 | −1.94 | −0.72 | −2.68 | −1.41 | −1.09 | −1.68 | −0.16 | 0.91 | 0.27 |
| miR_2385-<br>miR_2386-<br>miR_2423-<br>miR_2433 | 0.15 | −0.40 | −0.31 | 0.55 | −0.82 | −0.69 | −2.47 | 0.29 | −0.04 | 0.03 | −1.25 |
| miR_2387 | 0.28 | −0.05 | −0.20 | −0.10 | −1.06 | −0.12 | −0.24 | 0.42 | 0.21 | 0.06 | −0.55 |
| miR_2388 | 0.04 | 0.23 | 0.72 | 0.64 | 1.03 | 0.05 | 0.82 | −0.74 | −0.86 | 0.96 | 0.36 |
| miR_2389 | 0.11 | −0.07 | −0.14 | −0.13 | −0.16 | −0.05 | −0.53 | −0.22 | 0.21 | −0.56 | 0.01 |
| miR_2390 | 0.02 | −0.10 | −0.12 | −1.20 | −0.75 | −0.25 | 0.29 | 0.06 | 0.11 | −0.26 | −0.07 |
| miR_2392 | 0.14 | −0.58 | 0.10 | −0.25 | −0.18 | −0.02 | 0.18 | −1.16 | 0.72 | −0.02 | −0.22 |
| miR_2393 | 0.30 | −0.11 | 0.20 | 0.05 | 0.50 | 0.26 | 0.73 | −0.16 | 1.12 | 0.37 | 0.57 |
| miR_2394-<br>miR_2395 | 0.05 | −0.74 | −0.84 | −1.32 | −0.60 | −0.09 | 0.48 | −0.62 | 0.77 | 0.64 | 1.12 |
| miR_2396-<br>miR_2397-<br>miR_2398 | 0.06 | 1.69 | 0.66 | 1.25 | 1.60 | 0.85 | −0.81 | 0.52 | −0.87 | −1.17 | 0.56 |
| miR_2399 | 0.25 | 1.10 | 0.60 | 1.67 | 1.72 | 0.48 | −0.92 | 0.70 | −0.32 | −0.46 | 0.13 |
| miR_2400-<br>miR_2401-<br>miR_2402 | 0.46 | 0.99 | 0.32 | 1.27 | 2.04 | 0.21 | −1.09 | 0.49 | −0.85 | −0.53 | 0.66 |
| miR_2403 | 0.04 | 0.43 | 0.63 | 0.26 | 0.67 | 0.87 | 0.38 | −0.23 | −0.18 | 0.26 | 0.21 |
| miR_2405 | 0.30 | 0.88 | 0.34 | 1.53 | 1.91 | 0.07 | −1.13 | 0.42 | −0.75 | −0.91 | 0.62 |
| miR_2406 | 0.22 | 0.02 | −1.35 | 0.86 | 0.26 | −1.46 | −0.99 | −0.03 | −0.01 | −0.19 | −0.11 |
| miR_2407 | 0.14 | ND | 0.01 | −0.08 | −0.09 | 0.16 | −0.10 | −0.03 | 0.14 | −0.07 | 0.25 |
| miR_2409-<br>miR_2410-<br>miR_2411-<br>miR_2412 | 0.20 | 0.11 | −0.07 | 0.15 | −0.35 | −0.23 | −0.12 | 0.38 | 0.30 | 0.03 | 0.01 |
| miR_2413-<br>miR_2414-<br>miR_2415-<br>miR_2439-<br>miR_2440 | 0.24 | −0.37 | 0.33 | −0.34 | −0.77 | 0.17 | −1.00 | −1.80 | −1.44 | −0.25 | −0.82 |
| miR_2422 | 0.29 | −0.03 | −0.03 | −0.13 | −0.43 | 0.19 | 0.25 | 0.30 | 0.30 | −0.58 | 0.27 |
| miR_2424-<br>miR_2425 | −0.14 | −0.36 | 0.26 | −0.78 | −0.51 | 0.46 | 0.80 | 0.15 | −0.38 | 0.61 | 0.20 |
| miR_2426 | −0.10 | −0.06 | −0.07 | −0.17 | −0.02 | 0.02 | −0.22 | −0.10 | −0.13 | −0.58 | −0.09 |
| miR_2428 | 0.03 | −0.12 | −0.02 | 0.32 | 0.07 | 0.05 | −0.09 | 0.20 | 0.06 | −0.01 | 0.11 |
| miR_2429 | 0.11 | −0.40 | −0.56 | −0.51 | −0.45 | −0.76 | −0.05 | −0.26 | 0.01 | 0.26 | 0.07 |
| miR_2432-<br>miR_2433 | −0.07 | −0.52 | −0.47 | 0.28 | −0.89 | −0.71 | −1.81 | 0.26 | −0.07 | −0.41 | −1.28 |
| miR_2435-<br>miR_2436 | 0.06 | −0.56 | −0.49 | 0.96 | 0.46 | 0.01 | 0.22 | 0.28 | −0.21 | 0.27 | −0.73 |
| miR_2442 | −0.50 | −0.75 | −0.97 | −1.22 | −1.64 | −0.81 | −0.68 | −0.12 | 0.56 | −1.56 | −2.52 |
| miR_2446 | 0.15 | −0.10 | −0.42 | 0.32 | −0.16 | −0.61 | 0.26 | 0.45 | 0.59 | 0.73 | −1.31 |

TABLE 7 ratios_454premiRs: Contains ratio data generated on tumor versus normal adjacent tissues from a variety of tissues.

| | Tissue | | | | | | | | | | | |
|---|---|---|---|---|---|---|---|---|---|---|---|---|
| | Adrenal gland | | Bladder | | | | Colon | | Cervix | Duodenum | | Esophagus |
| MiR name | T/N-30 | T/N-30 | T/N-34 | T/N-46 | T/N-74 | T/N-ambion | T/N-47 | T/N-47 | T/N-ambion | T/N-79 | T/N-79 | T/N-ambion |
| premiR_09110 | ND | 0.15 | −0.11 | −0.10 | 0.18 | 0.02 | −0.05 | −0.05 | −0.08 | −0.06 | 0.09 | 0.22 |
| premiR_09111 | 0.10 | −0.22 | −0.11 | ND | −0.26 | −0.22 | 0.06 | −0.26 | −0.10 | −0.03 | −0.17 | −0.01 |
| premiR_09113 | −0.65 | −1.00 | ND | −0.22 | −0.87 | −0.24 | −0.57 | −0.76 | 0.17 | −0.72 | −0.72 | 0.18 |
| premiR_09114 | −0.37 | −0.38 | 0.58 | 0.22 | 0.17 | −0.08 | −0.25 | −0.32 | −0.09 | −0.26 | −0.56 | −0.24 |

TABLE 7-continued ratios_454premiRs: Contains ratio data generated on tumor versus normal adjacent tissues from a variety of tissues.

| | | | | | | | | | | | | |
|---|---|---|---|---|---|---|---|---|---|---|---|---|
| premiR_09115 | −0.32 | −0.22 | 0.54 | 0.26 | −0.71 | 0.08 | −0.86 | −0.53 | 0.30 | −0.70 | −0.37 | 0.53 |
| premiR_09116 | −0.21 | −0.25 | 0.38 | 0.05 | −0.50 | 0.01 | −0.48 | −0.42 | 0.33 | −1.48 | −1.58 | 0.19 |
| premiR_09118 | −0.82 | −0.53 | 0.10 | −0.26 | −1.09 | −0.12 | −0.36 | 0.12 | 0.97 | 0.07 | 0.35 | 0.78 |
| premiR_09128 | 2.02 | 1.40 | 1.35 | 1.06 | 1.44 | −0.27 | 0.61 | ND | 0.17 | 1.07 | 0.95 | 0.43 |
| premiR_09129 | 0.15 | −0.24 | ND | −0.07 | −0.60 | 0.32 | 0.19 | −0.09 | 0.03 | 0.00 | −0.10 | 0.07 |
| premiR_09131 | 0.09 | −0.13 | −0.11 | −0.08 | 0.04 | −0.23 | 0.10 | −0.34 | −0.22 | −0.01 | −0.19 | −0.13 |
| premiR_09135 | 0.14 | −0.26 | 0.04 | ND | −0.10 | −0.27 | −0.21 | −0.42 | −0.24 | −0.03 | −0.27 | −0.12 |
| premiR_09136 | 0.08 | 0.04 | −0.07 | ND | 0.07 | −0.10 | 0.11 | ND | −0.08 | ND | −0.12 | −0.09 |
| premiR_09138 | −0.29 | −0.41 | 0.05 | −0.17 | −0.69 | −0.03 | 0.33 | 0.21 | 0.13 | 0.52 | 0.48 | −0.04 |
| premiR_09141 | 1.02 | 1.15 | −0.41 | −0.56 | 0.51 | 0.16 | −0.81 | −1.53 | −0.17 | 0.46 | 0.34 | −0.39 |
| premiR_09143 | −0.05 | 0.21 | 0.09 | 0.08 | 0.07 | 0.20 | −0.09 | 0.16 | 0.24 | −0.14 | 0.04 | 0.25 |
| premiR_09144 | −0.38 | −0.79 | 0.31 | −0.13 | −0.67 | −0.08 | −0.20 | ND | 0.36 | −0.18 | −0.22 | 0.39 |
| premiR_09145 | ND | −0.08 | ND | ND | −0.07 | −0.34 | ND | −0.41 | −0.17 | ND | 0.00 | −0.14 |
| premiR_09148 | 0.06 | 0.14 | −0.05 | −0.02 | −0.10 | 0.12 | 0.03 | 0.00 | 0.01 | −0.04 | ND | 0.19 |
| premiR_09150 | −0.22 | −0.14 | 0.19 | −0.11 | −0.80 | −0.09 | −0.01 | −0.16 | −0.09 | −0.19 | −0.06 | 0.00 |
| premiR_09151-<br>premiR_09152-<br>premiR_09317-<br>premiR_09318-<br>premiR_09319-<br>premiR_09335-<br>premiR_09805 | −0.03 | −0.12 | −0.06 | ND | −0.01 | −0.04 | 0.02 | ND | −0.09 | ND | −0.12 | 0.02 |
| premiR_09154 | 0.11 | −0.14 | −0.08 | −0.14 | 0.32 | −0.16 | 0.04 | ND | −0.13 | ND | −0.23 | −0.04 |
| premiR_09156 | −0.28 | −0.48 | 0.24 | 0.13 | −0.57 | −0.22 | −0.18 | −0.01 | 0.22 | −0.52 | −0.57 | −0.07 |
| premiR_09157 | 0.02 | −0.20 | 0.00 | −0.15 | −0.73 | −0.14 | 0.07 | −0.18 | −0.18 | −0.01 | −0.16 | −0.08 |
| premiR_09161 | −0.75 | −0.29 | 0.84 | 1.66 | −0.71 | −1.18 | −0.26 | −0.24 | 0.02 | −0.02 | −0.01 | −0.42 |
| premiR_09163 | 0.11 | 0.26 | ND | −0.16 | −0.17 | −0.33 | −0.49 | −0.42 | −0.07 | −0.87 | −0.48 | −0.22 |
| premiR_09164 | 0.00 | 0.06 | −0.12 | −0.12 | −0.25 | 0.05 | 0.02 | −0.03 | 0.03 | 0.03 | 0.04 | 0.09 |
| premiR_09165 | −0.15 | −0.44 | 0.70 | −0.53 | −1.05 | −0.01 | 0.54 | 0.46 | 0.25 | −0.78 | −1.00 | 0.43 |
| premiR_09167 | 0.32 | 0.21 | 0.69 | −0.83 | −0.82 | 0.25 | −0.22 | −0.08 | 0.36 | −0.77 | −0.56 | 0.22 |
| premiR_09169-<br>premiR_09170-<br>premiR_09407 | −1.47 | −1.80 | 0.30 | −0.38 | −0.57 | 0.33 | 0.04 | 0.10 | 0.26 | −2.35 | −4.64 | −0.23 |
| premiR_09176 | −0.37 | −0.24 | 0.21 | −0.12 | 0.67 | 0.23 | 0.26 | 0.21 | −0.01 | 0.11 | 0.09 | −0.04 |
| premiR_09177 | 0.94 | 1.41 | 0.07 | 0.00 | 3.84 | −0.52 | 0.02 | 0.50 | 0.23 | 1.00 | 0.94 | 0.25 |
| premiR_09179 | 0.62 | 0.26 | 0.06 | 0.84 | −0.62 | 0.05 | 0.13 | ND | 0.27 | 0.13 | 0.18 | 0.24 |
| premiR_09180 | ND | −0.23 | −0.17 | ND | 0.13 | −0.33 | 0.09 | −0.44 | −0.31 | ND | −0.18 | −0.24 |
| premiR_09182 | −0.69 | −0.89 | 0.91 | −1.27 | −0.96 | 0.19 | 0.61 | 0.22 | 0.35 | −1.00 | −0.56 | 0.21 |
| premiR_09188-<br>premiR_09338-<br>premiR_09818 | −0.62 | −0.47 | 0.58 | 0.46 | 1.56 | −0.24 | −0.72 | −0.33 | −0.14 | −0.25 | −0.14 | 0.55 |
| premiR_09190 | −0.14 | 0.13 | −0.33 | 0.23 | −0.05 | 0.28 | −0.07 | 0.33 | 0.36 | 0.36 | 0.55 | 0.30 |
| premiR_09191 | 0.30 | 0.20 | 0.36 | 0.47 | 0.97 | −0.76 | −1.25 | −1.14 | 0.28 | −0.36 | −0.22 | 0.20 |
| premiR_09192 | 0.15 | 0.11 | −0.40 | −0.10 | 0.76 | 0.33 | 0.23 | ND | 0.24 | 0.70 | 0.58 | −0.37 |
| premiR_09194 | 0.11 | 0.03 | −0.09 | −0.05 | −0.06 | 0.09 | −0.01 | −0.15 | −0.01 | −0.01 | 0.11 | 0.15 |
| premiR_09195 | −0.64 | −0.05 | −0.31 | −0.18 | −0.79 | −1.90 | −0.10 | −0.13 | −0.24 | 0.30 | 0.28 | −0.03 |
| premiR_09197 | −0.99 | −0.80 | 0.47 | 1.15 | −0.75 | −0.13 | −1.77 | −0.69 | −0.08 | −0.22 | −0.40 | 0.46 |
| premiR_09198 | −0.66 | −1.13 | 0.82 | 0.32 | −0.46 | 0.24 | 0.34 | 0.63 | 0.40 | −0.25 | −1.21 | 0.42 |
| premiR_09201 | −0.28 | −0.25 | −0.94 | −1.36 | −0.06 | 0.55 | −0.17 | 0.36 | 0.82 | 0.14 | 0.29 | 0.87 |
| premiR_09206 | −0.18 | 0.31 | 0.86 | 0.24 | −0.70 | −0.44 | −0.01 | 0.21 | 0.39 | −0.13 | 0.26 | −0.21 |
| premiR_09208-<br>premiR_09398-<br>premiR_09404 | −0.78 | −0.52 | 0.10 | −0.05 | −0.96 | −0.37 | −0.98 | −0.89 | 0.92 | 0.40 | 0.45 | 0.94 |
| premiR_09210 | ND | −0.06 | −0.08 | 0.00 | −0.08 | −0.01 | −0.01 | −0.22 | −0.19 | ND | 0.02 | 0.05 |
| premiR_09211 | 0.25 | −0.02 | −0.20 | −0.07 | 0.23 | −0.15 | 0.08 | −0.33 | −0.19 | −0.01 | −0.07 | 0.00 |
| premiR_09212 | −0.22 | −0.49 | 0.17 | −0.27 | −0.87 | −0.14 | 0.31 | ND | −0.23 | 0.32 | 0.38 | −0.27 |
| premiR_09213 | −1.10 | −1.53 | 0.09 | −0.27 | −0.20 | 0.63 | −0.28 | 0.42 | 0.89 | 0.55 | −0.41 | 0.18 |
| premiR_09220 | −0.87 | −0.83 | 0.14 | 0.15 | −1.18 | 0.16 | −0.18 | ND | 0.21 | −0.78 | −0.68 | 0.22 |
| premiR_09222 | 0.09 | −0.02 | 0.00 | −0.42 | 0.39 | 0.27 | 0.14 | 0.03 | 0.08 | −0.30 | −0.19 | 0.08 |
| premiR_09223 | 0.01 | 0.05 | 0.05 | ND | −0.06 | 0.08 | −0.46 | −0.18 | 0.12 | −0.28 | −0.30 | 0.06 |
| premiR_09224 | −0.15 | 0.06 | −0.21 | −0.31 | −0.37 | 0.10 | 0.35 | ND | 0.10 | ND | −0.05 | 0.19 |
| premiR_09225 | −0.04 | 0.22 | −0.05 | −0.01 | −0.59 | 0.24 | −0.58 | 0.02 | 0.19 | −0.09 | 0.19 | 0.22 |
| premiR_09226 | −0.38 | −0.02 | 1.15 | 1.22 | −0.92 | −1.61 | −0.03 | −0.01 | 0.28 | −0.20 | −0.05 | −1.12 |
| premiR_09227 | 0.47 | −0.05 | 0.22 | 0.17 | −0.59 | −0.18 | −0.16 | −0.37 | 0.06 | −0.44 | −0.53 | 0.16 |
| premiR_09229 | −0.75 | −0.81 | 0.52 | 0.08 | −1.37 | −0.25 | −0.05 | 0.20 | 0.32 | −0.22 | 0.03 | −0.07 |
| premiR_09236 | 0.18 | 0.18 | −0.43 | −0.31 | −0.27 | 0.08 | 0.51 | ND | −0.04 | 0.60 | 0.21 | −0.04 |
| premiR_09240 | 0.86 | 0.62 | 0.35 | 0.19 | 0.24 | −0.03 | −0.54 | ND | −0.20 | −1.76 | −1.15 | −0.20 |
| premiR_09242 | −1.02 | −1.31 | 0.15 | 0.02 | −0.42 | 0.42 | −0.47 | 0.31 | 0.43 | 0.33 | −0.53 | 0.06 |
| premiR_09244-<br>premiR_09245-<br>premiR_09273 | 1.00 | 1.10 | −0.15 | 0.66 | ND | −0.33 | −0.45 | −1.30 | 0.01 | 0.05 | 0.68 | −0.08 |
| premiR_09245-<br>premiR_09273 | 1.26 | 0.69 | 0.27 | −0.95 | 0.80 | 0.59 | −1.10 | −1.40 | −0.14 | −0.57 | −0.71 | −0.21 |
| premiR_09246 | 0.06 | 0.00 | 0.18 | 0.37 | −0.42 | −0.71 | −0.12 | ND | 0.25 | 0.36 | 0.40 | 0.42 |
| premiR_09247 | 0.27 | −0.06 | −0.15 | −0.02 | 0.67 | −0.27 | 0.17 | −0.04 | −0.28 | 0.21 | 0.08 | −0.45 |
| premiR_09248 | −0.02 | 0.03 | −0.07 | 0.00 | 0.12 | −0.01 | 0.02 | −0.17 | −0.15 | ND | 0.02 | 0.06 |
| premiR_09249 | 0.25 | −0.28 | −0.10 | −0.05 | 0.15 | −0.33 | 0.18 | −0.33 | −0.29 | 0.02 | −0.26 | −0.17 |

TABLE 7-continued ratios_454premiRs: Contains ratio data generated on tumor versus normal adjacent tissues from a variety of tissues.

| | | | | | | | | | | | | |
|---|---|---|---|---|---|---|---|---|---|---|---|---|
| premiR_09250 | 0.30 | 0.30 | 1.01 | 1.06 | 1.26 | −0.53 | −0.75 | ND | 0.15 | −2.37 | −2.27 | 0.43 |
| premiR_09251 | −0.99 | −0.65 | ND | −0.59 | −1.56 | 0.06 | 0.25 | 0.16 | −0.02 | 0.17 | 0.17 | 0.01 |
| premiR_09252 | −0.38 | −0.23 | 0.19 | 0.20 | −1.00 | 0.11 | 0.67 | 0.63 | 0.35 | 0.03 | 0.43 | 0.32 |
| premiR_09255-premiR_09399-premiR_09904 | 0.23 | 0.38 | 0.06 | −0.13 | −0.27 | −0.03 | 0.11 | ND | −0.18 | −0.03 | −0.04 | −0.03 |
| premiR_09257 | −0.22 | 0.57 | −0.08 | ND | −0.13 | 0.47 | −0.02 | 0.42 | 0.46 | ND | 0.37 | 0.48 |
| premiR_09258 | 0.07 | 0.01 | 0.03 | −0.07 | 0.06 | 0.19 | 0.04 | −0.09 | −0.04 | ND | −0.02 | 0.09 |
| premiR_09262-premiR_09263 | 0.13 | 0.13 | 0.12 | −0.29 | 0.32 | 0.08 | −0.84 | ND | 0.02 | 0.93 | 0.77 | −0.16 |
| premiR_09264 | −0.32 | −0.39 | 0.55 | 0.21 | −0.99 | −0.15 | −0.12 | −0.05 | 0.19 | 0.03 | −0.02 | 0.14 |
| premiR_09266 | −0.31 | −0.33 | 0.00 | 0.82 | −0.71 | −0.12 | −0.42 | −0.28 | 0.12 | 0.22 | 0.30 | −0.64 |
| premiR_09268 | 0.03 | −0.45 | 0.92 | −1.37 | −0.72 | 0.04 | 0.88 | 0.67 | 0.48 | −0.59 | −0.30 | 0.72 |
| premiR_09270 | −0.30 | −0.73 | 0.60 | 0.76 | −0.14 | −0.13 | −0.17 | −0.34 | −0.12 | 0.48 | −0.11 | −0.33 |
| premiR_09272 | 1.06 | 1.13 | ND | 0.39 | 1.78 | −0.76 | 0.08 | −0.79 | 0.06 | 1.75 | 1.26 | −0.05 |
| premiR_09277 | −0.04 | −0.23 | 0.05 | −0.02 | −0.45 | −0.19 | 0.07 | −0.22 | −0.22 | −0.13 | −0.14 | −0.07 |
| premiR_09278 | −0.06 | 0.18 | 0.02 | 0.00 | −0.14 | 0.26 | −0.08 | 0.14 | 0.26 | −0.08 | 0.23 | 0.17 |
| premiR_09280 | −0.97 | −1.40 | ND | −0.50 | −0.94 | 0.16 | 0.02 | 0.65 | 0.36 | −0.57 | −0.41 | 0.32 |
| premiR_09281 | 0.02 | 0.12 | −0.07 | −0.02 | −0.34 | 0.17 | −0.03 | 0.03 | 0.05 | ND | ND | 0.27 |
| premiR_09283 | 0.20 | 0.00 | −0.18 | −0.20 | −0.01 | −0.04 | 0.35 | ND | −0.16 | ND | −0.09 | −0.02 |
| premiR_09284 | −0.56 | −1.07 | 0.14 | −0.46 | −0.94 | 0.22 | 0.35 | 0.41 | 0.19 | −0.17 | −0.30 | −0.07 |
| premiR_09285 | 0.06 | 0.25 | −0.11 | −0.07 | 0.03 | 0.26 | 0.07 | 0.06 | 0.15 | ND | 0.23 | 0.35 |
| premiR_09286 | −0.46 | −0.46 | 0.14 | 0.52 | −0.91 | 0.03 | −0.71 | −0.88 | −0.09 | −1.17 | −0.87 | 0.04 |
| premiR_09287 | 0.01 | 0.06 | 0.17 | −0.01 | −0.46 | 0.08 | −0.39 | ND | 0.03 | −0.12 | 0.01 | 0.10 |
| premiR_09289 | 0.07 | 0.35 | 0.16 | 0.11 | −0.51 | 0.23 | 0.01 | 0.30 | 0.29 | 0.00 | 0.25 | 0.21 |
| premiR_09291 | 0.00 | 0.00 | −0.10 | −0.14 | 0.05 | 0.01 | 0.04 | ND | −0.03 | −0.15 | −0.10 | −0.02 |
| premiR_09292 | 0.11 | −0.19 | −0.07 | −1.46 | −1.19 | 0.45 | −0.06 | 0.01 | 0.42 | −0.50 | −0.39 | 0.48 |
| premiR_09293 | −1.52 | −1.86 | 0.22 | 0.10 | −1.20 | −0.13 | 0.30 | 0.11 | 0.15 | −0.85 | −0.25 | −0.07 |
| premiR_09294 | 0.14 | −0.27 | −0.13 | −0.10 | 0.24 | −0.24 | 0.15 | −0.27 | −0.21 | −0.04 | −0.29 | −0.20 |
| premiR_09297 | −0.35 | −0.49 | −0.05 | 0.16 | 0.22 | −0.53 | 0.87 | 0.77 | −0.18 | 1.21 | 0.98 | −0.07 |
| premiR_09300 | −0.04 | −0.09 | 0.11 | 0.65 | 0.49 | −0.45 | −0.66 | −0.64 | 0.50 | −0.41 | −0.24 | 0.96 |
| premiR_09302 | −0.30 | −0.06 | 0.10 | 0.30 | −0.63 | 0.08 | −0.22 | 0.08 | 0.12 | −0.23 | 0.11 | 0.49 |
| premiR_09303 | −0.15 | −0.17 | 0.00 | 0.02 | −0.85 | −0.02 | −0.21 | ND | −0.13 | −0.36 | −0.37 | 0.00 |
| premiR_09304 | 0.45 | −0.15 | ND | 0.56 | −0.34 | −0.18 | −0.56 | −0.47 | 0.17 | −0.38 | −0.69 | 0.01 |
| premiR_09305 | 0.02 | −0.05 | −0.07 | −0.04 | −0.08 | 0.00 | 0.10 | −0.16 | 0.05 | −0.05 | −0.06 | 0.06 |
| premiR_09307 | ND | −0.10 | −0.07 | ND | −0.15 | −0.07 | 0.08 | ND | −0.11 | ND | −0.12 | −0.03 |
| premiR_09308 | 1.12 | 0.86 | −0.61 | 0.15 | 1.09 | 0.03 | 1.11 | 0.96 | −0.16 | 1.53 | 1.23 | 0.02 |
| premiR_09310 | 1.14 | 1.01 | −1.17 | 1.00 | 2.23 | −1.06 | 0.18 | −0.17 | −4.43 | 1.43 | 1.09 | −0.32 |
| premiR_09311 | −0.71 | −0.63 | 0.47 | 1.23 | −0.75 | −0.15 | −1.87 | ND | −0.08 | 0.12 | 0.05 | 0.56 |
| premiR_09313 | 0.05 | 0.18 | −0.11 | −0.02 | −0.53 | 0.19 | 0.12 | −0.02 | 0.10 | −0.07 | 0.18 | 0.29 |
| premiR_09314-premiR_09391 | −0.79 | −0.28 | −0.50 | −0.42 | −0.60 | −0.52 | 0.37 | 0.30 | −1.92 | 0.12 | 0.37 | 0.04 |
| premiR_09315-premiR_09390 | 0.01 | 0.54 | 0.05 | −0.10 | 0.44 | −0.11 | 0.11 | 0.48 | −1.03 | 0.31 | 0.39 | 0.65 |
| premiR_09320-premiR_09342 | 0.24 | −0.45 | 0.18 | 0.56 | −0.19 | −0.38 | −0.83 | −0.67 | −0.12 | −1.04 | −1.20 | 0.00 |
| premiR_09322-premiR_09323-premiR_09368 | 0.12 | −0.08 | 0.15 | 0.30 | −0.16 | −0.11 | −0.33 | −0.23 | 0.15 | −0.71 | −0.71 | −0.09 |
| premiR_09328-premiR_09385-premiR_09386-premiR_09387-premiR_09388-premiR_09389 | 1.81 | 1.57 | ND | 1.76 | ND | −0.61 | 1.08 | 0.46 | −4.05 | 0.53 | 0.83 | −0.22 |
| premiR_09328-premiR_09385-premiR_09386-premiR_09387-premiR_09388-premiR_09389 | 0.77 | 0.51 | 0.58 | 1.25 | 0.44 | −0.47 | 0.25 | 0.42 | −1.68 | 0.06 | −0.03 | −0.33 |
| premiR_09329 | 0.08 | 0.22 | −0.06 | −0.02 | −0.31 | 0.22 | −0.53 | 0.03 | 0.09 | −0.09 | 0.16 | 0.32 |
| premiR_09330 | 0.46 | 0.49 | 0.98 | 1.10 | 5.39 | −0.79 | −0.24 | −0.07 | −1.16 | −0.07 | −0.04 | 0.51 |
| premiR_09331 | −0.89 | −1.34 | 0.23 | −0.17 | −0.65 | 0.44 | 0.03 | ND | 0.40 | −0.79 | −2.68 | 0.15 |
| premiR_09332-premiR_09913 | −0.78 | −0.44 | 0.29 | −0.52 | −1.47 | 0.17 | −0.24 | −0.10 | 0.01 | −2.68 | −1.74 | 0.09 |
| premiR_09333 | ND | −0.06 | ND | −0.29 | −0.78 | −0.07 | 0.55 | 0.25 | −0.15 | 0.16 | 0.21 | −0.26 |
| premiR_09334 | −1.00 | −1.86 | 0.61 | −0.20 | −0.89 | −0.15 | 0.31 | 0.29 | −0.06 | 0.57 | 0.22 | −0.62 |
| premiR_09339 | 0.00 | −0.34 | 0.08 | 0.26 | −0.43 | −0.19 | −0.15 | −0.38 | −0.16 | −0.50 | −0.43 | −0.02 |
| premiR_09349-premiR_09350 | −0.90 | −0.79 | 0.37 | −1.22 | −0.95 | 0.27 | 0.45 | 0.50 | 0.45 | 0.09 | 0.27 | −0.04 |
| premiR_09351-premiR_09352-premiR_09353-premiR_09354-premiR_09355-premiR_09356- | ND | −0.11 | −0.14 | ND | 0.00 | −0.11 | 0.13 | −0.30 | −0.28 | 0.05 | ND | 0.05 |

TABLE 7-continued ratios_454premiRs: Contains ratio data generated on tumor versus normal adjacent tissues from a variety of tissues.

| | | | | | | | | | | | | |
|---|---|---|---|---|---|---|---|---|---|---|---|---|
| premiR_09357- | | | | | | | | | | | | |
| premiR_09358- | | | | | | | | | | | | |
| premiR_09359- | | | | | | | | | | | | |
| premiR_09360- | | | | | | | | | | | | |
| premiR_09361- | | | | | | | | | | | | |
| premiR_09362 | | | | | | | | | | | | |
| premiR_09363 | −0.22 | −0.10 | 0.23 | 0.41 | −0.52 | −0.08 | −0.44 | −0.41 | 0.40 | −0.46 | −0.41 | 0.02 |
| premiR_09364- | −0.10 | −0.34 | 0.06 | −0.14 | −0.73 | −0.09 | 0.40 | 0.22 | −0.30 | 0.35 | 0.44 | −0.18 |
| premiR_09365- | | | | | | | | | | | | |
| premiR_09366 | | | | | | | | | | | | |
| premiR_09367 | 0.07 | 0.18 | 0.40 | 0.03 | 0.06 | −0.07 | −0.83 | 0.19 | 0.20 | 0.09 | 0.28 | 0.16 |
| premiR_09369- | 1.25 | 1.28 | −0.48 | 0.38 | 1.38 | −0.42 | 0.43 | ND | −0.32 | 0.68 | 0.70 | −0.08 |
| premiR_09370 | | | | | | | | | | | | |
| premiR_09373 | −0.15 | 0.21 | ND | −0.07 | −0.50 | 0.53 | 0.17 | 0.35 | 0.42 | −1.39 | −0.63 | −0.07 |
| premiR_09374 | 0.00 | −0.06 | −0.06 | 0.01 | 0.03 | −0.07 | 0.04 | −0.17 | −0.01 | −0.03 | −0.03 | −0.01 |
| premiR_09375 | −0.20 | 0.04 | −0.34 | −0.28 | −0.20 | −0.42 | 0.22 | 0.18 | −1.32 | 0.51 | −0.04 | 0.00 |
| premiR_09380- | −1.45 | −1.55 | 0.27 | −1.59 | −0.88 | 0.11 | 0.37 | 0.62 | 0.09 | −6.17 | −2.38 | 0.11 |
| premiR_09381- | | | | | | | | | | | | |
| premiR_09382- | | | | | | | | | | | | |
| premiR_09412- | | | | | | | | | | | | |
| premiR_09413 | | | | | | | | | | | | |
| premiR_09392- | 0.10 | 0.01 | 0.01 | 0.04 | −0.30 | −0.01 | −0.03 | −0.08 | 0.04 | −0.08 | −0.12 | 0.12 |
| premiR_09843- | | | | | | | | | | | | |
| premiR_09847 | | | | | | | | | | | | |
| premiR_09393 | −0.52 | −0.26 | 0.17 | 0.16 | −1.42 | −0.16 | −0.42 | ND | 0.30 | −0.64 | −0.36 | 0.36 |
| premiR_09394 | −0.03 | 0.11 | ND | −0.36 | 0.00 | 0.08 | −0.05 | −0.10 | 0.02 | −0.03 | 0.13 | 0.20 |
| premiR_09396- | −0.01 | −0.25 | −0.14 | −0.07 | −0.83 | −0.16 | 0.18 | −0.35 | −0.30 | ND | −0.13 | −0.20 |
| premiR_09397 | | | | | | | | | | | | |
| premiR_09398 | 0.04 | 0.32 | −0.10 | 0.01 | 0.09 | 0.19 | −0.02 | 0.06 | 0.12 | ND | 0.22 | 0.30 |
| premiR_09398- | 0.16 | 0.35 | 0.51 | 0.53 | 0.18 | 0.28 | −1.10 | ND | 0.47 | −0.60 | −0.39 | 0.37 |
| premiR_09404 | | | | | | | | | | | | |
| premiR_09403- | −1.12 | −1.59 | 0.40 | −1.20 | −1.14 | 0.41 | 0.04 | 0.06 | 0.14 | −1.05 | −1.77 | 0.07 |
| premiR_09812 | | | | | | | | | | | | |
| premiR_09405 | 0.08 | 0.18 | −0.13 | −0.02 | −0.03 | 0.06 | 0.06 | −0.09 | 0.03 | −0.11 | 0.07 | 0.19 |
| premiR_09408- | 0.06 | 0.31 | ND | ND | −0.03 | 0.23 | ND | 0.15 | 0.23 | ND | 0.31 | 0.29 |
| premiR_09409 | | | | | | | | | | | | |
| premiR_09410- | 0.08 | −0.27 | −0.05 | −0.08 | −0.08 | −0.27 | −0.08 | −0.35 | −0.31 | −0.09 | −0.40 | −0.16 |
| premiR_09411- | | | | | | | | | | | | |
| premiR_09836 | | | | | | | | | | | | |
| premiR_09414- | −0.10 | −0.18 | 0.85 | 0.14 | −0.60 | −0.34 | 0.10 | −0.22 | −0.10 | −0.01 | −0.11 | −0.35 |
| premiR_09768 | | | | | | | | | | | | |
| premiR_09415 | ND | 0.18 | −0.15 | −0.18 | 0.08 | 0.05 | 0.05 | 0.04 | 0.13 | ND | 0.03 | 0.24 |
| premiR_09417 | 0.10 | −0.17 | −0.11 | 0.05 | 0.07 | −0.14 | 0.07 | −0.22 | 0.04 | −0.14 | −0.11 |
| premiR_09423 | ND | ND | ND | −0.45 | −1.03 | 0.48 | 0.03 | 0.36 | 0.36 | 0.23 | ND | 0.39 |
| premiR_09424 | 0.10 | −0.13 | −0.16 | −0.08 | 0.14 | −0.05 | 0.02 | −0.19 | −0.11 | −0.06 | −0.19 | −0.02 |
| premiR_09748 | −0.21 | −0.07 | 0.43 | 0.62 | 0.36 | −1.23 | −1.82 | −1.31 | 0.62 | −0.75 | −0.24 | 1.68 |
| premiR_09756 | ND | −0.12 | ND | −0.13 | −0.54 | −0.06 | −0.02 | 0.09 | 0.00 | −0.04 | 0.03 | 0.05 |
| premiR_09760- | 0.00 | −0.01 | 0.11 | ND | 0.24 | −0.08 | 0.06 | ND | −0.10 | ND | −0.03 | −0.14 |
| premiR_09886 | | | | | | | | | | | | |
| premiR_09761 | 0.33 | 0.15 | 0.22 | 0.13 | 0.69 | 0.25 | −0.44 | −0.17 | −0.02 | 0.23 | −0.03 | −0.17 |
| premiR_09764 | 0.80 | 0.60 | −0.04 | 0.06 | 0.80 | −0.01 | −0.43 | −0.13 | −0.10 | −0.14 | 0.27 | 0.13 |
| premiR_09766 | −0.18 | 0.20 | 0.09 | −0.10 | −0.51 | 0.37 | −0.12 | 0.18 | 0.33 | −0.35 | −0.06 | 0.32 |
| premiR_09769 | −0.46 | −0.08 | 0.49 | −0.63 | −0.54 | 0.37 | 0.24 | 0.54 | 0.39 | 0.12 | 0.31 | 0.45 |
| premiR_09770 | −0.02 | −0.04 | −0.13 | −0.03 | 0.11 | −0.11 | 0.09 | ND | −0.07 | ND | −0.24 | −0.12 |
| premiR_09771 | −0.05 | 0.19 | −0.04 | −0.09 | −0.02 | 0.24 | 0.28 | 0.13 | 0.16 | ND | 0.16 | 0.29 |
| premiR_09774 | −0.21 | 0.11 | 0.20 | 0.30 | −0.14 | −0.30 | −0.23 | −0.09 | −0.18 | −0.11 | −0.17 | 0.28 |
| premiR_09777 | −0.20 | −0.12 | 0.06 | −0.14 | −0.90 | −0.06 | 0.13 | −0.02 | −0.15 | 0.14 | 0.05 | −0.03 |
| premiR_09779- | −0.15 | −0.12 | 0.96 | −0.66 | −0.95 | 0.08 | 0.29 | 0.27 | −0.08 | −0.89 | −0.50 | 0.32 |
| premiR_09780 | | | | | | | | | | | | |
| premiR_09788 | −0.24 | −0.06 | 0.40 | ND | 0.11 | 0.07 | −0.02 | −0.10 | −0.05 | ND | −0.06 | 0.09 |
| premiR_09789 | −0.46 | −0.82 | 0.43 | −0.06 | −0.63 | −0.05 | 1.71 | 0.97 | 0.26 | −0.04 | 0.21 | −0.13 |
| premiR_09792 | 0.00 | −0.07 | −0.46 | −0.61 | −1.23 | 0.16 | −0.44 | ND | 0.01 | −0.32 | −0.43 | −0.19 |
| premiR_09793 | 0.00 | −0.13 | 0.00 | 0.01 | −0.07 | −0.04 | −0.10 | −0.18 | −0.10 | −0.04 | −0.20 | 0.00 |
| premiR_09794 | −0.64 | −0.63 | 0.10 | 0.59 | −0.67 | 0.01 | −0.40 | −0.56 | −0.07 | −0.84 | −0.67 | 0.10 |
| premiR_09795 | −0.08 | −0.30 | 0.05 | 0.12 | −0.24 | −0.29 | −0.18 | −0.45 | −0.29 | −0.18 | −0.24 | −0.12 |
| premiR_09799 | 0.01 | −0.20 | −0.13 | ND | −0.08 | −0.14 | 0.07 | ND | −0.17 | −0.06 | −0.30 | −0.16 |
| premiR_09803 | 0.03 | 0.02 | −0.09 | −0.03 | 0.14 | 0.02 | 0.05 | −0.02 | 0.05 | −0.02 | −0.01 | 0.15 |
| premiR_09804 | −0.19 | 0.10 | 0.85 | −0.04 | 0.31 | 0.16 | −0.58 | −0.17 | 0.22 | −1.20 | −0.79 | 0.63 |
| premiR_09814 | −0.42 | −0.67 | 0.21 | −0.34 | 0.23 | 0.63 | −0.35 | 0.13 | 0.63 | −0.42 | −0.51 | 0.42 |
| premiR_09816 | −0.69 | −1.00 | 0.50 | −0.94 | −0.90 | 0.34 | 0.01 | 0.07 | 0.02 | −0.44 | −0.67 | −0.07 |
| premiR_09817 | −0.21 | 0.25 | 0.14 | 0.01 | 0.06 | −0.06 | −0.50 | −0.02 | 0.33 | −0.37 | −0.09 | 0.28 |
| premiR_09827 | 0.91 | 0.61 | ND | −0.39 | 0.63 | 0.01 | 0.11 | 0.30 | 0.20 | 0.26 | 0.43 | 0.11 |
| premiR_09835 | −0.07 | 0.20 | ND | 0.01 | −0.27 | 0.22 | −0.40 | 0.13 | 0.37 | −0.40 | 0.00 | 0.28 |
| premiR_09844 | 0.33 | −0.90 | −0.32 | −0.28 | 0.46 | −1.35 | −0.34 | −1.27 | −0.94 | −0.11 | −1.51 | −0.09 |
| premiR_09845 | −0.38 | −0.50 | ND | −0.40 | −0.53 | 0.04 | −0.69 | −0.79 | 0.27 | −0.65 | −1.16 | 0.01 |
| premiR_09850 | −0.58 | −0.41 | 0.36 | −0.32 | −1.42 | −0.10 | −0.14 | ND | 0.17 | −3.05 | −2.15 | −0.19 |
| premiR_09852 | 0.45 | −0.23 | −0.09 | 0.01 | 0.18 | 0.11 | 0.37 | 0.16 | 0.06 | −0.07 | −0.29 | −0.03 |

TABLE 7-continued ratios__454premiRs: Contains ratio data generated on tumor versus normal adjacent tissues from a variety of tissues.

| | | | | | | | | | | | | |
|---|---|---|---|---|---|---|---|---|---|---|---|---|
| premiR_09853 | 0.52 | 0.19 | 0.02 | 0.24 | 0.28 | 0.42 | 0.22 | 0.23 | 0.58 | −0.27 | −0.16 | 0.07 |
| premiR_09854 | −0.17 | −0.22 | −0.08 | −0.20 | −0.81 | −0.01 | −0.22 | −0.36 | 0.02 | −1.70 | −1.56 | 0.05 |
| premiR_09859 | 0.06 | −0.24 | 0.01 | −0.33 | −0.70 | −0.04 | −0.27 | −0.23 | −0.05 | −0.89 | −0.83 | −0.02 |
| premiR_09863 | −0.27 | −0.27 | −0.42 | −0.39 | −0.90 | 0.11 | −0.22 | −0.37 | 0.28 | −2.78 | −2.45 | 0.28 |
| premiR_09865 | −0.11 | −0.09 | 0.04 | −0.16 | −0.68 | 0.03 | −0.50 | −0.52 | 0.28 | −1.95 | −1.85 | 0.12 |
| premiR_09867 | 0.39 | 0.09 | −0.02 | −0.27 | −0.37 | 0.03 | −0.36 | −0.57 | 0.38 | −2.08 | −1.86 | 0.04 |
| premiR_09867- premiR_09869 | −0.14 | −0.12 | 0.16 | −0.16 | −0.68 | 0.12 | −0.40 | ND | 0.17 | −2.45 | −2.62 | −0.02 |
| premiR_09868 | −0.18 | −0.19 | 0.20 | −0.14 | −0.85 | 0.09 | −0.33 | −0.33 | 0.20 | −1.91 | −2.21 | 0.17 |
| premiR_09870 | 0.02 | −0.20 | −0.04 | 0.02 | 0.02 | −0.26 | 0.02 | −0.35 | −0.21 | ND | −0.16 | −0.11 |
| premiR_09874 | 0.78 | 0.55 | ND | 1.02 | 2.72 | −1.08 | −0.33 | −0.53 | −0.56 | −0.68 | −1.16 | −0.07 |
| premiR_09875 | 0.09 | −0.19 | ND | ND | 0.08 | −0.06 | −0.21 | −0.32 | −0.22 | −0.13 | −0.50 | −0.08 |
| premiR_09877 | −0.69 | −0.71 | 0.43 | 1.21 | −0.69 | −0.15 | −1.67 | −0.92 | −0.05 | −0.02 | −0.28 | 0.50 |
| premiR_09881 | −0.51 | −0.73 | 0.66 | 0.14 | −0.71 | −0.08 | −0.41 | −0.54 | 0.17 | −0.16 | −0.32 | −0.01 |
| premiR_09883 | −1.08 | −1.42 | 0.24 | 0.37 | −0.65 | 0.00 | −0.56 | 0.01 | −0.01 | 0.45 | 0.33 | 0.11 |
| premiR_09897 | −0.63 | −0.64 | 0.01 | −0.47 | −0.69 | 0.41 | −0.21 | 0.03 | 0.36 | −0.10 | −0.14 | 0.06 |
| premiR_09899 | 0.19 | 0.16 | 0.06 | ND | −0.22 | 0.12 | 0.03 | 0.12 | 0.18 | −0.15 | 0.02 | 0.26 |
| premiR_09902 | 0.08 | −0.16 | −0.10 | −0.04 | 0.16 | −0.20 | 0.14 | −0.29 | −0.31 | −0.05 | −0.21 | −0.17 |
| premiR_09903 | −1.64 | −2.88 | 0.36 | 0.06 | −0.53 | −0.07 | −0.21 | 0.39 | −0.13 | −0.19 | −0.68 | −0.08 |
| premiR_09908 | −1.27 | −1.47 | −0.05 | −0.21 | −0.52 | −0.14 | −0.04 | −0.25 | −0.24 | −0.70 | −0.50 | −0.28 |
| premiR_09910 | ND | 0.16 | −0.08 | ND | −0.15 | 0.27 | 0.06 | ND | 0.35 | ND | 0.06 | 0.21 |
| premiR_09916 | 0.32 | 0.05 | 0.08 | −0.17 | 0.20 | −0.39 | −0.32 | 0.15 | 0.41 | −0.28 | −0.09 | 1.11 |

| | Tissue Kidney | | | | | | | | | |
|---|---|---|---|---|---|---|---|---|---|---|
| MiR name | T/N-48 | T/N-55 | T/N-55 | T/N-57 | T/N-57 | T/N-60 | T/N-61 | T/N-66 | T/N-73 | T/N-76 | T/N-81 |
| premiR_09110 | −0.03 | −0.08 | 0.06 | 0.09 | 0.05 | 0.53 | 0.07 | −0.03 | 0.08 | 0.05 | −0.06 |
| premiR_09111 | 0.00 | −0.03 | −0.14 | −0.04 | 0.02 | 0.27 | 0.16 | −0.01 | 0.11 | 0.00 | −0.08 |
| premiR_09113 | 0.42 | 0.11 | −0.12 | −0.96 | −0.97 | −0.68 | 0.00 | −0.13 | −0.33 | −1.93 | 0.24 |
| premiR_09114 | −0.06 | −0.12 | −0.53 | −0.56 | −0.17 | −0.36 | −0.09 | 0.47 | 0.13 | 0.08 | 0.46 |
| premiR_09115 | 0.21 | 0.17 | 0.37 | −0.80 | −0.76 | −0.46 | 0.24 | −0.19 | −1.17 | −0.75 | 0.36 |
| premiR_09116 | 0.38 | 0.20 | 0.31 | −0.77 | −0.78 | −0.37 | 0.06 | −0.70 | −0.72 | −1.58 | −0.58 |
| premiR_09118 | 0.73 | 0.46 | 0.75 | 0.06 | −0.09 | −0.23 | 0.55 | 0.76 | −0.65 | −0.48 | −0.06 |
| premiR_09128 | −0.30 | −0.02 | 0.40 | 0.74 | 0.50 | −0.19 | −0.11 | −1.15 | 0.19 | 0.94 | 1.15 |
| premiR_09129 | 0.25 | 0.57 | 0.28 | 0.43 | 0.15 | 0.18 | 0.26 | 0.29 | −0.77 | 0.12 | 0.06 |
| premiR_09131 | −0.05 | −0.14 | −0.22 | 0.23 | 0.08 | 0.53 | 0.16 | 0.04 | −0.06 | 0.07 | −0.07 |
| premiR_09135 | ND | −0.33 | −0.39 | −0.18 | −0.02 | 0.35 | −0.15 | 0.12 | −0.09 | 0.03 | −0.08 |
| premiR_09136 | −0.09 | −0.15 | −0.10 | 0.27 | 0.05 | 0.11 | −0.01 | 0.14 | −0.28 | 0.22 | 0.17 |
| premiR_09138 | −0.01 | −0.23 | 0.18 | 0.81 | 0.50 | 0.40 | 1.71 | 0.92 | −0.86 | −0.41 | 0.23 |
| premiR_09141 | −1.95 | −2.40 | −2.37 | −0.70 | −0.49 | 0.30 | −1.41 | 0.93 | 1.28 | 0.31 | −0.14 |
| premiR_09143 | ND | −0.02 | 0.28 | −0.16 | −0.01 | 0.20 | 0.08 | 0.07 | −0.05 | 0.10 | 0.44 |
| premiR_09144 | 0.48 | 0.38 | 0.28 | −0.13 | −0.15 | 0.12 | 0.05 | 0.64 | −0.38 | −1.21 | −0.62 |
| premiR_09145 | ND | ND | −0.23 | 0.15 | −0.19 | 0.43 | 0.15 | 0.04 | −0.05 | −0.06 | −0.03 |
| premiR_09148 | −0.03 | −0.10 | 0.11 | 0.03 | 0.00 | 0.31 | 0.12 | 0.04 | −0.09 | 0.03 | −0.09 |
| premiR_09150 | 0.20 | −0.08 | −0.04 | −0.68 | −0.34 | −0.54 | 0.13 | −0.16 | −0.07 | −0.50 | 0.14 |
| premiR_09151- premiR_09152- premiR_09317- premiR_09318- premiR_09319- premiR_09335- premiR_09805 | −0.10 | −0.48 | −0.07 | 0.07 | 0.01 | 0.18 | 0.08 | −0.05 | 0.03 | 0.04 | −0.09 |
| premiR_09154 | −0.01 | −0.37 | −0.19 | 0.19 | 0.05 | 0.29 | 0.07 | −0.10 | 0.00 | 0.03 | −0.09 |
| premiR_09156 | 0.39 | 0.04 | 0.11 | −0.37 | −0.36 | −0.23 | 0.00 | 0.67 | −0.15 | −0.78 | 0.14 |
| premiR_09157 | 0.05 | −0.12 | −0.13 | −0.09 | 0.00 | −0.20 | 0.36 | 0.13 | −0.24 | −0.22 | 0.01 |
| premiR_09161 | −0.16 | −0.07 | −0.11 | −0.53 | −0.26 | −0.68 | 0.18 | −0.24 | −0.72 | −0.52 | −0.19 |
| premiR_09163 | −0.03 | −0.04 | −0.09 | 0.05 | −0.03 | 0.32 | 0.19 | 0.09 | 0.02 | −0.07 | −0.02 |
| premiR_09164 | −0.01 | −0.06 | 0.00 | 0.10 | 0.05 | 0.43 | 0.19 | 0.00 | −0.08 | 0.04 | −0.03 |
| premiR_09165 | 1.21 | 0.60 | 0.03 | −0.05 | −0.07 | 1.48 | −0.36 | 1.70 | −0.50 | −0.21 | −0.34 |
| premiR_09167 | 0.48 | 0.03 | 0.16 | −0.21 | −0.33 | −0.28 | 0.95 | −0.49 | 0.41 | −0.86 | −0.48 |
| premiR_09169- premiR_09170- premiR_09407 | 1.11 | −0.22 | −0.02 | −0.44 | −0.32 | −0.14 | 0.40 | −0.89 | −0.52 | −1.66 | −0.69 |
| premiR_09176 | 0.10 | 0.07 | 0.12 | −0.24 | −0.11 | −0.05 | −0.21 | 0.28 | 0.29 | 0.34 | 0.78 |
| premiR_09177 | −0.59 | −0.08 | 0.33 | 1.53 | 0.92 | 0.90 | 0.24 | −0.14 | 0.28 | 1.13 | 0.62 |
| premiR_09179 | −0.32 | −0.31 | 0.23 | −0.15 | −0.23 | −0.49 | 0.35 | −0.65 | −1.28 | −1.27 | −0.10 |
| premiR_09180 | ND | −0.12 | −0.25 | 0.22 | 0.07 | 0.38 | 0.25 | 0.05 | −0.03 | 0.01 | −0.11 |
| premiR_09182 | 0.70 | 0.35 | 0.36 | −0.62 | −0.64 | 0.23 | −0.41 | 0.80 | 0.70 | −0.82 | −0.72 |
| premiR_09188- premiR_09338- premiR_09818 | 0.22 | 0.02 | −0.05 | −0.46 | −0.25 | −0.43 | 0.39 | −1.14 | −0.44 | −0.16 | −0.08 |
| premiR_09190 | 0.30 | 0.19 | 0.34 | 0.18 | 0.07 | 0.16 | −0.22 | −0.12 | 0.55 | 0.41 | 0.15 |
| premiR_09191 | −0.15 | 0.33 | 0.12 | −0.32 | −0.36 | 0.50 | −0.21 | −0.40 | 0.04 | 0.02 | −0.22 |
| premiR_09192 | −0.40 | −0.36 | −0.05 | 0.59 | 0.25 | 0.23 | −0.13 | 0.91 | −0.06 | 0.57 | 0.00 |

TABLE 7-continued ratios__454premiRs: Contains ratio data generated on tumor versus normal adjacent tissues from a variety of tissues.

| | | | | | | | | | | | |
|---|---|---|---|---|---|---|---|---|---|---|---|
| premiR_09194 | −0.02 | ND | −0.01 | 0.04 | 0.03 | 0.61 | 0.15 | 0.05 | −0.07 | 0.02 | −0.06 |
| premiR_09195 | ND | 0.63 | 0.20 | −0.66 | −0.37 | −0.22 | −0.34 | 0.55 | 0.31 | −0.49 | −0.34 |
| premiR_09197 | −0.46 | 0.84 | 0.46 | −0.27 | −0.33 | −0.22 | 0.15 | 1.44 | −2.44 | −0.20 | 0.01 |
| premiR_09198 | 0.87 | 0.87 | 0.51 | 0.52 | 0.50 | 0.87 | −0.47 | 0.97 | 0.52 | 1.19 | 0.49 |
| premiR_09201 | 0.47 | 0.98 | 0.62 | 0.32 | 0.16 | 0.17 | −0.36 | −0.19 | 0.21 | 0.05 | −0.65 |
| premiR_09206 | ND | 0.12 | 0.34 | 0.56 | 0.18 | 0.27 | 0.04 | −0.06 | −0.05 | 0.04 | −0.27 |
| premiR_09208-premiR_09398-premiR_09404 | 0.59 | −0.04 | 0.55 | −0.02 | −0.10 | 0.36 | 0.47 | 0.51 | −0.39 | −1.40 | −0.37 |
| premiR_09210 | ND | ND | −0.08 | 0.05 | 0.02 | 0.48 | 0.12 | 0.03 | 0.00 | 0.02 | −0.08 |
| premiR_09211 | −0.13 | −0.29 | −0.17 | 0.23 | 0.09 | 0.46 | 0.11 | 0.06 | −0.04 | 0.03 | −0.09 |
| premiR_09212 | −0.14 | −0.09 | 0.03 | 0.21 | 0.11 | −0.18 | 1.29 | −0.15 | −0.71 | −0.41 | 0.34 |
| premiR_09213 | 0.48 | 0.72 | 0.48 | 0.97 | 1.12 | 0.94 | 0.01 | 0.75 | −0.30 | 1.39 | 0.24 |
| premiR_09220 | 0.29 | 0.43 | 0.32 | −0.57 | −0.61 | −0.78 | 0.10 | 0.20 | −0.40 | −1.47 | −0.32 |
| premiR_09222 | 0.15 | −0.17 | −0.07 | −0.29 | −0.12 | −0.26 | 0.19 | 0.11 | 0.34 | −0.04 | 0.03 |
| premiR_09223 | ND | 0.22 | 0.12 | −0.49 | −0.17 | −0.18 | 0.00 | −0.08 | −0.01 | 0.05 | 0.19 |
| premiR_09224 | −0.03 | −0.34 | −0.02 | 0.08 | 0.04 | 0.20 | 0.18 | −0.03 | 0.34 | 0.07 | −0.14 |
| premiR_09225 | 0.00 | 0.06 | ND | −0.64 | −0.12 | 0.10 | −0.01 | 0.09 | −0.69 | ND | 0.10 |
| premiR_09226 | 0.02 | 0.09 | 0.02 | −0.54 | −0.13 | 0.22 | 0.18 | −0.21 | −0.39 | −0.11 | −0.10 |
| premiR_09227 | −0.01 | 0.37 | 0.04 | −0.48 | −0.49 | −0.99 | 0.03 | −0.34 | −1.14 | −1.14 | 0.15 |
| premiR_09229 | 0.49 | 0.10 | 0.27 | 0.52 | 0.24 | −0.34 | 2.10 | −0.12 | −0.44 | −1.17 | 0.10 |
| premiR_09236 | 0.03 | −0.32 | −0.17 | −0.12 | −0.05 | 0.25 | 0.12 | 0.46 | 0.90 | 0.06 | −0.02 |
| premiR_09240 | −1.37 | −1.35 | −1.24 | −1.28 | −1.24 | −0.98 | −1.23 | −0.72 | −0.81 | −0.26 | 0.41 |
| premiR_09242 | −0.02 | 0.86 | 0.30 | 0.13 | 0.28 | 0.61 | −0.66 | 0.93 | −0.65 | 0.19 | −0.13 |
| premiR_09244-premiR_09245-premiR_09273 | −1.69 | −2.86 | −3.05 | 0.01 | 0.05 | 0.25 | −1.82 | −0.31 | 0.35 | 0.63 | 0.22 |
| premiR_09245-premiR_09273 | −1.89 | −1.72 | −1.92 | −0.66 | −0.69 | −1.05 | −1.20 | −0.06 | −1.50 | −1.14 | −0.31 |
| premiR_09246 | −0.80 | −0.72 | −0.20 | 0.23 | 0.11 | −0.09 | 0.87 | −0.55 | −1.12 | −0.20 | 0.13 |
| premiR_09247 | −0.14 | −0.10 | −0.41 | 0.32 | 0.10 | 0.34 | 0.05 | −0.08 | 0.16 | 0.10 | 0.10 |
| premiR_09248 | −0.08 | −0.22 | −0.10 | 0.06 | 0.01 | 0.44 | 0.03 | 0.15 | −0.03 | 0.05 | −0.02 |
| premiR_09249 | −0.02 | −0.22 | −0.39 | 0.25 | 0.09 | 0.31 | 0.14 | −0.01 | −0.07 | 0.03 | −0.06 |
| premiR_09250 | 0.66 | −0.37 | 0.01 | −1.53 | −1.41 | −1.23 | 1.38 | −2.76 | −1.14 | −1.79 | −0.12 |
| premiR_09251 | 0.21 | 0.18 | 0.02 | −0.20 | −0.07 | −0.31 | 0.11 | 0.92 | −0.56 | −0.66 | −0.15 |
| premiR_09252 | 0.24 | −0.04 | 0.47 | −0.23 | −0.34 | −0.20 | 0.46 | −0.45 | −0.62 | −0.93 | −0.10 |
| premiR_09255-premiR_09399-premiR_09904 | −0.11 | −0.16 | 0.24 | −0.30 | −0.12 | −0.08 | 0.15 | −0.25 | −0.11 | −0.05 | 0.16 |
| premiR_09257 | ND | 0.06 | 0.44 | 0.06 | 0.02 | 0.24 | 0.28 | −0.14 | 0.05 | ND | −0.07 |
| premiR_09258 | ND | −0.12 | −0.05 | 0.17 | 0.09 | 0.39 | 0.16 | −0.04 | 0.03 | 0.03 | −0.11 |
| premiR_09262-premiR_09263 | −0.49 | −0.79 | −0.60 | 0.13 | 0.04 | 0.07 | −0.19 | 0.91 | 0.19 | 0.29 | −0.14 |
| premiR_09264 | 0.16 | −0.27 | 0.23 | −0.33 | −0.43 | −0.14 | 0.10 | 0.21 | −0.58 | −0.68 | 0.85 |
| premiR_09266 | 0.06 | −0.03 | −0.02 | −0.20 | −0.03 | 0.01 | 0.07 | 0.12 | 0.03 | −0.15 | −0.02 |
| premiR_09268 | 0.17 | 0.13 | 0.05 | −0.29 | −0.33 | 0.30 | −0.30 | 1.23 | 0.57 | −0.33 | −0.72 |
| premiR_09270 | −0.66 | 0.65 | −0.30 | −0.49 | −0.39 | −0.63 | −0.84 | 0.20 | −1.68 | 0.43 | 0.98 |
| premiR_09272 | −1.59 | −2.97 | −1.62 | 1.33 | 0.77 | 2.26 | −0.57 | 0.64 | −0.31 | 0.65 | 0.46 |
| premiR_09277 | 0.04 | −0.07 | −0.21 | −0.27 | −0.07 | −0.13 | 0.16 | 0.15 | −0.16 | −0.10 | 0.18 |
| premiR_09278 | ND | −0.21 | 0.10 | −0.21 | 0.00 | 0.12 | 0.04 | −0.02 | −0.14 | −0.07 | −0.05 |
| premiR_09280 | 0.17 | −0.09 | −0.02 | 0.54 | 0.45 | 0.43 | 0.26 | 0.27 | −0.71 | −0.26 | −0.08 |
| premiR_09281 | 0.01 | ND | 0.10 | ND | ND | 0.30 | ND | 0.02 | −0.05 | ND | −0.03 |
| premiR_09283 | −0.14 | −0.44 | −0.07 | 0.18 | 0.04 | 0.44 | 0.12 | −0.10 | −0.11 | 0.03 | −0.11 |
| premiR_09284 | 0.65 | −0.04 | 0.29 | 0.67 | 0.46 | 0.36 | 0.45 | 0.01 | −0.47 | −0.88 | 0.11 |
| premiR_09285 | 0.02 | ND | 0.19 | ND | ND | 0.64 | 0.06 | −0.02 | −0.01 | ND | −0.01 |
| premiR_09286 | 0.13 | 0.58 | −0.24 | −0.63 | −0.65 | −0.61 | 0.06 | −0.22 | −0.45 | −1.23 | 0.06 |
| premiR_09287 | −0.08 | −0.10 | 0.09 | −0.52 | −0.21 | −0.13 | 0.11 | −0.45 | −0.11 | −0.04 | 0.33 |
| premiR_09289 | 0.09 | 0.09 | 0.29 | −0.47 | −0.13 | −0.27 | 0.38 | −0.41 | −0.82 | −0.25 | 0.08 |
| premiR_09291 | −0.11 | −0.48 | −0.07 | 0.12 | 0.03 | 0.11 | 0.13 | −0.02 | −0.06 | 0.02 | −0.11 |
| premiR_09292 | −0.18 | 0.32 | −0.06 | −0.28 | −0.33 | −0.12 | −0.93 | 0.44 | −0.41 | −1.18 | −1.04 |
| premiR_09293 | −0.33 | −0.43 | −0.24 | −0.62 | −0.64 | −0.36 | 0.65 | 0.17 | −1.46 | −2.01 | −0.17 |
| premiR_09294 | 0.00 | −0.23 | −0.26 | 0.37 | 0.12 | 0.19 | 0.26 | 0.06 | −0.07 | 0.04 | −0.02 |
| premiR_09297 | −0.02 | 1.25 | 0.88 | 0.78 | 0.37 | 1.41 | 0.70 | 0.09 | −0.57 | 1.31 | 0.05 |
| premiR_09300 | 0.05 | −0.55 | 0.09 | 0.23 | 0.01 | 0.61 | 0.57 | −0.57 | −0.86 | −0.23 | −0.62 |
| premiR_09302 | −0.73 | −0.10 | 0.13 | −0.52 | −0.31 | −0.64 | −0.44 | −0.53 | −2.16 | −0.67 | 0.17 |
| premiR_09303 | −0.05 | −0.25 | −0.17 | −0.74 | −0.31 | −0.16 | 0.03 | −0.21 | 0.00 | −0.14 | −0.19 |
| premiR_09304 | 0.10 | 0.83 | −0.08 | −0.47 | −0.37 | −0.43 | 0.05 | 0.03 | 0.01 | −0.22 | 0.39 |
| premiR_09305 | ND | −0.07 | −0.03 | 0.10 | 0.07 | 0.35 | 0.19 | 0.02 | 0.01 | 0.00 | −0.13 |
| premiR_09307 | 0.02 | −0.36 | −0.17 | 0.07 | 0.03 | 0.24 | 0.09 | −0.07 | −0.04 | −0.02 | −0.11 |
| premiR_09308 | 0.03 | 0.21 | 0.23 | 0.26 | 0.05 | 0.14 | −0.26 | 0.41 | 0.08 | 0.31 | 0.25 |
| premiR_09310 | −2.38 | −3.42 | −3.42 | −0.67 | −0.68 | −0.89 | −1.76 | −0.31 | −0.67 | 0.28 | 0.34 |
| premiR_09311 | −0.78 | 0.72 | 0.39 | −0.43 | −0.43 | −0.25 | −0.12 | 1.37 | −2.22 | −0.30 | −0.19 |
| premiR_09313 | 0.03 | ND | 0.14 | ND | ND | 0.54 | 0.08 | 0.00 | −0.04 | −0.06 | −0.02 |
| premiR_09314-premiR_09391 | −0.26 | −0.60 | −0.09 | 1.21 | 1.15 | −0.20 | 1.41 | −0.26 | 0.76 | −0.96 | −0.54 |
| premiR_09315-premiR_09390 | −0.03 | −0.66 | 0.40 | 0.63 | 1.45 | 0.49 | 0.25 | −0.20 | 0.46 | 0.47 | 0.30 |

TABLE 7-continued ratios_454premiRs: Contains ratio data generated on tumor versus normal adjacent tissues from a variety of tissues.

| | | | | | | | | | | |
|---|---|---|---|---|---|---|---|---|---|---|
| premiR_09320-premiR_09342 | −0.06 | −0.14 | −0.55 | −0.75 | −0.55 | −0.68 | −0.08 | −0.27 | 0.10 | −0.47 | 0.17 |
| premiR_09322-premiR_09323-premiR_09368 | 0.26 | 0.38 | 0.04 | −0.29 | −0.29 | −0.29 | 0.22 | −0.29 | 0.08 | −0.72 | −0.05 |
| premiR_09328-premiR_09385-premiR_09386-premiR_09387-premiR_09388-premiR_09389 | −0.86 | −0.16 | −0.23 | 1.35 | 1.29 | 0.12 | −1.11 | 0.65 | −1.18 | 1.52 | 1.45 |
| premiR_09328-premiR_09385-premiR_09386-premiR_09387-premiR_09388-premiR_09389 | −0.05 | 0.20 | −0.37 | 0.07 | 0.41 | −0.77 | −0.74 | 0.32 | −1.26 | 0.02 | 0.03 |
| premiR_09329 | −0.05 | ND | 0.18 | ND | ND | 0.40 | −0.21 | −0.15 | −0.57 | 0.02 | 0.03 |
| premiR_09330 | −0.30 | −0.96 | −0.40 | −0.48 | −0.35 | −0.38 | −0.21 | −1.03 | 0.72 | 0.15 | 0.76 |
| premiR_09331 | 0.71 | 0.59 | 0.31 | −0.09 | 0.01 | −0.44 | 0.06 | 0.43 | −0.43 | −1.36 | −0.31 |
| premiR_09332-premiR_09913 | ND | 0.30 | 0.30 | −0.77 | −0.78 | −0.86 | 0.25 | −0.79 | −0.76 | −2.79 | −0.57 |
| premiR_09333 | 0.15 | −0.09 | −0.11 | 0.17 | 0.11 | 0.05 | 0.12 | 0.29 | −0.07 | −0.20 | −0.05 |
| premiR_09334 | 0.03 | 0.27 | 0.23 | −0.28 | −0.25 | −0.48 | 0.09 | 0.53 | −1.27 | −1.76 | 0.33 |
| premiR_09339 | ND | 0.04 | −0.12 | −0.45 | −0.23 | −0.55 | 0.59 | −0.12 | −0.25 | −0.52 | 0.40 |
| premiR_09349-premiR_09350 | 0.41 | −0.05 | 0.48 | 0.17 | 0.00 | 0.67 | 0.54 | 0.58 | 0.05 | −0.67 | −0.69 |
| premiR_09351-premiR_09352-premiR_09353-premiR_09354-premiR_09355-premiR_09356-premiR_09357-premiR_09358-premiR_09359-premiR_09360-premiR_09361-premiR_09362 | ND | −0.17 | −0.03 | 0.20 | 0.10 | 0.65 | 0.18 | 0.10 | 0.02 | 0.05 | −0.09 |
| premiR_09363 | 0.23 | 0.22 | −0.13 | −0.58 | −0.61 | −0.49 | −0.19 | 0.05 | 0.22 | −0.46 | 0.67 |
| premiR_09364-premiR_09365-premiR_09366 | 0.03 | −0.01 | 0.00 | 0.35 | 0.16 | 0.21 | 1.09 | 0.45 | −0.22 | −0.18 | 0.24 |
| premiR_09367 | −0.17 | 0.38 | 0.25 | −0.19 | −0.06 | 0.20 | 0.44 | −0.01 | −0.77 | −0.08 | −0.12 |
| premiR_09369-premiR_09370 | −0.97 | −0.56 | 0.07 | 0.27 | 0.20 | 1.14 | −0.43 | −0.81 | 2.07 | 1.50 | 0.29 |
| premiR_09373 | 0.70 | 0.05 | 0.38 | −0.03 | −0.09 | −0.60 | 2.84 | −0.93 | −0.32 | −1.63 | 0.65 |
| premiR_09374 | −0.01 | −0.09 | −0.06 | 0.16 | 0.07 | 0.34 | 0.17 | 0.01 | −0.04 | 0.02 | −0.12 |
| premiR_09375 | −0.17 | −0.77 | −0.17 | 0.63 | 0.80 | 0.05 | 1.21 | 0.01 | 1.41 | −0.85 | −0.43 |
| premiR_09380-premiR_09381-premiR_09382-premiR_09412-premiR_09413 | 1.45 | −0.80 | −0.52 | −0.70 | −0.73 | −0.45 | −0.63 | −1.21 | 0.31 | −2.31 | −0.81 |
| premiR_09392-premiR_09843-premiR_09847 | −0.09 | −0.13 | 0.02 | −0.08 | 0.00 | 0.33 | 0.23 | 0.01 | −0.14 | −0.01 | −0.03 |
| premiR_09393 | 0.20 | −0.19 | 0.20 | −0.55 | −0.37 | −0.52 | 0.16 | −0.44 | −0.31 | −0.85 | −0.24 |
| premiR_09394 | −0.07 | ND | 0.04 | 0.17 | 0.06 | 0.60 | 0.15 | 0.01 | −0.03 | −0.09 | 0.01 |
| premiR_09396-premiR_09397 | ND | −0.22 | −0.21 | −0.05 | 0.02 | 0.26 | 0.18 | 0.02 | 0.02 | −0.16 | −0.22 |
| premiR_09398 | ND | ND | ND | 0.06 | 0.06 | 0.40 | 0.12 | 0.05 | 0.00 | ND | −0.04 |
| premiR_09398-premiR_09404 | −0.14 | −0.16 | 0.33 | −0.44 | −0.22 | −0.35 | 0.06 | −0.06 | −0.03 | −0.37 | 0.32 |
| premiR_09403-premiR_09812 | 0.43 | −0.09 | −0.16 | 0.26 | 0.15 | 0.10 | 0.33 | 1.14 | −0.08 | −1.00 | 0.04 |
| premiR_09405 | −0.04 | −0.07 | 0.06 | 0.00 | 0.02 | 0.56 | 0.15 | 0.01 | −0.03 | ND | −0.10 |
| premiR_09408-premiR_09409 | 0.12 | ND | 0.24 | ND | 0.09 | 0.23 | 0.08 | ND | 0.00 | −0.02 | −0.08 |
| premiR_09410-premiR_09411-premiR_09836 | 0.07 | −0.14 | −0.32 | 0.17 | 0.08 | 0.32 | 0.36 | 0.00 | 0.00 | 0.06 | −0.13 |
| premiR_09414-premiR_09768 | 0.06 | −0.03 | −0.04 | 0.06 | 0.06 | 0.20 | 0.17 | 0.06 | −0.02 | −0.02 | −0.18 |
| premiR_09415 | 0.04 | −0.28 | 0.17 | 0.16 | 0.02 | 0.34 | 0.15 | −0.01 | −0.03 | 0.01 | −0.11 |
| premiR_09417 | ND | −0.10 | −0.21 | ND | 0.05 | 0.54 | 0.17 | ND | −0.02 | 0.02 | −0.10 |
| premiR_09423 | ND | 0.50 | ND | −0.15 | −0.08 | −0.26 | −0.34 | 0.16 | −0.01 | −0.10 | 0.04 |

TABLE 7-continued ratios_454premiRs: Contains ratio data generated on tumor versus normal adjacent tissues from a variety of tissues.

| | | | | | | | | | | | |
|---|---|---|---|---|---|---|---|---|---|---|---|
| premiR_09424 | −0.04 | −0.22 | −0.12 | 0.27 | 0.08 | 0.49 | 0.17 | 0.03 | −0.13 | 0.02 | −0.11 |
| premiR_09748 | 0.06 | −0.17 | 0.13 | −0.70 | −0.56 | −0.15 | −0.03 | −1.99 | −0.87 | −0.16 | −0.76 |
| premiR_09756 | 0.07 | −0.13 | −0.02 | 0.01 | −0.03 | 0.06 | 0.23 | −0.12 | −0.11 | −0.03 | 0.12 |
| premiR_09760-premiR_09886 | −0.04 | −0.41 | −0.05 | 0.17 | 0.05 | 0.32 | 0.14 | 0.03 | 0.02 | 0.02 | −0.05 |
| premiR_09761 | −0.01 | 0.07 | 0.01 | −0.34 | −0.12 | −0.28 | −0.60 | −0.15 | 1.04 | 0.28 | 0.38 |
| premiR_09764 | −0.60 | −1.00 | −0.31 | −0.22 | −0.08 | −0.05 | −0.47 | 0.20 | −0.29 | 0.23 | 0.16 |
| premiR_09766 | −0.04 | −0.17 | 0.25 | −0.58 | −0.22 | −0.08 | 0.04 | −0.25 | −0.09 | −0.17 | 0.09 |
| premiR_09769 | 0.32 | 0.10 | 0.58 | −0.33 | −0.28 | −0.09 | 0.17 | 0.57 | 0.33 | −0.55 | −0.79 |
| premiR_09770 | 0.03 | −0.31 | −0.19 | 0.14 | 0.06 | 0.36 | 0.10 | −0.01 | 0.05 | −0.02 | −0.08 |
| premiR_09771 | ND | 0.03 | 0.23 | 0.11 | 0.03 | 0.30 | 0.18 | −0.01 | −0.03 | 0.05 | −0.10 |
| premiR_09774 | 0.03 | −0.12 | −0.21 | −0.44 | −0.21 | −0.05 | 0.12 | −0.43 | −0.13 | −0.11 | 0.00 |
| premiR_09777 | 0.10 | −0.08 | −0.02 | −0.21 | −0.03 | 0.13 | 0.17 | 0.27 | −0.10 | −0.10 | −0.05 |
| premiR_09779-premiR_09780 | 0.87 | 0.45 | 0.35 | −0.25 | −0.35 | −0.07 | 0.72 | 0.69 | −0.30 | −1.18 | −0.43 |
| premiR_09788 | ND | −0.13 | 0.00 | −0.35 | −0.06 | −0.37 | 0.05 | −0.18 | −0.17 | −0.07 | −0.03 |
| premiR_09789 | 0.79 | 0.02 | 0.51 | 0.64 | 0.33 | 0.15 | 0.41 | 1.06 | 0.04 | 0.53 | 0.54 |
| premiR_09792 | −0.04 | 0.72 | 0.19 | −0.37 | −0.19 | −0.49 | −0.51 | 0.92 | −1.23 | −0.46 | −0.37 |
| premiR_09793 | 0.08 | 0.12 | −0.12 | −0.20 | −0.03 | 0.09 | 0.14 | −0.10 | 0.06 | −0.03 | −0.07 |
| premiR_09794 | −0.06 | 0.32 | −0.29 | −0.58 | −0.46 | −0.35 | 0.00 | 0.14 | −0.70 | −1.05 | 0.07 |
| premiR_09795 | −0.08 | −0.08 | −0.24 | −0.27 | −0.07 | −0.07 | 0.14 | −0.04 | −0.07 | −0.14 | 0.00 |
| premiR_09799 | −0.03 | −0.25 | −0.26 | 0.24 | 0.04 | 0.21 | 0.20 | 0.04 | −0.08 | 0.02 | −0.10 |
| premiR_09803 | 0.07 | −0.19 | 0.01 | 0.25 | 0.09 | 0.41 | 0.16 | 0.02 | −0.10 | 0.11 | −0.01 |
| premiR_09804 | 0.36 | −0.49 | −0.05 | −0.80 | −0.58 | −0.59 | −0.39 | −0.41 | 0.00 | −0.38 | 0.59 |
| premiR_09814 | 0.46 | 0.61 | 0.72 | 0.07 | 0.08 | 0.70 | −0.31 | 0.57 | −0.40 | 0.73 | 0.48 |
| premiR_09816 | 0.47 | 0.45 | 0.36 | −0.04 | −0.03 | 0.56 | −0.13 | 0.84 | −0.11 | 0.14 | −0.43 |
| premiR_09817 | ND | 0.02 | 0.13 | −0.59 | −0.30 | −0.47 | −0.08 | 0.07 | 0.28 | −0.75 | −0.19 |
| premiR_09827 | −0.24 | −0.30 | 0.08 | 0.00 | 0.06 | 0.32 | −0.10 | −0.58 | 0.16 | −0.17 | 0.37 |
| premiR_09835 | 0.12 | 0.09 | 0.37 | −0.22 | −0.11 | −0.41 | 0.21 | −0.33 | −0.07 | −0.13 | 0.12 |
| premiR_09844 | −0.05 | 0.10 | −2.10 | 1.75 | 0.97 | 0.96 | 0.27 | −0.11 | −0.63 | −0.16 | −0.35 |
| premiR_09845 | 0.05 | −0.26 | −0.23 | −0.46 | −0.35 | −0.13 | 1.21 | −0.34 | −0.80 | −1.43 | −0.24 |
| premiR_09850 | 1.31 | 0.31 | 0.21 | −0.83 | −0.84 | −0.88 | 0.45 | −0.88 | −0.47 | −2.97 | −0.50 |
| premiR_09852 | 0.71 | 0.44 | 0.08 | −0.36 | −0.31 | 0.22 | 0.21 | −0.15 | 0.05 | 0.35 | 0.59 |
| premiR_09853 | 0.98 | 0.93 | 0.18 | −0.61 | −0.64 | −0.29 | 0.13 | −0.41 | 0.62 | 0.24 | 0.39 |
| premiR_09854 | 0.66 | 0.18 | −0.49 | −0.77 | −0.74 | −0.67 | −0.08 | −0.42 | 1.03 | −1.71 | −0.52 |
| premiR_09859 | ND | 0.00 | −0.26 | −0.70 | −0.37 | −0.54 | −0.06 | −0.35 | 0.62 | −0.25 | −0.45 |
| premiR_09863 | 0.83 | 0.22 | −0.42 | −0.83 | −0.83 | −0.89 | −0.28 | −0.74 | 0.79 | −1.88 | −0.99 |
| premiR_09865 | 0.30 | 0.09 | −0.50 | −0.84 | −0.83 | −0.81 | −0.26 | −0.55 | 1.08 | −1.78 | −0.33 |
| premiR_09867 | 0.50 | 0.07 | −0.59 | −0.76 | −0.77 | −0.61 | −0.31 | −0.49 | 1.59 | −1.41 | −0.19 |
| premiR_09867-premiR_09869 | 0.28 | −0.71 | −0.74 | −1.50 | −1.46 | −0.84 | −0.34 | −1.08 | 0.95 | −2.18 | −0.44 |
| premiR_09868 | 0.73 | 0.16 | −0.52 | −0.83 | −0.83 | −0.88 | −0.19 | −0.67 | 0.96 | −1.83 | −0.87 |
| premiR_09870 | ND | ND | −0.27 | 0.13 | 0.05 | 0.23 | 0.20 | −0.03 | 0.05 | ND | −0.10 |
| premiR_09874 | 0.39 | −0.17 | −0.01 | −1.71 | −0.92 | 0.33 | −0.96 | −0.90 | 0.29 | 1.07 | −0.03 |
| premiR_09875 | ND | 0.13 | −0.19 | −0.49 | −0.10 | −0.10 | 0.21 | −0.11 | 0.00 | 0.15 | 0.05 |
| premiR_09877 | −0.43 | 0.97 | 0.40 | −0.41 | −0.41 | −0.45 | −0.02 | 1.19 | −2.03 | 0.98 | 0.09 |
| premiR_09881 | 0.16 | −0.10 | −0.11 | −1.27 | −1.24 | −0.74 | −0.08 | −0.28 | −0.49 | −1.99 | 0.15 |
| premiR_09883 | −0.34 | 0.56 | 0.49 | −0.82 | −0.78 | −0.40 | −0.14 | 1.19 | −1.23 | −0.63 | −0.03 |
| premiR_09897 | 0.80 | 0.61 | 0.56 | 0.02 | −0.08 | −0.48 | −0.01 | 0.37 | −0.69 | −0.46 | 0.01 |
| premiR_09899 | ND | 0.08 | 0.20 | −0.38 | −0.11 | −0.30 | −0.31 | −0.17 | 0.09 | −0.11 | 0.02 |
| premiR_09902 | 0.05 | 0.01 | −0.22 | 0.29 | 0.09 | 0.44 | 0.22 | 0.02 | 0.11 | 0.01 | −0.12 |
| premiR_09903 | 0.08 | −0.35 | −0.17 | −0.67 | −0.65 | −0.77 | 0.13 | −0.26 | −0.50 | −2.23 | −0.07 |
| premiR_09908 | −0.68 | −0.51 | −0.71 | −0.42 | −0.24 | −0.27 | −0.10 | −0.10 | −1.34 | −1.52 | 0.03 |
| premiR_09910 | ND | −0.37 | 0.19 | 0.03 | 0.02 | 0.23 | 0.21 | 0.01 | −0.17 | −0.03 | −0.06 |
| premiR_09916 | 0.20 | −0.07 | −0.07 | 0.04 | 0.06 | 0.43 | 0.28 | −0.81 | 0.42 | 0.06 | −0.41 |

| | Tissue | | | | | | | | | |
|---|---|---|---|---|---|---|---|---|---|---|
| | Liver | Lung | Mamma | | | | | | | Ovary |
| MiR name | T/N-ambion | T/N-ambion | T/N-32 | T/N-41 | T/N-43 | T/N-44 | T/N-45 | T/N-52 | T/N-53 | T/N-ambion | T/N-ambion |
| premiR_09110 | 0.06 | 0.10 | 0.01 | −0.11 | −0.05 | −0.13 | 0.02 | −0.28 | 0.15 | 0.19 | −0.05 |
| premiR_09111 | −0.15 | −0.22 | 0.25 | 0.02 | 0.00 | −0.27 | −0.05 | −0.11 | 0.04 | −0.28 | −0.12 |
| premiR_09113 | 0.09 | −0.05 | 0.14 | −0.13 | −0.41 | −0.28 | −0.04 | −0.43 | 0.60 | −0.36 | 0.26 |
| premiR_09114 | −0.07 | −0.20 | 0.00 | 0.36 | −0.14 | 0.17 | 0.40 | 0.18 | 0.14 | −0.31 | 0.20 |
| premiR_09115 | 0.20 | 0.07 | 0.45 | −0.44 | −0.15 | −0.39 | −0.22 | −0.84 | 0.50 | −0.32 | 0.24 |
| premiR_09116 | −0.32 | 0.09 | 0.19 | −0.32 | −0.42 | −1.02 | −0.52 | −0.18 | 0.30 | 0.09 | 0.36 |
| premiR_09118 | 0.36 | 0.45 | −0.01 | −0.83 | 0.06 | 0.31 | −0.26 | 0.02 | 0.39 | 0.20 | 0.52 |
| premiR_09128 | 0.37 | 0.63 | −0.56 | −0.69 | 1.35 | 0.76 | 0.43 | 1.14 | 0.50 | 0.58 | 0.32 |
| premiR_09129 | −0.20 | −0.31 | −0.07 | −0.11 | −0.04 | −0.05 | 0.24 | −0.35 | −0.03 | −0.40 | −0.03 |
| premiR_09131 | −0.24 | −0.23 | 0.17 | 0.15 | −0.04 | −0.28 | −0.06 | −0.26 | −0.19 | −0.16 | −0.18 |
| premiR_09135 | −0.21 | −0.22 | −0.14 | 0.00 | −0.08 | −0.10 | ND | −0.15 | −0.08 | −0.19 | −0.13 |
| premiR_09136 | −0.04 | −0.12 | 0.07 | −0.03 | −0.07 | 0.11 | ND | −0.23 | 0.01 | −0.03 | 0.14 |
| premiR_09138 | −0.36 | −0.04 | −0.12 | −0.56 | 0.11 | 0.55 | −0.25 | −0.68 | −0.24 | −0.89 | 0.02 |
| premiR_09141 | −0.30 | 0.05 | 0.09 | 1.05 | 0.25 | 0.36 | 0.20 | 1.40 | −0.98 | 0.31 | −0.09 |

TABLE 7-continued ratios_454premiRs: Contains ratio data generated on tumor versus normal adjacent tissues from a variety of tissues.

| | | | | | | | | | | |
|---|---|---|---|---|---|---|---|---|---|---|
| premiR_09143 | 0.28 | 0.20 | −0.09 | −0.15 | 0.14 | 0.08 | −0.11 | −0.11 | 0.30 | 0.29 | 0.25 |
| premiR_09144 | 0.13 | 0.04 | 1.03 | −0.32 | −0.03 | −0.86 | −0.28 | −1.83 | 0.28 | 0.20 | −0.18 |
| premiR_09145 | −0.23 | −0.11 | 0.15 | 0.29 | ND | 0.14 | ND | −0.14 | 0.02 | −0.18 | −0.24 |
| premiR_09148 | 0.13 | 0.13 | 0.10 | 0.15 | −0.02 | −0.01 | −0.05 | −0.24 | 0.18 | 0.15 | 0.06 |
| premiR_09150 | −0.09 | −0.02 | 0.07 | −0.13 | −0.02 | −0.37 | −0.08 | −0.20 | 0.06 | −0.05 | −0.13 |
| premiR_09151-premiR_09152-premiR_09317-premiR_09318-premiR_09319-premiR_09335-premiR_09805 | 0.00 | −0.03 | 0.10 | 0.24 | −0.01 | −0.06 | −0.12 | −0.31 | 0.04 | 0.00 | −0.02 |
| premiR_09154 | 0.07 | −0.19 | 0.11 | 0.24 | −0.12 | −0.15 | 0.02 | −0.19 | −0.13 | −0.05 | −0.25 |
| premiR_09156 | 0.10 | 0.19 | 0.20 | −0.26 | −0.14 | −0.25 | −0.35 | −0.39 | 0.42 | −0.26 | 0.16 |
| premiR_09157 | −0.20 | −0.22 | 0.12 | 0.11 | −0.06 | −0.18 | −0.17 | −0.28 | −0.18 | −0.27 | −0.18 |
| premiR_09161 | 0.13 | 0.25 | −0.26 | −0.31 | 0.13 | −0.21 | 0.22 | −0.14 | 0.04 | −0.07 | 0.00 |
| premiR_09163 | −0.24 | −0.21 | 0.02 | 0.27 | 0.01 | 0.78 | −0.05 | −0.03 | 0.08 | −0.01 | −0.06 |
| premiR_09164 | 0.00 | −0.01 | 0.09 | 0.05 | −0.04 | −0.06 | 0.04 | −0.17 | 0.04 | 0.09 | 0.05 |
| premiR_09165 | −0.02 | 0.08 | 1.28 | −0.51 | −0.56 | −0.27 | −0.36 | −1.34 | 0.42 | 0.56 | −0.46 |
| premiR_09167 | 0.15 | 0.27 | −0.03 | −0.24 | −0.97 | −1.34 | −0.70 | 0.20 | 0.40 | 0.38 | 0.24 |
| premiR_09169-premiR_09170-premiR_09407 | −0.27 | 0.18 | 0.14 | −0.60 | −0.62 | −1.73 | −0.74 | −0.13 | 0.19 | −0.81 | −0.04 |
| premiR_09176 | 0.21 | 0.05 | −0.29 | −0.39 | 0.30 | 0.48 | 0.17 | 0.19 | 0.28 | −0.16 | 0.22 |
| premiR_09177 | 0.43 | 0.51 | 0.82 | 0.01 | 1.40 | 0.44 | 0.22 | 0.07 | 0.76 | 0.93 | 0.55 |
| premiR_09179 | −0.07 | 0.20 | −0.32 | −0.18 | 0.59 | 0.04 | 0.23 | −0.26 | 0.05 | −0.03 | −0.02 |
| premiR_09180 | −0.35 | −0.26 | ND | ND | ND | −0.18 | ND | −0.24 | −0.11 | −0.21 | −0.23 |
| premiR_09182 | 0.21 | 0.04 | 0.98 | 0.44 | −1.02 | 0.19 | −0.54 | −1.17 | 0.88 | −0.32 | −0.24 |
| premiR_09188-premiR_09338-premiR_09818 | −0.10 | −0.10 | 0.03 | −0.04 | 0.12 | −0.11 | 0.57 | −0.04 | −0.03 | −0.22 | −0.09 |
| premiR_09190 | 0.09 | 0.35 | 0.04 | 0.10 | 0.10 | 0.31 | 0.02 | 0.24 | 0.16 | 0.41 | 0.27 |
| premiR_09191 | 0.67 | 0.46 | 0.89 | 0.64 | −0.24 | −0.07 | 0.69 | 0.22 | 0.93 | 1.02 | 0.70 |
| premiR_09192 | 0.05 | 0.09 | 0.23 | −0.30 | −0.04 | −0.20 | 0.20 | −0.10 | 0.04 | 0.28 | 0.18 |
| premiR_09194 | 0.03 | 0.06 | 0.00 | 0.09 | −0.04 | 0.02 | 0.02 | −0.24 | 0.10 | 0.14 | −0.07 |
| premiR_09195 | −0.35 | 0.46 | 0.99 | −0.84 | 0.15 | ND | −0.14 | 0.53 | 0.12 | 0.10 | −0.01 |
| premiR_09197 | −0.05 | −0.25 | 1.01 | 0.36 | −0.35 | −0.18 | −0.56 | −2.53 | 0.00 | −0.17 | −0.07 |
| premiR_09198 | 0.15 | 0.14 | 1.09 | −0.25 | −0.04 | 0.51 | 0.34 | −1.85 | 0.53 | 0.41 | −0.58 |
| premiR_09201 | −0.17 | −0.34 | −0.13 | 0.04 | −0.46 | −0.30 | −0.35 | −0.09 | 0.13 | 0.33 | 0.18 |
| premiR_09206 | 0.33 | 0.39 | −0.19 | 0.21 | 0.02 | 0.21 | 0.20 | −0.07 | 0.27 | 0.34 | 0.30 |
| premiR_09208-premiR_09398-premiR_09404 | 0.11 | 0.10 | 0.70 | −0.12 | −0.64 | −0.14 | 0.03 | −0.51 | 0.35 | −0.01 | 0.34 |
| premiR_09210 | −0.07 | 0.01 | ND | ND | −0.05 | −0.02 | −0.07 | −0.24 | 0.10 | 0.08 | −0.11 |
| premiR_09211 | −0.11 | −0.14 | 0.17 | 0.03 | −0.08 | −0.25 | −0.04 | −0.17 | −0.08 | −0.04 | −0.15 |
| premiR_09212 | −0.30 | −0.19 | −0.11 | −0.33 | −0.17 | 0.62 | −0.42 | −0.39 | −0.23 | −0.81 | −0.33 |
| premiR_09213 | −0.03 | −0.28 | 0.15 | −0.42 | 0.10 | 0.37 | −0.13 | −1.30 | 0.67 | −0.65 | −0.17 |
| premiR_09220 | 0.12 | 0.26 | 0.03 | −0.24 | −0.39 | −0.12 | 0.23 | −0.13 | 0.31 | 0.08 | 0.18 |
| premiR_09222 | 0.01 | −0.07 | −0.15 | 0.11 | 0.02 | 0.01 | −0.15 | 0.16 | 0.03 | 0.16 | −0.10 |
| premiR_09223 | 0.12 | 0.10 | −0.02 | −0.09 | −0.02 | ND | −0.20 | −0.05 | 0.30 | −0.10 | 0.16 |
| premiR_09224 | 0.01 | 0.07 | 0.20 | 0.31 | −0.11 | −0.18 | −0.08 | 0.02 | 0.20 | 0.01 | −0.01 |
| premiR_09225 | 0.29 | ND | 0.23 | 0.02 | 0.01 | 0.19 | 0.01 | −0.08 | ND | 0.07 | 0.21 |
| premiR_09226 | 0.19 | 0.45 | −0.60 | −0.17 | 0.34 | 0.11 | 0.80 | 0.26 | 0.31 | 0.25 | 0.24 |
| premiR_09227 | −0.10 | −0.13 | 0.25 | −0.09 | 0.30 | −0.05 | 0.31 | −0.08 | 0.23 | −0.47 | −0.01 |
| premiR_09229 | 0.24 | 0.31 | −0.03 | −0.18 | −0.14 | −0.28 | −0.11 | 0.15 | 0.28 | 0.33 | 0.36 |
| premiR_09236 | −0.10 | 0.00 | 0.09 | 0.80 | −0.06 | −0.10 | 0.21 | 0.34 | 0.17 | −0.24 | −0.08 |
| premiR_09240 | −0.15 | 0.19 | −0.16 | −0.32 | 0.88 | −0.10 | −0.41 | 0.66 | −0.27 | 0.33 | −0.01 |
| premiR_09242 | 0.11 | −0.17 | 0.97 | −0.03 | −0.49 | 0.30 | −0.11 | −1.53 | 0.44 | −0.72 | −0.64 |
| premiR_09244-premiR_09245-premiR_09273 | 0.16 | 0.18 | −0.53 | −0.13 | 2.03 | 1.17 | 0.79 | 3.98 | 0.81 | 2.05 | 0.85 |
| premiR_09245-premiR_09273 | −0.27 | −0.02 | −0.72 | 0.25 | −0.54 | −0.71 | −0.63 | 0.60 | −0.47 | 0.17 | −0.10 |
| premiR_09246 | 0.00 | −0.10 | −0.05 | −0.53 | 0.21 | 0.44 | 0.10 | −0.36 | −0.04 | −0.32 | 0.38 |
| premiR_09247 | −0.37 | −0.25 | 0.07 | 0.10 | 0.08 | −0.08 | −0.01 | 0.09 | −0.24 | −0.23 | −0.10 |
| premiR_09248 | −0.08 | −0.03 | 0.05 | ND | −0.05 | 0.02 | 0.05 | −0.16 | 0.09 | 0.10 | −0.12 |
| premiR_09249 | −0.25 | −0.30 | 0.11 | 0.07 | 0.00 | −0.23 | 0.02 | −0.23 | −0.21 | −0.29 | −0.33 |
| premiR_09250 | 0.19 | 0.13 | −0.06 | 0.33 | 0.97 | −1.21 | 0.12 | 0.10 | 0.60 | 0.47 | 0.51 |
| premiR_09251 | −0.13 | −0.08 | 0.22 | −0.11 | −0.29 | 0.01 | −0.11 | −0.25 | −0.04 | −0.55 | −0.04 |
| premiR_09252 | 0.22 | 0.44 | −0.41 | −0.46 | 0.12 | −0.05 | −0.14 | 0.05 | 0.17 | 0.07 | 0.17 |
| premiR_09255-premiR_09399-premiR_09904 | −0.12 | −0.07 | −0.01 | 0.04 | 0.03 | 0.09 | −0.27 | −0.09 | 0.01 | −0.09 | 0.13 |
| premiR_09257 | 0.38 | 0.40 | ND | 0.31 | ND | ND | ND | −0.14 | 0.38 | 0.48 | 0.41 |
| premiR_09258 | 0.01 | −0.07 | 0.10 | ND | −0.17 | −0.08 | 0.04 | −0.26 | 0.00 | 0.04 | −0.05 |
| premiR_09262-premiR_09263 | −0.19 | 0.04 | −0.07 | 0.38 | −0.10 | −0.08 | −0.17 | 0.28 | −0.29 | −0.84 | −0.35 |

TABLE 7-continued ratios_454premiRs: Contains ratio data generated on tumor versus normal adjacent tissues from a variety of tissues.

| | | | | | | | | | | | |
|---|---|---|---|---|---|---|---|---|---|---|---|
| premiR_09264 | 0.03 | 0.05 | 0.02 | −0.02 | −0.07 | 0.03 | −0.08 | −0.54 | 0.45 | 0.12 | 0.30 |
| premiR_09266 | −0.18 | 1.00 | 0.12 | 0.00 | 0.05 | −0.02 | −0.09 | 0.43 | −0.03 | 0.33 | −0.31 |
| premiR_09268 | 0.21 | 0.14 | 1.24 | 0.26 | −0.54 | 0.12 | −0.03 | −0.25 | 0.90 | 0.25 | −0.66 |
| premiR_09270 | 0.30 | −0.10 | 0.25 | −1.18 | −0.21 | 0.78 | 0.13 | −0.42 | 0.26 | −1.20 | 0.47 |
| premiR_09272 | −0.61 | 0.50 | −0.05 | −0.04 | 0.46 | 0.39 | 0.35 | 1.62 | 0.06 | 1.81 | −0.04 |
| premiR_09277 | −0.24 | −0.22 | 0.11 | 0.04 | −0.04 | −0.15 | −0.11 | −0.22 | −0.13 | −0.32 | −0.10 |
| premiR_09278 | 0.17 | 0.17 | 0.05 | 0.11 | −0.06 | 0.09 | −0.09 | −0.10 | 0.17 | 0.19 | 0.18 |
| premiR_09280 | −0.07 | 0.09 | 0.58 | −0.59 | −0.55 | −0.79 | −0.72 | −0.65 | 0.08 | −0.72 | −0.42 |
| premiR_09281 | 0.18 | 0.20 | −0.01 | 0.03 | ND | −0.02 | 0.02 | −0.11 | 0.39 | 0.30 | 0.07 |
| premiR_09283 | −0.05 | −0.10 | 0.25 | 0.13 | 0.02 | −0.28 | −0.13 | −0.31 | −0.03 | −0.05 | −0.29 |
| premiR_09284 | −0.30 | −0.20 | 0.16 | 0.02 | 0.37 | 0.13 | −0.55 | −0.42 | −0.24 | −0.70 | −0.31 |
| premiR_09285 | 0.24 | 0.22 | 0.11 | 0.09 | 0.00 | 0.09 | 0.09 | −0.20 | 0.32 | 0.37 | 0.14 |
| premiR_09286 | −0.04 | 0.00 | 0.10 | 0.02 | −0.48 | −0.36 | −0.17 | −0.04 | 0.41 | −0.01 | 0.30 |
| premiR_09287 | 0.17 | −0.01 | 0.10 | −0.18 | −0.03 | −0.09 | −0.03 | −0.25 | 0.22 | 0.16 | 0.07 |
| premiR_09289 | 0.30 | 0.29 | 0.00 | −0.36 | 0.05 | −0.04 | 0.00 | −0.14 | 0.30 | 0.33 | 0.33 |
| premiR_09291 | −0.04 | −0.05 | 0.13 | 0.21 | −0.10 | −0.18 | −0.15 | −0.25 | 0.04 | 0.00 | −0.10 |
| premiR_09292 | −0.07 | 0.09 | 0.30 | 0.06 | −0.79 | −0.44 | −0.53 | −0.59 | 0.31 | 0.60 | −0.22 |
| premiR_09293 | −0.50 | 0.12 | −0.07 | −0.98 | −1.14 | −0.66 | −0.57 | −0.87 | −0.02 | −1.70 | −0.25 |
| premiR_09294 | −0.26 | −0.32 | 0.11 | 0.18 | −0.02 | −0.24 | −0.13 | −0.29 | −0.30 | −0.20 | −0.27 |
| premiR_09297 | −0.08 | −0.19 | −0.43 | −1.26 | 0.36 | −0.13 | 0.20 | 0.04 | −0.56 | −0.51 | −0.02 |
| premiR_09300 | 0.55 | 0.15 | 0.77 | 0.46 | −0.28 | −0.56 | 0.13 | −0.90 | 0.65 | 1.14 | 0.43 |
| premiR_09302 | 0.19 | 0.14 | −0.18 | −0.20 | 0.02 | 0.29 | −0.01 | −0.10 | 0.21 | 0.01 | 0.21 |
| premiR_09303 | −0.05 | −0.09 | 0.08 | 0.01 | −0.09 | −0.17 | −0.06 | −0.17 | 0.11 | −0.07 | 0.09 |
| premiR_09304 | 0.15 | 0.00 | 0.21 | 0.26 | −0.08 | −0.15 | 0.40 | 0.19 | 0.46 | 0.24 | 0.37 |
| premiR_09305 | −0.02 | 0.04 | 0.08 | 0.16 | −0.05 | −0.16 | ND | −0.22 | 0.08 | 0.03 | −0.02 |
| premiR_09307 | −0.08 | −0.11 | 0.15 | 0.12 | −0.07 | ND | ND | −0.23 | 0.01 | 0.01 | 0.15 |
| premiR_09308 | 0.42 | 0.39 | −0.17 | 0.14 | 0.04 | 0.39 | 0.23 | 0.14 | 0.18 | 1.21 | −0.18 |
| premiR_09310 | 0.01 | 0.36 | −0.43 | 1.79 | 0.64 | 0.29 | 0.84 | 2.42 | 0.40 | 2.10 | 0.25 |
| premiR_09311 | 0.17 | −0.11 | 0.68 | 0.50 | −0.43 | 0.15 | −0.38 | −2.50 | 0.07 | −0.11 | 0.17 |
| premiR_09313 | 0.22 | 0.22 | 0.07 | 0.04 | 0.02 | −0.13 | 0.09 | −0.14 | 0.30 | 0.30 | 0.20 |
| premiR_09314-premiR_09391 | −0.12 | 0.52 | 0.50 | 0.66 | −0.37 | −1.44 | 0.28 | 0.43 | 0.09 | 0.48 | 0.15 |
| premiR_09315-premiR_09390 | 0.40 | 0.50 | −0.08 | 0.13 | 0.79 | 0.50 | −0.12 | 1.26 | 0.29 | 0.40 | 0.55 |
| premiR_09320-premiR_09342 | −0.37 | −0.29 | 0.10 | −0.13 | 0.03 | −0.56 | −0.20 | −0.07 | 0.09 | −0.23 | −0.18 |
| premiR_09322-premiR_09323-premiR_09368 | 0.01 | 0.06 | 0.19 | 0.01 | −0.09 | −0.08 | 0.08 | 0.37 | 0.28 | 0.15 | 0.21 |
| premiR_09328-premiR_09385-premiR_09386-premiR_09387-premiR_09388-premiR_09389 | 0.77 | 0.80 | −0.89 | −0.95 | 2.18 | 1.25 | 0.44 | 2.08 | 0.58 | 1.97 | 0.64 |
| premiR_09328-premiR_09385-premiR_09386-premiR_09387-premiR_09388-premiR_09389 | 0.75 | 0.63 | −0.82 | −0.23 | 1.34 | 1.24 | 0.47 | 1.46 | 0.66 | 0.68 | 0.68 |
| premiR_09329 | 0.24 | 0.27 | −0.07 | 0.12 | 0.01 | 0.02 | −0.05 | −0.17 | 0.30 | 0.32 | 0.11 |
| premiR_09330 | −0.30 | 0.30 | −0.11 | 0.58 | 1.72 | 0.82 | 1.20 | 1.92 | 0.88 | −0.09 | 0.97 |
| premiR_09331 | 0.38 | 0.13 | 0.77 | −0.29 | −0.12 | −0.28 | −0.05 | −1.31 | 0.88 | −0.19 | −0.59 |
| premiR_09332-premiR_09913 | −0.01 | 0.02 | 0.02 | −1.04 | −0.60 | −1.48 | −1.16 | −0.14 | 0.02 | −0.25 | −0.06 |
| premiR_09333 | −0.25 | −0.22 | −0.04 | −0.22 | −0.12 | −0.05 | −0.24 | −0.09 | −0.18 | −0.43 | −0.11 |
| premiR_09334 | −0.05 | −0.40 | 0.51 | −0.42 | −0.36 | 0.26 | −0.39 | −1.36 | −0.23 | −1.93 | 0.05 |
| premiR_09339 | −0.14 | −0.24 | 0.10 | 0.03 | 0.07 | −0.17 | −0.14 | −0.14 | −0.03 | −0.23 | −0.03 |
| premiR_09349-premiR_09350 | −0.03 | −0.32 | 0.29 | −0.22 | −0.41 | −0.35 | −1.00 | −0.96 | −0.08 | −0.93 | −0.29 |
| premiR_09351-premiR_09352-premiR_09353-premiR_09354-premiR_09355-premiR_09356-premiR_09357-premiR_09358-premiR_09359-premiR_09360-premiR_09361-premiR_09362 | −0.12 | −0.07 | ND | 0.10 | 0.05 | −0.24 | ND | −0.36 | −0.01 | −0.20 | −0.20 |
| premiR_09363 | 0.06 | 0.14 | 0.30 | 0.20 | −0.20 | −0.26 | 0.40 | 0.39 | 0.69 | 0.31 | 0.29 |
| premiR_09364-premiR_09365-premiR_09366 | −0.27 | −0.10 | −0.14 | −0.25 | −0.12 | 0.51 | −0.32 | −0.18 | −0.26 | −0.67 | −0.38 |

TABLE 7-continued ratios_454premiRs: Contains ratio data generated on tumor versus normal adjacent tissues from a variety of tissues.

| | | | | | | | | | | | |
|---|---|---|---|---|---|---|---|---|---|---|---|
| premiR_09367 | −0.20 | 0.24 | 0.46 | −0.48 | 0.00 | −0.18 | −0.02 | 0.14 | −0.13 | 0.32 | −0.23 |
| premiR_09369-premiR_09370 | −0.01 | 0.27 | −0.12 | 0.61 | 0.65 | 0.64 | 0.41 | 1.08 | −0.09 | 0.91 | 0.19 |
| premiR_09373 | 0.27 | 0.69 | −0.12 | −0.55 | −0.02 | −0.14 | −0.94 | 0.53 | 0.32 | 0.07 | 0.29 |
| premiR_09374 | −0.06 | −0.07 | 0.08 | ND | −0.08 | −0.15 | −0.08 | −0.18 | −0.06 | −0.05 | −0.08 |
| premiR_09375 | 0.03 | 0.22 | 0.16 | 0.63 | −0.30 | −0.60 | 0.30 | 0.42 | −0.05 | 0.28 | 0.14 |
| premiR_09380-premiR_09381-premiR_09382-premiR_09412-premiR_09413 | −0.66 | 0.05 | 0.14 | −0.65 | −0.32 | −0.98 | −1.34 | 0.33 | −0.52 | −0.50 | −0.37 |
| premiR_09392-premiR_09843-premiR_09847 | −0.01 | −0.03 | 0.11 | 0.17 | 0.02 | −0.15 | −0.09 | −0.27 | 0.04 | 0.02 | −0.09 |
| premiR_09393 | 0.07 | 0.10 | 0.13 | −0.26 | −0.06 | −0.18 | −0.29 | −0.12 | 0.28 | 0.08 | 0.08 |
| premiR_09394 | 0.11 | 0.14 | 0.09 | 0.15 | 0.02 | 0.29 | −0.03 | −0.08 | 0.15 | 0.21 | 0.07 |
| premiR_09396-premiR_09397 | −0.25 | −0.14 | 0.14 | 0.04 | −0.01 | −0.16 | ND | −0.20 | −0.05 | −0.22 | −0.24 |
| premiR_09398 | 0.22 | 0.12 | −0.01 | ND | 0.04 | 0.19 | ND | −0.07 | 0.31 | 0.29 | 0.20 |
| premiR_09398-premiR_09404 | 0.16 | 0.43 | 0.08 | 0.39 | 0.01 | 0.09 | −0.03 | 0.05 | 0.35 | 0.43 | 0.13 |
| premiR_09403-premiR_09812 | −0.27 | −0.16 | 0.85 | −0.15 | −1.02 | −1.24 | −1.07 | −1.09 | −0.16 | −1.15 | −0.32 |
| premiR_09405 | 0.09 | 0.12 | 0.10 | 0.14 | 0.03 | −0.05 | 0.04 | −0.28 | 0.18 | 0.14 | −0.07 |
| premiR_09408-premiR_09409 | 0.11 | 0.19 | −0.08 | 0.33 | −0.06 | ND | ND | −0.05 | 0.21 | 0.24 | 0.13 |
| premiR_09410-premiR_09411-premiR_09836 | −0.27 | −0.27 | 0.08 | 0.19 | −0.03 | −0.25 | −0.02 | −0.24 | −0.28 | −0.25 | −0.32 |
| premiR_09414-premiR_09768 | −0.01 | −0.09 | −0.14 | 0.15 | −0.01 | −0.13 | 0.13 | −0.11 | −0.04 | −0.07 | −0.08 |
| premiR_09415 | 0.13 | 0.03 | 0.14 | 0.17 | −0.09 | −0.04 | ND | −0.25 | 0.15 | 0.24 | 0.04 |
| premiR_09417 | −0.22 | −0.11 | ND | 0.14 | 0.00 | −0.23 | 0.03 | −0.25 | −0.01 | −0.10 | −0.16 |
| premiR_09423 | 0.32 | 0.26 | −0.14 | −0.19 | 0.08 | 0.61 | −0.08 | −0.15 | ND | 0.35 | 0.34 |
| premiR_09424 | −0.13 | −0.16 | 0.17 | 0.16 | −0.07 | −0.11 | −0.15 | −0.22 | −0.17 | −0.07 | −0.17 |
| premiR_09748 | 0.38 | 0.20 | 0.22 | 0.20 | 0.04 | −0.16 | 0.22 | −0.11 | 0.42 | 0.33 | 0.76 |
| premiR_09756 | −0.10 | 0.02 | ND | −0.10 | 0.00 | 0.38 | −0.05 | −0.11 | 0.11 | −0.10 | 0.04 |
| premiR_09760-premiR_09886 | −0.26 | 0.04 | 0.07 | 0.14 | −0.12 | ND | ND | −0.17 | 0.05 | −0.04 | −0.01 |
| premiR_09761 | 0.05 | 0.17 | −0.28 | 0.27 | 0.19 | 0.24 | 0.43 | 0.68 | 0.10 | 0.43 | 0.25 |
| premiR_09764 | 0.04 | 0.40 | −0.21 | −0.44 | 0.27 | 0.10 | −0.27 | 0.04 | 0.12 | 0.16 | 0.21 |
| premiR_09766 | 0.23 | 0.20 | −0.04 | 0.00 | −0.08 | ND | ND | −0.19 | 0.19 | 0.25 | 0.25 |
| premiR_09769 | 0.33 | 0.25 | 0.25 | −0.59 | −0.45 | 0.14 | −0.14 | −0.27 | 0.82 | −0.53 | 0.02 |
| premiR_09770 | −0.17 | −0.22 | 0.17 | 0.14 | −0.21 | −0.05 | ND | −0.22 | −0.08 | −0.08 | 0.05 |
| premiR_09771 | 0.15 | 0.16 | 0.07 | ND | ND | 0.21 | ND | −0.16 | 0.19 | 0.25 | 0.22 |
| premiR_09774 | −0.25 | −0.21 | −0.16 | −0.04 | −0.08 | −0.15 | −0.16 | −0.12 | −0.22 | −0.22 | −0.25 |
| premiR_09777 | −0.09 | −0.07 | 0.08 | −0.07 | −0.09 | 0.20 | −0.01 | −0.23 | −0.03 | −0.11 | −0.16 |
| premiR_09779-premiR_09780 | 0.22 | 0.28 | 0.71 | −0.13 | −0.09 | −0.08 | −0.26 | −0.89 | 0.45 | 0.04 | 0.10 |
| premiR_09788 | −0.14 | 0.05 | 0.02 | −0.05 | −0.06 | −0.18 | −0.07 | −0.20 | 0.12 | −0.02 | 0.06 |
| premiR_09789 | 0.50 | 0.95 | −0.78 | −1.20 | 1.10 | 0.39 | 0.27 | 0.73 | 0.44 | 0.12 | 0.01 |
| premiR_09792 | −0.22 | −0.90 | 0.36 | −0.51 | −0.73 | −0.68 | −0.23 | −0.54 | −0.18 | −0.72 | −0.28 |
| premiR_09793 | −0.09 | −0.10 | 0.09 | −0.03 | 0.06 | −0.12 | 0.05 | −0.15 | 0.06 | −0.07 | 0.00 |
| premiR_09794 | −0.32 | −0.17 | 0.24 | −0.29 | −0.47 | −0.04 | 0.09 | 0.14 | 0.02 | −0.43 | −0.13 |
| premiR_09795 | −0.24 | −0.24 | 0.07 | −0.02 | −0.02 | −0.26 | −0.03 | −0.20 | −0.07 | −0.18 | −0.31 |
| premiR_09799 | −0.12 | −0.27 | 0.07 | 0.18 | −0.25 | −0.03 | −0.25 | −0.29 | −0.22 | −0.18 | −0.50 |
| premiR_09803 | 0.00 | 0.02 | 0.12 | 0.20 | −0.03 | −0.14 | ND | −0.25 | 0.06 | 0.06 | 0.03 |
| premiR_09804 | 0.24 | 0.28 | 0.07 | −0.02 | −0.08 | −0.43 | −0.01 | 0.13 | 0.75 | 0.38 | 0.15 |
| premiR_09814 | 0.54 | 0.02 | 0.34 | 0.02 | 0.13 | −0.13 | −0.07 | −0.88 | 0.71 | 0.30 | 0.15 |
| premiR_09816 | −0.88 | −0.19 | 0.66 | −0.13 | −0.77 | 0.25 | −0.51 | −1.31 | 0.54 | −0.67 | −0.02 |
| premiR_09817 | 0.27 | 0.11 | 0.06 | −0.20 | −0.05 | −0.04 | −0.18 | 0.00 | 0.30 | 0.26 | 0.15 |
| premiR_09827 | 0.10 | 0.29 | −0.19 | 0.06 | 0.23 | 0.39 | 0.04 | 0.12 | 0.27 | 0.13 | 0.24 |
| premiR_09835 | 0.24 | 0.26 | −0.10 | 0.06 | −0.04 | ND | −0.08 | 0.03 | 0.35 | 0.32 | 0.30 |
| premiR_09844 | −1.22 | −0.98 | 0.38 | 0.34 | −0.55 | −0.80 | 0.24 | −0.63 | −1.18 | −0.44 | −1.52 |
| premiR_09845 | 0.14 | −0.08 | 0.25 | −0.81 | −0.19 | −1.11 | −0.51 | −0.66 | 0.49 | −0.76 | 0.77 |
| premiR_09850 | 0.02 | 0.08 | 0.06 | −0.46 | −0.55 | −1.55 | −0.97 | 0.07 | −0.02 | −0.12 | −0.11 |
| premiR_09852 | −0.16 | −0.19 | −0.11 | −0.24 | −0.30 | −0.07 | −0.13 | 0.00 | −0.56 | −0.18 | −0.63 |
| premiR_09853 | 0.01 | 0.00 | −0.33 | 0.17 | −0.29 | −0.01 | 0.16 | 0.43 | −0.49 | −0.06 | −0.55 |
| premiR_09854 | −0.27 | −0.15 | −0.07 | 0.12 | −1.08 | −0.54 | −0.25 | 0.30 | 0.22 | −0.09 | 0.09 |
| premiR_09859 | −0.21 | −0.14 | 0.03 | −0.32 | −0.51 | −0.30 | −0.18 | 0.08 | 0.17 | −0.22 | −0.07 |
| premiR_09863 | −0.11 | −0.04 | −0.15 | 0.10 | −0.84 | −1.01 | −0.60 | 0.35 | 0.41 | −0.08 | 0.30 |
| premiR_09865 | 0.00 | −0.07 | −0.20 | 0.09 | −1.05 | −0.73 | −0.20 | 0.51 | 0.42 | 0.08 | 0.54 |
| premiR_09867 | −0.07 | −0.07 | 0.13 | 0.56 | −0.71 | −0.83 | −0.23 | 0.78 | 0.48 | 0.10 | 0.51 |
| premiR_09867-premiR_09869 | 0.07 | −0.03 | −0.30 | 0.04 | −0.83 | −1.21 | −0.24 | 1.08 | 0.50 | −0.04 | 0.48 |
| premiR_09868 | −0.13 | −0.05 | −0.18 | −0.01 | −1.21 | −0.79 | 0.04 | 0.45 | 0.40 | −0.11 | 0.27 |
| premiR_09870 | −0.18 | −0.18 | 0.03 | ND | ND | −0.09 | 0.06 | −0.18 | −0.05 | −0.18 | −0.18 |

TABLE 7-continued ratios_454premiRs: Contains ratio data generated on tumor versus normal adjacent tissues from a variety of tissues.

| | | | | | | | | | | | |
|---|---|---|---|---|---|---|---|---|---|---|---|
| premiR_09874 | −0.07 | 0.53 | −0.80 | −0.82 | 0.96 | 0.37 | −0.55 | 0.68 | −0.39 | 0.62 | −0.46 |
| premiR_09875 | −0.20 | −0.17 | ND | ND | ND | ND | ND | −0.15 | −0.04 | −0.29 | −0.02 |
| premiR_09877 | 0.03 | −0.40 | 0.54 | 0.28 | −0.43 | 0.20 | 0.00 | −2.04 | 0.01 | −0.23 | 0.10 |
| premiR_09881 | 0.07 | −0.17 | 0.37 | 0.10 | −0.25 | −0.30 | 0.00 | −0.48 | 0.46 | −0.93 | 0.19 |
| premiR_09883 | 0.45 | −0.03 | 0.48 | −0.24 | −0.65 | 0.60 | −0.40 | −1.61 | −0.09 | −1.27 | 0.10 |
| premiR_09897 | −0.05 | −0.22 | −0.02 | −0.40 | 0.39 | −0.27 | −0.08 | −0.60 | 0.31 | 0.10 | 0.03 |
| premiR_09899 | 0.18 | 0.06 | 0.00 | −0.45 | −0.10 | −0.11 | −0.04 | −0.12 | 0.05 | 0.01 | 0.13 |
| premiR_09902 | −0.27 | −0.27 | 0.10 | 0.16 | −0.07 | −0.09 | ND | −0.25 | −0.25 | −0.19 | −0.29 |
| premiR_09903 | 0.01 | 0.30 | 0.28 | −0.77 | −0.81 | −0.59 | −0.66 | −0.14 | 0.06 | −1.08 | −0.04 |
| premiR_09908 | −0.32 | −0.21 | 0.15 | −0.78 | −1.29 | −0.46 | −0.12 | −0.61 | −0.28 | −2.04 | −0.31 |
| premiR_09910 | 0.26 | 0.18 | 0.11 | 0.07 | −0.06 | ND | ND | −0.23 | 0.23 | 0.28 | 0.52 |
| premiR_09916 | 0.31 | 0.27 | 0.42 | 0.28 | −0.10 | −0.32 | −0.03 | −0.02 | 0.35 | 1.03 | 0.24 |

| | Tissue | | | | | | | | | | |
|---|---|---|---|---|---|---|---|---|---|---|---|
| | Prostate | | | | | | | | Stomach | Uterus | |
| | T/N-ambion | | | | Rectal | | | | T/N-ambion | T/N-38 | T/N-ambion |
| MiR name | | T/N-31 | T/N-50 | T/N-62 | T/N-68 | T/N-69 | T/N-71 | T/N-85 | | | |
| premiR_09110 | 0.13 | −0.02 | −0.01 | 0.02 | 0.00 | 0.07 | −0.09 | −0.06 | 0.15 | −0.14 | 0.15 |
| premiR_09111 | −0.08 | 0.28 | 0.56 | 0.52 | 0.32 | 0.19 | −0.08 | 0.00 | −0.28 | −0.11 | 0.04 |
| premiR_09113 | 0.02 | 0.03 | 0.79 | 0.81 | 0.51 | 0.51 | 0.50 | 0.25 | −0.35 | 0.73 | 0.60 |
| premiR_09114 | 0.24 | −0.32 | 0.14 | 0.72 | 0.10 | −0.48 | 0.02 | −0.09 | −0.45 | 0.36 | 0.14 |
| premiR_09115 | 0.03 | −0.16 | 0.87 | −0.29 | −0.20 | 1.02 | 0.65 | −0.47 | −0.51 | 0.82 | 0.50 |
| premiR_09116 | 0.30 | 0.29 | 0.50 | 0.22 | 0.30 | 1.05 | 0.48 | −0.37 | −0.45 | 0.40 | 0.30 |
| premiR_09118 | 0.37 | 0.26 | 1.11 | 1.33 | 0.62 | 0.51 | 0.77 | −0.42 | −0.33 | 0.63 | 0.39 |
| premiR_09128 | 0.37 | 0.06 | −0.30 | 0.29 | 0.01 | −0.03 | 0.27 | 0.38 | −0.16 | 1.15 | 0.50 |
| premiR_09129 | −0.12 | −0.42 | −0.18 | −1.75 | −0.98 | 0.43 | 0.60 | −0.15 | −0.26 | 0.00 | −0.03 |
| premiR_09131 | −0.18 | −0.03 | −0.06 | −0.22 | −0.01 | 0.22 | −0.11 | −0.12 | −0.14 | −0.45 | −0.19 |
| premiR_09135 | −0.15 | 0.04 | 0.45 | 0.53 | 0.17 | −0.01 | 0.04 | 0.03 | −0.29 | 0.00 | −0.08 |
| premiR_09136 | −0.13 | −0.13 | −0.05 | −0.39 | −0.25 | 0.36 | 0.02 | −0.07 | 0.00 | −0.37 | 0.01 |
| premiR_09138 | −0.15 | −0.17 | 0.15 | −0.90 | −0.60 | −0.12 | 0.33 | 0.09 | 0.02 | −0.45 | −0.24 |
| premiR_09141 | 0.47 | 0.37 | −0.25 | 1.40 | 1.54 | −0.41 | −0.91 | 0.02 | 0.10 | 0.24 | −0.98 |
| premiR_09143 | 0.32 | −0.03 | 0.28 | 0.10 | 0.11 | 0.19 | 0.12 | 0.26 | 0.24 | 0.25 | 0.30 |
| premiR_09144 | 0.00 | −0.47 | 0.41 | −0.58 | −0.24 | 0.40 | 0.39 | −0.23 | −0.47 | 0.51 | 0.28 |
| premiR_09145 | −0.05 | ND | −0.18 | −0.16 | −0.39 | 0.26 | −0.19 | −0.34 | −0.14 | −0.93 | 0.02 |
| premiR_09148 | 0.16 | −0.02 | −0.02 | −0.16 | −0.11 | 0.20 | −0.12 | 0.01 | 0.16 | −0.45 | 0.18 |
| premiR_09150 | −0.04 | −0.12 | 0.24 | 0.06 | −0.05 | 0.25 | 0.13 | 0.21 | −0.04 | −0.16 | 0.06 |
| premiR_09151-<br>premiR_09152-<br>premiR_09317-<br>premiR_09318-<br>premiR_09319-<br>premiR_09335-<br>premiR_09805 | −0.05 | −0.07 | 0.02 | −0.05 | −0.11 | 0.36 | −0.08 | −0.11 | 0.02 | −0.58 | 0.04 |
| premiR_09154 | −0.07 | −0.01 | −0.07 | −0.05 | −0.05 | −0.18 | −0.27 | −0.03 | −0.03 | −0.34 | −0.13 |
| premiR_09156 | 0.16 | −0.12 | 0.52 | −0.30 | −0.12 | −0.04 | 0.45 | 0.35 | 0.00 | 0.64 | 0.42 |
| premiR_09157 | −0.15 | −0.12 | 0.19 | −0.10 | 0.00 | 0.13 | −0.07 | −0.09 | −0.04 | −0.40 | −0.18 |
| premiR_09161 | 0.04 | 0.64 | 1.02 | 0.61 | 0.28 | 0.70 | 0.51 | −0.04 | −0.44 | 0.31 | 0.04 |
| premiR_09163 | 0.00 | 0.33 | 0.42 | 0.33 | 0.14 | 0.24 | 0.03 | 0.05 | −0.30 | −0.06 | 0.08 |
| premiR_09164 | 0.04 | ND | −0.12 | −0.35 | −0.12 | 0.00 | 0.08 | 0.00 | 0.09 | −0.22 | 0.04 |
| premiR_09165 | −0.39 | −0.72 | −0.53 | −2.04 | −0.39 | −0.05 | −0.04 | −1.13 | −0.04 | 0.20 | 0.42 |
| premiR_09167 | 0.28 | 0.03 | 0.38 | 0.30 | −0.15 | 0.40 | 0.50 | −0.06 | −0.10 | −0.02 | 0.40 |
| premiR_09169-<br>premiR_09170-<br>premiR_09407 | 0.27 | −0.42 | 0.13 | −0.50 | −0.68 | 0.24 | 0.12 | −0.54 | 0.29 | 0.29 | 0.19 |
| premiR_09176 | 0.11 | −0.21 | −0.02 | 0.08 | −0.42 | 0.06 | 0.08 | 0.38 | −0.11 | 0.57 | 0.28 |
| premiR_09177 | 0.14 | −0.44 | −1.02 | −0.51 | −0.41 | 0.27 | −0.22 | 0.29 | −0.80 | 0.52 | 0.76 |
| premiR_09179 | 0.14 | −0.01 | 0.00 | −0.61 | −0.28 | 0.13 | 0.17 | 0.21 | 0.16 | 0.67 | 0.05 |
| premiR_09180 | −0.22 | ND | −0.12 | −0.29 | −0.08 | 0.14 | −0.30 | −0.14 | −0.18 | −0.70 | −0.11 |
| premiR_09182 | 0.04 | 0.00 | −0.98 | −0.38 | −0.67 | −1.30 | −0.36 | −0.45 | −0.16 | −0.29 | 0.88 |
| premiR_09188-<br>premiR_09338-<br>premiR_09818 | 0.05 | 1.27 | 1.55 | 0.99 | 0.82 | 1.81 | 0.78 | −0.53 | −0.40 | 0.41 | −0.03 |
| premiR_09190 | 0.62 | −0.18 | 0.32 | 0.51 | 0.49 | 0.03 | 0.40 | 0.08 | 0.22 | 0.23 | 0.16 |
| premiR_09191 | 0.41 | 0.39 | −0.18 | 0.54 | 0.61 | −0.16 | 0.22 | 0.25 | −0.88 | 1.34 | 0.93 |
| premiR_09192 | 0.19 | −0.10 | −0.90 | −0.38 | −0.13 | 0.79 | 0.14 | 0.23 | −0.16 | 0.57 | 0.04 |
| premiR_09194 | 0.09 | −0.04 | −0.02 | −0.13 | −0.08 | 0.22 | −0.07 | −0.05 | 0.09 | −0.38 | 0.10 |
| premiR_09195 | −0.16 | 1.34 | 0.20 | 1.12 | 2.18 | −0.06 | −0.29 | 0.39 | 0.09 | −0.03 | 0.12 |
| premiR_09197 | −0.03 | −0.95 | 0.43 | −4.04 | −1.49 | 0.56 | 1.19 | 0.42 | −0.53 | 1.26 | 0.00 |
| premiR_09198 | −0.19 | −0.90 | −0.41 | −1.20 | −1.00 | −0.51 | 0.23 | −0.12 | −0.14 | −0.27 | 0.53 |
| premiR_09201 | 0.37 | 0.18 | 0.00 | 0.53 | −0.32 | 0.40 | 0.19 | −0.12 | −0.24 | −0.52 | 0.13 |
| premiR_09206 | 0.34 | 1.15 | 0.23 | 0.08 | −0.03 | 0.23 | −0.12 | −0.12 | 0.45 | −0.61 | 0.27 |

TABLE 7-continued ratios_454premiRs: Contains ratio data generated on tumor versus normal adjacent tissues from a variety of tissues.

| | | | | | | | | | | | |
|---|---|---|---|---|---|---|---|---|---|---|---|
| premiR_09208-<br>premiR_09398-<br>premiR_09404 | 0.18 | 0.11 | 1.24 | 2.85 | 1.57 | 0.83 | 0.67 | −0.58 | −1.06 | 0.99 | 0.35 |
| premiR_09210 | 0.03 | −0.03 | 0.00 | −0.06 | 0.03 | 0.26 | −0.20 | −0.04 | −0.06 | −0.46 | 0.10 |
| premiR_09211 | −0.07 | 0.07 | −0.10 | −0.28 | 0.04 | 0.15 | −0.20 | −0.08 | 0.00 | −0.25 | −0.08 |
| premiR_09212 | −0.24 | −0.02 | 0.28 | −0.55 | −0.44 | −0.26 | 0.34 | 0.08 | −0.22 | −0.34 | −0.23 |
| premiR_09213 | −0.02 | −0.41 | −0.44 | −0.83 | −1.39 | −0.18 | 0.47 | 0.21 | 0.02 | 0.15 | 0.67 |
| premiR_09220 | 0.05 | −0.16 | 0.17 | −0.20 | −0.14 | −0.14 | 0.53 | −0.03 | −0.06 | 0.56 | 0.31 |
| premiR_09222 | 0.10 | −0.03 | −0.19 | 0.73 | 0.06 | −0.23 | −0.05 | 0.32 | 0.02 | 0.49 | 0.03 |
| premiR_09223 | 0.19 | −0.03 | 0.47 | 0.47 | 0.49 | 0.39 | 0.37 | 0.10 | −0.09 | 0.35 | 0.30 |
| premiR_09224 | 0.27 | 0.23 | 0.40 | 0.76 | 0.63 | 0.07 | −0.37 | 0.05 | 0.00 | −0.43 | 0.20 |
| premiR_09225 | ND | −0.01 | −0.01 | −0.50 | −0.07 | 0.53 | 0.66 | 0.30 | 0.12 | 0.49 | ND |
| premiR_09226 | 0.02 | 1.59 | 0.62 | 0.52 | 0.14 | 0.43 | 0.51 | 0.02 | 0.13 | 0.14 | 0.31 |
| premiR_09227 | 0.05 | −0.27 | 0.42 | −0.21 | −0.08 | 0.40 | 0.68 | −0.01 | −0.28 | 0.62 | 0.23 |
| premiR_09229 | 0.36 | 0.20 | 0.46 | 0.36 | 0.14 | 0.36 | 0.48 | −0.06 | 0.08 | 0.58 | 0.28 |
| premiR_09236 | 0.19 | 0.63 | 0.80 | 1.29 | 1.31 | −0.11 | −0.59 | 0.21 | −0.20 | 0.06 | 0.17 |
| premiR_09240 | 0.36 | −0.05 | −0.13 | −0.53 | −0.21 | −0.15 | 0.23 | 0.12 | 0.00 | 1.06 | −0.27 |
| premiR_09242 | −0.27 | −0.94 | −0.33 | −1.35 | −1.34 | −0.45 | 0.58 | −0.11 | −0.15 | 0.69 | 0.44 |
| premiR_09244-<br>premiR_09245-<br>premiR_09273 | 0.27 | 0.50 | 0.09 | 1.99 | 1.19 | 0.09 | −0.02 | 0.98 | 0.76 | 1.44 | 0.81 |
| premiR_09245-<br>premiR_09273 | 0.36 | 0.02 | −0.95 | −0.75 | −0.07 | −0.98 | −1.35 | −1.03 | −0.05 | 0.42 | −0.47 |
| premiR_09246 | −0.26 | 0.88 | 0.95 | 0.82 | 0.57 | 1.18 | 0.85 | 0.17 | −1.03 | 0.47 | −0.04 |
| premiR_09247 | −0.14 | −0.11 | −0.25 | 0.15 | 0.26 | −0.02 | −0.26 | 0.18 | −0.60 | 0.04 | −0.24 |
| premiR_09248 | 0.01 | −0.02 | 0.06 | −0.03 | −0.05 | 0.20 | −0.19 | −0.01 | −0.01 | −0.52 | 0.09 |
| premiR_09249 | −0.22 | −0.10 | −0.29 | −0.35 | −0.16 | 0.02 | −0.22 | −0.10 | −0.17 | −0.33 | −0.21 |
| premiR_09250 | 0.33 | −0.29 | 0.33 | −0.86 | −0.84 | 0.46 | 0.66 | −0.88 | −0.50 | 1.32 | 0.60 |
| premiR_09251 | −0.06 | −0.51 | −0.04 | −1.32 | −0.75 | −0.34 | 0.34 | 0.41 | −0.04 | −0.10 | −0.04 |
| premiR_09252 | 0.32 | 0.37 | 0.39 | 0.06 | −0.21 | 0.27 | 0.75 | 0.39 | 0.48 | 0.47 | 0.17 |
| premiR_09255-<br>premiR_09399-<br>premiR_09904 | −0.08 | −0.26 | −0.19 | −0.23 | −0.71 | 0.23 | −0.24 | −0.37 | −0.07 | ND | 0.01 |
| premiR_09257 | 0.48 | −0.02 | 0.02 | 0.01 | 0.03 | 0.26 | −0.19 | −0.07 | 0.60 | −0.42 | 0.38 |
| premiR_09258 | 0.01 | −0.02 | 0.01 | −0.11 | 0.01 | 0.25 | −0.22 | −0.17 | −0.01 | −0.61 | 0.00 |
| premiR_09262-<br>premiR_09263 | 0.17 | 0.21 | 0.82 | 0.82 | 0.48 | −0.31 | −0.51 | 0.18 | 0.22 | 0.19 | −0.29 |
| premiR_09264 | 0.18 | 0.41 | 0.53 | 0.29 | 0.26 | 0.43 | 0.64 | 0.32 | −0.22 | 0.83 | 0.45 |
| premiR_09266 | −0.04 | 0.41 | 0.86 | 0.49 | 0.38 | 0.39 | 0.60 | 0.51 | 0.83 | 0.44 | −0.03 |
| premiR_09268 | −0.15 | 0.02 | −1.32 | −0.72 | −0.34 | −1.26 | −0.50 | −0.47 | −0.06 | 0.11 | 0.90 |
| premiR_09270 | −0.16 | −0.49 | 0.67 | −0.22 | −0.27 | 0.60 | 0.98 | 0.55 | −0.01 | 0.86 | 0.26 |
| premiR_09272 | 0.19 | 2.01 | 0.97 | 1.83 | 4.17 | 1.48 | −0.07 | 0.83 | 0.26 | 0.95 | 0.06 |
| premiR_09277 | −0.19 | −0.10 | 0.15 | −0.16 | 0.04 | 0.17 | 0.05 | 0.03 | −0.12 | −0.30 | −0.13 |
| premiR_09278 | 0.27 | 0.07 | 0.22 | 0.23 | 0.10 | 0.16 | 0.04 | 0.09 | 0.27 | −0.14 | 0.17 |
| premiR_09280 | −0.21 | −0.40 | 0.02 | 0.04 | −1.08 | 0.38 | 0.82 | 0.74 | 0.48 | 0.26 | 0.08 |
| premiR_09281 | 0.24 | −0.03 | 0.14 | 0.02 | −0.10 | 0.28 | 0.07 | 0.08 | 0.17 | −0.45 | 0.39 |
| premiR_09283 | −0.03 | −0.09 | −0.07 | −0.18 | −0.06 | 0.27 | −0.23 | −0.14 | −0.03 | −0.43 | −0.03 |
| premiR_09284 | −0.17 | −0.45 | −0.59 | −2.03 | −1.23 | 0.01 | 0.23 | 0.52 | −0.45 | 0.40 | −0.24 |
| premiR_09285 | 0.26 | −0.02 | −0.04 | −0.44 | −0.03 | 0.30 | −0.02 | −0.01 | 0.27 | −0.44 | 0.32 |
| premiR_09286 | 0.19 | −0.38 | 0.40 | −0.18 | 0.21 | 0.48 | 0.57 | −0.38 | −0.66 | 0.49 | 0.41 |
| premiR_09287 | 0.14 | 0.42 | 0.66 | 0.41 | 0.33 | 0.68 | 0.57 | 0.33 | 0.03 | −0.10 | 0.22 |
| premiR_09289 | 0.32 | 0.16 | 0.27 | −0.08 | −0.25 | 0.00 | 0.49 | −0.10 | 0.35 | 0.36 | 0.30 |
| premiR_09291 | 0.01 | −0.13 | −0.08 | −0.30 | −0.17 | 0.25 | −0.29 | −0.15 | 0.05 | −0.74 | 0.04 |
| premiR_09292 | 0.19 | −0.55 | −0.63 | −0.89 | −0.59 | −0.33 | 0.19 | −0.77 | 0.14 | −0.04 | 0.31 |
| premiR_09293 | −0.09 | −0.01 | 0.84 | 0.39 | 0.38 | 0.48 | 0.47 | −0.41 | 0.07 | −0.47 | −0.02 |
| premiR_09294 | −0.15 | 0.00 | −0.15 | −0.19 | 0.06 | 0.10 | −0.29 | −0.22 | −0.12 | −0.28 | −0.30 |
| premiR_09297 | −0.39 | 0.45 | −0.03 | −0.05 | −0.14 | 0.34 | 0.79 | −0.12 | −0.34 | −1.29 | −0.56 |
| premiR_09300 | 0.16 | 0.28 | 0.31 | 0.31 | 0.54 | 1.71 | 1.00 | 0.06 | −0.79 | 0.51 | 0.65 |
| premiR_09302 | 0.18 | 0.21 | 0.79 | 0.35 | −0.13 | 0.52 | 0.58 | −0.20 | 0.02 | 0.50 | 0.21 |
| premiR_09303 | −0.06 | −0.04 | 0.49 | 0.33 | 0.15 | 0.22 | 0.15 | 0.10 | −0.04 | −0.18 | 0.11 |
| premiR_09304 | 0.10 | 0.42 | 0.35 | 0.17 | 0.20 | 0.53 | 0.49 | 0.26 | −0.24 | 0.63 | 0.46 |
| premiR_09305 | 0.09 | −0.10 | −0.10 | −0.20 | 0.06 | 0.04 | −0.19 | −0.15 | 0.07 | −0.49 | 0.08 |
| premiR_09307 | −0.03 | −0.05 | −0.05 | −0.26 | −0.14 | 0.21 | −0.21 | −0.11 | −0.03 | −0.54 | 0.01 |
| premiR_09308 | 0.23 | 1.54 | 0.18 | 0.59 | 1.37 | 1.42 | 0.87 | 0.19 | 0.89 | 0.12 | 0.18 |
| premiR_09310 | 0.18 | 0.97 | 0.91 | 2.65 | 3.71 | 1.17 | 0.56 | 1.08 | −0.24 | −0.45 | 0.40 |
| premiR_09311 | 0.22 | −0.55 | 0.57 | −2.90 | −1.63 | 0.20 | 1.00 | 0.20 | −0.53 | 1.56 | 0.07 |
| premiR_09313 | 0.25 | −0.04 | 0.12 | 0.04 | −0.08 | 0.37 | −0.01 | −0.02 | 0.20 | −0.37 | 0.30 |
| premiR_09314-<br>premiR_09391 | 0.04 | 0.19 | −0.15 | 0.38 | 0.91 | 0.28 | −1.16 | −0.38 | 0.46 | −0.33 | 0.09 |
| premiR_09315-<br>premiR_09390 | 0.19 | 0.09 | −0.06 | 0.31 | 0.22 | 0.11 | −0.51 | 0.03 | 0.01 | −0.17 | 0.29 |
| premiR_09320-<br>premiR_09342 | −0.05 | −0.26 | 0.11 | 0.12 | 0.30 | 0.29 | 0.25 | −0.27 | −0.36 | 0.45 | 0.09 |
| premiR_09322-<br>premiR_09323-<br>premiR_09368 | 0.08 | 0.03 | 0.29 | 0.34 | 0.39 | 0.14 | 0.28 | 0.41 | −0.17 | 0.33 | 0.28 |

TABLE 7-continued ratios_454premiRs: Contains ratio data generated on tumor versus normal adjacent tissues from a variety of tissues.

| | | | | | | | | | | | |
|---|---|---|---|---|---|---|---|---|---|---|---|
| premiR_09328-premiR_09385-premiR_09386-premiR_09387-premiR_09388-premiR_09389 | 0.23 | 0.24 | −1.26 | −0.18 | 1.77 | 1.05 | 0.95 | 0.53 | 1.65 | 0.67 | 0.58 |
| premiR_09328-premiR_09385-premiR_09386-premiR_09387-premiR_09388-premiR_09389 | 0.27 | −0.11 | 0.11 | −0.03 | 0.99 | 0.41 | 0.85 | −0.16 | 1.10 | 0.19 | 0.66 |
| premiR_09329 | 0.28 | 0.04 | 0.28 | 0.40 | 0.02 | 0.33 | 0.18 | 0.17 | 0.24 | 0.28 | 0.30 |
| premiR_09330 | −0.01 | 0.46 | 0.05 | 0.89 | −0.03 | −0.06 | −0.28 | −0.77 | −0.79 | 0.69 | 0.88 |
| premiR_09331 | 0.01 | −0.40 | −0.51 | −1.35 | −0.74 | −0.09 | 0.61 | −0.48 | −0.15 | 0.22 | 0.88 |
| premiR_09332-premiR_09913 | 0.12 | −0.71 | −0.32 | −1.21 | −1.13 | −0.37 | −0.06 | −1.50 | 0.02 | 0.15 | 0.02 |
| premiR_09333 | −0.29 | 0.09 | 0.37 | 0.18 | −0.21 | 0.26 | 0.40 | 0.94 | −0.29 | −0.37 | −0.18 |
| premiR_09334 | −0.15 | −0.43 | 0.20 | −0.24 | −0.67 | 0.27 | 0.77 | 0.39 | 0.14 | 0.01 | −0.23 |
| premiR_09339 | −0.16 | 0.08 | 0.34 | 0.14 | 0.10 | 0.26 | 0.12 | −0.08 | −0.30 | −0.26 | −0.03 |
| premiR_09349-premiR_09350 | −0.23 | −0.45 | −0.68 | −0.44 | −0.59 | −0.26 | −0.14 | 0.11 | 0.49 | −0.08 | −0.08 |
| premiR_09351-premiR_09352-premiR_09353-premiR_09354-premiR_09355-premiR_09356-premiR_09357-premiR_09358-premiR_09359-premiR_09360-premiR_09361-premiR_09362 | −0.04 | 0.02 | −0.16 | −0.25 | 0.05 | 0.12 | −0.23 | −0.13 | −0.09 | −0.42 | −0.01 |
| premiR_09363 | 0.22 | 0.05 | 0.40 | 0.64 | 0.75 | 0.55 | 0.34 | 0.60 | −0.35 | 0.47 | 0.69 |
| premiR_09364-premiR_09365-premiR_09366 | −0.25 | −0.22 | −0.06 | −0.69 | −0.49 | −0.25 | 0.13 | 0.10 | −0.26 | −0.12 | −0.26 |
| premiR_09367 | 0.08 | 0.43 | −0.08 | 0.31 | 0.78 | 0.99 | 0.31 | 0.21 | 0.18 | 0.61 | −0.13 |
| premiR_09369-premiR_09370 | −0.10 | 0.03 | −0.47 | 0.77 | 1.02 | −0.11 | −0.75 | 0.58 | 0.00 | 0.40 | −0.09 |
| premiR_09373 | 0.70 | 0.34 | 1.40 | 1.35 | −0.01 | 1.27 | 0.98 | 0.24 | 0.50 | 0.53 | 0.32 |
| premiR_09374 | 0.05 | −0.18 | −0.06 | −0.20 | −0.10 | 0.11 | −0.24 | −0.11 | 0.03 | −0.65 | −0.06 |
| premiR_09375 | −0.04 | 0.35 | −0.15 | 1.03 | 0.80 | −0.05 | −0.85 | −0.01 | −0.07 | −0.48 | −0.05 |
| premiR_09380-premiR_09381-premiR_09382-premiR_09412-premiR_09413 | 0.28 | −0.43 | −0.54 | 0.36 | −1.17 | −0.52 | −1.53 | −1.20 | −0.86 | −0.84 | −0.52 |
| premiR_09392-premiR_09843-premiR_09847 | −0.10 | −0.10 | −0.13 | −0.33 | −0.01 | 0.08 | −0.19 | −0.26 | 0.07 | −0.53 | 0.04 |
| premiR_09393 | 0.22 | 0.33 | 0.87 | 0.74 | 0.42 | 0.92 | 0.40 | −0.26 | −0.45 | 0.51 | 0.28 |
| premiR_09394 | 0.16 | 0.01 | −0.02 | −0.06 | −0.47 | 0.24 | −0.11 | −0.11 | 0.13 | −0.54 | 0.15 |
| premiR_09396-premiR_09397 | −0.19 | −0.23 | −0.04 | −0.05 | 0.02 | 0.15 | −0.23 | 0.03 | −0.16 | −0.51 | −0.05 |
| premiR_09398 | ND | −0.03 | −0.15 | −0.19 | −0.04 | 0.15 | −0.19 | −0.01 | 0.25 | −0.34 | 0.31 |
| premiR_09398-premiR_09404 | 0.45 | −0.12 | 0.42 | 0.38 | 0.28 | 0.67 | 0.63 | 0.44 | 0.34 | 0.70 | 0.35 |
| premiR_09403-premiR_09812 | −0.07 | −0.64 | −0.04 | −1.33 | −1.20 | −0.71 | 0.06 | −0.10 | −0.05 | 0.24 | −0.16 |
| premiR_09405 | 0.13 | 0.01 | 0.13 | −0.03 | −0.06 | 0.33 | −0.09 | −0.10 | 0.14 | −0.45 | 0.18 |
| premiR_09408-premiR_09409 | 0.28 | 0.02 | −0.10 | −0.14 | −0.06 | 0.18 | −0.17 | −0.23 | 0.29 | ND | 0.21 |
| premiR_09410-premiR_09411-premiR_09836 | −0.21 | −0.12 | −0.05 | −0.26 | −0.01 | 0.05 | −0.21 | −0.23 | −0.21 | −0.47 | −0.28 |
| premiR_09414-premiR_09768 | −0.04 | 0.58 | 0.49 | 0.74 | 0.27 | 0.29 | −0.21 | 0.16 | −0.04 | −0.70 | −0.04 |
| premiR_09415 | 0.14 | −0.07 | −0.06 | −0.22 | 0.04 | 0.25 | −0.26 | −0.11 | 0.21 | −0.56 | 0.15 |
| premiR_09417 | −0.10 | −0.04 | −0.09 | −0.14 | −0.06 | 0.21 | −0.23 | −0.09 | −0.07 | −0.56 | −0.01 |
| premiR_09423 | ND | 0.50 | −0.05 | −0.55 | −1.09 | −0.01 | 0.77 | 0.28 | 0.37 | −0.01 | ND |
| premiR_09424 | −0.04 | −0.01 | −0.17 | −0.30 | −0.12 | 0.10 | −0.39 | −0.18 | −0.04 | −0.55 | −0.17 |
| premiR_09748 | 0.31 | 2.15 | 1.94 | 2.21 | 2.76 | 2.47 | 1.48 | −0.81 | −1.60 | 0.96 | 0.42 |
| premiR_09756 | 0.04 | 0.07 | 0.47 | 0.19 | −0.10 | 0.23 | 0.12 | 0.13 | −0.04 | −0.41 | 0.11 |
| premiR_09760-premiR_09886 | 0.03 | −0.02 | −0.08 | −0.15 | 0.22 | 0.23 | −0.22 | −0.14 | 0.10 | −0.49 | 0.05 |

TABLE 7-continued ratios_454premiRs: Contains ratio data generated on tumor versus normal adjacent tissues from a variety of tissues.

| | | | | | | | | | | |
|---|---|---|---|---|---|---|---|---|---|---|
| premiR_09761 | 0.28 | 0.14 | −0.12 | 0.83 | 0.18 | −0.34 | −0.22 | 0.12 | −0.24 | 0.38 | 0.10 |
| premiR_09764 | 0.10 | −0.01 | −0.36 | −0.14 | 0.41 | −0.09 | −0.02 | 0.11 | 0.01 | 0.53 | 0.12 |
| premiR_09766 | 0.28 | 0.03 | 0.21 | 0.22 | 0.03 | 0.16 | −0.13 | 0.02 | 0.34 | −0.06 | 0.19 |
| premiR_09769 | 0.02 | −0.12 | 0.32 | 0.70 | −0.45 | −0.69 | 0.01 | 0.16 | 0.09 | 0.78 | 0.82 |
| premiR_09770 | −0.17 | −0.07 | −0.01 | −0.18 | 0.09 | 0.31 | −0.17 | −0.10 | −0.13 | −0.57 | −0.08 |
| premiR_09771 | 0.23 | −0.03 | −0.05 | −0.11 | −0.02 | 0.18 | −0.24 | −0.08 | 0.30 | −0.65 | 0.19 |
| premiR_09774 | −0.11 | 0.16 | 0.79 | 0.48 | 0.18 | 0.52 | 0.28 | −0.13 | −0.20 | 0.09 | −0.22 |
| premiR_09777 | −0.01 | 0.09 | 0.27 | 0.38 | −0.11 | 0.15 | 0.07 | 0.25 | −0.03 | −0.29 | −0.03 |
| premiR_09779-premiR_09780 | 0.22 | −0.22 | −0.45 | −0.79 | −0.41 | −1.05 | 0.06 | −0.67 | 0.06 | 0.28 | 0.45 |
| premiR_09788 | 0.00 | −0.09 | 0.27 | 0.08 | −0.02 | 0.24 | −0.04 | 0.09 | 0.05 | −0.43 | 0.12 |
| premiR_09789 | 0.63 | 0.43 | 0.64 | 0.00 | 0.38 | 1.54 | 1.06 | 1.01 | 1.19 | 0.67 | 0.44 |
| premiR_09792 | −0.06 | −0.77 | −0.49 | −3.35 | −1.50 | −0.23 | 0.28 | −0.73 | −0.57 | −1.05 | −0.18 |
| premiR_09793 | 0.02 | −0.05 | 0.11 | 0.03 | −0.04 | 0.29 | 0.10 | 0.21 | −0.11 | −0.53 | 0.06 |
| premiR_09794 | 0.16 | −0.04 | 0.49 | 0.22 | 0.22 | 0.48 | 0.37 | −0.47 | −0.71 | 0.27 | 0.02 |
| premiR_09795 | −0.21 | −0.16 | 0.27 | −0.02 | 0.03 | 0.22 | −0.05 | −0.05 | −0.24 | −0.40 | −0.07 |
| premiR_09799 | −0.14 | −0.04 | −0.14 | −0.21 | −0.01 | 0.14 | −0.23 | −0.05 | 0.05 | −0.87 | −0.22 |
| premiR_09803 | 0.08 | −0.04 | −0.05 | −0.20 | −0.01 | 0.13 | −0.19 | −0.15 | 0.14 | −0.62 | 0.06 |
| premiR_09804 | 0.42 | 0.30 | 0.49 | 1.07 | 0.61 | 1.01 | 0.58 | 1.16 | −0.30 | 0.66 | 0.75 |
| premiR_09814 | 0.37 | −0.38 | −1.01 | −1.64 | −1.18 | 0.02 | 0.61 | 0.22 | 0.12 | 0.35 | 0.71 |
| premiR_09816 | −0.11 | −0.57 | −0.88 | −1.39 | −0.99 | −0.81 | 0.03 | −0.31 | 0.22 | −0.04 | 0.54 |
| premiR_09817 | 0.25 | 0.19 | −0.03 | 0.89 | 0.66 | 0.24 | 0.39 | 0.35 | −0.17 | 0.65 | 0.30 |
| premiR_09827 | 0.25 | −0.19 | −0.48 | −0.18 | −0.69 | −0.25 | −0.07 | 0.29 | 0.10 | 0.52 | 0.27 |
| premiR_09835 | 0.41 | 0.21 | 0.64 | 0.40 | 0.38 | 0.28 | 0.54 | 0.48 | 0.15 | 0.15 | 0.35 |
| premiR_09844 | −1.02 | −0.02 | −0.09 | 0.11 | 0.12 | 0.32 | −0.32 | −0.40 | −1.06 | −0.89 | −1.18 |
| premiR_09845 | −0.19 | −0.51 | 0.54 | −0.05 | −0.17 | 0.88 | 0.30 | 0.04 | −0.66 | 1.06 | 0.49 |
| premiR_09850 | 0.15 | −0.12 | 0.01 | −0.35 | −0.48 | 0.06 | 0.05 | −1.32 | −0.30 | 0.32 | −0.02 |
| premiR_09852 | −0.15 | −0.26 | −0.08 | −0.06 | −0.55 | −0.01 | −0.07 | −0.37 | −0.50 | −0.07 | −0.56 |
| premiR_09853 | 0.11 | −0.36 | 0.06 | 0.42 | −0.66 | −0.34 | −0.47 | −0.64 | −0.42 | −0.38 | −0.49 |
| premiR_09854 | 0.11 | −0.02 | 0.43 | 0.83 | −0.17 | −0.63 | −0.74 | −1.00 | −0.45 | 0.05 | 0.22 |
| premiR_09859 | 0.02 | −0.23 | 0.35 | 0.63 | 0.04 | −0.21 | −0.31 | −0.53 | −0.40 | 0.14 | 0.17 |
| premiR_09863 | 0.30 | −0.08 | 0.61 | 0.90 | −0.26 | −0.54 | −0.60 | −0.79 | −0.53 | 0.21 | 0.41 |
| premiR_09865 | 0.28 | −0.02 | 0.48 | 0.85 | −0.12 | −0.52 | −0.60 | −0.90 | −0.56 | 0.28 | 0.42 |
| premiR_09867 | 0.31 | 0.22 | 0.59 | 1.09 | 0.05 | −0.40 | −0.82 | −0.64 | −0.52 | 0.10 | 0.48 |
| premiR_09867-premiR_09869 | 0.28 | 0.12 | 0.72 | 1.23 | 0.17 | 0.08 | −0.45 | −0.73 | −0.63 | 0.03 | 0.50 |
| premiR_09868 | 0.24 | −0.31 | 0.53 | 0.91 | −0.16 | −0.55 | −0.77 | −0.91 | −0.49 | 0.11 | 0.40 |
| premiR_09870 | −0.09 | −0.03 | −0.06 | −0.12 | −0.04 | 0.14 | −0.24 | −0.13 | −0.12 | −0.77 | −0.05 |
| premiR_09874 | 0.09 | −0.12 | −0.37 | 0.52 | −0.23 | −0.54 | 0.06 | −0.07 | 0.50 | 0.89 | −0.39 |
| premiR_09875 | −0.15 | ND | 0.14 | 0.24 | −0.04 | 0.07 | −0.03 | −0.12 | −0.31 | −0.24 | −0.04 |
| premiR_09877 | 0.16 | −0.65 | 0.42 | −3.05 | −1.64 | 0.04 | 1.02 | 0.27 | −0.65 | 1.16 | 0.01 |
| premiR_09881 | −0.10 | −0.02 | 1.10 | 1.15 | 0.74 | 1.05 | 0.90 | 0.48 | −0.33 | 0.75 | 0.46 |
| premiR_09883 | 0.09 | −0.42 | 0.41 | −0.81 | −1.19 | −0.36 | 0.73 | 0.08 | 0.10 | 1.56 | −0.09 |
| premiR_09897 | 0.17 | −0.32 | −0.84 | −1.71 | −1.02 | 0.00 | 0.68 | 0.29 | −0.11 | 0.41 | 0.31 |
| premiR_09899 | 0.15 | 0.00 | 0.09 | 0.43 | −0.14 | −0.26 | −0.29 | 0.01 | 0.09 | 0.27 | 0.05 |
| premiR_09902 | −0.13 | −0.02 | −0.16 | −0.16 | −0.07 | 0.05 | −0.28 | −0.19 | −0.17 | −0.74 | −0.25 |
| premiR_09903 | −0.21 | −0.46 | 0.93 | −0.35 | −0.81 | 0.35 | 0.36 | 0.30 | −0.12 | 0.96 | 0.06 |
| premiR_09908 | −0.27 | −0.29 | 0.12 | −0.44 | −0.17 | −0.39 | −0.28 | −1.76 | −0.26 | −1.01 | −0.28 |
| premiR_09910 | 0.28 | −0.09 | −0.08 | −0.15 | −0.07 | 0.37 | −0.21 | −0.08 | 0.39 | −0.49 | 0.23 |
| premiR_09916 | 0.36 | 0.69 | 1.09 | 1.16 | 1.04 | 1.88 | 1.39 | 0.24 | −0.19 | 0.13 | 0.35 |

Tissue specific expression of a microRNA can be identified with Table 8 (tissuespecificity_index_454miRs) and Table 9 (tissuespecificity_index_454premiRs). A positive tissue specificity index value indicates a higher prevalence of this microRNA in a sample compared to the average, whereas a negative value indicates lower levels of the specific microRNA. E.g. Seq ID 113 gives negative values for e.g. uterus, stomach, prostate and colon indicating lower or no expression of this microRNA in these tissues. This indicates that the expression of this microRNA is limited to a number of tissues.

| Lengthy table referenced here | Lengthy table referenced here |
| --- | --- |
| US08188255-20120529-T00001 | US08188255-20120529-T00004 |
| Please refer to the end of the specification for access instructions. | Please refer to the end of the specification for access instructions. |

| Lengthy table referenced here | Lengthy table referenced here |
| --- | --- |
| US08188255-20120529-T00002 | US08188255-20120529-T00005 |
| Please refer to the end of the specification for access instructions. | Please refer to the end of the specification for access instructions. |

| Lengthy table referenced here | Lengthy table referenced here |
| --- | --- |
| US08188255-20120529-T00003 | US08188255-20120529-T00006 |
| Please refer to the end of the specification for access instructions. | Please refer to the end of the specification for access instructions. |

LENGTHY TABLES

The patent contains a lengthy table section. A copy of the table is available in electronic form from the USPTO web site (http://seqdata.uspto.gov/?pageRequest=docDetail&DocID=US08188255B2). An electronic copy of the table will also be available from the USPTO upon request and payment of the fee set forth in 37 CFR 1.19(b)(3).

The invention claimed is:

1. An isolated compound which comprises a contiguous nucleobase sequence of 12 to 20 nucleobases, wherein the contiguous sequence is identical or complementary to a contiguous nucleotide sequence present in a nucleic acid sequence selected from the group consisting of SEQ ID NOs: 469, 470, 471, and/or 472.

2. The compound according to claim 1, wherein the contiguous nucleobase sequence is in the form of an oligonucleotide.

3. The compound according to claim 1, wherein the contiguous nucleotide sequence comprises at least one nucleotide analogue.

4. A conjugate comprising the compound according to claim 1, and at least one non-nucleobase moiety covalently attached thereto.

5. A composition comprising a compound according to claim 1, or the conjugate according to claim 4, and at least one pharmaceutically acceptable diluent, carrier, salt or adjuvant.

6. The compound of claim 1, wherein said compound is a detection probe.

7. The compound of claim 6, wherein the contiguous nucleobase sequence forms a recognition sequence which is able to specifically hybridize or is complementary to, a RNA selected from the group consisting of SEQ ID NOs:469, 470, 471 and/or 472.

8. The compound of claim 6, wherein the oligonucleotide comprises nucleoside analogues with regular spacing over part or the entire nucleobases sequence.

9. The compound of claim 8, wherein the regular spacing is a nucleotide analogue at every second, third or fourth nucleobase position, or combination thereof.

10. A collection of detection probes which comprises at least one compound according to claim 6, and at least one further detection probe.

11. The collection of detection probes according to claim 10, which comprises at least one detection probe pair, and optionally at least one further detection probe, wherein one first member of the detection probe pair specifically hybridizes to, or is complementary to, a mature miRNA selected from the odd numbered SEQ IDs No 1-407, or the SEQ IDs listed in the first column of table 3, and the second member of the detection probe pair hybridizes, or is complementary to, the corresponding pre-mature miRNA even numbered SEQ IDs NO 2-408, or the SEQ IDs listed in the second column of table 3, wherein either the first member of the detection probe pair is unable to specifically hybridize to, or is not complementary to, the pre-mature miRNA, and/or the second member of the detection probe pair is unable to specifically hybridze to, or is not complementary to, the mature miRNA.

12. The collection of detection probes according to claim 11, which comprises at least two of said nonidentical detection probe pairs.

13. The collection of detection probes according to claim 10, which comprises at least one further detection probe comprising a recognition sequence consisting of nucleobases, wherein the detection probe is able to specifically hybridze to at least one RNA selected from the group comprising: hsa mIR 21, hsa-Let 7i, hsa miR 101, hsa miR 145, hsa miR 9, hsa miR122a, hsa miR 128b, hsa miR 149, hsa miR 125a, hsa miR 143, hsa miR 136, and hsa-miR 205.

14. The collection of detection probes according to claim 10, which further comprises at least one detection probe comprising a recognition sequence consisting of nucleobases, wherein the detection probe is able to specifically hybridze to at least one mRNA or DNA sequence associated with cancer.

15. The collection of detection probes according to claim 10 which comprises at least 5 detection probes.

16. The collection of detection probes according to 15, which comprises at least 30 detection probes.

17. A kit for the characterization of cancer, the kit comprising at least one compound according to claim 6, or a collection of detection probes according to claim 10.

18. A kit according to claim 17, wherein the kit is in the form of, or comprises, an oligonucleotide array.

19. The compound according to claim 3, wherein said nucleotide analogue is a LNA.

20. The compound of claim 1, wherein said compound has a total of 12 to 30 nucleobases.

21. The compound of claim 1, wherein said contiguous sequence is identical to a contiguous sequence present in a nucleic acid sequence selected from the group consisting of SEQ ID NOs: 469, 470, 471, and 472.

22. The compound of claim 21, wherein said compound comprises the sequence of SEQ ID NO: 469, 470, 471, or 472.

23. The compound of claim 22, wherein said compound consists of the sequence of SEQ ID NO: 469, 470, 471, or 472.

24. The compound of claim 1, wherein said contiguous sequence is complementary to a contiguous sequence present in a nucleic acid sequence selected from the group consisting of SEQ ID NOs: 469, 470, 471, and 472.

25. The compound of claim 24, wherein said compound comprises a sequence complementary to SEQ ID NO: 469, 470, 471, or 472.

26. The compound of claim 25 wherein said compound consists of a sequence complementary to SEQ ID NO: 469, 470, 471, or 472.

* * * * *